(12) United States Patent
Cirpus et al.

(10) Patent No.: US 7,893,320 B2
(45) Date of Patent: Feb. 22, 2011

(54) METHOD FOR PRODUCING MULTIPLE UNSATURATED FATTY ACIDS IN PLANTS

(75) Inventors: Petra Cirpus, Mannheim (DE); Andreas Renz, Limburgerhof (DE); Jens Lerchl, Svalöv (SE); Anne-Marie Kuijpers, Otterstadt (DE)

(73) Assignee: BASF Plant Science GmbH (DE)

( * ) Notice: Subject to any disclaimer, the term of this patent is extended or adjusted under 35 U.S.C. 154(b) by 1716 days.

(21) Appl. No.: 10/511,621

(22) PCT Filed: Apr. 25, 2003

(86) PCT No.: PCT/EP03/04297

§ 371 (c)(1), (2), (4) Date: Oct. 19, 2004

(87) PCT Pub. No.: WO03/093482

PCT Pub. Date: Nov. 13, 2003

(65) Prior Publication Data

US 2007/0028326 A1 Feb. 1, 2007

(30) Foreign Application Priority Data

Apr. 29, 2002 (DE) .............................. 102 19 203

(51) Int. Cl.
*C12N 15/82* (2006.01)
*A01H 5/00* (2006.01)
(52) U.S. Cl. ..................................... 800/281; 800/298
(58) Field of Classification Search ....................... None
See application file for complete search history.

(56) References Cited

U.S. PATENT DOCUMENTS

| | | | |
|---|---|---|---|
| 5,614,393 A | 3/1997 | Thomas et al. | |
| 6,043,411 A | 3/2000 | Nishizawa et al. | |
| 6,075,183 A * | 6/2000 | Knutzon et al. ............. | 800/281 |
| 7,067,285 B2 * | 6/2006 | Mukerji et al. ............. | 435/71.1 |
| 2004/0111763 A1 | 6/2004 | Heinz et al. | |

FOREIGN PATENT DOCUMENTS

| | | |
|---|---|---|
| CA | 2378423 A1 | 1/2001 |
| EP | 0550162 | 7/1993 |
| EP | 0794250 | 9/1997 |
| WO | WO-91/13972 | 9/1991 |
| WO | WO-93/06712 | 4/1993 |
| WO | WO-93/11245 | 6/1993 |
| WO | WO-94/11516 | 5/1994 |
| WO | WO-94/18337 | 8/1994 |
| WO | WO-95/18222 | 7/1995 |
| WO | WO-96/21022 | 7/1996 |
| WO | WO-97/21340 | 6/1997 |
| WO | WO-97/30582 | 8/1997 |
| WO | WO-98/46763 | 10/1998 |
| WO | WO-98/46764 | 10/1998 |
| WO | WO-98/46765 | 10/1998 |
| WO | WO-98/46776 | 10/1998 |
| WO | WO-99/27111 | 6/1999 |
| WO | WO-00/21557 | 4/2000 |
| WO | WO-01/02591 | 1/2001 |
| WO | WO-01/59128 | 8/2001 |

OTHER PUBLICATIONS

Broun et al, Science 282: 1315-1317, Nov. 13, 1998.*
Van de Loo et al, PNAS, USA 92: 6743-6747, Jul. 1995.*
Doerks et al, TIG 14(60: 248-250, Jun. 1998.*
Smith et al, Nature Biotechnology 15: 1222-1223, Nov. 15, 1997.*
Brenner, S.E., TIG 15(4): 132-133, Apr. 1999.*
Bork et al, TIG 12(10): 425-427, Oct. 1996.*
DeLuca, V., AgBiotech News and Information 5(6): 225N-229N, 1993.*
Parker-Barnes et al, PNAS, USA 97(15): 8284-8289, Jul. 18, 2000.*
Beaudoin et al, PNAS, USA 97(12): 6421-6426, Jun. 6, 2000.*
GenEMBL Accession AX214446, Heinz et al, Sep. 6, 2001.*
Girke et al. Plant J 15:39-48, 1998.*
Alonso, D. Lopez, et al., "Plants as 'chemical factories' for the production of polyunsaturated fatty acids", Biotechnology Advances, vol. 18, 2000, pp. 481-497.
Sayanova, Olga, et al., "Expression of a borage desaturase cDNA containing an N-terminal cytochrome b5 domain results in the accumulation of high levels of Δ6 -desaturated fatty acids in transgenic tobacco." Proc. Natl. Acad. Sci. USA, vol. 94, 1997, pp. 4211-4216.
Stukey, Joseph et al., "The OLE1 Gene of *Saccharomyces cerevisiae* Encodes the Δ9 Fatty Acid Desaturase and Can Be Functionally Replaced by the Rat Stearoyl-CoA Desaturase Gene", The Journal of Biological Chemistry, vol. 265, No. 33, 1990, pp. 20144-20149.
McKeon, Tom, et al., "Stearoyl-Acyl Carrier Protein Desaturase from Safflower Seeds." Methods in Enzymology, vol. 71, 1981, pp. 275-281.
Huang, Yung-Sheng, et al., "Cloning of Δ12-and Δ6-Desaturases from *Mortierella alpine* and Recombinant Production of γ-Linolenic Acid in *Saccharomyces cerevisiae*." Lipids, vol. 34, No. 7, 1999, pp. 649-659.

(Continued)

*Primary Examiner* — Elizabeth F McElwain
(74) *Attorney, Agent, or Firm* — Connolly Bove Lodge & Hutz LLP

(57) ABSTRACT

The present invention relates to a method for the production of fatty acid esters which comprise unsaturated fatty acids with at least three double bonds, and to free unsaturated fatty acids with a content of at least 1% by weight based on the total fatty acids present in the plants, by expressing at least one nucleic acid sequence which encodes a polypeptide with Δ6-desaturase activity and at least one nucleic acid sequence which encodes a polypeptide with Δ6-elongase activity. Advantageously, these nucleic acid sequences can, if appropriate, be expressed in the transgenic plant together with a third nucleic acid sequence which encodes a polypeptide with Δ5-desaturase activity. The invention furthermore relates to the use of defined nucleic acid sequences which encode polypeptides with a Δ6-desaturase activity, Δ6-elongase activity or Δ5-desaturase activity selected from a group of nucleic acid sequences, and/or to the use of nucleic acid constructs comprising the abovementioned nucleic acid sequences.

21 Claims, 3 Drawing Sheets

OTHER PUBLICATIONS

Wada, Hajime, et al., "Enhancement of chilling tolerance of a cyanobacterium by genetic manipulation of fatty acid desaturation." Nature, vol. 347, No. 6288, 1990, pp. 200-203.

Wang, Xuemin, et al., "Biosynthesis and regulation of linolenic acid in higher plants." Plant Physiology and Biochemistry, vol. 26, No. 6, 1988, pp. 777-792.

* cited by examiner

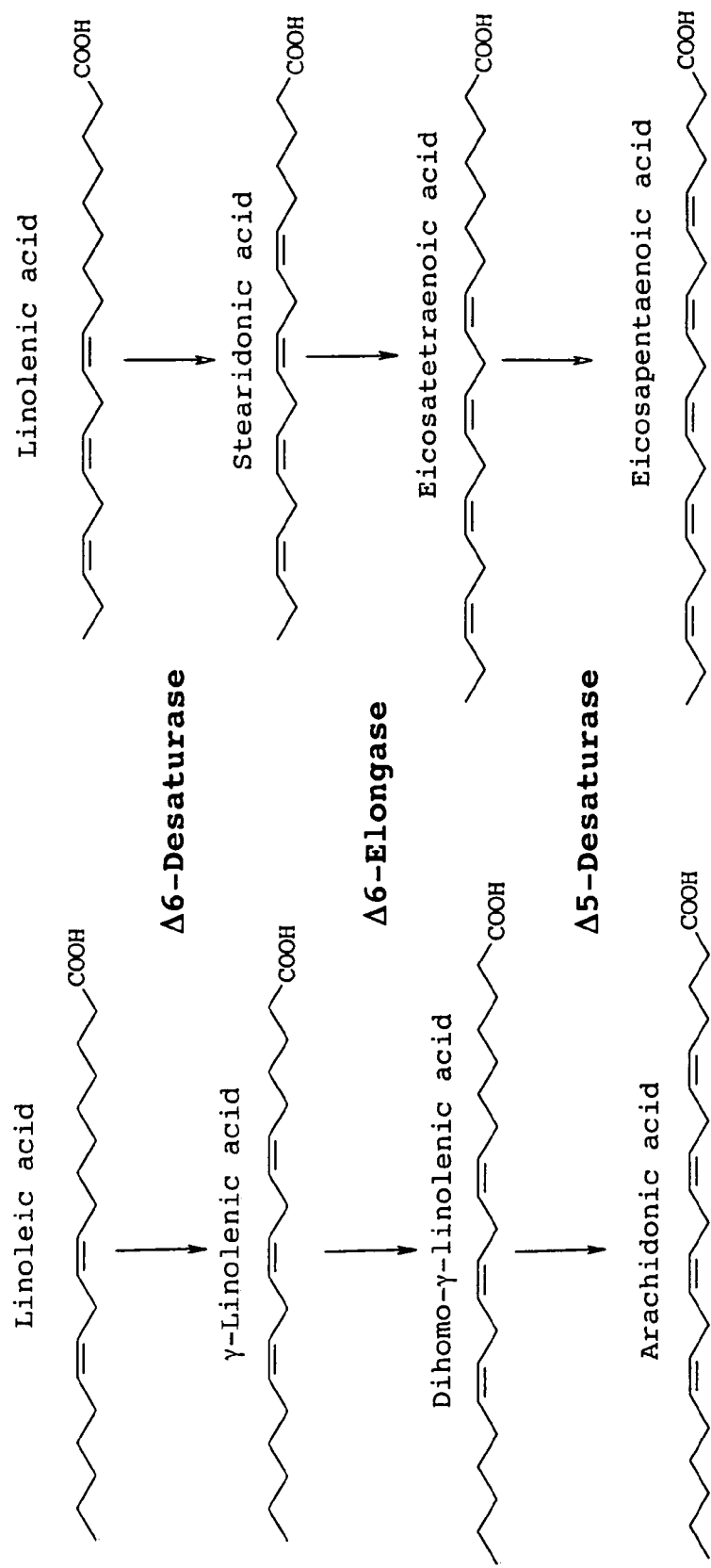
Figure 1: Biosynthesis chain

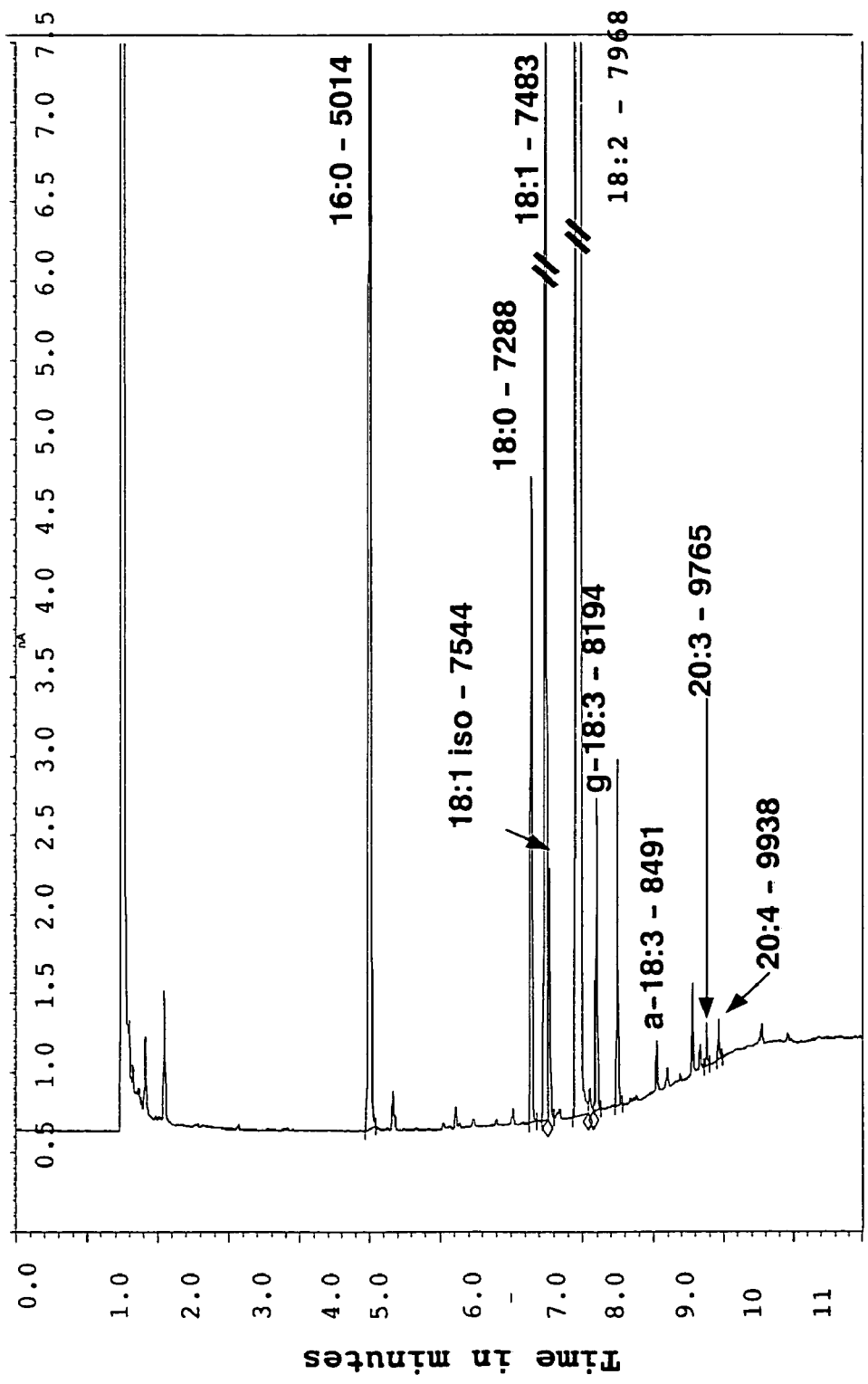
Figure 2: Fatty acid profile of transgenic tobacco seeds

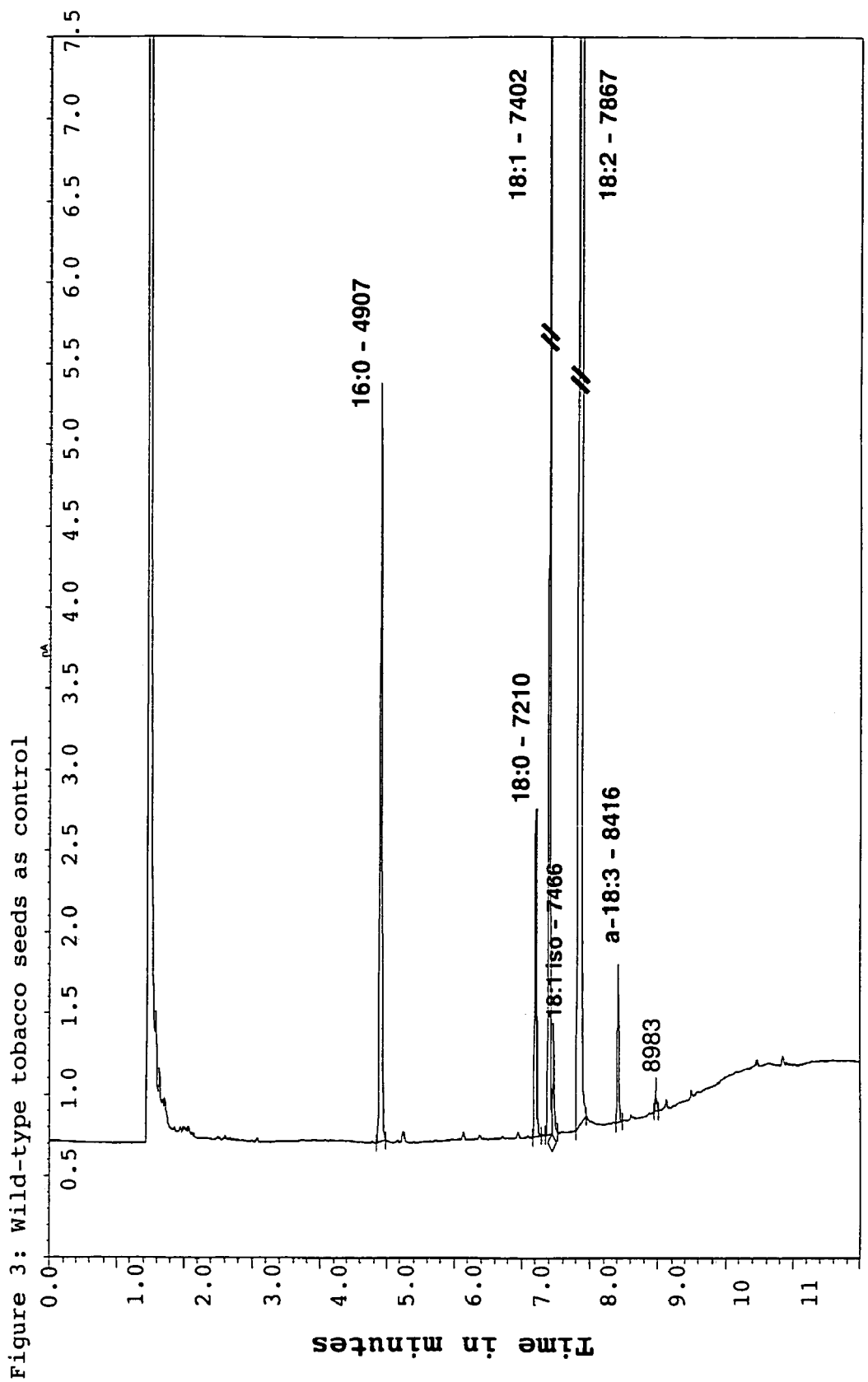

SEQUENCE LISTING

```
<160> NUMBER OF SEQ ID NOS: 65

<210> SEQ ID NO 1
<211> LENGTH: 1687
<212> TYPE: DNA
<213> ORGANISM: Borago officinalis
<220> FEATURE:
<221> NAME/KEY: CDS
<222> LOCATION: (42)..(1388)
<223> OTHER INFORMATION: D6-desaturase

<400> SEQUENCE: 1
tatctgccta ccctcccaaa gagagtagtc attttcatc a atg gct gct caa atc      56
                                             Met Ala Ala Gln Ile
                                               1               5 aag aaa tac att acc tca gat gaa ctc aag aac cac gat aaa ccc gga     104
Lys Lys Tyr Ile Thr Ser Asp Glu Leu Lys Asn His Asp Lys Pro Gly
                10                  15                  20 gat cta tgg atc tcg att caa ggg aaa gcc tat gat gtt tcg gat tgg     152
Asp Leu Trp Ile Ser Ile Gln Gly Lys Ala Tyr Asp Val Ser Asp Trp
            25                  30                  35 gtg aaa gac cat cca ggt ggc agc ttt ccc ttg aag agt ctt gct ggt     200
Val Lys Asp His Pro Gly Gly Ser Phe Pro Leu Lys Ser Leu Ala Gly
        40                  45                  50 caa gag gta act gat gca ttt gtt gca ttc cat cct gcc tct aca tgg     248
Gln Glu Val Thr Asp Ala Phe Val Ala Phe His Pro Ala Ser Thr Trp
    55                  60                  65 aag aat ctt gat aag ttt ttc act ggg tat tat ctt aaa gat tac tct     296
Lys Asn Leu Asp Lys Phe Phe Thr Gly Tyr Tyr Leu Lys Asp Tyr Ser
70                  75                  80                  85 gtt tct gag gtt tct aaa gat tat agg aag ctt gtg ttt gag ttt tct     344
Val Ser Glu Val Ser Lys Asp Tyr Arg Lys Leu Val Phe Glu Phe Ser
                90                  95                 100 aaa atg ggt ttg tat gac aaa aaa ggt cat att atg ttt gca act ttg     392
Lys Met Gly Leu Tyr Asp Lys Lys Gly His Ile Met Phe Ala Thr Leu
            105                 110                 115 tgc ttt ata gca atg ctg ttt gct atg agt gtt tat ggg gtt ttg ttt     440
Cys Phe Ile Ala Met Leu Phe Ala Met Ser Val Tyr Gly Val Leu Phe
        120                 125                 130 tgt gag ggt gtt ttg gta cat ttg ttt tct ggg tgt ttg atg ggg ttt     488
Cys Glu Gly Val Leu Val His Leu Phe Ser Gly Cys Leu Met Gly Phe
    135                 140                 145 ctt tgg att cag agt ggt tgg att gga cat gat gct ggg cat tat atg     536
Leu Trp Ile Gln Ser Gly Trp Ile Gly His Asp Ala Gly His Tyr Met
150                 155                 160                 165
```

-continued

| | | |
|---|---|---|
| gta gtg tct gat tca agg ctt aat aag ttt atg ggt att ttt gct gca<br>Val Val Ser Asp Ser Arg Leu Asn Lys Phe Met Gly Ile Phe Ala Ala<br>170 175 180 | 584 |
| aat tgt ctt tca gga ata agt att ggt tgg tgg aaa tgg aac cat aat<br>Asn Cys Leu Ser Gly Ile Ser Ile Gly Trp Trp Lys Trp Asn His Asn<br>185 190 195 | 632 |
| gca cat cac att gcc tgt aat agc ctt gaa tat gac cct gat tta caa<br>Ala His His Ile Ala Cys Asn Ser Leu Glu Tyr Asp Pro Asp Leu Gln<br>200 205 210 | 680 |
| tat ata cca ttc ctt gtt gtg tct tcc aag ttt ttt ggt tca ctc acc<br>Tyr Ile Pro Phe Leu Val Val Ser Ser Lys Phe Phe Gly Ser Leu Thr<br>215 220 225 | 728 |
| tct cat ttc tat gag aaa agg ttg act ttt gac tct tta tca aga ttc<br>Ser His Phe Tyr Glu Lys Arg Leu Thr Phe Asp Ser Leu Ser Arg Phe<br>230 235 240 245 | 776 |
| ttt gta agt tat caa cat tgg aca ttt tac cct att atg tgt gct gct<br>Phe Val Ser Tyr Gln His Trp Thr Phe Tyr Pro Ile Met Cys Ala Ala<br>250 255 260 | 824 |
| agg ctc aat atg tat gta caa tct ctc ata atg ttg ttg acc aag aga<br>Arg Leu Asn Met Tyr Val Gln Ser Leu Ile Met Leu Leu Thr Lys Arg<br>265 270 275 | 872 |
| aat gtg tcc tat cga gct cat gaa ctc ttg gga tgc cta gtg ttc tcg<br>Asn Val Ser Tyr Arg Ala His Glu Leu Leu Gly Cys Leu Val Phe Ser<br>280 285 290 | 920 |
| att tgg tac ccg ttg ctt gtt tct tgt ttg cct aat tgg ggt gaa aga<br>Ile Trp Tyr Pro Leu Leu Val Ser Cys Leu Pro Asn Trp Gly Glu Arg<br>295 300 305 | 968 |
| att atg ttt gtt att gca agt ttg tca gtg act gga atg caa caa gtt<br>Ile Met Phe Val Ile Ala Ser Leu Ser Val Thr Gly Met Gln Gln Val<br>310 315 320 325 | 1016 |
| cag ttc tcc ttg aac cac ttc tct tca agt gtt tat gtt gga aag cct<br>Gln Phe Ser Leu Asn His Phe Ser Ser Ser Val Tyr Val Gly Lys Pro<br>330 335 340 | 1064 |
| aaa ggg aat aat tgg ttt gag aaa caa acg gat ggg aca ctt gac att<br>Lys Gly Asn Asn Trp Phe Glu Lys Gln Thr Asp Gly Thr Leu Asp Ile<br>345 350 355 | 1112 |
| tct tgt cct cct tgg atg gat tgg ttt cat ggt gga ttg caa ttc caa<br>Ser Cys Pro Pro Trp Met Asp Trp Phe His Gly Gly Leu Gln Phe Gln<br>360 365 370 | 1160 |
| att gag cat cat ttg ttt ccc aag atg cct aga tgc aac ctt agg aaa<br>Ile Glu His His Leu Phe Pro Lys Met Pro Arg Cys Asn Leu Arg Lys<br>375 380 385 | 1208 |
| atc tcg ccc tac gtg atc gag tta tgc aag aaa cat aat ttg cct tac<br>Ile Ser Pro Tyr Val Ile Glu Leu Cys Lys Lys His Asn Leu Pro Tyr<br>390 395 400 405 | 1256 |
| aat tat gca tct ttc tcc aag gcc aat gaa atg aca ctc aga aca ttg<br>Asn Tyr Ala Ser Phe Ser Lys Ala Asn Glu Met Thr Leu Arg Thr Leu<br>410 415 420 | 1304 |
| agg aac aca gca ttg cag gct agg gat ata acc aag ccg ctc ccg aag<br>Arg Asn Thr Ala Leu Gln Ala Arg Asp Ile Thr Lys Pro Leu Pro Lys<br>425 430 435 | 1352 |
| aat ttg gta tgg gaa gct ctt cac act cat ggt taa aattacccctt<br>Asn Leu Val Trp Glu Ala Leu His Thr His Gly<br>440 445 | 1398 |
| agttcatgta ataatttgag attatgtatc tcctatgttt gtgtcttgtc ttggttctac | 1458 |
| ttgttggagt cattgcaact tgtctttttat ggtttattag atgttttta atatattta | 1518 |
| gaggttttgc tttcatctcc attattgatg aataaggagt tgcatattgt caattgttgt | 1578 |
| gctcaatatc tgatattttg gaatgtactt tgtaccactg tgtttcagt tgaagctcat | 1638 | gtgtacttct atagactttg tttaaatggt tatgaaaaaa aaaaaaaaa    1687

<210> SEQ ID NO 2
<211> LENGTH: 448
<212> TYPE: PRT
<213> ORGANISM: Borago officinalis

<400> SEQUENCE: 2

Met Ala Ala Gln Ile Lys Lys Tyr Ile Thr Ser Asp Glu Leu Lys Asn
 1               5                  10                  15

His Asp Lys Pro Gly Asp Leu Trp Ile Ser Ile Gln Gly Lys Ala Tyr
            20                  25                  30

Asp Val Ser Asp Trp Val Lys Asp His Pro Gly Gly Ser Phe Pro Leu
        35                  40                  45

Lys Ser Leu Ala Gly Gln Glu Val Thr Asp Ala Phe Val Ala Phe His
    50                  55                  60

Pro Ala Ser Thr Trp Lys Asn Leu Asp Lys Phe Phe Thr Gly Tyr Tyr
65                  70                  75                  80

Leu Lys Asp Tyr Ser Val Ser Glu Val Ser Lys Asp Tyr Arg Lys Leu
                85                  90                  95

Val Phe Glu Phe Ser Lys Met Gly Leu Tyr Asp Lys Lys Gly His Ile
            100                 105                 110

Met Phe Ala Thr Leu Cys Phe Ile Ala Met Leu Phe Ala Met Ser Val
        115                 120                 125

Tyr Gly Val Leu Phe Cys Glu Gly Val Leu Val His Leu Phe Ser Gly
    130                 135                 140

Cys Leu Met Gly Phe Leu Trp Ile Gln Ser Gly Trp Ile Gly His Asp
145                 150                 155                 160

Ala Gly His Tyr Met Val Val Ser Asp Ser Arg Leu Asn Lys Phe Met
                165                 170                 175

Gly Ile Phe Ala Ala Asn Cys Leu Ser Gly Ile Ser Ile Gly Trp Trp
            180                 185                 190

Lys Trp Asn His Asn Ala His His Ile Ala Cys Asn Ser Leu Glu Tyr
        195                 200                 205

Asp Pro Asp Leu Gln Tyr Ile Pro Phe Leu Val Val Ser Ser Lys Phe
    210                 215                 220

Phe Gly Ser Leu Thr Ser His Phe Tyr Glu Lys Arg Leu Thr Phe Asp
225                 230                 235                 240

Ser Leu Ser Arg Phe Phe Val Ser Tyr Gln His Trp Thr Phe Tyr Pro
                245                 250                 255

Ile Met Cys Ala Ala Arg Leu Asn Met Tyr Val Gln Ser Leu Ile Met
            260                 265                 270

Leu Leu Thr Lys Arg Asn Val Ser Tyr Arg Ala His Glu Leu Leu Gly
        275                 280                 285

Cys Leu Val Phe Ser Ile Trp Tyr Pro Leu Leu Val Ser Cys Leu Pro
    290                 295                 300

Asn Trp Gly Glu Arg Ile Met Phe Val Ile Ala Ser Leu Ser Val Thr
305                 310                 315                 320

Gly Met Gln Gln Val Gln Phe Ser Leu Asn His Phe Ser Ser Ser Val
                325                 330                 335

Tyr Val Gly Lys Pro Lys Gly Asn Asn Trp Phe Glu Lys Gln Thr Asp
            340                 345                 350

Gly Thr Leu Asp Ile Ser Cys Pro Pro Trp Met Asp Trp Phe His Gly
        355                 360                 365

-continued

```
Gly Leu Gln Phe Gln Ile Glu His His Leu Phe Pro Lys Met Pro Arg
    370                 375                 380
Cys Asn Leu Arg Lys Ile Ser Pro Tyr Val Ile Glu Leu Cys Lys Lys
385                 390                 395                 400
His Asn Leu Pro Tyr Asn Tyr Ala Ser Phe Ser Lys Ala Asn Glu Met
                405                 410                 415
Thr Leu Arg Thr Leu Arg Asn Thr Ala Leu Gln Ala Arg Asp Ile Thr
            420                 425                 430
Lys Pro Leu Pro Lys Asn Leu Val Trp Glu Ala Leu His Thr His Gly
        435                 440                 445
```

<210> SEQ ID NO 3
<211> LENGTH: 1192
<212> TYPE: DNA
<213> ORGANISM: Physcomitrella patens
<220> FEATURE:
<221> NAME/KEY: CDS
<222> LOCATION: (58)..(930)
<223> OTHER INFORMATION: D6-elongase

<400> SEQUENCE: 3

```
ctgcttcgtc tcatcttggg ggtgtgattc gggagtgggt tgagttggtg gagcgca         57 atg gag gtc gtg gag aga ttc tac ggt gag ttg gat ggg aag gtc tcg       105
Met Glu Val Val Glu Arg Phe Tyr Gly Glu Leu Asp Gly Lys Val Ser
  1               5                  10                  15 cag ggc gtg aat gca ttg ctg ggt agt ttt ggg gtg gag ttg acg gat       153
Gln Gly Val Asn Ala Leu Leu Gly Ser Phe Gly Val Glu Leu Thr Asp
             20                  25                  30 acg ccc act acc aaa ggc ttg ccc ctc gtt gac agt ccc aca ccc atc       201
Thr Pro Thr Thr Lys Gly Leu Pro Leu Val Asp Ser Pro Thr Pro Ile
         35                  40                  45 gtc ctc ggt gtt tct gta tac ttg act att gtc att gga ggg ctt ttg       249
Val Leu Gly Val Ser Val Tyr Leu Thr Ile Val Ile Gly Gly Leu Leu
     50                  55                  60 tgg ata aag gcc agg gat ctg aaa ccg cgc gcc tcg gag cca ttt ttg       297
Trp Ile Lys Ala Arg Asp Leu Lys Pro Arg Ala Ser Glu Pro Phe Leu
 65                  70                  75                  80 ctc caa gct ttg gtg ctt gtg cac aac ctg ttc tgt ttt gcg ctc agt       345
Leu Gln Ala Leu Val Leu Val His Asn Leu Phe Cys Phe Ala Leu Ser
                 85                  90                  95 ctg tat atg tgc gtg ggc atc gct tat cag gct att acc tgg cgg tac       393
Leu Tyr Met Cys Val Gly Ile Ala Tyr Gln Ala Ile Thr Trp Arg Tyr
            100                 105                 110 tct ctc tgg ggc aat gca tac aat cct aaa cat aaa gag atg gcg att       441
Ser Leu Trp Gly Asn Ala Tyr Asn Pro Lys His Lys Glu Met Ala Ile
        115                 120                 125 ctg gta tac ttg ttc tac atg tct aag tac gtg gaa ttc atg gat acc       489
Leu Val Tyr Leu Phe Tyr Met Ser Lys Tyr Val Glu Phe Met Asp Thr
    130                 135                 140 gtt atc atg ata ctg aag cgc agc acc agg caa ata agc ttc ctc cac       537
Val Ile Met Ile Leu Lys Arg Ser Thr Arg Gln Ile Ser Phe Leu His
145                 150                 155                 160 gtt tat cat cat tct tca att tcc ctc att tgg tgg gct att gct cat       585
Val Tyr His His Ser Ser Ile Ser Leu Ile Trp Trp Ala Ile Ala His
                165                 170                 175 cac gct cct ggc ggt gaa gca tat tgg tct gcg gct ctg aac tca gga       633
His Ala Pro Gly Gly Glu Ala Tyr Trp Ser Ala Ala Leu Asn Ser Gly
            180                 185                 190 gtg cat gtt ctc atg tat gcg tat tac ttc ttg gct gcc tgc ctt cga       681
```

```
Val His Val Leu Met Tyr Ala Tyr Tyr Phe Leu Ala Ala Cys Leu Arg
        195                 200                 205 agt agc cca aag tta aaa aat aag tac ctt ttt tgg ggc agg tac ttg        729
Ser Ser Pro Lys Leu Lys Asn Lys Tyr Leu Phe Trp Gly Arg Tyr Leu
    210                 215                 220 aca caa ttc caa atg ttc cag ttt atg ctg aac tta gtg cag gct tac        777
Thr Gln Phe Gln Met Phe Gln Phe Met Leu Asn Leu Val Gln Ala Tyr
225                 230                 235                 240 tac gac atg aaa acg aat gcg cca tat cca caa tgg ctg atc aag att        825
Tyr Asp Met Lys Thr Asn Ala Pro Tyr Pro Gln Trp Leu Ile Lys Ile
                245                 250                 255 ttg ttc tac tac atg atc tcg ttg ctg ttt ctt ttc ggc aat ttt tac        873
Leu Phe Tyr Tyr Met Ile Ser Leu Leu Phe Leu Phe Gly Asn Phe Tyr
            260                 265                 270 gta caa aaa tac atc aaa ccc tct gac gga aag caa aag gga gct aaa        921
Val Gln Lys Tyr Ile Lys Pro Ser Asp Gly Lys Gln Lys Gly Ala Lys
        275                 280                 285 act gag tga gctgtatcaa gccatagaaa ctctattatg ttagaacctg                970
Thr Glu
    290 aagttggtgc tttcttatct ccacttatct tttaagcagc atcagttttg aaatgatgtg     1030 tgggcgtggt ctgcaagtag tcatcaatat aatcggcctg agcacttcag atggattgtt     1090 agaacatgag taaaagcggt tattacggtg tttattttgt accaaatcac cgcacgggtg     1150 aattgaaata tttcagattt gatcaatttc atctgaaaaa aa                        1192

<210> SEQ ID NO 4
<211> LENGTH: 290
<212> TYPE: PRT
<213> ORGANISM: Physcomitrella patens

<400> SEQUENCE: 4

Met Glu Val Val Glu Arg Phe Tyr Gly Glu Leu Asp Gly Lys Val Ser
1               5                   10                  15

Gln Gly Val Asn Ala Leu Leu Gly Ser Phe Gly Val Glu Leu Thr Asp
            20                  25                  30

Thr Pro Thr Thr Lys Gly Leu Pro Leu Val Asp Ser Pro Thr Pro Ile
        35                  40                  45

Val Leu Gly Val Ser Val Tyr Leu Thr Ile Val Ile Gly Gly Leu Leu
    50                  55                  60

Trp Ile Lys Ala Arg Asp Leu Lys Pro Arg Ala Ser Glu Pro Phe Leu
65                  70                  75                  80

Leu Gln Ala Leu Val Leu Val His Asn Leu Phe Cys Phe Ala Leu Ser
                85                  90                  95

Leu Tyr Met Cys Val Gly Ile Ala Tyr Gln Ala Ile Thr Trp Arg Tyr
            100                 105                 110

Ser Leu Trp Gly Asn Ala Tyr Asn Pro Lys His Lys Glu Met Ala Ile
        115                 120                 125

Leu Val Tyr Leu Phe Tyr Met Ser Lys Tyr Val Glu Phe Met Asp Thr
    130                 135                 140

Val Ile Met Ile Leu Lys Arg Ser Thr Arg Gln Ile Ser Phe Leu His
145                 150                 155                 160

Val Tyr His His Ser Ser Ile Ser Leu Ile Trp Trp Ala Ile Ala His
                165                 170                 175

His Ala Pro Gly Gly Glu Ala Tyr Trp Ser Ala Ala Leu Asn Ser Gly
            180                 185                 190
```

```
Val His Val Leu Met Tyr Ala Tyr Tyr Phe Leu Ala Ala Cys Leu Arg
        195                 200                 205

Ser Ser Pro Lys Leu Lys Asn Lys Tyr Leu Phe Trp Gly Arg Tyr Leu
210                 215                 220

Thr Gln Phe Gln Met Phe Gln Phe Met Leu Asn Leu Val Gln Ala Tyr
225                 230                 235                 240

Tyr Asp Met Lys Thr Asn Ala Pro Tyr Pro Gln Trp Leu Ile Lys Ile
                245                 250                 255

Leu Phe Tyr Tyr Met Ile Ser Leu Leu Phe Leu Phe Gly Asn Phe Tyr
                260                 265                 270

Val Gln Lys Tyr Ile Lys Pro Ser Asp Gly Lys Gln Lys Gly Ala Lys
            275                 280                 285

Thr Glu
    290

<210> SEQ ID NO 5
<211> LENGTH: 1054
<212> TYPE: DNA
<213> ORGANISM: Thraustochytrium
<220> FEATURE:
<221> NAME/KEY: CDS
<222> LOCATION: (43)..(858)
<223> OTHER INFORMATION: D6-elongase

<400> SEQUENCE: 5
gaattcggca cgagagcgcg cggagcggag acctcggccg cg atg atg gag ccg        54
                                              Met Met Glu Pro
                                                1 ctc gac agg tac agg gcg ctg gcg gag ctc gcc gcg agg tac gcc agc     102
Leu Asp Arg Tyr Arg Ala Leu Ala Glu Leu Ala Ala Arg Tyr Ala Ser
  5                  10                  15                  20 tcg gcg gcc ttc aag tgg caa gtc acg tac gac gcc aag gac agc ttc     150
Ser Ala Ala Phe Lys Trp Gln Val Thr Tyr Asp Ala Lys Asp Ser Phe
                 25                  30                  35 gtc ggg ccc ctg gga atc cgg gag ccg ctc ggg ctc ctg gtg ggc tcc     198
Val Gly Pro Leu Gly Ile Arg Glu Pro Leu Gly Leu Leu Val Gly Ser
             40                  45                  50 gtg gtc ctc tac ctg agc ctg ctg gcc gtg gtc tac gcg ctg cgg aac     246
Val Val Leu Tyr Leu Ser Leu Leu Ala Val Val Tyr Ala Leu Arg Asn
         55                  60                  65 tac ctt ggc ggc ctc atg gcg ctc cgc agc gtg cat aac ctc ggg ctc     294
Tyr Leu Gly Gly Leu Met Ala Leu Arg Ser Val His Asn Leu Gly Leu
     70                  75                  80 tgc ctc ttc tcg ggc gcc gtg tgg atc tac acg agc tac ctc atg atc     342
Cys Leu Phe Ser Gly Ala Val Trp Ile Tyr Thr Ser Tyr Leu Met Ile
 85                  90                  95                 100 cag gat ggg cac ttt cgc agc ctc gag gcg gca acg tgc gag ccg ctc     390
Gln Asp Gly His Phe Arg Ser Leu Glu Ala Ala Thr Cys Glu Pro Leu
                105                 110                 115 aag cat ccg cac ttc cag ctc atc agc ttg ctc ttt gcg ctg tcc aag     438
Lys His Pro His Phe Gln Leu Ile Ser Leu Leu Phe Ala Leu Ser Lys
            120                 125                 130 atc tgg gag tgg ttc gac acg gtg ctc ctc atc gtc aag ggc aac aag     486
Ile Trp Glu Trp Phe Asp Thr Val Leu Leu Ile Val Lys Gly Asn Lys
        135                 140                 145 ctc cgc ttc ctg cac gtc ttg cac cac gcc acg acc ttt tgg ctc tac     534
Leu Arg Phe Leu His Val Leu His His Ala Thr Thr Phe Trp Leu Tyr
    150                 155                 160 gcc atc gac cac atc ttt ctc tcg tcc atc aag tac ggc gtc gcg gtc     582
Ala Ile Asp His Ile Phe Leu Ser Ser Ile Lys Tyr Gly Val Ala Val
```

-continued

```
aat gct ttc atc cac acc gtc atg tac gcg cac tac ttc cgc cca ttc      630
Asn Ala Phe Ile His Thr Val Met Tyr Ala His Tyr Phe Arg Pro Phe
                185                 190                 195 ccg aag ggc ttg cgc ccg ctt att acg cag ttg cag atc gtc cag ttc      678
Pro Lys Gly Leu Arg Pro Leu Ile Thr Gln Leu Gln Ile Val Gln Phe
        200                 205                 210 att ttc agc atc ggc atc cat acc gcc att tac tgg cac tac gac tgc      726
Ile Phe Ser Ile Gly Ile His Thr Ala Ile Tyr Trp His Tyr Asp Cys
215                 220                 225 gag ccg ctc gtg cat acc cac ttt tgg gaa tac gtc acg ccc tac ctt      774
Glu Pro Leu Val His Thr His Phe Trp Glu Tyr Val Thr Pro Tyr Leu
    230                 235                 240 ttc gtc gtg ccc ttc ctc atc ctc ttt ttc aat ttt tac ctg cag cag      822
Phe Val Val Pro Phe Leu Ile Leu Phe Phe Asn Phe Tyr Leu Gln Gln
245                 250                 255                 260 tac gtc ctc gcg ccc gca aaa acc aag aag gca tag ccacgtaaca            868
Tyr Val Leu Ala Pro Ala Lys Thr Lys Lys Ala
                265                 270 gtagaccagc agcgccgagg acgcgtgccg cgttatcgcg aagcacgaaa taaagaagat     928
catttgattc aacgaggcta cttgcggcca cgagaaaaaa aaaaaaaaaa aaaaaaaaaa     988
aaaaaaaaaa aaaaaaaaaa aaaaaaaaaa aaaaaaaaaa aaaaaaaaaa aaaaaaaaaa    1048
ctcgag                                                               1054

<210> SEQ ID NO 6
<211> LENGTH: 271
<212> TYPE: PRT
<213> ORGANISM: Thraustochytrium

<400> SEQUENCE: 6

Met Met Glu Pro Leu Asp Arg Tyr Arg Ala Leu Ala Glu Leu Ala Ala
1               5                   10                  15

Arg Tyr Ala Ser Ser Ala Ala Phe Lys Trp Gln Val Thr Tyr Asp Ala
            20                  25                  30

Lys Asp Ser Phe Val Gly Pro Leu Gly Ile Arg Glu Pro Leu Gly Leu
        35                  40                  45

Leu Val Gly Ser Val Val Leu Tyr Leu Ser Leu Leu Ala Val Val Tyr
    50                  55                  60

Ala Leu Arg Asn Tyr Leu Gly Gly Leu Met Ala Leu Arg Ser Val His
65                  70                  75                  80

Asn Leu Gly Leu Cys Leu Phe Ser Gly Ala Val Trp Ile Tyr Thr Ser
                85                  90                  95

Tyr Leu Met Ile Gln Asp Gly His Phe Arg Ser Leu Glu Ala Ala Thr
            100                 105                 110

Cys Glu Pro Leu Lys His Pro His Phe Gln Leu Ile Ser Leu Leu Phe
        115                 120                 125

Ala Leu Ser Lys Ile Trp Glu Trp Phe Asp Thr Val Leu Leu Ile Val
    130                 135                 140

Lys Gly Asn Lys Leu Arg Phe Leu His Val Leu His His Ala Thr Thr
145                 150                 155                 160

Phe Trp Leu Tyr Ala Ile Asp His Ile Phe Leu Ser Ser Ile Lys Tyr
                165                 170                 175

Gly Val Ala Val Asn Ala Phe Ile His Thr Val Met Tyr Ala His Tyr
            180                 185                 190

Phe Arg Pro Phe Pro Lys Gly Leu Arg Pro Leu Ile Thr Gln Leu Gln
```

-continued

```
                      195                 200                 205
Ile Val Gln Phe Ile Phe Ser Ile Gly Ile His Thr Ala Ile Tyr Trp
    210                 215                 220

His Tyr Asp Cys Glu Pro Leu Val His Thr His Phe Trp Glu Tyr Val
225                 230                 235                 240

Thr Pro Tyr Leu Phe Val Val Pro Phe Leu Ile Leu Phe Phe Asn Phe
                245                 250                 255

Tyr Leu Gln Gln Tyr Val Leu Ala Pro Ala Lys Thr Lys Lys Ala
            260                 265                 270

<210> SEQ ID NO 7
<211> LENGTH: 2040
<212> TYPE: DNA
<213> ORGANISM: Ceratodon purpureus
<220> FEATURE:
<221> NAME/KEY: CDS
<222> LOCATION: (176)..(1627)
<223> OTHER INFORMATION: D6-desaturase

<400> SEQUENCE: 7
ctcaggcagg tctcagttga tgagacgctg agttctgaat cctttgagct gtgtcaggct      60
cggcacttgt gggatggtga aggagtgatc gatcaggagt gcaggagctg cattagtttc     120
tcagggtcga tcaggttatt ctgaaaaagg ctgcgtctgt gagcagtttg caaaa atg     178
                                                                Met
                                                                  1 gcc ctc gtt acc gac ttt ctg aac ttt ctg ggc acg aca tgg agc aag     226
Ala Leu Val Thr Asp Phe Leu Asn Phe Leu Gly Thr Thr Trp Ser Lys
             5                  10                  15 tac agc gtg tac acc cat agc tat gct gga aac tat ggg cct act ttg     274
Tyr Ser Val Tyr Thr His Ser Tyr Ala Gly Asn Tyr Gly Pro Thr Leu
         20                  25                  30 aag cac gcc aaa aag gtt tct gct caa ggt aaa act gcg gga cag aca     322
Lys His Ala Lys Lys Val Ser Ala Gln Gly Lys Thr Ala Gly Gln Thr
     35                  40                  45 ctg aga cag aga tcg gtg cag gac aaa aag cca ggc act tac tct ctg     370
Leu Arg Gln Arg Ser Val Gln Asp Lys Lys Pro Gly Thr Tyr Ser Leu
 50                  55                  60                  65 gcc gat gtt gct tct cac gac agg cct gga gac tgc tgg atg atc gtc     418
Ala Asp Val Ala Ser His Asp Arg Pro Gly Asp Cys Trp Met Ile Val
                 70                  75                  80 aaa gag aag gtg tat gat att agc cgt ttt gcg gac gac cac cct gga     466
Lys Glu Lys Val Tyr Asp Ile Ser Arg Phe Ala Asp Asp His Pro Gly
             85                  90                  95 ggg acg gta att agc acc tac ttt ggg cgg gat ggc aca gac gtt ttc     514
Gly Thr Val Ile Ser Thr Tyr Phe Gly Arg Asp Gly Thr Asp Val Phe
        100                 105                 110 gca aca ttc cat cca cct gcc gca tgg aag caa ctc aat gac tac tac     562
Ala Thr Phe His Pro Pro Ala Ala Trp Lys Gln Leu Asn Asp Tyr Tyr
    115                 120                 125 att gga gac ctt gct agg gaa gag ccc ctt gat gaa ttg ctt aaa gac     610
Ile Gly Asp Leu Ala Arg Glu Glu Pro Leu Asp Glu Leu Leu Lys Asp
130                 135                 140                 145 tac aga gat atg aga gcc gag ttt gtt aga gaa ggg ctt ttc aag agt     658
Tyr Arg Asp Met Arg Ala Glu Phe Val Arg Glu Gly Leu Phe Lys Ser
                150                 155                 160 tcc aag gcc tgg ttc ctg ctt cag act ctg att aat gca gct ctc ttt     706
Ser Lys Ala Trp Phe Leu Leu Gln Thr Leu Ile Asn Ala Ala Leu Phe
            165                 170                 175 gct gcg agc att gcg act atc tgt tac gac aag agt tac tgg gct att     754
```

```
              Ala Ala Ser Ile Ala Thr Ile Cys Tyr Asp Lys Ser Tyr Trp Ala Ile
                      180                 185                 190 gtg ctg tca gcc agt ttg atg ggt ctc ttc gtc caa cag tgt gga tgg            802
Val Leu Ser Ala Ser Leu Met Gly Leu Phe Val Gln Gln Cys Gly Trp
    195                 200                 205 ctt gcc cat gat ttc ctt cat caa cag gtc ttt gag aac cgt acc gcg            850
Leu Ala His Asp Phe Leu His Gln Gln Val Phe Glu Asn Arg Thr Ala
210                 215                 220                 225 aac tcc ttc ttt ggc tat ttg ttc ggc aat tgc gtg ctt ggc ttt agt            898
Asn Ser Phe Phe Gly Tyr Leu Phe Gly Asn Cys Val Leu Gly Phe Ser
                    230                 235                 240 gta tca tgg tgg agg acg aag cac aac att cat cat act gct ccg aat            946
Val Ser Trp Trp Arg Thr Lys His Asn Ile His His Thr Ala Pro Asn
                245                 250                 255 gag tgc gac gaa cag tac aca cct cta gac gaa gac att gat act ctc            994
Glu Cys Asp Glu Gln Tyr Thr Pro Leu Asp Glu Asp Ile Asp Thr Leu
        260                 265                 270 ccc atc att gcc tgg agc aag gaa att ttg gcc acc gtt gag agc aag           1042
Pro Ile Ile Ala Trp Ser Lys Glu Ile Leu Ala Thr Val Glu Ser Lys
    275                 280                 285 aga att ttg cga gtg ctt caa tat cag cac tac atg att ctg cct cta           1090
Arg Ile Leu Arg Val Leu Gln Tyr Gln His Tyr Met Ile Leu Pro Leu
290                 295                 300                 305 ttg ttc atg gcc cgg tac agt tgg act ttt gga agt ttg ctc ttc aca           1138
Leu Phe Met Ala Arg Tyr Ser Trp Thr Phe Gly Ser Leu Leu Phe Thr
                    310                 315                 320 ttc aat cct gat ttg agc acg acc aag gga ttg ata gag aag gga aca           1186
Phe Asn Pro Asp Leu Ser Thr Thr Lys Gly Leu Ile Glu Lys Gly Thr
                325                 330                 335 gtt gct ttt cac tac gcc tgg ttc agt tgg gct gcg ttc cat att ttg           1234
Val Ala Phe His Tyr Ala Trp Phe Ser Trp Ala Ala Phe His Ile Leu
            340                 345                 350 ccg ggt gtc gct aag cct ctt gcg tgg atg gta gca act gag ctt gtg           1282
Pro Gly Val Ala Lys Pro Leu Ala Trp Met Val Ala Thr Glu Leu Val
        355                 360                 365 gcc ggt ttg ttg ttg gga ttc gtg ttt acg ttg agt cac aat gga aag           1330
Ala Gly Leu Leu Leu Gly Phe Val Phe Thr Leu Ser His Asn Gly Lys
370                 375                 380                 385 gag gtt tac aat gaa tcg aag gac ttc gtg aga gcc cag gtt att acc           1378
Glu Val Tyr Asn Glu Ser Lys Asp Phe Val Arg Ala Gln Val Ile Thr
                    390                 395                 400 acc cgt aac acc aag cga ggc tgg ttc aac gat tgg ttc act ggg gga           1426
Thr Arg Asn Thr Lys Arg Gly Trp Phe Asn Asp Trp Phe Thr Gly Gly
                405                 410                 415 ctc gac acc cag att gag cat cac ctg ttt cca aca atg ccc agg cac           1474
Leu Asp Thr Gln Ile Glu His His Leu Phe Pro Thr Met Pro Arg His
            420                 425                 430 aac tac ccc aag atc gca cct cag gtc gag gct ctt tgc aag aag cac           1522
Asn Tyr Pro Lys Ile Ala Pro Gln Val Glu Ala Leu Cys Lys Lys His
        435                 440                 445 ggc ctc gag tac gat aat gtc tcc gtc gtt ggt gcc tct gtc gcg gtt           1570
Gly Leu Glu Tyr Asp Asn Val Ser Val Val Gly Ala Ser Val Ala Val
450                 455                 460                 465 gtg aag gcg ctc aag gaa att gct gat gaa gcg tca att cgg ctt cac           1618
Val Lys Ala Leu Lys Glu Ile Ala Asp Glu Ala Ser Ile Arg Leu His
                    470                 475                 480 gct cac taa gaaatcgtcg aactttgact attcattttt ttcgcctggc                   1667
Ala His tacctcaaat gttcgggagc aggtgcttgg cagtgtgttc aaccggagcg cactgaaaat         1727
```

```
gtgcagaatc catttccaga aattaccatt cctagctaaa tcttcttttt accaggtcgg   1787
atatatgaaa ctttttgat gcaacaagta gcattcaatt gaagacattg ttcgagatat   1847
aattcgcagt gtttctattc agcgggcata cgtactagtc catatcggcg gttgccgaga   1907
gtttacatta ttagttggca caacgagtag atctagtgta aatttctatt ccgcatgta   1967 atattactct gaatatatac cgttatctat tttcctaaaa aaaaaaaaaa aaaaaaaaa   2027 aaaaaaaaaa aaa                                                     2040

<210> SEQ ID NO 8
<211> LENGTH: 483
<212> TYPE: PRT
<213> ORGANISM: Ceratodon purpureus

<400> SEQUENCE: 8
```

Met Ala Leu Val Thr Asp Phe Leu Asn Phe Leu Gly Thr Thr Trp Ser
1               5                   10                  15

Lys Tyr Ser Val Tyr Thr His Ser Tyr Ala Gly Asn Tyr Gly Pro Thr
            20                  25                  30

Leu Lys His Ala Lys Lys Val Ser Ala Gln Gly Lys Thr Ala Gly Gln
        35                  40                  45

Thr Leu Arg Gln Arg Ser Val Gln Asp Lys Lys Pro Gly Thr Tyr Ser
    50                  55                  60

Leu Ala Asp Val Ala Ser His Asp Arg Pro Gly Asp Cys Trp Met Ile
65                  70                  75                  80

Val Lys Glu Lys Val Tyr Asp Ile Ser Arg Phe Ala Asp Asp His Pro
                85                  90                  95

Gly Gly Thr Val Ile Ser Thr Tyr Phe Gly Arg Asp Gly Thr Asp Val
            100                 105                 110

Phe Ala Thr Phe His Pro Pro Ala Ala Trp Lys Gln Leu Asn Asp Tyr
        115                 120                 125

Tyr Ile Gly Asp Leu Ala Arg Glu Glu Pro Leu Asp Glu Leu Leu Lys
    130                 135                 140

Asp Tyr Arg Asp Met Arg Ala Glu Phe Val Arg Glu Gly Leu Phe Lys
145                 150                 155                 160

Ser Ser Lys Ala Trp Phe Leu Leu Gln Thr Leu Ile Asn Ala Ala Leu
                165                 170                 175

Phe Ala Ala Ser Ile Ala Thr Ile Cys Tyr Asp Lys Ser Tyr Trp Ala
            180                 185                 190

Ile Val Leu Ser Ala Ser Leu Met Gly Leu Phe Val Gln Gln Cys Gly
        195                 200                 205

Trp Leu Ala His Asp Phe Leu His Gln Gln Val Phe Glu Asn Arg Thr
    210                 215                 220

Ala Asn Ser Phe Phe Gly Tyr Leu Phe Gly Asn Cys Val Leu Gly Phe
225                 230                 235                 240

Ser Val Ser Trp Trp Arg Thr Lys His Asn Ile His His Thr Ala Pro
                245                 250                 255

Asn Glu Cys Asp Glu Gln Tyr Thr Pro Leu Asp Glu Asp Ile Asp Thr
            260                 265                 270

Leu Pro Ile Ile Ala Trp Ser Lys Glu Ile Leu Ala Thr Val Glu Ser
        275                 280                 285

Lys Arg Ile Leu Arg Val Leu Gln Tyr Gln His Tyr Met Ile Leu Pro
    290                 295                 300

Leu Leu Phe Met Ala Arg Tyr Ser Trp Thr Phe Gly Ser Leu Leu Phe

```
                305                 310                 315                 320
Thr Phe Asn Pro Asp Leu Ser Thr Thr Lys Gly Leu Ile Glu Lys Gly
                325                 330                 335

Thr Val Ala Phe His Tyr Ala Trp Phe Ser Trp Ala Ala Phe His Ile
                340                 345                 350

Leu Pro Gly Val Ala Lys Pro Leu Ala Trp Met Val Ala Thr Glu Leu
                355                 360                 365

Val Ala Gly Leu Leu Gly Phe Val Phe Thr Leu Ser His Asn Gly
                370                 375             380

Lys Glu Val Tyr Asn Glu Ser Lys Asp Phe Val Arg Ala Gln Val Ile
385                 390                 395                 400

Thr Thr Arg Asn Thr Lys Arg Gly Trp Phe Asn Asp Trp Phe Thr Gly
                405                 410                 415

Gly Leu Asp Thr Gln Ile Glu His His Leu Phe Pro Thr Met Pro Arg
                420                 425                 430

His Asn Tyr Pro Lys Ile Ala Pro Gln Val Glu Ala Leu Cys Lys Lys
                435                 440                 445

His Gly Leu Glu Tyr Asp Asn Val Ser Val Val Gly Ala Ser Val Ala
            450                 455                 460

Val Val Lys Ala Leu Lys Glu Ile Ala Asp Glu Ala Ser Ile Arg Leu
465                 470                 475                 480

His Ala His

<210> SEQ ID NO 9
<211> LENGTH: 1467
<212> TYPE: DNA
<213> ORGANISM: Ceratodon purpureus
<220> FEATURE:
<221> NAME/KEY: CDS
<222> LOCATION: (10)..(1461)
<223> OTHER INFORMATION: D6-desaturase

<400> SEQUENCE: 9 ggatccaaa atg gcc ctc gtt acc gac ttt ctg aac ttt ctg ggc acg aca        51
          Met Ala Leu Val Thr Asp Phe Leu Asn Phe Leu Gly Thr Thr
            1               5                   10 tgg agc aag tac agc gtg tac acc cat agc tat gct gga aac tat ggg        99
Trp Ser Lys Tyr Ser Val Tyr Thr His Ser Tyr Ala Gly Asn Tyr Gly
 15                  20                  25                  30 cct act ttg aag cac gcc aaa aag gtt tct gct caa ggt aaa act gcg       147
Pro Thr Leu Lys His Ala Lys Lys Val Ser Ala Gln Gly Lys Thr Ala
                 35                  40                  45 gga cag aca ctg aga cag aga tcg gtg cag gac aaa aag cca ggc act       195
Gly Gln Thr Leu Arg Gln Arg Ser Val Gln Asp Lys Lys Pro Gly Thr
             50                  55                  60 tac tct ctg gcc gat gtt gct tct cac gac agg cct gga gac tgc tgg       243
Tyr Ser Leu Ala Asp Val Ala Ser His Asp Arg Pro Gly Asp Cys Trp
         65                  70                  75 atg atc gtc aaa gag aag gtg tat gat att agc cgt ttt gcg gac gac       291
Met Ile Val Lys Glu Lys Val Tyr Asp Ile Ser Arg Phe Ala Asp Asp
     80                  85                  90 cac cct gga ggg acg gta att agc acc tac ttt ggg cgg gat ggc aca       339
His Pro Gly Gly Thr Val Ile Ser Thr Tyr Phe Gly Arg Asp Gly Thr
 95                 100                 105                 110 gac gtt ttc gca aca ttc cat cca cct gcc gca tgg aag caa ctc aat       387
Asp Val Phe Ala Thr Phe His Pro Pro Ala Ala Trp Lys Gln Leu Asn
                115                 120                 125 gac tac tac att gga gac ctt gct agg gaa gag ccc ctt gat gaa ttg       435
```

```
                Asp Tyr Tyr Ile Gly Asp Leu Ala Arg Glu Glu Pro Leu Asp Glu Leu
                            130                 135                 140 ctt aaa gac tac aga gat atg aga gcc gag ttt gtt aga gaa ggg ctt          483
Leu Lys Asp Tyr Arg Asp Met Arg Ala Glu Phe Val Arg Glu Gly Leu
        145                 150                 155 ttc aag agt tcc aag gcc tgg ttc ctg ctt cag act ctg att aat gca          531
Phe Lys Ser Ser Lys Ala Trp Phe Leu Leu Gln Thr Leu Ile Asn Ala
    160                 165                 170 gct ctc ttt gct gcg agc att gcg act atc tgt tac gac aag agt tac          579
Ala Leu Phe Ala Ala Ser Ile Ala Thr Ile Cys Tyr Asp Lys Ser Tyr
175                 180                 185                 190 tgg gct att gtg ctg tca gcc agt ttg atg ggt ctc ttc gtc caa cag          627
Trp Ala Ile Val Leu Ser Ala Ser Leu Met Gly Leu Phe Val Gln Gln
                195                 200                 205 tgt gga tgg ctt gcc cat gat ttc ctt cat caa cag gtc ttt gag aac          675
Cys Gly Trp Leu Ala His Asp Phe Leu His Gln Gln Val Phe Glu Asn
            210                 215                 220 cgt acc gcg aac tcc ttc ttt ggc tat ttg ttc ggc aat tgc gtg ctt          723
Arg Thr Ala Asn Ser Phe Phe Gly Tyr Leu Phe Gly Asn Cys Val Leu
        225                 230                 235 ggc ttt agt gta tca tgg tgg agg acg aag cac aac att cat cat act          771
Gly Phe Ser Val Ser Trp Trp Arg Thr Lys His Asn Ile His His Thr
    240                 245                 250 gct ccg aat gag tgc gac gaa cag tac aca cct cta gac gaa gac att          819
Ala Pro Asn Glu Cys Asp Glu Gln Tyr Thr Pro Leu Asp Glu Asp Ile
255                 260                 265                 270 gat act ctc ccc atc att gcc tgg agc aag gaa att ttg gcc acc gtt          867
Asp Thr Leu Pro Ile Ile Ala Trp Ser Lys Glu Ile Leu Ala Thr Val
                275                 280                 285 gag agc aag aga att ttg cga gtg ctt caa tat cag cac tac atg att          915
Glu Ser Lys Arg Ile Leu Arg Val Leu Gln Tyr Gln His Tyr Met Ile
            290                 295                 300 ctg cct cta ttg ttc atg gcc cgg tac agt tgg act ttt gga agt ttg          963
Leu Pro Leu Leu Phe Met Ala Arg Tyr Ser Trp Thr Phe Gly Ser Leu
        305                 310                 315 ctc ttc aca ttc aat cct gat ttg agc acg acc aag gga tta ata gag         1011
Leu Phe Thr Phe Asn Pro Asp Leu Ser Thr Thr Lys Gly Leu Ile Glu
    320                 325                 330 aag gga aca gtt gct ttt cac tac gcc tgg ttc agt tgg gct gcg ttc         1059
Lys Gly Thr Val Ala Phe His Tyr Ala Trp Phe Ser Trp Ala Ala Phe
335                 340                 345                 350 cat att ttg ccg ggt gtc gct aag cct ctt gcg tgg atg gta gca act         1107
His Ile Leu Pro Gly Val Ala Lys Pro Leu Ala Trp Met Val Ala Thr
                355                 360                 365 gag ctt gtg gcc ggt ttg ttg ttg gga ttc gtg ttt acg ttg agt cac         1155
Glu Leu Val Ala Gly Leu Leu Leu Gly Phe Val Phe Thr Leu Ser His
            370                 375                 380 aat gga aag gag gtt tac aat gaa tcg aag gac ttc gtg aga gcc cag         1203
Asn Gly Lys Glu Val Tyr Asn Glu Ser Lys Asp Phe Val Arg Ala Gln
        385                 390                 395 gtt att acc acc cgt aac acc aag cga ggc tgg ttc aac gat tgg ttc         1251
Val Ile Thr Thr Arg Asn Thr Lys Arg Gly Trp Phe Asn Asp Trp Phe
    400                 405                 410 act ggg gga ctc gac acc cag att gag cat cac ctg ttt cca aca atg         1299
Thr Gly Gly Leu Asp Thr Gln Ile Glu His His Leu Phe Pro Thr Met
415                 420                 425                 430 ccc agg cac aac tac ccc aag atc gca cct cag gtc gag gct ctt tgc         1347
Pro Arg His Asn Tyr Pro Lys Ile Ala Pro Gln Val Glu Ala Leu Cys
                435                 440                 445
```

-continued

```
aag aag cac ggc ctc gag tac gat aat gtc tcc gtc gtt ggt gcc tct    1395
Lys Lys His Gly Leu Glu Tyr Asp Asn Val Ser Val Val Gly Ala Ser
        450                 455                 460 gtc gcg gtt gtg aag gcg ctc aag gaa att gct gat gaa gcg tca att    1443
Val Ala Val Val Lys Ala Leu Lys Glu Ile Ala Asp Glu Ala Ser Ile
465                 470                 475 cgg ctt cac gct cac taa gtcgac                                     1467
Arg Leu His Ala His
    480
```

<210> SEQ ID NO 10
<211> LENGTH: 483
<212> TYPE: PRT
<213> ORGANISM: Ceratodon purpureus

<400> SEQUENCE: 10

```
Met Ala Leu Val Thr Asp Phe Leu Asn Phe Leu Gly Thr Thr Trp Ser
1               5                   10                  15

Lys Tyr Ser Val Tyr Thr His Ser Tyr Ala Gly Asn Tyr Gly Pro Thr
            20                  25                  30

Leu Lys His Ala Lys Lys Val Ser Ala Gln Gly Lys Thr Ala Gly Gln
        35                  40                  45

Thr Leu Arg Gln Arg Ser Val Gln Asp Lys Lys Pro Gly Thr Tyr Ser
    50                  55                  60

Leu Ala Asp Val Ala Ser His Asp Arg Pro Gly Asp Cys Trp Met Ile
65                  70                  75                  80

Val Lys Glu Lys Val Tyr Asp Ile Ser Arg Phe Ala Asp His Pro
                85                  90                  95

Gly Gly Thr Val Ile Ser Thr Tyr Phe Gly Arg Asp Gly Thr Asp Val
            100                 105                 110

Phe Ala Thr Phe His Pro Pro Ala Ala Trp Lys Gln Leu Asn Asp Tyr
        115                 120                 125

Tyr Ile Gly Asp Leu Ala Arg Glu Glu Pro Leu Asp Glu Leu Leu Lys
    130                 135                 140

Asp Tyr Arg Asp Met Arg Ala Glu Phe Val Arg Glu Gly Leu Phe Lys
145                 150                 155                 160

Ser Ser Lys Ala Trp Phe Leu Leu Gln Thr Leu Ile Asn Ala Ala Leu
                165                 170                 175

Phe Ala Ala Ser Ile Ala Thr Ile Cys Tyr Asp Lys Ser Tyr Trp Ala
            180                 185                 190

Ile Val Leu Ser Ala Ser Leu Met Gly Leu Phe Val Gln Gln Cys Gly
        195                 200                 205

Trp Leu Ala His Asp Phe Leu His Gln Gln Val Phe Glu Asn Arg Thr
    210                 215                 220

Ala Asn Ser Phe Phe Gly Tyr Leu Phe Gly Asn Cys Val Leu Gly Phe
225                 230                 235                 240

Ser Val Ser Trp Trp Arg Thr Lys His Asn Ile His His Thr Ala Pro
                245                 250                 255

Asn Glu Cys Asp Glu Gln Tyr Thr Pro Leu Asp Glu Asp Ile Asp Thr
            260                 265                 270

Leu Pro Ile Ile Ala Trp Ser Lys Glu Ile Leu Ala Thr Val Glu Ser
        275                 280                 285

Lys Arg Ile Leu Arg Val Leu Gln Tyr Gln His Tyr Met Ile Leu Pro
    290                 295                 300

Leu Leu Phe Met Ala Arg Tyr Ser Trp Thr Phe Gly Ser Leu Leu Phe
305                 310                 315                 320
```

```
Thr Phe Asn Pro Asp Leu Ser Thr Thr Lys Gly Leu Ile Glu Lys Gly
            325                 330                 335

Thr Val Ala Phe His Tyr Ala Trp Phe Ser Trp Ala Ala Phe His Ile
            340                 345                 350

Leu Pro Gly Val Ala Lys Pro Leu Ala Trp Met Val Ala Thr Glu Leu
            355                 360                 365

Val Ala Gly Leu Leu Gly Phe Val Phe Thr Leu Ser His Asn Gly
            370                 375                 380

Lys Glu Val Tyr Asn Glu Ser Lys Asp Phe Val Arg Ala Gln Val Ile
385                 390                 395                 400

Thr Thr Arg Asn Thr Lys Arg Gly Trp Phe Asn Asp Trp Phe Thr Gly
            405                 410                 415

Gly Leu Asp Thr Gln Ile Glu His His Leu Phe Pro Thr Met Pro Arg
            420                 425                 430

His Asn Tyr Pro Lys Ile Ala Pro Gln Val Glu Ala Leu Cys Lys Lys
            435                 440                 445

His Gly Leu Glu Tyr Asp Asn Val Ser Val Val Gly Ala Ser Val Ala
            450                 455                 460

Val Val Lys Ala Leu Lys Glu Ile Ala Asp Glu Ala Ser Ile Arg Leu
465                 470                 475                 480

His Ala His

<210> SEQ ID NO 11
<211> LENGTH: 2160
<212> TYPE: DNA
<213> ORGANISM: Ceratodon purpureus
<220> FEATURE:
<221> NAME/KEY: CDS
<222> LOCATION: (159)..(1721)
<223> OTHER INFORMATION: D6-desaturase

<400> SEQUENCE: 11
cggaggtctc ttgtcgttct tggagtctgt gtcgagcttg aatgcggta ggcgcggccg      60 tttcgtggtt ttggcgttgg cattgcgcga gggcggacag tgggagtgcg ggaggtctgt     120
ttgtgcatga cgaggtggtt gtaatcttcg ccggcaga atg gtg tcc cag ggc ggc     176
                                            Met Val Ser Gln Gly Gly
                                            1               5 ggt ctc tcg cag ggt tcc att gaa gaa aac att gac gtt gag cac ttg      224
Gly Leu Ser Gln Gly Ser Ile Glu Glu Asn Ile Asp Val Glu His Leu
            10                  15                  20 gca acg atg ccc ctc gtc agt gac ttc cta aat gtc ctg gga acg act      272
Ala Thr Met Pro Leu Val Ser Asp Phe Leu Asn Val Leu Gly Thr Thr
        25                  30                  35 ttg ggc cag tgg agt ctt tcc act aca ttc gct ttc aag agg ctc acg      320
Leu Gly Gln Trp Ser Leu Ser Thr Thr Phe Ala Phe Lys Arg Leu Thr
    40                  45                  50 act aag aaa cac agt tcg gac atc tcg gtg gag gca caa aaa gaa tcg      368
Thr Lys Lys His Ser Ser Asp Ile Ser Val Glu Ala Gln Lys Glu Ser
55                  60                  65                  70 gtt gcg cgg ggg cca gtt gag aat att tct caa tcg gtt gcg cag ccc      416
Val Ala Arg Gly Pro Val Glu Asn Ile Ser Gln Ser Val Ala Gln Pro
            75                  80                  85 atc agg cgg agg tgg gtg cag gat aaa aag ccg gtt act tac agc ctg      464
Ile Arg Arg Arg Trp Val Gln Asp Lys Lys Pro Val Thr Tyr Ser Leu
        90                  95                  100 aag gat gta gct tcg cac gat atg ccc cag gac tgc tgg att ata atc      512
Lys Asp Val Ala Ser His Asp Met Pro Gln Asp Cys Trp Ile Ile Ile
```

-continued

```
              105                 110                 115
aaa gag aag gtg tat gat gtg agc acc ttc gct gag cag cac cct gga         560
Lys Glu Lys Val Tyr Asp Val Ser Thr Phe Ala Glu Gln His Pro Gly
    120                 125                 130 ggc acg gtt atc aac acc tac ttc gga cga gac gcc aca gat gtt ttc         608
Gly Thr Val Ile Asn Thr Tyr Phe Gly Arg Asp Ala Thr Asp Val Phe
135                 140                 145                 150 tct act ttc cac gca tcc acc tca tgg aag att ctt cag aat ttc tac         656
Ser Thr Phe His Ala Ser Thr Ser Trp Lys Ile Leu Gln Asn Phe Tyr
                    155                 160                 165 atc ggg aac ctt gtt agg gag gag ccg act ttg gag ctg ctg aag gag         704
Ile Gly Asn Leu Val Arg Glu Glu Pro Thr Leu Glu Leu Leu Lys Glu
                170                 175                 180 tac aga gag ttg aga gcc ctt ttc ttg aga gaa cag ctt ttc aag agt         752
Tyr Arg Glu Leu Arg Ala Leu Phe Leu Arg Glu Gln Leu Phe Lys Ser
            185                 190                 195 tcc aaa tcc tac tac ctt ttc aag act ctc ata aat gtt tcc att gtt         800
Ser Lys Ser Tyr Tyr Leu Phe Lys Thr Leu Ile Asn Val Ser Ile Val
        200                 205                 210 gcc aca agc att gcg ata atc agt ctg tac aag tct tac cgg gcg gtt         848
Ala Thr Ser Ile Ala Ile Ile Ser Leu Tyr Lys Ser Tyr Arg Ala Val
215                 220                 225                 230 ctg tta tca gcc agt ttg atg ggc ttg ttt att caa cag tgc gga tgg         896
Leu Leu Ser Ala Ser Leu Met Gly Leu Phe Ile Gln Gln Cys Gly Trp
                    235                 240                 245 ttg tct cac gat ttt cta cac cat cag gta ttt gag aca cgc tgg ctc         944
Leu Ser His Asp Phe Leu His His Gln Val Phe Glu Thr Arg Trp Leu
                250                 255                 260 aat gac gtt gtt ggc tat gtg gtc ggc aac gtt gtt ctg gga ttc agt         992
Asn Asp Val Val Gly Tyr Val Val Gly Asn Val Val Leu Gly Phe Ser
            265                 270                 275 gtc tcg tgg tgg aag acc aag cac aac ctg cat cat gct gct ccg aat        1040
Val Ser Trp Trp Lys Thr Lys His Asn Leu His His Ala Ala Pro Asn
        280                 285                 290 gaa tgc gac caa aag tac aca ccg att gat gag gat att gat act ctc        1088
Glu Cys Asp Gln Lys Tyr Thr Pro Ile Asp Glu Asp Ile Asp Thr Leu
295                 300                 305                 310 ccc atc att gct tgg agt aaa gat ctc ttg gcc act gtt gag agc aag        1136
Pro Ile Ile Ala Trp Ser Lys Asp Leu Leu Ala Thr Val Glu Ser Lys
                    315                 320                 325 acc atg ttg cga gtt ctt cag tac cag cac cta ttc ttt ttg gtt ctt        1184
Thr Met Leu Arg Val Leu Gln Tyr Gln His Leu Phe Phe Leu Val Leu
                330                 335                 340 ttg acg ttt gcc cgg gcg agt tgg cta ttt tgg agc gcg gcc ttc act        1232
Leu Thr Phe Ala Arg Ala Ser Trp Leu Phe Trp Ser Ala Ala Phe Thr
            345                 350                 355 ctc agg ccc gag ttg acc ctt ggc gag aag ctt ttg gag agg gga acg        1280
Leu Arg Pro Glu Leu Thr Leu Gly Glu Lys Leu Leu Glu Arg Gly Thr
        360                 365                 370 atg gct ttg cac tac att tgg ttt aat agt gtt gcg ttt tat ctg ctc        1328
Met Ala Leu His Tyr Ile Trp Phe Asn Ser Val Ala Phe Tyr Leu Leu
375                 380                 385                 390 ccc gga tgg aaa cca gtt gta tgg atg gtg gtc agc gag ctc atg tct        1376
Pro Gly Trp Lys Pro Val Val Trp Met Val Val Ser Glu Leu Met Ser
                    395                 400                 405 ggt ttc ctg ctg gga tac gta ttt gta ctc agt cac aat gga atg gag        1424
Gly Phe Leu Leu Gly Tyr Val Phe Val Leu Ser His Asn Gly Met Glu
                410                 415                 420 gtg tac aat acg tca aag gac ttc gtg aat gcc cag att gca tcg act        1472
```

```
Val Tyr Asn Thr Ser Lys Asp Phe Val Asn Ala Gln Ile Ala Ser Thr
        425                 430                 435 cgc gac atc aaa gca ggg gtg ttt aat gat tgg ttc acc gga ggt ctc   1520
Arg Asp Ile Lys Ala Gly Val Phe Asn Asp Trp Phe Thr Gly Gly Leu
    440                 445                 450 aac aga cag att gag cat cat cta ttt cca acg atg ccc agg cac aac   1568
Asn Arg Gln Ile Glu His His Leu Phe Pro Thr Met Pro Arg His Asn
455                 460                 465                 470 ctt aat aaa att tct cct cac gtg gag act ttg tgc aag aag cat gga   1616
Leu Asn Lys Ile Ser Pro His Val Glu Thr Leu Cys Lys Lys His Gly
                475                 480                 485 ctg gtc tac gaa gac gtg agc atg gct tcg ggc act tac cgg gtt ttg   1664
Leu Val Tyr Glu Asp Val Ser Met Ala Ser Gly Thr Tyr Arg Val Leu
            490                 495                 500 aaa aca ctt aag gac gtt gcc gat gct gct tca cac cag cag ctt gct   1712
Lys Thr Leu Lys Asp Val Ala Asp Ala Ala Ser His Gln Gln Leu Ala
        505                 510                 515 gcg agt tga ggcatcgcag cactcgtcga aacattttg tctgttatag            1761
Ala Ser
520 tgttcatatg tgatcgaggg gaaaaggtcc catgctctga tctattcttc tgtagccaat  1821 attttcaat tgaaaggagg ttcctcactt atcttccatc tatcgttgca catcctgcat   1881 cagagttagc gttggagtaa tgttaagcac ttgtagatta tgcccaccat tgccacattt  1941 ctgttcggtt acaatcgttt gattccatgc tatcctccgt gttcatctcg ttgttataag  2001 caagcttgaa aaacatgct acgagattgg cagacgttgt cttggcagct gtagaggttg   2061 gttccattca ttgtgtagta cagaactctc tcgtccctgt ttctctacat tacttgttac  2121 atagtgactt tcattcacag caaaaaaaaa aaaaaaaaa                        2160

<210> SEQ ID NO 12
<211> LENGTH: 520
<212> TYPE: PRT
<213> ORGANISM: Ceratodon purpureus

<400> SEQUENCE: 12

Met Val Ser Gln Gly Gly Gly Leu Ser Gln Gly Ser Ile Glu Glu Asn
1               5                   10                  15

Ile Asp Val Glu His Leu Ala Thr Met Pro Leu Val Ser Asp Phe Leu
            20                  25                  30

Asn Val Leu Gly Thr Thr Leu Gly Gln Trp Ser Leu Ser Thr Thr Phe
        35                  40                  45

Ala Phe Lys Arg Leu Thr Thr Lys Lys His Ser Ser Asp Ile Ser Val
    50                  55                  60

Glu Ala Gln Lys Glu Ser Val Ala Arg Gly Pro Val Glu Asn Ile Ser
65                  70                  75                  80

Gln Ser Val Ala Gln Pro Ile Arg Arg Trp Val Gln Asp Lys Lys
                85                  90                  95

Pro Val Thr Tyr Ser Leu Lys Asp Val Ala Ser His Asp Met Pro Gln
            100                 105                 110

Asp Cys Trp Ile Ile Ile Lys Glu Lys Val Tyr Asp Val Ser Thr Phe
        115                 120                 125

Ala Glu Gln His Pro Gly Gly Thr Val Ile Asn Thr Tyr Phe Gly Arg
    130                 135                 140

Asp Ala Thr Asp Val Phe Ser Thr Phe His Ala Ser Thr Ser Trp Lys
145                 150                 155                 160
```

-continued

```
Ile Leu Gln Asn Phe Tyr Ile Gly Asn Leu Val Arg Glu Pro Thr
                165                 170                 175
Leu Glu Leu Leu Lys Glu Tyr Arg Glu Leu Arg Ala Leu Phe Leu Arg
            180                 185                 190
Glu Gln Leu Phe Lys Ser Ser Lys Ser Tyr Tyr Leu Phe Lys Thr Leu
            195                 200                 205
Ile Asn Val Ser Ile Val Ala Thr Ser Ile Ala Ile Ile Ser Leu Tyr
210                 215                 220
Lys Ser Tyr Arg Ala Val Leu Leu Ser Ala Ser Leu Met Gly Leu Phe
225                 230                 235                 240
Ile Gln Gln Cys Gly Trp Leu Ser His Asp Phe Leu His His Gln Val
                245                 250                 255
Phe Glu Thr Arg Trp Leu Asn Asp Val Val Gly Tyr Val Val Gly Asn
            260                 265                 270
Val Val Leu Gly Phe Ser Val Ser Trp Trp Lys Thr Lys His Asn Leu
        275                 280                 285
His His Ala Ala Pro Asn Glu Cys Asp Gln Lys Tyr Thr Pro Ile Asp
    290                 295                 300
Glu Asp Ile Asp Thr Leu Pro Ile Ile Ala Trp Ser Lys Asp Leu Leu
305                 310                 315                 320
Ala Thr Val Glu Ser Lys Thr Met Leu Arg Val Leu Gln Tyr Gln His
                325                 330                 335
Leu Phe Phe Leu Val Leu Leu Thr Phe Ala Arg Ala Ser Trp Leu Phe
            340                 345                 350
Trp Ser Ala Ala Phe Thr Leu Arg Pro Glu Leu Thr Leu Gly Glu Lys
        355                 360                 365
Leu Leu Glu Arg Gly Thr Met Ala Leu His Tyr Ile Trp Phe Asn Ser
    370                 375                 380
Val Ala Phe Tyr Leu Leu Pro Gly Trp Lys Pro Val Val Trp Met Val
385                 390                 395                 400
Val Ser Glu Leu Met Ser Gly Phe Leu Leu Gly Tyr Val Phe Val Leu
                405                 410                 415
Ser His Asn Gly Met Glu Val Tyr Asn Thr Ser Lys Asp Phe Val Asn
            420                 425                 430
Ala Gln Ile Ala Ser Thr Arg Asp Ile Lys Ala Gly Val Phe Asn Asp
        435                 440                 445
Trp Phe Thr Gly Gly Leu Asn Arg Gln Ile Glu His His Leu Phe Pro
    450                 455                 460
Thr Met Pro Arg His Asn Leu Asn Lys Ile Ser Pro His Val Glu Thr
465                 470                 475                 480
Leu Cys Lys Lys His Gly Leu Val Tyr Glu Asp Val Ser Met Ala Ser
                485                 490                 495
Gly Thr Tyr Arg Val Leu Lys Thr Leu Lys Asp Val Ala Asp Ala Ala
            500                 505                 510
Ser His Gln Gln Leu Ala Ala Ser
        515                 520

<210> SEQ ID NO 13
<211> LENGTH: 1434
<212> TYPE: DNA
<213> ORGANISM: Phaeodactylum tricornutum
<220> FEATURE:
<221> NAME/KEY: CDS
<222> LOCATION: (1)..(1434)
<223> OTHER INFORMATION: D6-desaturase
```

<400> SEQUENCE: 13

```
atg ggc aaa gga ggg gac gct cgg gcc tcg aag ggc tca acg gcg gct      48
Met Gly Lys Gly Gly Asp Ala Arg Ala Ser Lys Gly Ser Thr Ala Ala
1               5                   10                  15 cgc aag atc agt tgg cag gaa gtc aag acc cac gcg tct ccg gag gac      96
Arg Lys Ile Ser Trp Gln Glu Val Lys Thr His Ala Ser Pro Glu Asp
            20                  25                  30 gcc tgg atc att cac tcc aat aag gtc tac gac gtg tcc aac tgg cac     144
Ala Trp Ile Ile His Ser Asn Lys Val Tyr Asp Val Ser Asn Trp His
        35                  40                  45 gaa cat ccc gga ggc gcc gtc att ttc acg cac gcc ggt gac gac atg     192
Glu His Pro Gly Gly Ala Val Ile Phe Thr His Ala Gly Asp Asp Met
    50                  55                  60 acg gac att ttc gct gcc ttt cac gca ccc gga tcg cag tcg ctc atg     240
Thr Asp Ile Phe Ala Ala Phe His Ala Pro Gly Ser Gln Ser Leu Met
65                  70                  75                  80 aag aag ttc tac att ggc gaa ttg ctc ccg gaa acc acc ggc aag gag     288
Lys Lys Phe Tyr Ile Gly Glu Leu Leu Pro Glu Thr Thr Gly Lys Glu
                85                  90                  95 ccg cag caa atc gcc ttt gaa aag ggc tac cgc gat ctg cgc tcc aaa     336
Pro Gln Gln Ile Ala Phe Glu Lys Gly Tyr Arg Asp Leu Arg Ser Lys
            100                 105                 110 ctc atc atg atg ggc atg ttc aag tcc aac aag tgg ttc tac gtc tac     384
Leu Ile Met Met Gly Met Phe Lys Ser Asn Lys Trp Phe Tyr Val Tyr
        115                 120                 125 aag tgc ctc agc aac atg gcc att tgg gcc gcc gcc tgt gct ctc gtc     432
Lys Cys Leu Ser Asn Met Ala Ile Trp Ala Ala Ala Cys Ala Leu Val
    130                 135                 140 ttt tac tcg gac cgc ttc tgg gta cac ctg gcc agc gcc gtc atg ctg     480
Phe Tyr Ser Asp Arg Phe Trp Val His Leu Ala Ser Ala Val Met Leu
145                 150                 155                 160 gga aca ttc ttt cag cag tcg gga tgg ttg gca cac gac ttt ctg cac     528
Gly Thr Phe Phe Gln Gln Ser Gly Trp Leu Ala His Asp Phe Leu His
                165                 170                 175 cac cag gtc ttc acc aag cgc aag cac ggg gat ctc gga gga ctc ttt     576
His Gln Val Phe Thr Lys Arg Lys His Gly Asp Leu Gly Gly Leu Phe
            180                 185                 190 tgg ggg aac ctc atg cag ggt tac tcc gta cag tgg tgg aaa aac aag     624
Trp Gly Asn Leu Met Gln Gly Tyr Ser Val Gln Trp Trp Lys Asn Lys
        195                 200                 205 cac aac gga cac cac gcc gtc ccc aac ctc cac tgc tcc tcc gca gtc     672
His Asn Gly His His Ala Val Pro Asn Leu His Cys Ser Ser Ala Val
    210                 215                 220 gcg caa gat ggg gac ccg gac atc gat acc atg ccc ctt ctc gcc tgg     720
Ala Gln Asp Gly Asp Pro Asp Ile Asp Thr Met Pro Leu Leu Ala Trp
225                 230                 235                 240 tcc gtc cag caa gcc cag tct tac cgg gaa ctc caa gcc gac gga aag     768
Ser Val Gln Gln Ala Gln Ser Tyr Arg Glu Leu Gln Ala Asp Gly Lys
                245                 250                 255 gat tcg ggt ttg gtc aag ttc atg atc cgt aac caa tcc tac ttt tac     816
Asp Ser Gly Leu Val Lys Phe Met Ile Arg Asn Gln Ser Tyr Phe Tyr
            260                 265                 270 ttt ccc atc ttg ttg ctc gcc cgc ctg tcg tgg ttg aac gag tcc ttc     864
Phe Pro Ile Leu Leu Leu Ala Arg Leu Ser Trp Leu Asn Glu Ser Phe
        275                 280                 285 aag tgc gcc ttt ggg ctt gga gct gcg tcg gag aac gct gct ctc gaa     912
Lys Cys Ala Phe Gly Leu Gly Ala Ala Ser Glu Asn Ala Ala Leu Glu
    290                 295                 300 ctc aag gcc aag ggt ctt cag tac ccc ctt ttt gaa aag gct ggc atc     960
```

-continued

```
Leu Lys Ala Lys Gly Leu Gln Tyr Pro Leu Leu Glu Lys Ala Gly Ile
305                 310                 315                 320 ctg ctg cac tac gct tgg atg ctt aca gtt tcg tcc ggc ttt gga cgc      1008
Leu Leu His Tyr Ala Trp Met Leu Thr Val Ser Ser Gly Phe Gly Arg
                325                 330                 335 ttc tcg ttc gcg tac acc gca ttt tac ttt cta acc gcg acc gcg tcc      1056
Phe Ser Phe Ala Tyr Thr Ala Phe Tyr Phe Leu Thr Ala Thr Ala Ser
            340                 345                 350 tgt gga ttc ttg ctc gcc att gtc ttt ggc ctc ggc cac aac ggc atg      1104
Cys Gly Phe Leu Leu Ala Ile Val Phe Gly Leu Gly His Asn Gly Met
        355                 360                 365 gcc acc tac aat gcc gac gcc cgt ccg gac ttc tgg aag ctc caa gtc      1152
Ala Thr Tyr Asn Ala Asp Ala Arg Pro Asp Phe Trp Lys Leu Gln Val
    370                 375                 380 acc acg act cgc aac gtc acg ggc gga cac ggt ttc ccc caa gcc ttt      1200
Thr Thr Thr Arg Asn Val Thr Gly Gly His Gly Phe Pro Gln Ala Phe
385                 390                 395                 400 gtc gac tgg ttc tgt ggt ggc ctc cag tac caa gtc gac cac cac tta      1248
Val Asp Trp Phe Cys Gly Gly Leu Gln Tyr Gln Val Asp His His Leu
                405                 410                 415 ttc ccc agc ctg ccc cga cac aat ctg gcc aag aca cac gca ctg gtc      1296
Phe Pro Ser Leu Pro Arg His Asn Leu Ala Lys Thr His Ala Leu Val
            420                 425                 430 gaa tcg ttc tgc aag gag tgg ggt gtc cag tac cac gaa gcc gac ctt      1344
Glu Ser Phe Cys Lys Glu Trp Gly Val Gln Tyr His Glu Ala Asp Leu
        435                 440                 445 gtg gac ggg acc atg gaa gtc ttg cac cat ttg ggc agc gtg gcc ggc      1392
Val Asp Gly Thr Met Glu Val Leu His His Leu Gly Ser Val Ala Gly
    450                 455                 460 gaa ttc gtc gtg gat ttt gta cgc gat gga ccc gcc atg taa              1434
Glu Phe Val Val Asp Phe Val Arg Asp Gly Pro Ala Met
465                 470                 475
```

<210> SEQ ID NO 14
<211> LENGTH: 477
<212> TYPE: PRT
<213> ORGANISM: Phaeodactylum tricornutum

<400> SEQUENCE: 14

```
Met Gly Lys Gly Gly Asp Ala Arg Ala Ser Lys Gly Ser Thr Ala Ala
1               5                   10                  15

Arg Lys Ile Ser Trp Gln Glu Val Lys Thr His Ala Ser Pro Glu Asp
            20                  25                  30

Ala Trp Ile Ile His Ser Asn Lys Val Tyr Asp Val Ser Asn Trp His
        35                  40                  45

Glu His Pro Gly Gly Ala Val Ile Phe Thr His Ala Gly Asp Asp Met
    50                  55                  60

Thr Asp Ile Phe Ala Ala Phe His Ala Pro Gly Ser Gln Ser Leu Met
65                  70                  75                  80

Lys Lys Phe Tyr Ile Gly Glu Leu Leu Pro Glu Thr Thr Gly Lys Glu
                85                  90                  95

Pro Gln Gln Ile Ala Phe Glu Lys Gly Tyr Arg Asp Leu Arg Ser Lys
            100                 105                 110

Leu Ile Met Met Gly Met Phe Lys Ser Asn Lys Trp Phe Tyr Val Tyr
        115                 120                 125

Lys Cys Leu Ser Asn Met Ala Ile Trp Ala Ala Ala Cys Ala Leu Val
    130                 135                 140

Phe Tyr Ser Asp Arg Phe Trp Val His Leu Ala Ser Ala Val Met Leu
```

```
                145                 150                 155                 160
Gly Thr Phe Phe Gln Gln Ser Gly Trp Leu Ala His Asp Phe Leu His
                165                 170                 175
His Gln Val Phe Thr Lys Arg Lys His Gly Asp Leu Gly Gly Leu Phe
                180                 185                 190
Trp Gly Asn Leu Met Gln Gly Tyr Ser Val Gln Trp Trp Lys Asn Lys
                195                 200                 205
His Asn Gly His His Ala Val Pro Asn Leu His Cys Ser Ser Ala Val
        210                 215                 220
Ala Gln Asp Gly Asp Pro Asp Ile Asp Thr Met Pro Leu Leu Ala Trp
225                 230                 235                 240
Ser Val Gln Gln Ala Gln Ser Tyr Arg Glu Leu Gln Ala Asp Gly Lys
                245                 250                 255
Asp Ser Gly Leu Val Lys Phe Met Ile Arg Asn Gln Ser Tyr Phe Tyr
                260                 265                 270
Phe Pro Ile Leu Leu Leu Ala Arg Leu Ser Trp Leu Asn Glu Ser Phe
                275                 280                 285
Lys Cys Ala Phe Gly Leu Gly Ala Ala Ser Glu Asn Ala Ala Leu Glu
                290                 295                 300
Leu Lys Ala Lys Gly Leu Gln Tyr Pro Leu Leu Glu Lys Ala Gly Ile
305                 310                 315                 320
Leu Leu His Tyr Ala Trp Met Leu Thr Val Ser Ser Gly Phe Gly Arg
                325                 330                 335
Phe Ser Phe Ala Tyr Thr Ala Phe Tyr Phe Leu Thr Ala Thr Ala Ser
                340                 345                 350
Cys Gly Phe Leu Leu Ala Ile Val Phe Gly Leu Gly His Asn Gly Met
                355                 360                 365
Ala Thr Tyr Asn Ala Asp Ala Arg Pro Asp Phe Trp Lys Leu Gln Val
                370                 375                 380
Thr Thr Thr Arg Asn Val Thr Gly Gly His Gly Phe Pro Gln Ala Phe
385                 390                 395                 400
Val Asp Trp Phe Cys Gly Gly Leu Gln Tyr Gln Val Asp His His Leu
                405                 410                 415
Phe Pro Ser Leu Pro Arg His Asn Leu Ala Lys Thr His Ala Leu Val
                420                 425                 430
Glu Ser Phe Cys Lys Glu Trp Gly Val Gln Tyr His Glu Ala Asp Leu
                435                 440                 445
Val Asp Gly Thr Met Glu Val Leu His His Leu Gly Ser Val Ala Gly
        450                 455                 460
Glu Phe Val Val Asp Phe Val Arg Asp Gly Pro Ala Met
465                 470                 475

<210> SEQ ID NO 15
<211> LENGTH: 1563
<212> TYPE: DNA
<213> ORGANISM: Ceratodon purpureus
<220> FEATURE:
<221> NAME/KEY: CDS
<222> LOCATION: (1)..(1563)
<223> OTHER INFORMATION: D6-desaturase

<400> SEQUENCE: 15 atg gtg tcc cag ggc ggc ggt ctc tcg cag ggt tcc att gaa gaa aac     48
Met Val Ser Gln Gly Gly Gly Leu Ser Gln Gly Ser Ile Glu Glu Asn
 1               5                  10                  15 att gac gtt gag cac ttg gca acg atg ccc ctc gtc agt gac ttc cta     96
```

```
             Ile Asp Val Glu His Leu Ala Thr Met Pro Leu Val Ser Asp Phe Leu
                      20                  25                  30 aat gtc ctg gga acg act ttg ggc cag tgg agt ctt tcc act aca ttc           144
Asn Val Leu Gly Thr Thr Leu Gly Gln Trp Ser Leu Ser Thr Thr Phe
             35                  40                  45 gct ttc aag agg ctc acg act aag aaa cac agt tcg gac atc tcg gtg           192
Ala Phe Lys Arg Leu Thr Thr Lys Lys His Ser Ser Asp Ile Ser Val
         50                  55                  60 gag gca caa aaa gaa tcg gtt gcg cgg ggg cca gtt gag aat att tct           240
Glu Ala Gln Lys Glu Ser Val Ala Arg Gly Pro Val Glu Asn Ile Ser
 65                  70                  75                  80 caa tcg gtt gcg cag ccc atc agg cgg agg tgg gtg cag gat aaa aag           288
Gln Ser Val Ala Gln Pro Ile Arg Arg Arg Trp Val Gln Asp Lys Lys
                 85                  90                  95 ccg gtt act tac agc ctg aag gat gta gct tcg cac gat atg ccc cag           336
Pro Val Thr Tyr Ser Leu Lys Asp Val Ala Ser His Asp Met Pro Gln
            100                 105                 110 gac tgc tgg att ata atc aaa gag aag gtg tat gat gtg agc acc ttc           384
Asp Cys Trp Ile Ile Ile Lys Glu Lys Val Tyr Asp Val Ser Thr Phe
        115                 120                 125 gct gag cag cac cct gga ggc acg gtt atc aac acc tac ttc gga cga           432
Ala Glu Gln His Pro Gly Gly Thr Val Ile Asn Thr Tyr Phe Gly Arg
130                 135                 140 gac gcc aca gat gtt ttc tct act ttc cac gca tcc acc tca tgg aag           480
Asp Ala Thr Asp Val Phe Ser Thr Phe His Ala Ser Thr Ser Trp Lys
145                 150                 155                 160 att ctt cag aat ttc tac atc ggg aac ctt gtt agg gag gag ccg act           528
Ile Leu Gln Asn Phe Tyr Ile Gly Asn Leu Val Arg Glu Glu Pro Thr
                165                 170                 175 ttg gag ctg ctg aag gag tac aga gag ttg aga gcc ctt ttc ttg aga           576
Leu Glu Leu Leu Lys Glu Tyr Arg Glu Leu Arg Ala Leu Phe Leu Arg
            180                 185                 190 gaa cag ctt ttc aag agt tcc aaa tcc tac tac ctt ttc aag act ctc           624
Glu Gln Leu Phe Lys Ser Ser Lys Ser Tyr Tyr Leu Phe Lys Thr Leu
        195                 200                 205 ata aat gtt tcc att gtt gcc aca agc att gcg ata atc agt ctg tac           672
Ile Asn Val Ser Ile Val Ala Thr Ser Ile Ala Ile Ile Ser Leu Tyr
    210                 215                 220 aag tct tac cgg gcg gtt ctg tta tca gcc agt ttg atg ggc ttg ttt           720
Lys Ser Tyr Arg Ala Val Leu Leu Ser Ala Ser Leu Met Gly Leu Phe
225                 230                 235                 240 att caa cag tgc gga tgg ttg tct cac gat ttt cta cac cat cag gta           768
Ile Gln Gln Cys Gly Trp Leu Ser His Asp Phe Leu His His Gln Val
                245                 250                 255 ttt gag aca cgc tgg ctc aat gac gtt gtt ggc tat gtg gtc ggc aac           816
Phe Glu Thr Arg Trp Leu Asn Asp Val Val Gly Tyr Val Val Gly Asn
            260                 265                 270 gtt gtt ctg gga ttc agt gtc tcg tgg tgg aag acc aag cac aac ctg           864
Val Val Leu Gly Phe Ser Val Ser Trp Trp Lys Thr Lys His Asn Leu
        275                 280                 285 cat cat gct gct ccg aat gaa tgc gac caa aag tac aca ccg att gat           912
His His Ala Ala Pro Asn Glu Cys Asp Gln Lys Tyr Thr Pro Ile Asp
    290                 295                 300 gag gat att gat act ctc ccc atc att gct tgg agt aaa gat ctc ttg           960
Glu Asp Ile Asp Thr Leu Pro Ile Ile Ala Trp Ser Lys Asp Leu Leu
305                 310                 315                 320 gcc act gtt gag agc aag acc atg ttg cga gtt ctt cag tac cag cac          1008
Ala Thr Val Glu Ser Lys Thr Met Leu Arg Val Leu Gln Tyr Gln His
                325                 330                 335
```

```
cta ttc ttt ttg gtt ctt ttg acg ttt gcc cgg gcg agt tgg cta ttt      1056
Leu Phe Phe Leu Val Leu Leu Thr Phe Ala Arg Ala Ser Trp Leu Phe
            340                 345                 350 tgg agc gcg gcc ttc act ctc agg ccc gag ttg acc ctt ggc gag aag      1104
Trp Ser Ala Ala Phe Thr Leu Arg Pro Glu Leu Thr Leu Gly Glu Lys
355                 360                 365 ctt ttg gag agg gga acg atg gct ttg cac tac att tgg ttt aat agt      1152
Leu Leu Glu Arg Gly Thr Met Ala Leu His Tyr Ile Trp Phe Asn Ser
        370                 375                 380 gtt gcg ttt tat ctg ctc ccc gga tgg aaa cca gtt gta tgg atg gtg      1200
Val Ala Phe Tyr Leu Leu Pro Gly Trp Lys Pro Val Val Trp Met Val
385                 390                 395                 400 gtc agc gag ctc atg tct ggt ttc ctg ctg gga tac gta ttt gta ctc      1248
Val Ser Glu Leu Met Ser Gly Phe Leu Leu Gly Tyr Val Phe Val Leu
            405                 410                 415 agt cac aat gga atg gag gtg tac aat acg tca aag gac ttc gtg aat      1296
Ser His Asn Gly Met Glu Val Tyr Asn Thr Ser Lys Asp Phe Val Asn
        420                 425                 430 gcc cag att gca tcg act cgc gac atc aaa gca ggg gtg ttt aat gat      1344
Ala Gln Ile Ala Ser Thr Arg Asp Ile Lys Ala Gly Val Phe Asn Asp
    435                 440                 445 tgg ttc acc gga ggt ctc aac aga cag att gag cat cat cta ttt cca      1392
Trp Phe Thr Gly Gly Leu Asn Arg Gln Ile Glu His His Leu Phe Pro
450                 455                 460 acg atg ccc agg cac aac ctt aat aaa att tct cct cac gtg gag act      1440
Thr Met Pro Arg His Asn Leu Asn Lys Ile Ser Pro His Val Glu Thr
465                 470                 475                 480 ttg tgc aag aag cat gga ctg gtc tac gaa gac gtg agc atg gct tcg      1488
Leu Cys Lys Lys His Gly Leu Val Tyr Glu Asp Val Ser Met Ala Ser
            485                 490                 495 ggc act tac cgg gtt ttg aaa aca ctt aag gac gtt gcc gat gct gct      1536
Gly Thr Tyr Arg Val Leu Lys Thr Leu Lys Asp Val Ala Asp Ala Ala
        500                 505                 510 tca cac cag cag ctt gct gcg agt tga                                  1563
Ser His Gln Gln Leu Ala Ala Ser
    515                 520

<210> SEQ ID NO 16
<211> LENGTH: 520
<212> TYPE: PRT
<213> ORGANISM: Ceratodon purpureus

<400> SEQUENCE: 16

Met Val Ser Gln Gly Gly Gly Leu Ser Gln Gly Ser Ile Glu Glu Asn
 1               5                  10                  15

Ile Asp Val Glu His Leu Ala Thr Met Pro Leu Val Ser Asp Phe Leu
            20                  25                  30

Asn Val Leu Gly Thr Thr Leu Gly Gln Trp Ser Leu Ser Thr Thr Phe
        35                  40                  45

Ala Phe Lys Arg Leu Thr Thr Lys Lys His Ser Ser Asp Ile Ser Val
    50                  55                  60

Glu Ala Gln Lys Glu Ser Val Ala Arg Gly Pro Val Glu Asn Ile Ser
65                  70                  75                  80

Gln Ser Val Ala Gln Pro Ile Arg Arg Arg Trp Val Gln Asp Lys Lys
            85                  90                  95

Pro Val Thr Tyr Ser Leu Lys Asp Val Ala Ser His Asp Met Pro Gln
           100                 105                 110

Asp Cys Trp Ile Ile Ile Lys Glu Lys Val Tyr Asp Val Ser Thr Phe
       115                 120                 125
```

```
Ala Glu Gln His Pro Gly Gly Thr Val Ile Asn Thr Tyr Phe Gly Arg
    130                 135                 140

Asp Ala Thr Asp Val Phe Ser Thr Phe His Ala Ser Thr Ser Trp Lys
145                 150                 155                 160

Ile Leu Gln Asn Phe Tyr Ile Gly Asn Leu Val Arg Glu Pro Thr
                165                 170                 175

Leu Glu Leu Leu Lys Glu Tyr Arg Glu Leu Arg Ala Leu Phe Leu Arg
                180                 185                 190

Glu Gln Leu Phe Lys Ser Ser Lys Ser Tyr Tyr Leu Phe Lys Thr Leu
                195                 200                 205

Ile Asn Val Ser Ile Val Ala Thr Ser Ile Ala Ile Ser Leu Tyr
    210                 215                 220

Lys Ser Tyr Arg Ala Val Leu Leu Ser Ala Ser Leu Met Gly Leu Phe
225                 230                 235                 240

Ile Gln Gln Cys Gly Trp Leu Ser His Asp Phe Leu His His Gln Val
                245                 250                 255

Phe Glu Thr Arg Trp Leu Asn Asp Val Val Gly Tyr Val Val Gly Asn
                260                 265                 270

Val Val Leu Gly Phe Ser Val Ser Trp Trp Lys Thr Lys His Asn Leu
        275                 280                 285

His His Ala Ala Pro Asn Glu Cys Asp Gln Lys Tyr Thr Pro Ile Asp
    290                 295                 300

Glu Asp Ile Asp Thr Leu Pro Ile Ile Ala Trp Ser Lys Asp Leu Leu
305                 310                 315                 320

Ala Thr Val Glu Ser Lys Thr Met Leu Arg Val Leu Gln Tyr Gln His
                325                 330                 335

Leu Phe Phe Leu Val Leu Leu Thr Phe Ala Arg Ala Ser Trp Leu Phe
                340                 345                 350

Trp Ser Ala Ala Phe Thr Leu Arg Pro Glu Leu Thr Leu Gly Glu Lys
        355                 360                 365

Leu Leu Glu Arg Gly Thr Met Ala Leu His Tyr Ile Trp Phe Asn Ser
    370                 375                 380

Val Ala Phe Tyr Leu Leu Pro Gly Trp Lys Pro Val Val Trp Met Val
385                 390                 395                 400

Val Ser Glu Leu Met Ser Gly Phe Leu Leu Gly Tyr Val Phe Val Leu
                405                 410                 415

Ser His Asn Gly Met Glu Val Tyr Asn Thr Ser Lys Asp Phe Val Asn
                420                 425                 430

Ala Gln Ile Ala Ser Thr Arg Asp Ile Lys Ala Gly Val Phe Asn Asp
        435                 440                 445

Trp Phe Thr Gly Gly Leu Asn Arg Gln Ile Glu His His Leu Phe Pro
    450                 455                 460

Thr Met Pro Arg His Asn Leu Asn Lys Ile Ser Pro His Val Glu Thr
465                 470                 475                 480

Leu Cys Lys Lys His Gly Leu Val Tyr Glu Asp Val Ser Met Ala Ser
                485                 490                 495

Gly Thr Tyr Arg Val Leu Lys Thr Leu Lys Asp Val Ala Asp Ala Ala
                500                 505                 510

Ser His Gln Gln Leu Ala Ala Ser
        515                 520

<210> SEQ ID NO 17
<211> LENGTH: 1578
```

```
<212> TYPE: DNA
<213> ORGANISM: Physcomitrella patens
<220> FEATURE:
<221> NAME/KEY: CDS
<222> LOCATION: (1)..(1578)
<223> OTHER INFORMATION: D6-desaturase

<400> SEQUENCE: 17 atg gta ttc gcg ggc ggt gga ctt cag cag ggc tct ctc gaa gaa aac      48
Met Val Phe Ala Gly Gly Gly Leu Gln Gln Gly Ser Leu Glu Glu Asn
 1               5                  10                  15 atc gac gtc gag cac att gcc agt atg tct ctc ttc agc gac ttc ttc      96
Ile Asp Val Glu His Ile Ala Ser Met Ser Leu Phe Ser Asp Phe Phe
             20                  25                  30 agt tat gtg tct tca act gtt ggt tcg tgg agc gta cac agt ata caa     144
Ser Tyr Val Ser Ser Thr Val Gly Ser Trp Ser Val His Ser Ile Gln
         35                  40                  45 cct ttg aag cgc ctg acg agt aag aag cgt gtt tcg gaa agc gct gcc     192
Pro Leu Lys Arg Leu Thr Ser Lys Lys Arg Val Ser Glu Ser Ala Ala
     50                  55                  60 gtg caa tgt ata tca gct gaa gtt cag aga aat tcg agt acc cag gga     240
Val Gln Cys Ile Ser Ala Glu Val Gln Arg Asn Ser Ser Thr Gln Gly
 65                  70                  75                  80 act gcg gag gca ctc gca gaa tca gtc gtg aag ccc acg aga cga agg     288
Thr Ala Glu Ala Leu Ala Glu Ser Val Val Lys Pro Thr Arg Arg Arg
                 85                  90                  95 tca tct cag tgg aag aag tcg aca cac ccc cta tca gaa gta gca gta     336
Ser Ser Gln Trp Lys Lys Ser Thr His Pro Leu Ser Glu Val Ala Val
            100                 105                 110 cac aac aag cca agc gat tgc tgg att gtt gta aaa aac aag gtg tat     384
His Asn Lys Pro Ser Asp Cys Trp Ile Val Val Lys Asn Lys Val Tyr
        115                 120                 125 gat gtt tcc aat ttt gcg gac gag cat ccc gga gga tca gtt att agt     432
Asp Val Ser Asn Phe Ala Asp Glu His Pro Gly Gly Ser Val Ile Ser
    130                 135                 140 act tat ttt gga cga gac ggc aca gat gtt ttc tct agt ttt cat gca     480
Thr Tyr Phe Gly Arg Asp Gly Thr Asp Val Phe Ser Ser Phe His Ala
145                 150                 155                 160 gct tct aca tgg aaa att ctt caa gac ttt tac att ggt gac gtg gag     528
Ala Ser Thr Trp Lys Ile Leu Gln Asp Phe Tyr Ile Gly Asp Val Glu
                165                 170                 175 agg gtg gag ccg act cca gag ctg ctg aaa gat ttc cga gaa atg aga     576
Arg Val Glu Pro Thr Pro Glu Leu Leu Lys Asp Phe Arg Glu Met Arg
            180                 185                 190 gct ctt ttc ctg agg gag caa ctt ttc aaa agt tcg aaa ttg tac tat     624
Ala Leu Phe Leu Arg Glu Gln Leu Phe Lys Ser Ser Lys Leu Tyr Tyr
        195                 200                 205 gtt atg aag ctg ctc acg aat gtt gct att ttt gct gcg agc att gca     672
Val Met Lys Leu Leu Thr Asn Val Ala Ile Phe Ala Ala Ser Ile Ala
    210                 215                 220 ata ata tgt tgg agc aag act att tca gcg gtt ttg gct tca gct tgt     720
Ile Ile Cys Trp Ser Lys Thr Ile Ser Ala Val Leu Ala Ser Ala Cys
225                 230                 235                 240 atg atg gct ctg tgt ttc caa cag tgc gga tgg cta tcc cat gat ttt     768
Met Met Ala Leu Cys Phe Gln Gln Cys Gly Trp Leu Ser His Asp Phe
                245                 250                 255 ctc cac aat cag gtg ttt gag aca cgc tgg ctt aat gaa gtt gtc ggg     816
Leu His Asn Gln Val Phe Glu Thr Arg Trp Leu Asn Glu Val Val Gly
            260                 265                 270 tat gtg atc ggc aac gcc gtt ctg ggg ttt agt aca ggg tgg tgg aag     864
Tyr Val Ile Gly Asn Ala Val Leu Gly Phe Ser Thr Gly Trp Trp Lys
```

```
                    275                 280                 285
gag aag cat aac ctt cat cat gct gct cca aat gaa tgc gat cag act    912
Glu Lys His Asn Leu His His Ala Ala Pro Asn Glu Cys Asp Gln Thr
    290                 295                 300 tac caa cca att gat gaa gat att gat act ctc ccc ctc att gcc tgg    960
Tyr Gln Pro Ile Asp Glu Asp Ile Asp Thr Leu Pro Leu Ile Ala Trp
305                 310                 315                 320 agc aag gac ata ctg gcc aca gtt gag aat aag aca ttc ttg cga atc   1008
Ser Lys Asp Ile Leu Ala Thr Val Glu Asn Lys Thr Phe Leu Arg Ile
                325                 330                 335 ctc caa tac cag cat ctg ttc ttc atg ggt ctg tta ttt ttc gcc cgt   1056
Leu Gln Tyr Gln His Leu Phe Phe Met Gly Leu Leu Phe Phe Ala Arg
        340                 345                 350 ggt agt tgg ctc ttt tgg agc tgg aga tat acc tct aca gca gtg ctc   1104
Gly Ser Trp Leu Phe Trp Ser Trp Arg Tyr Thr Ser Thr Ala Val Leu
            355                 360                 365 tca cct gtc gac agg ttg ttg gag aag gga act gtt ctg ttt cac tac   1152
Ser Pro Val Asp Arg Leu Leu Glu Lys Gly Thr Val Leu Phe His Tyr
    370                 375                 380 ttt tgg ttc gtc ggg aca gcg tgc tat ctt ctc cct ggt tgg aag cca   1200
Phe Trp Phe Val Gly Thr Ala Cys Tyr Leu Leu Pro Gly Trp Lys Pro
385                 390                 395                 400 tta gta tgg atg gcg gtg act gag ctc atg tcc ggc atg ctg ctg ggc   1248
Leu Val Trp Met Ala Val Thr Glu Leu Met Ser Gly Met Leu Leu Gly
                405                 410                 415 ttt gta ttt gta ctt agc cac aat ggg atg gag gtt tat aat tcg tct   1296
Phe Val Phe Val Leu Ser His Asn Gly Met Glu Val Tyr Asn Ser Ser
        420                 425                 430 aaa gaa ttc gtg agt gca cag atc gta tcc aca cgg gat atc aaa gga   1344
Lys Glu Phe Val Ser Ala Gln Ile Val Ser Thr Arg Asp Ile Lys Gly
            435                 440                 445 aac ata ttc aac gac tgg ttc act ggt ggc ctt aac agg caa ata gag   1392
Asn Ile Phe Asn Asp Trp Phe Thr Gly Gly Leu Asn Arg Gln Ile Glu
    450                 455                 460 cat cat ctt ttc cca aca atg ccc agg cat aat tta aac aaa ata gca   1440
His His Leu Phe Pro Thr Met Pro Arg His Asn Leu Asn Lys Ile Ala
465                 470                 475                 480 cct aga gtg gag gtg ttc tgt aag aaa cac ggt ctg gtg tac gaa gac   1488
Pro Arg Val Glu Val Phe Cys Lys Lys His Gly Leu Val Tyr Glu Asp
                485                 490                 495 gta tct att gct acc ggc act tgc aag gtt ttg aaa gca ttg aag gaa   1536
Val Ser Ile Ala Thr Gly Thr Cys Lys Val Leu Lys Ala Leu Lys Glu
        500                 505                 510 gtc gcg gag gct gcg gca gag cag cat gct acc acc agt taa           1578
Val Ala Glu Ala Ala Ala Glu Gln His Ala Thr Thr Ser
            515                 520                 525

<210> SEQ ID NO 18
<211> LENGTH: 525
<212> TYPE: PRT
<213> ORGANISM: Physcomitrella patens

<400> SEQUENCE: 18

Met Val Phe Ala Gly Gly Gly Leu Gln Gln Gly Ser Leu Glu Glu Asn
1               5                   10                  15

Ile Asp Val Glu His Ile Ala Ser Met Ser Leu Phe Ser Asp Phe Phe
                20                  25                  30

Ser Tyr Val Ser Ser Thr Val Gly Ser Trp Ser Val His Ser Ile Gln
        35                  40                  45
```

-continued

Pro Leu Lys Arg Leu Thr Ser Lys Arg Val Ser Glu Ala Ala
    50                  55                  60

Val Gln Cys Ile Ser Ala Glu Val Gln Arg Asn Ser Ser Thr Gln Gly
65                  70                  75                  80

Thr Ala Glu Ala Leu Ala Glu Ser Val Val Lys Pro Thr Arg Arg Arg
                85                  90                  95

Ser Ser Gln Trp Lys Lys Ser Thr His Pro Leu Ser Glu Val Ala Val
                100                 105                 110

His Asn Lys Pro Ser Asp Cys Trp Ile Val Lys Asn Lys Val Tyr
    115                 120                 125

Asp Val Ser Asn Phe Ala Asp Glu His Pro Gly Gly Ser Val Ile Ser
    130                 135                 140

Thr Tyr Phe Gly Arg Asp Gly Thr Asp Val Phe Ser Ser Phe His Ala
145                 150                 155                 160

Ala Ser Thr Trp Lys Ile Leu Gln Asp Phe Tyr Ile Gly Asp Val Glu
                165                 170                 175

Arg Val Glu Pro Thr Pro Glu Leu Leu Lys Asp Phe Arg Glu Met Arg
                180                 185                 190

Ala Leu Phe Leu Arg Glu Gln Leu Phe Lys Ser Lys Leu Tyr Tyr
    195                 200                 205

Val Met Lys Leu Leu Thr Asn Val Ala Ile Phe Ala Ala Ser Ile Ala
    210                 215                 220

Ile Ile Cys Trp Ser Lys Thr Ile Ser Ala Val Leu Ala Ser Ala Cys
225                 230                 235                 240

Met Met Ala Leu Cys Phe Gln Cys Gly Trp Leu Ser His Asp Phe
                245                 250                 255

Leu His Asn Gln Val Phe Glu Thr Arg Trp Leu Asn Glu Val Val Gly
    260                 265                 270

Tyr Val Ile Gly Asn Ala Val Leu Gly Phe Ser Thr Gly Trp Trp Lys
    275                 280                 285

Glu Lys His Asn Leu His His Ala Ala Pro Asn Glu Cys Asp Gln Thr
290                 295                 300

Tyr Gln Pro Ile Asp Glu Asp Ile Asp Thr Leu Pro Leu Ile Ala Trp
305                 310                 315                 320

Ser Lys Asp Ile Leu Ala Thr Val Glu Asn Lys Thr Phe Leu Arg Ile
                325                 330                 335

Leu Gln Tyr Gln His Leu Phe Phe Met Gly Leu Leu Phe Phe Ala Arg
                340                 345                 350

Gly Ser Trp Leu Phe Trp Ser Trp Arg Tyr Thr Ser Thr Ala Val Leu
                355                 360                 365

Ser Pro Val Asp Arg Leu Leu Glu Lys Gly Thr Val Leu Phe His Tyr
370                 375                 380

Phe Trp Phe Val Gly Thr Ala Cys Tyr Leu Leu Pro Gly Trp Lys Pro
385                 390                 395                 400

Leu Val Trp Met Ala Val Thr Glu Leu Met Ser Gly Met Leu Leu Gly
                405                 410                 415

Phe Val Phe Val Leu Ser His Asn Gly Met Glu Val Tyr Asn Ser Ser
                420                 425                 430

Lys Glu Phe Val Ser Ala Gln Ile Val Ser Thr Arg Asp Ile Lys Gly
                435                 440                 445

Asn Ile Phe Asn Asp Trp Phe Thr Gly Gly Leu Asn Arg Gln Ile Glu
    450                 455                 460

His His Leu Phe Pro Thr Met Pro Arg His Asn Leu Asn Lys Ile Ala

```
                         465                 470                 475                 480
                     Pro Arg Val Glu Val Phe Cys Lys Lys His Gly Leu Val Tyr Glu Asp
                                         485                 490                 495

Val Ser Ile Ala Thr Gly Thr Cys Lys Val Leu Lys Ala Leu Lys Glu
                                 500                 505                 510

Val Ala Glu Ala Ala Ala Glu Gln His Ala Thr Thr Ser
                                 515                 520                 525

<210> SEQ ID NO 19
<211> LENGTH: 837
<212> TYPE: DNA
<213> ORGANISM: Phytophthora infestans
<220> FEATURE:
<221> NAME/KEY: CDS
<222> LOCATION: (1)..(837)
<223> OTHER INFORMATION: D6-elongase

<400> SEQUENCE: 19 atg tcg act gag cta ctg cag agc tac tac gcg tgg gcc aac gcc acg        48
Met Ser Thr Glu Leu Leu Gln Ser Tyr Tyr Ala Trp Ala Asn Ala Thr
  1               5                  10                  15 gag gcc aag ctg ctg gac tgg gtc gac cct gag ggc ggc tgg aag gtg        96
Glu Ala Lys Leu Leu Asp Trp Val Asp Pro Glu Gly Gly Trp Lys Val
             20                  25                  30 cat cct atg gca gac tac ccc cta gcc aac ttc tcc agc gtc tac gcc       144
His Pro Met Ala Asp Tyr Pro Leu Ala Asn Phe Ser Ser Val Tyr Ala
         35                  40                  45 atc tgc gtc gga tac ttg ctc ttc gta atc ttc ggc acg gcc ctg atg       192
Ile Cys Val Gly Tyr Leu Leu Phe Val Ile Phe Gly Thr Ala Leu Met
     50                  55                  60 aaa atg gga gtc ccc gcc atc aag acc agt cca tta cag ttt gtg tac       240
Lys Met Gly Val Pro Ala Ile Lys Thr Ser Pro Leu Gln Phe Val Tyr
 65                  70                  75                  80 aac ccc atc caa gtc att gcc tgc tct tat atg tgc gtg gag gcc gcc       288
Asn Pro Ile Gln Val Ile Ala Cys Ser Tyr Met Cys Val Glu Ala Ala
                 85                  90                  95 atc cag gcc tac cgc aac ggc tac acc gcc gcc ccg tgc aac gcc ttt       336
Ile Gln Ala Tyr Arg Asn Gly Tyr Thr Ala Ala Pro Cys Asn Ala Phe
            100                 105                 110 aag tcc gac gac ccc gtc atg ggc aac gtt ctg tac ctc ttc tat ctc       384
Lys Ser Asp Asp Pro Val Met Gly Asn Val Leu Tyr Leu Phe Tyr Leu
        115                 120                 125 tcc aag atg ctc gac ctg tgc gac aca gtc ttc att atc cta gga aag       432
Ser Lys Met Leu Asp Leu Cys Asp Thr Val Phe Ile Ile Leu Gly Lys
    130                 135                 140 aag tgg aaa cag ctt tcc atc ttg cac gtg tac cac cac ctt acc gtg       480
Lys Trp Lys Gln Leu Ser Ile Leu His Val Tyr His His Leu Thr Val
145                 150                 155                 160 ctt ttc gtc tac tat gtg acg ttc cgc gcc gct cag gac ggg gac tca       528
Leu Phe Val Tyr Tyr Val Thr Phe Arg Ala Ala Gln Asp Gly Asp Ser
                165                 170                 175 tat gct acc atc gtg ctc aac ggc ttc gtg cac acc atc atg tac act       576
Tyr Ala Thr Ile Val Leu Asn Gly Phe Val His Thr Ile Met Tyr Thr
            180                 185                 190 tac tac ttc gtc agc gcc cac acg cgc aac att tgg tgg aag aag tac       624
Tyr Tyr Phe Val Ser Ala His Thr Arg Asn Ile Trp Trp Lys Lys Tyr
        195                 200                 205 ctc acg cgc att cag ctt atc cag ttc gtg acc atg aac gtg cag ggc       672
Leu Thr Arg Ile Gln Leu Ile Gln Phe Val Thr Met Asn Val Gln Gly
    210                 215                 220
```

```
tac ctg acc tac tct cga cag tgc cca ggc atg cct cct aag gtg ccg     720
Tyr Leu Thr Tyr Ser Arg Gln Cys Pro Gly Met Pro Pro Lys Val Pro
225                 230                 235                 240 ctc atg tac ctt gtg tac gtg cag tca ctc ttc tgg ctc ttc atg aat     768
Leu Met Tyr Leu Val Tyr Val Gln Ser Leu Phe Trp Leu Phe Met Asn
                245                 250                 255 ttc tac att cgc gcg tac gtg ttc ggc ccc aag aaa ccg gcc gtg gag     816
Phe Tyr Ile Arg Ala Tyr Val Phe Gly Pro Lys Lys Pro Ala Val Glu
            260                 265                 270 gaa tcg aag aag aag ttg taa                                         837
Glu Ser Lys Lys Lys Leu
        275

<210> SEQ ID NO 20
<211> LENGTH: 278
<212> TYPE: PRT
<213> ORGANISM: Phytophthora infestans

<400> SEQUENCE: 20

Met Ser Thr Glu Leu Leu Gln Ser Tyr Tyr Ala Trp Ala Asn Ala Thr
1               5                   10                  15

Glu Ala Lys Leu Leu Asp Trp Val Asp Pro Glu Gly Gly Trp Lys Val
            20                  25                  30

His Pro Met Ala Asp Tyr Pro Leu Ala Asn Phe Ser Ser Val Tyr Ala
        35                  40                  45

Ile Cys Val Gly Tyr Leu Leu Phe Val Ile Phe Gly Thr Ala Leu Met
    50                  55                  60

Lys Met Gly Val Pro Ala Ile Lys Thr Ser Pro Leu Gln Phe Val Tyr
65                  70                  75                  80

Asn Pro Ile Gln Val Ile Ala Cys Ser Tyr Met Cys Val Glu Ala Ala
                85                  90                  95

Ile Gln Ala Tyr Arg Asn Gly Tyr Thr Ala Ala Pro Cys Asn Ala Phe
            100                 105                 110

Lys Ser Asp Asp Pro Val Met Gly Asn Val Leu Tyr Leu Phe Tyr Leu
        115                 120                 125

Ser Lys Met Leu Asp Leu Cys Asp Thr Val Phe Ile Ile Leu Gly Lys
    130                 135                 140

Lys Trp Lys Gln Leu Ser Ile Leu His Val Tyr His Leu Thr Val
145                 150                 155                 160

Leu Phe Val Tyr Tyr Val Thr Phe Arg Ala Ala Gln Asp Gly Asp Ser
                165                 170                 175

Tyr Ala Thr Ile Val Leu Asn Gly Phe Val His Thr Ile Met Tyr Thr
            180                 185                 190

Tyr Tyr Phe Val Ser Ala His Thr Arg Asn Ile Trp Trp Lys Lys Tyr
        195                 200                 205

Leu Thr Arg Ile Gln Leu Ile Gln Phe Val Thr Met Asn Val Gln Gly
    210                 215                 220

Tyr Leu Thr Tyr Ser Arg Gln Cys Pro Gly Met Pro Pro Lys Val Pro
225                 230                 235                 240

Leu Met Tyr Leu Val Tyr Val Gln Ser Leu Phe Trp Leu Phe Met Asn
                245                 250                 255

Phe Tyr Ile Arg Ala Tyr Val Phe Gly Pro Lys Lys Pro Ala Val Glu
            260                 265                 270

Glu Ser Lys Lys Lys Leu
        275
```

<210> SEQ ID NO 21
<211> LENGTH: 1410
<212> TYPE: DNA
<213> ORGANISM: Phaeodactylum tricornutum
<220> FEATURE:
<221> NAME/KEY: CDS
<222> LOCATION: (1)..(1410)
<223> OTHER INFORMATION: D5-desaturase

<400> SEQUENCE: 21

```
atg gct ccg gat gcg gat aag ctt cga caa cgc cag acg act gcg gta        48
Met Ala Pro Asp Ala Asp Lys Leu Arg Gln Arg Gln Thr Thr Ala Val
 1               5                  10                  15 gcg aag cac aat gct gct acc ata tcg acg cag gaa cgc ctt tgc agt        96
Ala Lys His Asn Ala Ala Thr Ile Ser Thr Gln Glu Arg Leu Cys Ser
                20                  25                  30 ctg tct tcg ctc aaa ggc gaa gaa gtc tgc atc gac gga atc atc tat       144
Leu Ser Ser Leu Lys Gly Glu Glu Val Cys Ile Asp Gly Ile Ile Tyr
            35                  40                  45 gac ctc caa tca ttc gat cat ccc ggg ggt gaa acg atc aaa atg ttt       192
Asp Leu Gln Ser Phe Asp His Pro Gly Gly Glu Thr Ile Lys Met Phe
        50                  55                  60 ggt ggc aac gat gtc act gta cag tac aag atg att cac ccg tac cat       240
Gly Gly Asn Asp Val Thr Val Gln Tyr Lys Met Ile His Pro Tyr His
 65                  70                  75                  80 acc gag aag cat ttg gaa aag atg aag cgt gtc ggc aag gtg acg gat       288
Thr Glu Lys His Leu Glu Lys Met Lys Arg Val Gly Lys Val Thr Asp
                85                  90                  95 ttc gtc tgc gag tac aag ttc gat acc gaa ttt gaa cgc gaa atc aaa       336
Phe Val Cys Glu Tyr Lys Phe Asp Thr Glu Phe Glu Arg Glu Ile Lys
               100                 105                 110 cga gaa gtc ttc aag att gtg cga cga ggc aag gat ttc ggt act ttg       384
Arg Glu Val Phe Lys Ile Val Arg Arg Gly Lys Asp Phe Gly Thr Leu
           115                 120                 125 gga tgg ttc ttc cgt gcg ttt tgc tac att gcc att ttc ttc tac ctg       432
Gly Trp Phe Phe Arg Ala Phe Cys Tyr Ile Ala Ile Phe Phe Tyr Leu
       130                 135                 140 cag tac cat tgg gtc acc acg gga acc tct tgg ctg ctg gcc gtg gcc       480
Gln Tyr His Trp Val Thr Thr Gly Thr Ser Trp Leu Leu Ala Val Ala
145                 150                 155                 160 tac gga atc tcc caa gcg atg att ggc atg aat gtc cag cac gat gcc       528
Tyr Gly Ile Ser Gln Ala Met Ile Gly Met Asn Val Gln His Asp Ala
                165                 170                 175 aac cac ggg gcc acc tcc aag cgt ccc tgg gtc aac gac atg cta ggc       576
Asn His Gly Ala Thr Ser Lys Arg Pro Trp Val Asn Asp Met Leu Gly
            180                 185                 190 ctc ggt gcg gat ttt att ggt ggt tcc aag tgg ctc tgg cag gaa caa       624
Leu Gly Ala Asp Phe Ile Gly Gly Ser Lys Trp Leu Trp Gln Glu Gln
        195                 200                 205 cac tgg acc cac cac gct tac acc aat cac gcc gag atg gat ccc gat       672
His Trp Thr His His Ala Tyr Thr Asn His Ala Glu Met Asp Pro Asp
    210                 215                 220 agc ttt ggt gcc gaa cca atg ctc cta ttc aac gac tat ccc ttg gat       720
Ser Phe Gly Ala Glu Pro Met Leu Leu Phe Asn Asp Tyr Pro Leu Asp
225                 230                 235                 240 cat ccc gct cgt acc tgg cta cat cgc ttt caa gca ttc ttt tac atg       768
His Pro Ala Arg Thr Trp Leu His Arg Phe Gln Ala Phe Phe Tyr Met
                245                 250                 255 ccc gtc ttg gct gga tac tgg ttg tcc gct gtc ttc aat cca caa att       816
Pro Val Leu Ala Gly Tyr Trp Leu Ser Ala Val Phe Asn Pro Gln Ile
            260                 265                 270
```

-continued

```
ctt gac ctc cag caa cgc ggc gca ctt tcc gtc ggt atc cgt ctc gac    864
Leu Asp Leu Gln Gln Arg Gly Ala Leu Ser Val Gly Ile Arg Leu Asp
            275                 280                 285 aac gct ttc att cac tcg cga cgc aag tat gcg gtt ttc tgg cgg gct    912
Asn Ala Phe Ile His Ser Arg Arg Lys Tyr Ala Val Phe Trp Arg Ala
        290                 295                 300 gtg tac att gcg gtg aac gtg att gct ccg ttt tac aca aac tcc ggc    960
Val Tyr Ile Ala Val Asn Val Ile Ala Pro Phe Tyr Thr Asn Ser Gly
305                 310                 315                 320 ctc gaa tgg tcc tgg cgt gtc ttt gga aac atc atg ctc atg ggt gtg   1008
Leu Glu Trp Ser Trp Arg Val Phe Gly Asn Ile Met Leu Met Gly Val
                325                 330                 335 gcg gaa tcg ctc gcg ctg gcg gtc ctg ttt tcg ttg tcg cac aat ttc   1056
Ala Glu Ser Leu Ala Leu Ala Val Leu Phe Ser Leu Ser His Asn Phe
            340                 345                 350 gaa tcc gcg gat cgc gat ccg acc gcc cca ctg aaa aag acg gga gaa   1104
Glu Ser Ala Asp Arg Asp Pro Thr Ala Pro Leu Lys Lys Thr Gly Glu
        355                 360                 365 cca gtc gac tgg ttc aag aca cag gtc gaa act tcc tgc act tac ggt   1152
Pro Val Asp Trp Phe Lys Thr Gln Val Glu Thr Ser Cys Thr Tyr Gly
370                 375                 380 gga ttc ctt tcc ggt tgc ttc acg gga ggt ctc aac ttt cag gtt gaa   1200
Gly Phe Leu Ser Gly Cys Phe Thr Gly Gly Leu Asn Phe Gln Val Glu
385                 390                 395                 400 cac cac ttg ttc cca cgc atg agc agc gct tgg tat ccc tac att gcc   1248
His His Leu Phe Pro Arg Met Ser Ser Ala Trp Tyr Pro Tyr Ile Ala
                405                 410                 415 ccc aag gtc cgc gaa att tgc gcc aaa cac ggc gtc cac tac gcc tac   1296
Pro Lys Val Arg Glu Ile Cys Ala Lys His Gly Val His Tyr Ala Tyr
            420                 425                 430 tac ccg tgg atc cac caa aac ttt ctc tcc acc gtc cgc tac atg cac   1344
Tyr Pro Trp Ile His Gln Asn Phe Leu Ser Thr Val Arg Tyr Met His
        435                 440                 445 gcg gcc ggg acc ggt gcc aac tgg cgc cag atg gcc aga gaa aat ccc   1392
Ala Ala Gly Thr Gly Ala Asn Trp Arg Gln Met Ala Arg Glu Asn Pro
450                 455                 460 ttg acc gga cgg gcg taa                                            1410
Leu Thr Gly Arg Ala
465
```

<210> SEQ ID NO 22
<211> LENGTH: 469
<212> TYPE: PRT
<213> ORGANISM: Phaeodactylum tricornutum

<400> SEQUENCE: 22

```
Met Ala Pro Asp Ala Asp Lys Leu Arg Gln Arg Gln Thr Thr Ala Val
 1               5                  10                  15

Ala Lys His Asn Ala Ala Thr Ile Ser Thr Gln Glu Arg Leu Cys Ser
                20                  25                  30

Leu Ser Ser Leu Lys Gly Glu Glu Val Cys Ile Asp Gly Ile Ile Tyr
            35                  40                  45

Asp Leu Gln Ser Phe Asp His Pro Gly Gly Glu Thr Ile Lys Met Phe
        50                  55                  60

Gly Gly Asn Asp Val Thr Val Gln Tyr Lys Met Ile His Pro Tyr His
 65                  70                  75                  80

Thr Glu Lys His Leu Glu Lys Met Lys Arg Val Gly Lys Val Thr Asp
                85                  90                  95

Phe Val Cys Glu Tyr Lys Phe Asp Thr Glu Phe Glu Arg Glu Ile Lys
```

```
                  100                 105                 110
Arg Glu Val Phe Lys Ile Val Arg Arg Gly Lys Asp Phe Gly Thr Leu
            115                 120                 125
Gly Trp Phe Phe Arg Ala Phe Cys Tyr Ile Ala Ile Phe Phe Tyr Leu
        130                 135                 140
Gln Tyr His Trp Val Thr Thr Gly Thr Ser Trp Leu Leu Ala Val Ala
145                 150                 155                 160
Tyr Gly Ile Ser Gln Ala Met Ile Gly Met Asn Val Gln His Asp Ala
                165                 170                 175
Asn His Gly Ala Thr Ser Lys Arg Pro Trp Val Asn Asp Met Leu Gly
            180                 185                 190
Leu Gly Ala Asp Phe Ile Gly Gly Ser Lys Trp Leu Trp Gln Glu Gln
        195                 200                 205
His Trp Thr His His Ala Tyr Thr Asn His Ala Glu Met Asp Pro Asp
    210                 215                 220
Ser Phe Gly Ala Glu Pro Met Leu Leu Phe Asn Asp Tyr Pro Leu Asp
225                 230                 235                 240
His Pro Ala Arg Thr Trp Leu His Arg Phe Gln Ala Phe Phe Tyr Met
                245                 250                 255
Pro Val Leu Ala Gly Tyr Trp Leu Ser Ala Val Phe Asn Pro Gln Ile
            260                 265                 270
Leu Asp Leu Gln Gln Arg Gly Ala Leu Ser Val Gly Ile Arg Leu Asp
        275                 280                 285
Asn Ala Phe Ile His Ser Arg Arg Lys Tyr Ala Val Phe Trp Arg Ala
    290                 295                 300
Val Tyr Ile Ala Val Asn Val Ile Ala Pro Phe Tyr Thr Asn Ser Gly
305                 310                 315                 320
Leu Glu Trp Ser Trp Arg Val Phe Gly Asn Ile Met Leu Met Gly Val
                325                 330                 335
Ala Glu Ser Leu Ala Leu Ala Val Leu Phe Ser Leu Ser His Asn Phe
            340                 345                 350
Glu Ser Ala Asp Arg Asp Pro Thr Ala Pro Leu Lys Lys Thr Gly Glu
        355                 360                 365
Pro Val Asp Trp Phe Lys Thr Gln Val Glu Thr Ser Cys Thr Tyr Gly
    370                 375                 380
Gly Phe Leu Ser Gly Cys Phe Thr Gly Gly Leu Asn Phe Gln Val Glu
385                 390                 395                 400
His His Leu Phe Pro Arg Met Ser Ser Ala Trp Tyr Pro Tyr Ile Ala
                405                 410                 415
Pro Lys Val Arg Glu Ile Cys Ala Lys His Gly Val His Tyr Ala Tyr
            420                 425                 430
Tyr Pro Trp Ile His Gln Asn Phe Leu Ser Thr Val Arg Tyr Met His
        435                 440                 445
Ala Ala Gly Thr Gly Ala Asn Trp Arg Gln Met Ala Arg Glu Asn Pro
    450                 455                 460
Leu Thr Gly Arg Ala
465

<210> SEQ ID NO 23
<211> LENGTH: 1344
<212> TYPE: DNA
<213> ORGANISM: Caenorhabditis elegans
<220> FEATURE:
<221> NAME/KEY: CDS
<222> LOCATION: (1)..(1344)
```

<223> OTHER INFORMATION: D5-desaturase

<400> SEQUENCE: 23

```
atg gta tta cga gag caa gag cat gag cca ttc ttc att aaa att gat        48
Met Val Leu Arg Glu Gln Glu His Glu Pro Phe Phe Ile Lys Ile Asp
 1               5                  10                  15 gga aaa tgg tgt caa att gac gat gct gtc ctg aga tca cat cca ggt        96
Gly Lys Trp Cys Gln Ile Asp Asp Ala Val Leu Arg Ser His Pro Gly
             20                  25                  30 ggt agt gca att act acc tat aaa aat atg gat gcc act acc gta ttc      144
Gly Ser Ala Ile Thr Thr Tyr Lys Asn Met Asp Ala Thr Thr Val Phe
         35                  40                  45 cac aca ttc cat act ggt tct aaa gaa gcg tat caa tgg ctg aca gaa      192
His Thr Phe His Thr Gly Ser Lys Glu Ala Tyr Gln Trp Leu Thr Glu
     50                  55                  60 ttg aaa aaa gag tgc cct aca caa gaa cca gag atc cca gat att aag      240
Leu Lys Lys Glu Cys Pro Thr Gln Glu Pro Glu Ile Pro Asp Ile Lys
 65                  70                  75                  80 gat gac cca atc aaa gga att gat gat gtg aac atg gga act ttc aat      288
Asp Asp Pro Ile Lys Gly Ile Asp Asp Val Asn Met Gly Thr Phe Asn
                 85                  90                  95 att tct gag aaa cga tct gcc caa ata aat aaa agt ttc act gat cta      336
Ile Ser Glu Lys Arg Ser Ala Gln Ile Asn Lys Ser Phe Thr Asp Leu
            100                 105                 110 cgt atg cga gtt cgt gca gaa gga ctt atg gat gga tct cct ttg ttc      384
Arg Met Arg Val Arg Ala Glu Gly Leu Met Asp Gly Ser Pro Leu Phe
        115                 120                 125 tac att aga aaa att ctt gaa aca atc ttc aca att ctt ttt gca ttc      432
Tyr Ile Arg Lys Ile Leu Glu Thr Ile Phe Thr Ile Leu Phe Ala Phe
    130                 135                 140 tac ctt caa tac cac aca tat tat ctt cca tca gct att cta atg gga      480
Tyr Leu Gln Tyr His Thr Tyr Tyr Leu Pro Ser Ala Ile Leu Met Gly
145                 150                 155                 160 gtt gcg tgg caa caa ttg gga tgg tta atc cat gaa ttc gca cat cat      528
Val Ala Trp Gln Gln Leu Gly Trp Leu Ile His Glu Phe Ala His His
                165                 170                 175 cag ttg ttc aaa aac aga tac tac aat gat ttg gcc agc tat ttc gtt      576
Gln Leu Phe Lys Asn Arg Tyr Tyr Asn Asp Leu Ala Ser Tyr Phe Val
            180                 185                 190 gga aac ttt tta caa gga ttc tca tct ggt ggt tgg aaa gag cag cac      624
Gly Asn Phe Leu Gln Gly Phe Ser Ser Gly Gly Trp Lys Glu Gln His
        195                 200                 205 aat gtg cat cac gca gcc aca aat gtt gtt gga cga gac gga gat ctt      672
Asn Val His His Ala Ala Thr Asn Val Val Gly Arg Asp Gly Asp Leu
    210                 215                 220 gat tta gtc cca ttc tat gct aca gtg gca gaa cat ctc aac aat tat      720
Asp Leu Val Pro Phe Tyr Ala Thr Val Ala Glu His Leu Asn Asn Tyr
225                 230                 235                 240 tct cag gat tca tgg gtt atg act cta ttc aga tgg caa cat gtt cat      768
Ser Gln Asp Ser Trp Val Met Thr Leu Phe Arg Trp Gln His Val His
                245                 250                 255 tgg aca ttc atg tta cca ttc ctc cgt ctc tcg tgg ctt ctt cag tca      816
Trp Thr Phe Met Leu Pro Phe Leu Arg Leu Ser Trp Leu Leu Gln Ser
            260                 265                 270 atc att ttt gtt agt cag atg cca act cat tat tat gac tat tac aga      864
Ile Ile Phe Val Ser Gln Met Pro Thr His Tyr Tyr Asp Tyr Tyr Arg
        275                 280                 285 aat act gcg att tat gaa cag gtt ggc ctc tct ttg cac tgg gct tgg      912
Asn Thr Ala Ile Tyr Glu Gln Val Gly Leu Ser Leu His Trp Ala Trp
    290                 295                 300
```

-continued

```
tca ttg ggt caa ttg tat ttc cta ccc gat tgg tca act aga ata atg    960
Ser Leu Gly Gln Leu Tyr Phe Leu Pro Asp Trp Ser Thr Arg Ile Met
305                 310                 315                 320 ttc ttc ctt gtt tct cat ctt gtt gga ggt ttc ctg ctc tct cat gta   1008
Phe Phe Leu Val Ser His Leu Val Gly Gly Phe Leu Leu Ser His Val
                325                 330                 335 gtt act ttc aat cat tat tca gtg gag aag ttt gca ttg agc tcg aac   1056
Val Thr Phe Asn His Tyr Ser Val Glu Lys Phe Ala Leu Ser Ser Asn
            340                 345                 350 atc atg tca aat tac gct tgt ctt caa atc atg acc aca aga aat atg   1104
Ile Met Ser Asn Tyr Ala Cys Leu Gln Ile Met Thr Thr Arg Asn Met
        355                 360                 365 aga cct gga aga ttc att gac tgg ctt tgg gga ggt ctt aac tat cag   1152
Arg Pro Gly Arg Phe Ile Asp Trp Leu Trp Gly Gly Leu Asn Tyr Gln
370                 375                 380 att gag cac cat ctt ttc cca acg atg cca cga cac aac ttg aac act   1200
Ile Glu His His Leu Phe Pro Thr Met Pro Arg His Asn Leu Asn Thr
385                 390                 395                 400 gtt atg cca ctt gtt aag gag ttt gca gca gca aat ggt tta cca tac   1248
Val Met Pro Leu Val Lys Glu Phe Ala Ala Ala Asn Gly Leu Pro Tyr
                405                 410                 415 atg gtc gac gat tat ttc aca gga ttc tgg ctt gaa att gag caa ttc   1296
Met Val Asp Asp Tyr Phe Thr Gly Phe Trp Leu Glu Ile Glu Gln Phe
            420                 425                 430 cga aat att gca aat gtt gct gct aaa ttg act aaa aag att gcc tag   1344
Arg Asn Ile Ala Asn Val Ala Ala Lys Leu Thr Lys Lys Ile Ala
        435                 440                 445

<210> SEQ ID NO 24
<211> LENGTH: 447
<212> TYPE: PRT
<213> ORGANISM: Caenorhabditis elegans

<400> SEQUENCE: 24

Met Val Leu Arg Glu Gln Glu His Glu Pro Phe Phe Ile Lys Ile Asp
1               5                   10                  15

Gly Lys Trp Cys Gln Ile Asp Asp Ala Val Leu Arg Ser His Pro Gly
                20                  25                  30

Gly Ser Ala Ile Thr Thr Tyr Lys Asn Met Asp Ala Thr Thr Val Phe
            35                  40                  45

His Thr Phe His Thr Gly Ser Lys Glu Ala Tyr Gln Trp Leu Thr Glu
        50                  55                  60

Leu Lys Lys Glu Cys Pro Thr Gln Glu Pro Glu Ile Pro Asp Ile Lys
65                  70                  75                  80

Asp Asp Pro Ile Lys Gly Ile Asp Val Asn Met Gly Thr Phe Asn
                85                  90                  95

Ile Ser Glu Lys Arg Ser Ala Gln Ile Asn Lys Ser Phe Thr Asp Leu
            100                 105                 110

Arg Met Arg Val Arg Ala Glu Gly Leu Met Asp Gly Ser Pro Leu Phe
        115                 120                 125

Tyr Ile Arg Lys Ile Leu Glu Thr Ile Phe Thr Ile Leu Phe Ala Phe
    130                 135                 140

Tyr Leu Gln Tyr His Thr Tyr Tyr Leu Pro Ser Ala Ile Leu Met Gly
145                 150                 155                 160

Val Ala Trp Gln Gln Leu Gly Trp Leu Ile His Glu Phe Ala His His
                165                 170                 175

Gln Leu Phe Lys Asn Arg Tyr Tyr Asn Asp Leu Ala Ser Tyr Phe Val
```

-continued

```
                180                 185                 190
Gly Asn Phe Leu Gln Gly Phe Ser Ser Gly Trp Lys Glu Gln His
                195                 200                 205

Asn Val His His Ala Ala Thr Asn Val Val Gly Arg Asp Gly Asp Leu
    210                 215                 220

Asp Leu Val Pro Phe Tyr Ala Thr Val Ala Glu His Leu Asn Asn Tyr
225                 230                 235                 240

Ser Gln Asp Ser Trp Val Met Thr Leu Phe Arg Trp Gln His Val His
                245                 250                 255

Trp Thr Phe Met Leu Pro Phe Leu Arg Leu Ser Trp Leu Leu Gln Ser
                260                 265                 270

Ile Ile Phe Val Ser Gln Met Pro Thr His Tyr Tyr Asp Tyr Tyr Arg
                275                 280                 285

Asn Thr Ala Ile Tyr Glu Gln Val Gly Leu Ser Leu His Trp Ala Trp
    290                 295                 300

Ser Leu Gly Gln Leu Tyr Phe Leu Pro Asp Trp Ser Thr Arg Ile Met
305                 310                 315                 320

Phe Phe Leu Val Ser His Leu Val Gly Gly Phe Leu Leu Ser His Val
                325                 330                 335

Val Thr Phe Asn His Tyr Ser Val Glu Lys Phe Ala Leu Ser Ser Asn
                340                 345                 350

Ile Met Ser Asn Tyr Ala Cys Leu Gln Ile Met Thr Thr Arg Asn Met
            355                 360                 365

Arg Pro Gly Arg Phe Ile Asp Trp Leu Trp Gly Gly Leu Asn Tyr Gln
            370                 375                 380

Ile Glu His His Leu Phe Pro Thr Met Pro Arg His Asn Leu Asn Thr
385                 390                 395                 400

Val Met Pro Leu Val Lys Glu Phe Ala Ala Asn Gly Leu Pro Tyr
                405                 410                 415

Met Val Asp Asp Tyr Phe Thr Gly Phe Trp Leu Glu Ile Glu Gln Phe
                420                 425                 430

Arg Asn Ile Ala Asn Val Ala Ala Lys Leu Thr Lys Lys Ile Ala
            435                 440                 445
```

<210> SEQ ID NO 25
<211> LENGTH: 954
<212> TYPE: DNA
<213> ORGANISM: Mortierella alpina
<220> FEATURE:
<221> NAME/KEY: CDS
<222> LOCATION: (1)..(954)
<223> OTHER INFORMATION: D6-elongase

<400> SEQUENCE: 25

```
atg gcc gcc gca atc ttg gac aag gtc aac ttc ggc att gat cag ccc     48
Met Ala Ala Ala Ile Leu Asp Lys Val Asn Phe Gly Ile Asp Gln Pro
 1               5                  10                  15 ttc gga atc aag ctc gac acc tac ttt gct cag gcc tat gaa ctc gtc     96
Phe Gly Ile Lys Leu Asp Thr Tyr Phe Ala Gln Ala Tyr Glu Leu Val
                20                  25                  30 acc gga aag tcc atc gac tcc ttc gtc ttc cag gag ggc gtc acg cct    144
Thr Gly Lys Ser Ile Asp Ser Phe Val Phe Gln Glu Gly Val Thr Pro
            35                  40                  45 ctc tcg acc cag aga gag gtc gcc atg tgg act atc act tac ttc gtc    192
Leu Ser Thr Gln Arg Glu Val Ala Met Trp Thr Ile Thr Tyr Phe Val
        50                  55                  60 gtc atc ttt ggt ggt cgc cag atc atg aag agc cag gac gcc ttc aag    240
```

```
Val Ile Phe Gly Gly Arg Gln Ile Met Lys Ser Gln Asp Ala Phe Lys
 65                  70                  75                  80 ctc aag ccc ctc ttc atc ctc cac aac ttc ctc ctg acg atc gcg tcc      288
Leu Lys Pro Leu Phe Ile Leu His Asn Phe Leu Leu Thr Ile Ala Ser
                 85                  90                  95 gga tcg ctg ttg ctg ttc atc gag aac ctg gtc ccc atc ctc gcc          336
Gly Ser Leu Leu Leu Phe Ile Glu Asn Leu Val Pro Ile Leu Ala
            100                 105                 110 aga aac gga ctt ttc tac gcc atc tgc gac gac ggt gcc tgg acc cag      384
Arg Asn Gly Leu Phe Tyr Ala Ile Cys Asp Asp Gly Ala Trp Thr Gln
                115                 120                 125 cgc ctc gag ctc ctc tac tac ctc aac tac ctg gtc aag tac tgg gag      432
Arg Leu Glu Leu Leu Tyr Tyr Leu Asn Tyr Leu Val Lys Tyr Trp Glu
130                 135                 140 ttg gcc gac acc gtc ttt ttg gtc ctc aag aag aag cct ctt gag ttc      480
Leu Ala Asp Thr Val Phe Leu Val Leu Lys Lys Lys Pro Leu Glu Phe
145                 150                 155                 160 ctg cac tac ttc cac cac tcg atg acc atg gtt ctc tgc ttt gtc cag      528
Leu His Tyr Phe His His Ser Met Thr Met Val Leu Cys Phe Val Gln
                165                 170                 175 ctt gga gga tac act tca gtg tcc tgg gtc cct att acc ctc aac ttg      576
Leu Gly Gly Tyr Thr Ser Val Ser Trp Val Pro Ile Thr Leu Asn Leu
            180                 185                 190 act gtc cac gtc ttc atg tac tac tac atg cgc tcc gct gcc ggt          624
Thr Val His Val Phe Met Tyr Tyr Tyr Met Arg Ser Ala Ala Gly
                195                 200                 205 gtt cgc atc tgg tgg aag cag tac ttg acc act ctc cag atc gtc cag      672
Val Arg Ile Trp Trp Lys Gln Tyr Leu Thr Thr Leu Gln Ile Val Gln
210                 215                 220 ttc gtt ctt gac ctc gga ttc atc tac ttc tgc gcc tac acc tac ttc      720
Phe Val Leu Asp Leu Gly Phe Ile Tyr Phe Cys Ala Tyr Thr Tyr Phe
225                 230                 235                 240 gcc ttc acc tac ttc ccc tgg gct ccc aac gtc ggc aag tgc gcc ggt      768
Ala Phe Thr Tyr Phe Pro Trp Ala Pro Asn Val Gly Lys Cys Ala Gly
                245                 250                 255 acc gag ggt gct gct ctc ttt ggc tgc gga ctc ctc tcc agc tat ctc      816
Thr Glu Gly Ala Ala Leu Phe Gly Cys Gly Leu Leu Ser Ser Tyr Leu
            260                 265                 270 ttg ctc ttt atc aac ttc tac cgc att acc tac aat gcc aag gcc aag      864
Leu Leu Phe Ile Asn Phe Tyr Arg Ile Thr Tyr Asn Ala Lys Ala Lys
                275                 280                 285 gca gcc aag gag cgt gga agc aac ttt acc ccc aag act gtc aag tcc      912
Ala Ala Lys Glu Arg Gly Ser Asn Phe Thr Pro Lys Thr Val Lys Ser
290                 295                 300 ggc gga tcg ccc aag aag ccc tcc aag agc aag cac atc taa              954
Gly Gly Ser Pro Lys Lys Pro Ser Lys Ser Lys His Ile
305                 310                 315

<210> SEQ ID NO 26
<211> LENGTH: 317
<212> TYPE: PRT
<213> ORGANISM: Mortierella alpina

<400> SEQUENCE: 26

Met Ala Ala Ala Ile Leu Asp Lys Val Asn Phe Gly Ile Asp Gln Pro
 1               5                  10                  15

Phe Gly Ile Lys Leu Asp Thr Tyr Phe Ala Gln Ala Tyr Glu Leu Val
                20                  25                  30

Thr Gly Lys Ser Ile Asp Ser Phe Val Phe Gln Glu Gly Val Thr Pro
            35                  40                  45
```

-continued

```
Leu Ser Thr Gln Arg Glu Val Ala Met Trp Thr Ile Thr Tyr Phe Val
    50                  55                  60

Val Ile Phe Gly Gly Arg Gln Ile Met Lys Ser Gln Asp Ala Phe Lys
 65                  70                  75                  80

Leu Lys Pro Leu Phe Ile Leu His Asn Phe Leu Thr Ile Ala Ser
                 85                  90                  95

Gly Ser Leu Leu Leu Leu Phe Ile Glu Asn Leu Val Pro Ile Leu Ala
                100                 105                 110

Arg Asn Gly Leu Phe Tyr Ala Ile Cys Asp Asp Gly Ala Trp Thr Gln
                115                 120                 125

Arg Leu Glu Leu Leu Tyr Tyr Leu Asn Tyr Leu Val Lys Tyr Trp Glu
            130                 135                 140

Leu Ala Asp Thr Val Phe Leu Val Leu Lys Lys Pro Leu Glu Phe
145                 150                 155                 160

Leu His Tyr Phe His His Ser Met Thr Met Val Leu Cys Phe Val Gln
                165                 170                 175

Leu Gly Gly Tyr Thr Ser Val Ser Trp Val Pro Ile Thr Leu Asn Leu
                180                 185                 190

Thr Val His Val Phe Met Tyr Tyr Tyr Met Arg Ser Ala Ala Gly
        195                 200                 205

Val Arg Ile Trp Trp Lys Gln Tyr Leu Thr Thr Leu Gln Ile Val Gln
210                 215                 220

Phe Val Leu Asp Leu Gly Phe Ile Tyr Phe Cys Ala Tyr Thr Tyr Phe
225                 230                 235                 240

Ala Phe Thr Tyr Phe Pro Trp Ala Pro Asn Val Gly Lys Cys Ala Gly
                245                 250                 255

Thr Glu Gly Ala Ala Leu Phe Gly Cys Gly Leu Leu Ser Ser Tyr Leu
            260                 265                 270

Leu Leu Phe Ile Asn Phe Tyr Arg Ile Thr Tyr Asn Ala Lys Ala Lys
            275                 280                 285

Ala Ala Lys Glu Arg Gly Ser Asn Phe Thr Pro Lys Thr Val Lys Ser
        290                 295                 300

Gly Gly Ser Pro Lys Lys Pro Ser Lys Ser Lys His Ile
305                 310                 315
```

<210> SEQ ID NO 27
<211> LENGTH: 1320
<212> TYPE: DNA
<213> ORGANISM: Thraustochytrium
<220> FEATURE:
<221> NAME/KEY: CDS
<222> LOCATION: (1)..(1320)
<223> OTHER INFORMATION: D5-desaturase

<400> SEQUENCE: 27

```
atg ggc aag ggc agc gag ggc cgc agc gcg gcg cgc gag atg acg gcc     48
Met Gly Lys Gly Ser Glu Gly Arg Ser Ala Ala Arg Glu Met Thr Ala
 1               5                  10                  15 gag gcg aac ggc gac aag cgg aaa acg att ctg atc gag ggc gtc ctg     96
Glu Ala Asn Gly Asp Lys Arg Lys Thr Ile Leu Ile Glu Gly Val Leu
                 20                  25                  30 tac gac gcg acg aac ttt aag cac ccg ggc ggt tcg atc atc aac ttc    144
Tyr Asp Ala Thr Asn Phe Lys His Pro Gly Gly Ser Ile Ile Asn Phe
             35                  40                  45 ttg acc gag ggc gag gcc ggc gtg gac gcg acg cag gcg tac cgc gag    192
Leu Thr Glu Gly Glu Ala Gly Val Asp Ala Thr Gln Ala Tyr Arg Glu
 50                  55                  60
```

-continued

| | | |
|---|---|---|
| ttt cat cag cgg tcc ggc aag gcc gac aag tac ctc aag tcg ctg ccg<br>Phe His Gln Arg Ser Gly Lys Ala Asp Lys Tyr Leu Lys Ser Leu Pro<br>65                          70                       75                    80 | 240 |

```
ttt cat cag cgg tcc ggc aag gcc gac aag tac ctc aag tcg ctg ccg      240
Phe His Gln Arg Ser Gly Lys Ala Asp Lys Tyr Leu Lys Ser Leu Pro
 65                  70                  75                  80 aag ctg gat gcg tcc aag gtg gag tcg cgg ttc tcg gcc aaa gag cag      288
Lys Leu Asp Ala Ser Lys Val Glu Ser Arg Phe Ser Ala Lys Glu Gln
                 85                  90                  95 gcg cgg cgc gac gcc atg acg cgc gac tac gcg gcc ttt cgc gag gag      336
Ala Arg Arg Asp Ala Met Thr Arg Asp Tyr Ala Ala Phe Arg Glu Glu
            100                 105                 110 ctc gtc gcc gag ggg tac ttt gac ccg tcg atc ccg cac atg att tac      384
Leu Val Ala Glu Gly Tyr Phe Asp Pro Ser Ile Pro His Met Ile Tyr
        115                 120                 125 cgc gtc gtg gag atc gtg gcg ctc ttc gcg ctc tcg ttc tgg ctc atg      432
Arg Val Val Glu Ile Val Ala Leu Phe Ala Leu Ser Phe Trp Leu Met
    130                 135                 140 tcc aag gcc tcg ccc acc tcg ctc gtg ctg ggc gtg gtg atg aac ggc      480
Ser Lys Ala Ser Pro Thr Ser Leu Val Leu Gly Val Val Met Asn Gly
145                 150                 155                 160 att gcg cag ggc cgc tgc ggc tgg gtc atg cac gag atg ggc cac ggg      528
Ile Ala Gln Gly Arg Cys Gly Trp Val Met His Glu Met Gly His Gly
                165                 170                 175 tcg ttc acg ggc gtc atc tgg ctc gac gac cgg atg tgc gag ttc ttc      576
Ser Phe Thr Gly Val Ile Trp Leu Asp Asp Arg Met Cys Glu Phe Phe
            180                 185                 190 tac ggc gtc ggc tgc ggc atg agc ggg cac tac tgg aag aac cag cac      624
Tyr Gly Val Gly Cys Gly Met Ser Gly His Tyr Trp Lys Asn Gln His
        195                 200                 205 agc aag cac cac gcc gcg ccc aac cgc ctc gag cac gat gtc gat ctc      672
Ser Lys His His Ala Ala Pro Asn Arg Leu Glu His Asp Val Asp Leu
    210                 215                 220 aac acg ctg ccc ctg gtc gcc ttt aac gag cgc gtc gtg cgc aag gtc      720
Asn Thr Leu Pro Leu Val Ala Phe Asn Glu Arg Val Val Arg Lys Val
225                 230                 235                 240 aag ccg gga tcg ctg ctg gcg ctc tgg ctg cgc gtg cag gcg tac ctc      768
Lys Pro Gly Ser Leu Leu Ala Leu Trp Leu Arg Val Gln Ala Tyr Leu
                245                 250                 255 ttt gcg ccc gtc tcg tgc ctg ctc atc ggc ctt ggc tgg acg ctc tac      816
Phe Ala Pro Val Ser Cys Leu Leu Ile Gly Leu Gly Trp Thr Leu Tyr
            260                 265                 270 ctg cac ccg cgc tac atg ctg cgc acc aag cgg cac atg gag ttc gtc      864
Leu His Pro Arg Tyr Met Leu Arg Thr Lys Arg His Met Glu Phe Val
        275                 280                 285 tgg atc ttc gcg cgc tac att ggc tgg ttc tcg ctc atg ggc gct ctc      912
Trp Ile Phe Ala Arg Tyr Ile Gly Trp Phe Ser Leu Met Gly Ala Leu
    290                 295                 300 ggc tac tcg ccg ggc acc tcg gtc ggg atg tac ctg tgc tcg ttc ggc      960
Gly Tyr Ser Pro Gly Thr Ser Val Gly Met Tyr Leu Cys Ser Phe Gly
305                 310                 315                 320 ctc ggc tgc att tac att ttc ctg cag ttc gcc gtc agc cac acg cac     1008
Leu Gly Cys Ile Tyr Ile Phe Leu Gln Phe Ala Val Ser His Thr His
                325                 330                 335 ctg ccg gtg acc aac ccg gag gac cag ctg cac tgg ctc gag tac gcg     1056
Leu Pro Val Thr Asn Pro Glu Asp Gln Leu His Trp Leu Glu Tyr Ala
            340                 345                 350 gcc gac cac acg gtg aac att agc acc aag tcc tgg ctc gtc acg tgg     1104
Ala Asp His Thr Val Asn Ile Ser Thr Lys Ser Trp Leu Val Thr Trp
        355                 360                 365 tgg atg tcg aac ctg aac ttt cag atc gag cac cac ctc ttc ccc acg     1152
Trp Met Ser Asn Leu Asn Phe Gln Ile Glu His His Leu Phe Pro Thr
```

```
                    370              375              380
gcg ccg cag ttc cgc ttc aag gaa atc agt cct cgc gtc gag gcc ctc    1200
Ala Pro Gln Phe Arg Phe Lys Glu Ile Ser Pro Arg Val Glu Ala Leu
385                 390              395              400 ttc aag cgc cac aac ctc ccg tac tac gac ctg ccc tac acg agc gcg    1248
Phe Lys Arg His Asn Leu Pro Tyr Tyr Asp Leu Pro Tyr Thr Ser Ala
                405              410              415 gtc tcg acc acc ttt gcc aat ctt tat tcc gtc ggc cac tcg gtc ggc    1296
Val Ser Thr Thr Phe Ala Asn Leu Tyr Ser Val Gly His Ser Val Gly
            420              425              430 gcc gac acc aag aag cag gac tga                                    1320
Ala Asp Thr Lys Lys Gln Asp
            435

<210> SEQ ID NO 28
<211> LENGTH: 439
<212> TYPE: PRT
<213> ORGANISM: Thraustochytrium

<400> SEQUENCE: 28

Met Gly Lys Gly Ser Glu Gly Arg Ser Ala Ala Arg Glu Met Thr Ala
1               5                   10                  15

Glu Ala Asn Gly Asp Lys Arg Lys Thr Ile Leu Ile Glu Gly Val Leu
            20                  25                  30

Tyr Asp Ala Thr Asn Phe Lys His Pro Gly Gly Ser Ile Ile Asn Phe
        35                  40                  45

Leu Thr Glu Gly Glu Ala Gly Val Asp Ala Thr Gln Ala Tyr Arg Glu
    50                  55                  60

Phe His Gln Arg Ser Gly Lys Ala Asp Lys Tyr Leu Lys Ser Leu Pro
65                  70                  75                  80

Lys Leu Asp Ala Ser Lys Val Glu Ser Arg Phe Ser Ala Lys Glu Gln
                85                  90                  95

Ala Arg Arg Asp Ala Met Thr Arg Asp Tyr Ala Ala Phe Arg Glu Glu
            100                 105                 110

Leu Val Ala Glu Gly Tyr Phe Asp Pro Ser Ile Pro His Met Ile Tyr
        115                 120                 125

Arg Val Val Glu Ile Val Ala Leu Phe Ala Leu Ser Phe Trp Leu Met
    130                 135                 140

Ser Lys Ala Ser Pro Thr Ser Leu Val Leu Gly Val Val Met Asn Gly
145                 150                 155                 160

Ile Ala Gln Gly Arg Cys Gly Trp Val Met His Glu Met Gly His Gly
                165                 170                 175

Ser Phe Thr Gly Val Ile Trp Leu Asp Asp Arg Met Cys Glu Phe Phe
            180                 185                 190

Tyr Gly Val Gly Cys Gly Met Ser Gly His Tyr Trp Lys Asn Gln His
        195                 200                 205

Ser Lys His His Ala Ala Pro Asn Arg Leu Glu His Asp Val Asp Leu
    210                 215                 220

Asn Thr Leu Pro Leu Val Ala Phe Asn Glu Arg Val Val Arg Lys Val
225                 230                 235                 240

Lys Pro Gly Ser Leu Leu Ala Leu Trp Leu Arg Val Gln Ala Tyr Leu
                245                 250                 255

Phe Ala Pro Val Ser Cys Leu Leu Ile Gly Leu Gly Trp Thr Leu Tyr
            260                 265                 270

Leu His Pro Arg Tyr Met Leu Arg Thr Lys Arg His Met Glu Phe Val
        275                 280                 285
```

-continued

```
Trp Ile Phe Ala Arg Tyr Ile Gly Trp Phe Ser Leu Met Gly Ala Leu
            290                 295                 300
Gly Tyr Ser Pro Gly Thr Ser Val Gly Met Tyr Leu Cys Ser Phe Gly
305                 310                 315                 320
Leu Gly Cys Ile Tyr Ile Phe Leu Gln Phe Ala Val Ser His Thr His
                325                 330                 335
Leu Pro Val Thr Asn Pro Glu Asp Gln Leu His Trp Leu Glu Tyr Ala
            340                 345                 350
Ala Asp His Thr Val Asn Ile Ser Thr Lys Ser Trp Leu Val Thr Trp
        355                 360                 365
Trp Met Ser Asn Leu Asn Phe Gln Ile Glu His His Leu Phe Pro Thr
    370                 375                 380
Ala Pro Gln Phe Arg Phe Lys Glu Ile Ser Pro Arg Val Glu Ala Leu
385                 390                 395                 400
Phe Lys Arg His Asn Leu Pro Tyr Tyr Asp Leu Pro Tyr Thr Ser Ala
                405                 410                 415
Val Ser Thr Thr Phe Ala Asn Leu Tyr Ser Val Gly His Ser Val Gly
            420                 425                 430
Ala Asp Thr Lys Lys Gln Asp
        435

<210> SEQ ID NO 29
<211> LENGTH: 957
<212> TYPE: DNA
<213> ORGANISM: Mortierella alpina
<220> FEATURE:
<221> NAME/KEY: CDS
<222> LOCATION: (1)..(957)
<223> OTHER INFORMATION: D6-elongase

<400> SEQUENCE: 29 atg gag tcg att gcg cca ttc ctc cca tca aag atg ccg caa gat ctg      48
Met Glu Ser Ile Ala Pro Phe Leu Pro Ser Lys Met Pro Gln Asp Leu
  1               5                  10                  15 ttt atg gac ctt gcc acc gct atc ggt gtc cgg gcc gcg ccc tat gtc      96
Phe Met Asp Leu Ala Thr Ala Ile Gly Val Arg Ala Ala Pro Tyr Val
                 20                  25                  30 gat cct ctc gag gcc gcg ctg gtg gcc cag gcc gag aag tac atc ccc     144
Asp Pro Leu Glu Ala Ala Leu Val Ala Gln Ala Glu Lys Tyr Ile Pro
             35                  40                  45 acg att gtc cat cac acg cgt ggg ttc ctg gtc gcg gtg gag tcg cct     192
Thr Ile Val His His Thr Arg Gly Phe Leu Val Ala Val Glu Ser Pro
         50                  55                  60 ttg gcc cgt gag ctg ccg ttg atg aac ccg ttc cac gtg ctg ttg atc     240
Leu Ala Arg Glu Leu Pro Leu Met Asn Pro Phe His Val Leu Leu Ile
     65                  70                  75                  80 gtg ctc gct tat ttg gtc acg gtc ttt gtg ggc atg cag atc atg aag     288
Val Leu Ala Tyr Leu Val Thr Val Phe Val Gly Met Gln Ile Met Lys
                 85                  90                  95 aac ttt gag cgg ttc gag gtc aag acg ttt tcg ctc ctg cac aac ttt     336
Asn Phe Glu Arg Phe Glu Val Lys Thr Phe Ser Leu Leu His Asn Phe
                100                 105                 110 tgt ctg gtc tcg atc agc gcc tac atg tgc ggt ggg atc ctg tac gag     384
Cys Leu Val Ser Ile Ser Ala Tyr Met Cys Gly Gly Ile Leu Tyr Glu
            115                 120                 125 gct tat cag gcc aac tat gga ctg ttt gag aac gct gct gat cat acc     432
Ala Tyr Gln Ala Asn Tyr Gly Leu Phe Glu Asn Ala Ala Asp His Thr
        130                 135                 140
```

```
ttc aag ggt ctt cct atg gcc aag atg atc tgg ctc ttc tac ttc tcc    480
Phe Lys Gly Leu Pro Met Ala Lys Met Ile Trp Leu Phe Tyr Phe Ser
145                 150                 155                 160 aag atc atg gag ttt gtc gac acc atg atc atg gtc ctc aag aag aac    528
Lys Ile Met Glu Phe Val Asp Thr Met Ile Met Val Leu Lys Lys Asn
                165                 170                 175 aac cgc cag atc tcc ttc ttg cac gtt tac cac cac agc tcc atc ttc    576
Asn Arg Gln Ile Ser Phe Leu His Val Tyr His His Ser Ser Ile Phe
            180                 185                 190 acc atc tgg tgg ttg gtc acc ttt gtt gca ccc aac ggt gaa gcc tac    624
Thr Ile Trp Trp Leu Val Thr Phe Val Ala Pro Asn Gly Glu Ala Tyr
        195                 200                 205 ttc tct gcg gcg ttg aac tcg ttc atc cat gtg atc atg tac ggc tac    672
Phe Ser Ala Ala Leu Asn Ser Phe Ile His Val Ile Met Tyr Gly Tyr
    210                 215                 220 tac ttc ttg tcg gcc ttg ggc ttc aag cag gtg tcg ttc atc aag ttc    720
Tyr Phe Leu Ser Ala Leu Gly Phe Lys Gln Val Ser Phe Ile Lys Phe
225                 230                 235                 240 tac atc acg cgc tcg cag atg aca cag ttc tgc atg atg tcg gtc cag    768
Tyr Ile Thr Arg Ser Gln Met Thr Gln Phe Cys Met Met Ser Val Gln
                245                 250                 255 tct tcc tgg gac atg tac gcc atg aag gtc ctt ggc cgc ccc gga tac    816
Ser Ser Trp Asp Met Tyr Ala Met Lys Val Leu Gly Arg Pro Gly Tyr
            260                 265                 270 ccc ttc ttc atc acg gct ctg ctt tgg ttc tac atg tgg acc atg ctc    864
Pro Phe Phe Ile Thr Ala Leu Leu Trp Phe Tyr Met Trp Thr Met Leu
        275                 280                 285 ggt ctc ttc tac aac ttt tac aga aag aac gcc aag ttg gcc aag cag    912
Gly Leu Phe Tyr Asn Phe Tyr Arg Lys Asn Ala Lys Leu Ala Lys Gln
    290                 295                 300 gcc aag gcc gac gct gcc aag gag aag gca agg aag ttg cag taa        957
Ala Lys Ala Asp Ala Ala Lys Glu Lys Ala Arg Lys Leu Gln
305                 310                 315

<210> SEQ ID NO 30
<211> LENGTH: 318
<212> TYPE: PRT
<213> ORGANISM: Mortierella alpina

<400> SEQUENCE: 30

Met Glu Ser Ile Ala Pro Phe Leu Pro Ser Lys Met Pro Gln Asp Leu
1               5                   10                  15

Phe Met Asp Leu Ala Thr Ala Ile Gly Val Arg Ala Ala Pro Tyr Val
            20                  25                  30

Asp Pro Leu Glu Ala Ala Leu Ala Gln Ala Glu Lys Tyr Ile Pro
        35                  40                  45

Thr Ile Val His His Thr Arg Gly Phe Leu Val Ala Val Glu Ser Pro
    50                  55                  60

Leu Ala Arg Glu Leu Pro Leu Met Asn Pro Phe His Val Leu Leu Ile
65                  70                  75                  80

Val Leu Ala Tyr Leu Val Thr Val Phe Val Gly Met Gln Ile Met Lys
                85                  90                  95

Asn Phe Glu Arg Phe Glu Val Lys Thr Phe Ser Leu Leu His Asn Phe
            100                 105                 110

Cys Leu Val Ser Ile Ser Ala Tyr Met Cys Gly Gly Ile Leu Tyr Glu
        115                 120                 125

Ala Tyr Gln Ala Asn Tyr Gly Leu Phe Glu Asn Ala Ala Asp His Thr
    130                 135                 140
```

```
Phe Lys Gly Leu Pro Met Ala Lys Met Ile Trp Leu Phe Tyr Phe Ser
145                 150                 155                 160

Lys Ile Met Glu Phe Val Asp Thr Met Ile Met Val Leu Lys Lys Asn
                165                 170                 175

Asn Arg Gln Ile Ser Phe Leu His Val Tyr His His Ser Ser Ile Phe
            180                 185                 190

Thr Ile Trp Trp Leu Val Thr Phe Val Ala Pro Asn Gly Glu Ala Tyr
        195                 200                 205

Phe Ser Ala Ala Leu Asn Ser Phe Ile His Val Ile Met Tyr Gly Tyr
    210                 215                 220

Tyr Phe Leu Ser Ala Leu Gly Phe Lys Gln Val Ser Phe Ile Lys Phe
225                 230                 235                 240

Tyr Ile Thr Arg Ser Gln Met Thr Gln Phe Cys Met Met Ser Val Gln
                245                 250                 255

Ser Ser Trp Asp Met Tyr Ala Met Lys Val Leu Gly Arg Pro Gly Tyr
                260                 265                 270

Pro Phe Phe Ile Thr Ala Leu Leu Trp Phe Tyr Met Trp Thr Met Leu
            275                 280                 285

Gly Leu Phe Tyr Asn Phe Tyr Arg Lys Asn Ala Lys Leu Ala Lys Gln
290                 295                 300

Ala Lys Ala Asp Ala Ala Lys Glu Lys Ala Arg Lys Leu Gln
305                 310                 315
```

<210> SEQ ID NO 31
<211> LENGTH: 1374
<212> TYPE: DNA
<213> ORGANISM: Mortierella alpina
<220> FEATURE:
<221> NAME/KEY: CDS
<222> LOCATION: (1)..(1374)
<223> OTHER INFORMATION: D6-desaturase

<400> SEQUENCE: 31

```
atg gct gct gct ccc agt gtg agg acg ttt act cgg gcc gag gtt ttg        48
Met Ala Ala Ala Pro Ser Val Arg Thr Phe Thr Arg Ala Glu Val Leu
  1               5                  10                  15 aat gcc gag gct ctg aat gag ggc aag aag gat gcc gag gca ccc ttc        96
Asn Ala Glu Ala Leu Asn Glu Gly Lys Lys Asp Ala Glu Ala Pro Phe
                 20                  25                  30 ttg atg atc atc gac aac aag gtg tac gat gtt cgc gag ttc gtc cct       144
Leu Met Ile Ile Asp Asn Lys Val Tyr Asp Val Arg Glu Phe Val Pro
             35                  40                  45 gat cat ccc ggt gga agt gtg att ctc acg cac gtt ggc aag gac ggc       192
Asp His Pro Gly Gly Ser Val Ile Leu Thr His Val Gly Lys Asp Gly
         50                  55                  60 act gac gtc ttt gac act ttt cac ccc gag gct gct tgg gag act ctt       240
Thr Asp Val Phe Asp Thr Phe His Pro Glu Ala Ala Trp Glu Thr Leu
 65                  70                  75                  80 gcc aac ttt tac gtt ggt gat att gac gag agc gac cgc gat atc aag       288
Ala Asn Phe Tyr Val Gly Asp Ile Asp Glu Ser Asp Arg Asp Ile Lys
                 85                  90                  95 aat gat gac ttt gcg gcc gag gtc cgc aag ctg cgt acc ttg ttc cag       336
Asn Asp Asp Phe Ala Ala Glu Val Arg Lys Leu Arg Thr Leu Phe Gln
            100                 105                 110 tct ctt ggt tac tac gat tct tcc aag gca tac tac gcc ttc aag gtc       384
Ser Leu Gly Tyr Tyr Asp Ser Ser Lys Ala Tyr Tyr Ala Phe Lys Val
        115                 120                 125 tcg ttc aac ctc tgc atc tgg ggt ttg tcg acg gtc att gtg gcc aag       432
Ser Phe Asn Leu Cys Ile Trp Gly Leu Ser Thr Val Ile Val Ala Lys
```

```
              130                 135                 140
tgg ggc cag acc tcg acc ctc gcc aac gtg ctc tcg gct gcg ctt ttg      480
Trp Gly Gln Thr Ser Thr Leu Ala Asn Val Leu Ser Ala Ala Leu Leu
145                 150                 155                 160 ggt ctg ttc tgg cag cag tgc gga tgg ttg gct cac gac ttt ttg cat      528
Gly Leu Phe Trp Gln Gln Cys Gly Trp Leu Ala His Asp Phe Leu His
                165                 170                 175 cac cag gtc ttc cag gac cgt ttc tgg ggt gat ctt ttc ggc gcc ttc      576
His Gln Val Phe Gln Asp Arg Phe Trp Gly Asp Leu Phe Gly Ala Phe
            180                 185                 190 ttg gga ggt gtc tgc cag ggc ttc tcg tcc tcg tgg tgg aag gac aag      624
Leu Gly Gly Val Cys Gln Gly Phe Ser Ser Ser Trp Trp Lys Asp Lys
        195                 200                 205 cac aac act cac cac gcc gcc ccc aac gtc cac ggc gag gat ccc gac      672
His Asn Thr His His Ala Ala Pro Asn Val His Gly Glu Asp Pro Asp
    210                 215                 220 att gac acc cac cct ctg ttg acc tgg agt gag cat gcg ttg gag atg      720
Ile Asp Thr His Pro Leu Leu Thr Trp Ser Glu His Ala Leu Glu Met
225                 230                 235                 240 ttc tcg gat gtc cca gat gag gag ctg acc cgc atg tgg tcg cgt ttc      768
Phe Ser Asp Val Pro Asp Glu Glu Leu Thr Arg Met Trp Ser Arg Phe
                245                 250                 255 atg gtc ctg aac cag acc tgg ttt tac ttc ccc att ctc tcg ttt gcc      816
Met Val Leu Asn Gln Thr Trp Phe Tyr Phe Pro Ile Leu Ser Phe Ala
            260                 265                 270 cgt ctc tcc tgg tgc ctc cag tcc att ctc ttt gtg ctg cct aac ggt      864
Arg Leu Ser Trp Cys Leu Gln Ser Ile Leu Phe Val Leu Pro Asn Gly
        275                 280                 285 cag gcc cac aag ccc tcg ggc gcg cgt gtg ccc atc tcg ttg gtc gag      912
Gln Ala His Lys Pro Ser Gly Ala Arg Val Pro Ile Ser Leu Val Glu
    290                 295                 300 cag ctg tcg ctt gcg atg cac tgg acc tgg tac ctc gcc acc atg ttc      960
Gln Leu Ser Leu Ala Met His Trp Thr Trp Tyr Leu Ala Thr Met Phe
305                 310                 315                 320 ctg ttc atc aag gat ccc gtc aac atg ctg gtg tac ttt ttg gtg tcg     1008
Leu Phe Ile Lys Asp Pro Val Asn Met Leu Val Tyr Phe Leu Val Ser
                325                 330                 335 cag gcg gtg tgc gga aac ttg ttg gcg atc gtg ttc tcg ctc aac cac     1056
Gln Ala Val Cys Gly Asn Leu Leu Ala Ile Val Phe Ser Leu Asn His
            340                 345                 350 aac ggt atg cct gtg atc tcg aag gag gag gcg gtc gat atg gat ttc     1104
Asn Gly Met Pro Val Ile Ser Lys Glu Glu Ala Val Asp Met Asp Phe
        355                 360                 365 ttc acg aag cag atc atc acg ggt cgt gat gtc cac ccg ggt cta ttt     1152
Phe Thr Lys Gln Ile Ile Thr Gly Arg Asp Val His Pro Gly Leu Phe
    370                 375                 380 gcc aac tgg ttc acg ggt gga ttg aac tat cag atc gag cac cac ttg     1200
Ala Asn Trp Phe Thr Gly Gly Leu Asn Tyr Gln Ile Glu His His Leu
385                 390                 395                 400 ttc cct tcg atg cct cgc cac aac ttt tca aag atc cag cct gct gtc     1248
Phe Pro Ser Met Pro Arg His Asn Phe Ser Lys Ile Gln Pro Ala Val
                405                 410                 415 gag acc ctg tgc aaa aag tac aat gtc cga tac cac acc acc ggt atg     1296
Glu Thr Leu Cys Lys Lys Tyr Asn Val Arg Tyr His Thr Thr Gly Met
            420                 425                 430 atc gag gga act gca gag gtc ttt agc cgt ctg aac gag gtc tcc aag     1344
Ile Glu Gly Thr Ala Glu Val Phe Ser Arg Leu Asn Glu Val Ser Lys
        435                 440                 445 gct gcc tcc aag atg ggt aag gcg cag taa                             1374
```

```
Ala Ala Ser Lys Met Gly Lys Ala Gln
    450             455
```

<210> SEQ ID NO 32
<211> LENGTH: 457
<212> TYPE: PRT
<213> ORGANISM: Mortierella alpina

<400> SEQUENCE: 32

```
Met Ala Ala Ala Pro Ser Val Arg Thr Phe Thr Arg Ala Glu Val Leu
  1               5                  10                  15

Asn Ala Glu Ala Leu Asn Glu Gly Lys Lys Asp Ala Glu Ala Pro Phe
             20                  25                  30

Leu Met Ile Ile Asp Asn Lys Val Tyr Asp Val Arg Glu Phe Val Pro
         35                  40                  45

Asp His Pro Gly Gly Ser Val Ile Leu Thr His Val Gly Lys Asp Gly
 50                  55                  60

Thr Asp Val Phe Asp Thr Phe His Pro Glu Ala Ala Trp Glu Thr Leu
 65                  70                  75                  80

Ala Asn Phe Tyr Val Gly Asp Ile Asp Glu Ser Asp Arg Asp Ile Lys
                 85                  90                  95

Asn Asp Asp Phe Ala Ala Glu Val Arg Lys Leu Arg Thr Leu Phe Gln
            100                 105                 110

Ser Leu Gly Tyr Tyr Asp Ser Ser Lys Ala Tyr Tyr Ala Phe Lys Val
        115                 120                 125

Ser Phe Asn Leu Cys Ile Trp Gly Leu Ser Thr Val Ile Val Ala Lys
    130                 135                 140

Trp Gly Gln Thr Ser Thr Leu Ala Asn Val Leu Ser Ala Ala Leu Leu
145                 150                 155                 160

Gly Leu Phe Trp Gln Gln Cys Gly Trp Leu Ala His Asp Phe Leu His
                165                 170                 175

His Gln Val Phe Gln Asp Arg Phe Trp Gly Asp Leu Phe Gly Ala Phe
            180                 185                 190

Leu Gly Gly Val Cys Gln Gly Phe Ser Ser Ser Trp Trp Lys Asp Lys
        195                 200                 205

His Asn Thr His His Ala Ala Pro Asn Val His Gly Glu Asp Pro Asp
    210                 215                 220

Ile Asp Thr His Pro Leu Leu Thr Trp Ser Glu His Ala Leu Glu Met
225                 230                 235                 240

Phe Ser Asp Val Pro Asp Glu Glu Leu Thr Arg Met Trp Ser Arg Phe
                245                 250                 255

Met Val Leu Asn Gln Thr Trp Phe Tyr Phe Pro Ile Leu Ser Phe Ala
            260                 265                 270

Arg Leu Ser Trp Cys Leu Gln Ser Ile Leu Phe Val Leu Pro Asn Gly
        275                 280                 285

Gln Ala His Lys Pro Ser Gly Ala Arg Val Pro Ile Ser Leu Val Glu
    290                 295                 300

Gln Leu Ser Leu Ala Met His Trp Thr Trp Tyr Leu Ala Thr Met Phe
305                 310                 315                 320

Leu Phe Ile Lys Asp Pro Val Asn Met Leu Val Tyr Phe Leu Val Ser
                325                 330                 335

Gln Ala Val Cys Gly Asn Leu Leu Ala Ile Val Phe Ser Leu Asn His
            340                 345                 350

Asn Gly Met Pro Val Ile Ser Lys Glu Glu Ala Val Asp Met Asp Phe
        355                 360                 365
```

```
Phe Thr Lys Gln Ile Ile Thr Gly Arg Asp Val His Pro Gly Leu Phe
        370                 375                 380

Ala Asn Trp Phe Thr Gly Gly Leu Asn Tyr Gln Ile Glu His His Leu
385                 390                 395                 400

Phe Pro Ser Met Pro Arg His Asn Phe Ser Lys Ile Gln Pro Ala Val
                405                 410                 415

Glu Thr Leu Cys Lys Lys Tyr Asn Val Arg Tyr His Thr Thr Gly Met
            420                 425                 430

Ile Glu Gly Thr Ala Glu Val Phe Ser Arg Leu Asn Glu Val Ser Lys
        435                 440                 445

Ala Ala Ser Lys Met Gly Lys Ala Gln
    450                 455

<210> SEQ ID NO 33
<211> LENGTH: 3598
<212> TYPE: DNA
<213> ORGANISM: Unknown
<220> FEATURE:
<223> OTHER INFORMATION: Sequence constitutes a plant
      promoter-terminator expression cassette in vector
      pUC19

<400> SEQUENCE: 33
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cggcgcgccg agctcctcga     420
gcaaatttac acattgccac taaacgtcta aacccttgta atttgttttt gttttactat     480
gtgtgttatg tatttgattt gcgataaatt tttatatttg gtactaaatt tataacacct     540
tttatgctaa cgtttgccaa cacttagcaa tttgcaagtt gattaattga ttctaaatta     600
tttttgtctt ctaaatacat atactaatca actggaaatg taaatatttg ctaatatttc     660
tactatagga gaattaaagt gagtgaatat ggtaccacaa ggtttggaga tttaattgtt     720
gcaatgctgc atggatggca tatacaccaa acattcaata attcttgagg ataataatgg     780
taccacacaa gatttgaggt gcatgaacgt cacgtggaca aaaggtttag taattttttca     840 agacaacaat gttaccacac acaagttttg aggtgcatgc atggatgccc tgtggaaagt     900
ttaaaaatat tttggaaatg atttgcatgg aagccatgtg taaaaccatg acatccactt     960
ggaggatgca ataatgaaga aaactacaaa tttacatgca actagttatg catgtagtct    1020
atataatgag gattttgcaa tactttcatt catacacact cactaagttt tacacgatta    1080
taatttcttc atagccagcc caccgcggtg ggcggccgcc tgcagtctag aaggcctcct    1140
gctttaatga gatatgcgag acgcctatga tcgcatgata tttgctttca attctgttgt    1200
gcacgttgta aaaacctga gcatgtgtag ctcagatcct taccgccggt ttcggttcat    1260
tctaatgaat atatcacccg ttactatcgt attttttatga ataatattct ccgttcaatt    1320
tactgattgt ccgtcgacga attcgagctc ggcgcgccaa gcttggcgta atcatggtca    1380
tagctgtttc ctgtgtgaaa ttgttatccg ctcacaattc cacacaacat acgagccgga    1440
```

```
agcataaagt gtaaagcctg gggtgcctaa tgagtgagct aactcacatt aattgcgttg    1500
cgctcactgc ccgctttcca gtcgggaaac ctgtcgtgcc agctgcatta atgaatcggc    1560
caacgcgcgg ggagaggcgg tttgcgtatt gggcgctctt ccgcttcctc gctcactgac    1620
tcgctgcgct cggtcgttcg gctgcggcga gcggtatcag ctcactcaaa ggcggtaata    1680
cggttatcca cagaatcagg ggataacgca ggaaagaaca tgtgagcaaa aggccagcaa    1740
aaggccagga accgtaaaaa ggccgcgttg ctggcgtttt tccataggct ccgcccccct    1800
gacgagcatc acaaaaatcg acgctcaagt cagaggtggc gaaacccgac aggactataa    1860
agataccagg cgtttccccc tggaagctcc ctcgtgcgct ctcctgttcc gaccctgccg    1920
cttaccggat acctgtccgc ctttctccct tcgggaagcg tggcgctttc tcatagctca    1980
cgctgtaggt atctcagttc ggtgtaggtc gttcgctcca agctgggctg tgtgcacgaa    2040
ccccccgttc agcccgaccg ctgcgcctta tccggtaact atcgtcttga gtccaacccg    2100
gtaagacacg acttatcgcc actggcagca gccactggta acaggattag cagagcgagg    2160
tatgtaggcg gtgctacaga gttcttgaag tggtggccta actacggcta cactagaagg    2220
acagtatttg gtatctgcgc tctgctgaag ccagttacct tcggaaaaag agttggtagc    2280
tcttgatccg gcaaacaaac caccgctggt agcggtggtt tttttgtttg caagcagcag    2340
attacgcgca gaaaaaaagg atctcaagaa gatcctttga tcttttctac ggggtctgac    2400
gctcagtgga acgaaaactc acgttaaggg attttggtca tgagattatc aaaaaggatc    2460
ttcacctaga tccttttaaa ttaaaaatga agttttaaat caatctaaag tatatatgag    2520
taaacttggt ctgacagtta ccaatgctta atcagtgagg cacctatctc agcgatctgt    2580
ctatttcgtt catccatagt tgcctgactc cccgtcgtgt agataactac gatacgggag    2640
ggcttaccat ctggccccag tgctgcaatg ataccgcgag acccacgctc accggctcca    2700
gatttatcag caataaacca gccagccgga agggccgagc gcagaagtgg tcctgcaact    2760
ttatccgcct ccatccagtc tattaattgt tgccgggaag ctagagtaag tagttcgcca    2820
gttaatagtt tgcgcaacgt tgttgccatt gctacaggca tcgtggtgtc acgctcgtcg    2880
tttggtatgg cttcattcag ctccggttcc caacgatcaa ggcgagttac atgatccccc    2940
atgttgtgca aaaagcggt tagctccttc ggtcctccga tcgttgtcag aagtaagttg    3000
gccgcagtgt tatcactcat ggttatggca gcactgcata attctcttac tgtcatgcca    3060
tccgtaagat gcttttctgt gactggtgag tactcaacca agtcattctg agaatagtgt    3120
atgcggcgac cgagttgctc ttgcccggcg tcaatacggg ataataccgc gccacatagc    3180
agaactttaa aagtgctcat cattggaaaa cgttcttcgg ggcgaaaact ctcaaggatc    3240
ttaccgctgt tgagatccag ttcgatgtaa cccactcgtg cacccaactg atcttcagca    3300
tcttttactt tcaccagcgt ttctgggtga gcaaaaacag gaaggcaaaa tgccgcaaaa    3360
aagggaataa gggcgacacg gaaatgttga atactcatac tcttcctttt tcaatattat    3420
tgaagcattt atcagggtta ttgtctcatg agcggataca tatttgaatg tatttagaaa    3480
aataaacaaa taggggttcc gcgcacattt ccccgaaaag tgccacctga cgtctaagaa    3540
accattatta tcatgacatt aacctataaa aataggcgta tcacgaggcc ctttcgtc      3598
```

<210> SEQ ID NO 34
<211> LENGTH: 3590
<212> TYPE: DNA
<213> ORGANISM: Unknown
<220> FEATURE:
<223> OTHER INFORMATION: Sequence constitutes a plant promoter-terminator expression cassette in vector pUC19

<400> SEQUENCE: 34

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cggcgcgccg agctcctcga     420
gcaaatttac acattgccac taaacgtcta aaccc ttgta atttgttttt gttttactat     480
gtgtgttatg tatttgattt gcgataaatt tttatatttg gtactaaatt tataacacct     540
tttatgctaa cgtttgccaa cacttagcaa tttgcaagtt gattaattga ttctaaatta     600
tttttgtctt ctaaatacat atactaatca actggaaatg taaatatttg ctaatatttc     660
tactatagga gaattaaagt gagtgaatat ggtaccacaa ggtttggaga tttaattgtt     720
gcaatgctgc atggatggca tatacaccaa acattcaata attcttgagg ataataatgg     780
taccacacaa gatttgaggt gcatgaacgt cacgtggaca aaaggtttag taattttca     840
agacaacaat gttaccacac acaagttttg aggtgcatgc atggatgccc tgtggaaagt     900
ttaaaaatat tttggaaatg atttgcatgg aagccatgtg taaaaccatg acatccactt     960
ggaggatgca ataatgaaga aaactacaaa tttacatgca actagttatg catgtagtct    1020
atataatgag gattttgcaa tactttcatt catacacact cactaagttt tacacgatta    1080
taatttcttc atagccagcg gatccgatat cgggcccgct agcgttaacc ctgctttaat    1140
gagatatgcg agacgcctat gatcgcatga tatttgcttt caattctgtt gtgcacgttg    1200
taaaaaacct gagcatgtgt agctcagatc cttaccgccg gtttcggttc attctaatga    1260
atatatcacc cgttactatc gtatttttat gaataatatt ctccgttcaa tttactgatt    1320
gtccgtcgac gaattcgagc tcggcgcgcc aagcttggcg taatcatggt catagctgtt    1380
tcctgtgtga attgttatc cgctcacaat tccacacaac atacgagccg gaagcataaa    1440
gtgtaaagcc tggggtgcct aatgagtgag ctaactcaca ttaattgcgt tgcgctcact    1500
gcccgctttc cagtcgggaa acctgtcgtg ccagctgcat taatgaatcg gccaacgcgc    1560
ggggagaggc ggtttgcgta ttgggcgctc ttccgcttcc tcgctcactg actcgctgcg    1620
ctcggtcgtt cggctgcggc gagcggtatc agctcactca aaggcggtaa tacggttatc    1680
cacagaatca ggggataacg caggaaagaa catgtgagca aaaggccagc aaaaggccag    1740
gaaccgtaaa aaggccgcgt tgctggcgtt tttccatagg ctccgccccc ctgacgagca    1800
tcacaaaaat cgacgctcaa gtcagaggtg gcgaaacccg acaggactat aaagatacca    1860
ggcgtttccc cctggaagct ccctcgtgcg ctctcctgtt ccgaccctgc cgcttaccgg    1920
atacctgtcc gcctttctcc cttcgggaag cgtggcgctt tctcatagct cacgctgtag    1980
gtatctcagt tcggtgtagg tcgttcgctc caagctgggc tgtgtgcacg aaccccccgt    2040
tcagcccgac cgctgcgcct tatccggtaa ctatcgtctt gagtccaacc cggtaagaca    2100
cgacttatcg ccactggcag cagccactgg taacaggatt agcagagcga ggtatgtagg    2160
cggtgctaca gagttcttga agtggtggcc taactacggc tacactagaa ggacagtatt    2220
```

```
tggtatctgc gctctgctga agccagttac cttcggaaaa agagttggta gctcttgatc    2280
cggcaaacaa accaccgctg gtagcggtgg ttttttttgtt tgcaagcagc agattacgcg    2340
cagaaaaaaa ggatctcaag aagatccttt gatcttttct acggggtctg acgctcagtg    2400
gaacgaaaac tcacgttaag ggattttggt catgagatta tcaaaaagga tcttcaccta    2460 gatccttttta aattaaaaat gaagttttaa atcaatctaa agtatatatg agtaaacttg    2520
gtctgacagt taccaatgct taatcagtga ggcacctatc tcagcgatct gtctatttcg    2580
ttcatccata gttgcctgac tccccgtcgt gtagataact acgatacggg agggcttacc    2640
atctggcccc agtgctgcaa tgataccgcg agacccacgc tcaccggctc cagatttatc    2700
agcaataaac cagccagccg aagggccga gcgcagaagt ggtcctgcaa ctttatccgc    2760
ctccatccag tctattaatt gttgccggga agctagagta agtagttcgc cagttaatag    2820
tttgcgcaac gttgttgcca ttgctacagg catcgtggtg tcacgctcgt cgtttggtat    2880
ggcttcattc agctccggtt cccaacgatc aaggcgagtt acatgatccc ccatgttgtg    2940
caaaaaagcg gttagctcct tcggtcctcc gatcgttgtc agaagtaagt tggccgcagt    3000
gttatcactc atggttatgg cagcactgca taattctctt actgtcatgc catccgtaag    3060
atgcttttct gtgactggtg agtactcaac caagtcattc tgagaatagt gtatgcggcg    3120
accgagttgc tcttgcccgg cgtcaatacg ggataatacc gcgccacata gcagaacttt    3180
aaaagtgctc atcattggaa aacgttcttc ggggcgaaaa ctctcaagga tcttaccgct    3240
gttgagatcc agttcgatgt aacccactcg tgcacccaac tgatcttcag catcttttac    3300
tttcaccagc gtttctgggt gagcaaaaac aggaaggcaa aatgccgcaa aaaagggaat    3360
aagggcgaca cggaaatgtt gaatactcat actcttcctt tttcaatatt attgaagcat    3420
ttatcagggt tattgtctca tgagcggata catatttgaa tgtatttaga aaaataaaca    3480
aataggggtt ccgcgcacat ttccccgaaa agtgccacct gacgtctaag aaaccattat    3540
tatcatgaca ttaacctata aaaataggcg tatcacgagg ccctttcgtc                3590

<210> SEQ ID NO 35
<211> LENGTH: 3584
<212> TYPE: DNA
<213> ORGANISM: Unknown
<220> FEATURE:
<223> OTHER INFORMATION: Sequence constitutes a plant
      promoter-terminator expression cassette in vector
      pUC19

<400> SEQUENCE: 35
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cggcgcgccg agctcctcga    420
gcaaatttac acattgccac taaacgtcta acccttgta atttgttttt gttttactat    480
gtgtgttatg tatttgattt gcgataaatt tttatatttg gtactaaatt tataacacct    540
tttatgctaa cgtttgccaa cacttagcaa tttgcaagtt gattaattga ttctaaatta    600
tttttgtctt ctaaatacat atactaatca actggaaatg taaatatttg ctaatatttc    660
```

```
tactatagga gaattaaagt gagtgaatat ggtaccacaa ggtttggaga tttaattgtt    720
gcaatgctgc atggatggca tatacaccaa acattcaata attcttgagg ataataatgg    780
taccacacaa gatttgaggt gcatgaacgt cacgtggaca aaaggtttag taatttttca    840
agacaacaat gttaccacac acaagttttg aggtgcatgc atggatgccc tgtggaaagt    900
ttaaaaatat tttggaaatg atttgcatgg aagccatgtg taaaaccatg acatccactt    960
ggaggatgca ataatgaaga aaactacaaa tttacatgca actagttatg catgtagtct   1020
atataatgag gattttgcaa tactttcatt catacacact cactaagttt tacacgatta   1080
taatttcttc atagccagca gatctgccgg catcgatccc gggccatggc ctgctttaat   1140
gagatatgcg agacgcctat gatcgcatga tatttgcttt caattctgtt gtgcacgttg   1200
taaaaaacct gagcatgtgt agctcagatc cttaccgccg gtttcggttc attctaatga   1260
atatatcacc cgttactatc gtattttat gaataatatt ctccgttcaa tttactgatt   1320
gtccgtcgac gagctcggcg cgccaagctt ggcgtaatca tggtcatagc tgtttcctgt   1380
gtgaaattgt tatccgctca caattccaca acatacga gccggaagca taaagtgtaa   1440
agcctggggt gcctaatgag tgagctaact cacattaatt gcgttgcgct cactgcccgc   1500
tttccagtcg ggaaacctgt cgtgccagct gcattaatga atcggccaac gcgcggggag   1560
aggcggtttg cgtattgggc gctcttccgc ttcctcgctc actgactcgc tgcgctcggt   1620
cgttcggctg cggcgagcgg tatcagctca ctcaaaggcg gtaatacggt tatccacaga   1680
atcaggggat aacgcaggaa agaacatgtg agcaaaaggc cagcaaaagg ccaggaaccg   1740
taaaaaggcc gcgttgctgg cgttttccca taggctccgc cccctgacg agcatcacaa   1800 aaatcgacgc tcaagtcaga ggtggcgaaa cccgacagga ctataaagat accaggcgtt   1860
tccccctgga agctccctcg tgcgctctcc tgttccgacc ctgccgctta ccggatacct   1920
gtccgccttt ctcccttcgg gaagcgtggc gctttctcat agctcacgct gtaggtatct   1980
cagttcggtg taggtcgttc gctccaagct gggctgtgtg cacgaacccc ccgttcagcc   2040
cgaccgctgc gccttatccg gtaactatcg tcttgagtcc aacccggtaa gacacgactt   2100
atcgccactg gcagcagcca ctggtaacag gattagcaga gcgaggtatg taggcggtgc   2160
tacagagttc ttgaagtggt ggcctaacta cggctacact agaaggacag tatttggtat   2220
ctgcgctctg ctgaagccag ttaccttcgg aaaaagagtt ggtagctctt gatccggcaa   2280
acaaaccacc gctggtagcg gtggtttttt tgtttgcaag cagcagatta cgcgcagaaa   2340
aaaaggatct caagaagatc ctttgatctt ttctacgggg tctgacgctc agtggaacga   2400
aaactcacgt taagggattt tggtcatgag attatcaaaa aggatcttca cctagatcct   2460
tttaaattaa aaatgaagtt ttaaatcaat ctaaagtata tatgagtaaa cttggtctga   2520
cagttaccaa tgcttaatca gtgaggcacc tatctcagcg atctgtctat ttcgttcatc   2580
catagttgcc tgactccccg tcgtgtagat aactacgata cgggagggct taccatctgg   2640
ccccagtgct gcaatgatac cgcgagaccc acgctcaccg gctccagatt tatcagcaat   2700
aaaccagcca gccggaaggg ccgagcgcag aagtggtcct gcaactttat ccgcctccat   2760
ccagtctatt aattgttgcc gggaagctag agtaagtagt tcgccagtta atagtttgcg   2820
caacgttgtt gccattgcta caggcatcgt ggtgtcacgc tcgtcgtttg gtatggcttc   2880
attcagctcc ggttcccaac gatcaaggcg agttacatga tccccatgt tgtgcaaaaa   2940 agcggttagc tccttcggtc ctccgatcgt tgtcagaagt aagttggccg cagtgttatc   3000
```

```
actcatggtt atggcagcac tgcataattc tcttactgtc atgccatccg taagatgctt    3060
ttctgtgact ggtgagtact caaccaagtc attctgagaa tagtgtatgc ggcgaccgag    3120
ttgctcttgc ccggcgtcaa tacgggataa taccgcgcca catagcagaa ctttaaaagt    3180
gctcatcatt ggaaaacgtt cttcggggcg aaaactctca aggatcttac cgctgttgag    3240
atccagttcg atgtaaccca ctcgtgcacc caactgatct tcagcatctt ttactttcac    3300
cagcgtttct gggtgagcaa aaacaggaag gcaaaatgcc gcaaaaaagg gaataagggc    3360
gacacggaaa tgttgaatac tcatactctt ccttttttcaa tattattgaa gcatttatca    3420
gggttattgt ctcatgagcg gatacatatt tgaatgtatt tagaaaaata aacaaatagg    3480
ggttccgcgc acatttcccc gaaaagtgcc acctgacgtc taagaaacca ttattatcat    3540
gacattaacc tataaaaata ggcgtatcac gaggcccttt cgtc                    3584
```

<210> SEQ ID NO 36
<211> LENGTH: 4507
<212> TYPE: DNA
<213> ORGANISM: Unknown
<220> FEATURE:
<223> OTHER INFORMATION: Sequence constitutes a plant
      promoter-terminator expression cassette in vector
      pUC19

<400> SEQUENCE: 36

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cggcgcgccg agctcctcga     420
gcaaatttac acattgccac taaacgtcta aaccccttgta atttgttttt gttttactat     480
gtgtgttatg tatttgattt gcgataaatt tttatatttg gtactaaatt tataacacct     540
tttatgctaa cgtttgccaa cacttagcaa tttgcaagtt gattaattga ttctaaatta     600 ttttttgtctt ctaaatacat atactaatca actggaaatg taaatatttg ctaatatttc     660
tactatagga gaattaaagt gagtgaatat ggtaccacaa ggtttggaga tttaattgtt     720
gcaatgctgc atggatggca tatacaccaa acattcaata attcttgagg ataataatgg     780
taccacacaa gatttgaggt gcatgaacgt cacgtggaca aaaggtttag taattttttca     840 agacaacaat gttaccacac acaagttttg aggtgcatgc atggatgccc tgtggaaagt     900
ttaaaaatat tttggaaatg atttgcatgg aagccatgtg taaaaccatg acatccactt     960
ggaggatgca ataatgaaga aaactacaaa tttacatgca actagttatg catgtagtct    1020
atataatgag gattttgcaa tactttcatt catacacact cactaagttt tacacgatta    1080
taatttcttc atagccagcc caccgcgtgtg ggcggccgcc tgcagtctag aaggcctcct    1140
gctttaatga gatatgcgag acgcctatga tcgcatgata tttgctttca attctgttgt    1200
gcacgttgta aaaaacctga gcatgtgtag ctcagatcct taccgccggt ttcggttcat    1260
tctaatgaat atatcacccg ttactatcgt atttttatga ataatattct ccgttcaatt    1320
tactgattgt ccgtcgagca aatttacaca ttgccactaa acgtctaaac ccttgtaatt    1380
tgtttttgtt ttactatgtg tgttatgtat ttgatttgcg ataaattttt atatttggta    1440
```

```
ctaaatttat aacacctttt atgctaacgt ttgccaacac ttagcaattt gcaagttgat    1500
taattgattc taaattattt ttgtcttcta aatacatata ctaatcaact ggaaatgtaa    1560
atatttgcta atatttctac tataggagaa ttaaagtgag tgaatatggt accacaaggt    1620
ttggagattt aattgttgca atgctgcatg gatggcatat acaccaaaca ttcaataatt    1680
cttgaggata ataatggtac cacacaagat ttgaggtgca tgaacgtcac gtggacaaaa    1740
ggtttagtaa tttttcaaga caacaatgtt accacacaca agttttgagg tgcatgcatg    1800
gatgccctgt ggaaagttta aaatatttt ggaaatgatt tgcatggaag ccatgtgtaa     1860
aaccatgaca tccacttgga ggatgcaata atgaagaaaa ctacaaattt acatgcaact    1920
agttatgcat gtagtctata taatgaggat tttgcaatac tttcattcat acacactcac    1980
taagttttac acgattataa tttcttcata gccagcggat ccgatatcgg gccgctagc    2040 gttaaccctg ctttaatgag atatgcgaga cgcctatgat cgcatgatat ttgctttcaa    2100
ttctgttgtg cacgttgtaa aaaacctgag catgtgtagc tcagatcctt accgccggtt    2160
tcggttcatt ctaatgaata tatcacccgt tactatcgta ttttatgaa taatattctc     2220 cgttcaattt actgattgtc cgtcgacgaa ttcgagctcg gcgcgccaag cttggcgtaa    2280
tcatggtcat agctgtttcc tgtgtgaaat tgttatccgc tcacaattcc acacaacata    2340
cgagccggaa gcataaagtg taaagcctgg ggtgcctaat gagtgagcta actcacatta    2400
attgcgttgc gctcactgcc cgcttttcag tcgggaaacc tgtcgtgcca gctgcattaa    2460
tgaatcggcc aacgcgcggg gagaggcggt ttgcgtattg ggcgctcttc cgcttcctcg    2520
ctcactgact cgctgcgctc ggtcgttcgg ctgcggcgag cggtatcagc tcactcaaag    2580
gcggtaatac ggttatccac agaatcaggg gataacgcag gaaagaacat gtgagcaaaa    2640
ggccagcaaa aggccaggaa ccgtaaaaag gccgcgttgc tggcgttttt ccataggctc    2700
cgcccccctg acgagcatca caaaaatcga cgctcaagtc agaggtggcg aaacccgaca    2760
ggactataaa gataccaggc gtttccccct ggaagctccc tcgtgcgctc tcctgttccg    2820
accctgccgc ttaccggata cctgtccgcc tttctccctt cgggaagcgt ggcgctttct    2880
catagctcac gctgtaggta tctcagttcg gtgtaggtcg ttcgctccaa gctgggctgt    2940
gtgcacgaac cccccgttca gcccgaccgc tgcgccttat ccggtaacta tcgtcttgag    3000
tccaacccgg taagacacga cttatcgcca ctggcagcag ccactggtaa caggattagc    3060
agagcgaggt atgtaggcgg tgctacagag ttcttgaagt ggtggcctaa ctacggctac    3120
actagaagga cagtatttgg tatctgcgct ctgctgaagc cagttacctt cggaaaaaga    3180
gttggtagct cttgatccgg caaacaaacc accgctggta gcggtggttt ttttgtttgc    3240
aagcagcaga ttacgcgcag aaaaaaagga tctcaagaag atcctttgat cttttctacg    3300
gggtctgacg ctcagtggaa cgaaaactca cgttaaggga ttttggtcat gagattatca    3360
aaaaggatct tcacctagat ccttttaaat taaaaatgaa gttttaaatc aatctaaagt    3420
atatatgagt aaacttggtc tgacagttac caatgcttaa tcagtgaggc acctatctca    3480
gcgatctgtc tatttcgttc atccatagtt gcctgactcc ccgtcgtgta gataactacg    3540
atacgggagg gcttaccatc tggccccagt gctgcaatga taccgcgaga cccacgctca    3600
ccggctccag atttatcagc aataaaccag ccagccggaa gggccgagcg cagaagtggt    3660
cctgcaactt tatccgcctc catccagtct attaattgtt gccgggaagc tagagtaagt    3720
agttcgccag ttaatagttt cgcaacgtt gttgccattg ctacaggcat cgtggtgtca    3780
```

```
cgctcgtcgt ttggtatggc ttcattcagc tccggttccc aacgatcaag gcgagttaca    3840
tgatccccca tgttgtgcaa aaaagcggtt agctccttcg gtcctccgat cgttgtcaga    3900
agtaagttgg ccgcagtgtt atcactcatg gttatggcag cactgcataa ttctcttact    3960
gtcatgccat ccgtaagatg cttttctgtg actggtgagt actcaaccaa gtcattctga    4020
gaatagtgta tgcggcgacc gagttgctct tgcccggcgt caatacggga taataccgcg    4080
ccacatagca gaactttaaa agtgctcatc attggaaaac gttcttcggg gcgaaaactc    4140
tcaaggatct taccgctgtt gagatccagt tcgatgtaac ccactcgtgc acccaactga    4200
tcttcagcat cttttacttt caccagcgtt tctgggtgag caaaaacagg aaggcaaaat    4260
gccgcaaaaa agggaataag ggcgacacgg aaatgttgaa tactcatact cttccttttt    4320
caatattatt gaagcattta tcagggttat tgtctcatga gcggatacat atttgaatgt    4380
atttagaaaa ataaacaaat aggggttccg cgcacatttc cccgaaaagt gccacctgac    4440
gtctaagaaa ccattattat catgacatta acctataaaa ataggcgtat cacgaggccc    4500
tttcgtc                                                              4507
```

<210> SEQ ID NO 37
<211> LENGTH: 5410
<212> TYPE: DNA
<213> ORGANISM: Unknown
<220> FEATURE:
<223> OTHER INFORMATION: Sequence constitutes a plant
      promoter-terminator expression cassette in vector
      pUC19

<400> SEQUENCE: 37

```
ttttggaaat gatttgcatg gaagccatgt gtaaaaccat gacatccact tggaggatgc      60
aataatgaag aaaactacaa atttacatgc aactagttat gcatgtagtc tatataatga     120
ggattttgca atactttcat tcatacacac tcactaagtt ttacacgatt ataatttctt     180
catagccagc ggatccgata tcgggcccgc tagcgttaac cctgctttaa tgagatatgc     240
gagacgccta tgatcgcatg atatttgctt tcaattctgt tgtgcacgtt gtaaaaaacc     300
tgagcatgtg tagctcagat ccttaccgcc ggtttcggtt cattctaatg aatatatcac     360
ccgttactat cgtatttta tgaataatat tctccgttca atttactgat tgtccgtcga     420
gcaaatttac acattgccac taaacgtcta aacccttgta atttgttttt gttttactat     480
gtgtgttatg tatttgattt gcgataaatt tttatatttg gtactaaatt tataacacct     540
tttatgctaa cgtttgccaa cacttagcaa tttgcaagtt gattaattga ttctaaatta     600
tttttgtctt ctaaatacat atactaatca actggaaatg taaatatttg ctaatatttc     660
tactatagga gaattaaagt gagtgaatat ggtaccacaa ggtttggaga tttaattgtt     720
gcaatgctgc atggatggca tatacaccaa acattcaata attcttgagg ataataatgg     780
taccacacaa gatttgaggt gcatgaacgt cacgtggaca aaaggtttag taattttca     840 agacaacaat gttaccacac acaagttttg aggtgcatgc atggatgccc tgtggaaagt     900
ttaaaaatat tttggaaatg atttgcatgg aagccatgtg taaaaccatg acatccactt     960
ggaggatgca ataatgaaga aaactacaaa tttacatgca actagttatg catgtagtct    1020
atataatgag gattttgcaa tactttcatt catacacact cactaagttt tacacgatta    1080
taatttcttc atagccagca gatctgccgg catcgatccc gggccatggc ctgctttaat    1140
gagatatgcg agacgcctat gatcgcatga tatttgcttt caattctgtt gtgcacgttg    1200
taaaaaacct gagcatgtgt agctcagatc cttaccgccg gtttcggttc attctaatga    1260
```

```
atatatcacc cgttactatc gtattttat gaataatatt ctccgttcaa tttactgatt    1320
gtccgtcgac gagctcggcg cgccaagctt ggcgtaatca tggtcatagc tgtttcctgt    1380
gtgaaattgt tatccgctca caattccaca acatacga gccggaagca taaagtgtaa      1440
agcctggggt gcctaatgag tgagctaact cacattaatt gcgttgcgct cactgcccgc    1500
tttccagtcg ggaaacctgt cgtgccagct gcattaatga atcggccaac gcgcgggag     1560
aggcggtttg cgtattgggc gctcttccgc ttcctcgctc actgactcgc tgcgctcggt    1620
cgttcggctg cggcgagcgg tatcagctca ctcaaaggcg gtaatacggt tatccacaga    1680
atcaggggat aacgcaggaa agaacatgtg agcaaaaggc cagcaaaagg ccaggaaccg    1740
taaaaaggcc gcgttgctgg cgtttttcca taggctccgc ccccctgacg agcatcacaa    1800
aaatcgacgc tcaagtcaga ggtggcgaaa cccgacagga ctataaagat accaggcgtt    1860
tccccctgga agctccctcg tgcgctctcc tgttccgacc ctgccgctta ccggatacct    1920
gtccgccttt ctcccttcgg gaagcgtggc gctttctcat agctcacgct gtaggtatct    1980
cagttcggtg taggtcgttc gctccaagct gggctgtgtg cacgaaccc cgttcagcc     2040
cgaccgctgc gccttatccg gtaactatcg tcttgagtcc aacccggtaa gacacgactt    2100
atcgccactg gcagcagcca ctggtaacag gattagcaga gcgaggtatg taggcggtgc    2160
tacagagttc ttgaagtggt ggcctaacta cggctacact agaaggacag tatttggtat    2220
ctgcgctctg ctgaagccag ttaccttcgg aaaaagagtt ggtagctctt gatccggcaa    2280
acaaaccacc gctggtagcg gtggtttttt tgtttgcaag cagcagatta cgcgcagaaa    2340
aaaaggatct caagaagatc ctttgatctt ttctacgggg tctgacgctc agtggaacga    2400
aaactcacgt taagggattt tggtcatgag attatcaaaa aggatcttca cctagatcct    2460
tttaaattaa aaatgaagtt ttaaatcaat ctaaagtata tatgagtaaa cttggtctga    2520
cagttaccaa tgcttaatca gtgaggcacc tatctcagcg atctgtctat ttcgttcatc    2580
catagttgcc tgactccccg tcgtgtagat aactacgata cgggagggct taccatctgg    2640
ccccagtgct gcaatgatac cgcgagaccc acgctcaccg gctccagatt tatcagcaat    2700
aaaccagcca gccggaaggg ccgagcgcag aagtggtcct gcaactttat ccgcctccat    2760
ccagtctatt aattgttgcc gggaagctag agtaagtagt tcgccagtta atagtttgcg    2820
caacgttgtt gccattgcta caggcatcgt ggtgtcacgc tcgtcgtttg gtatggcttc    2880
attcagctcc ggttcccaac gatcaaggcg agttacatga tccccatgt tgtgcaaaaa    2940
agcggttagc tccttcggtc ctccgatcgt tgtcagaagt aagttggccg cagtgttatc    3000
actcatggtt atggcagcac tgcataattc tcttactgtc atgccatccg taagatgctt    3060
ttctgtgact ggtgagtact caaccaagtc attctgagaa tagtgtatgc ggcgaccgag    3120
ttgctcttgc ccggcgtcaa tacgggataa taccgcgcca catagcagaa ctttaaaagt    3180
gctcatcatt ggaaaacgtt cttcggggcg aaaactctca aggatcttac cgctgttgag    3240
atccagttcg atgtaaccca ctcgtgcacc caactgatct tcagcatctt ttactttcac    3300
cagcgtttct gggtgagcaa aaacaggaag gcaaaatgcc gcaaaaaagg gaataagggc    3360
gacacggaaa tgttgaatac tcatactctt cctttttcaa tattattgaa gcatttatca    3420
gggttattgt ctcatgagcg gatacatatt tgaatgtatt tagaaaaata aacaaatagg    3480
ggttccgcgc acatttcccc gaaaagtgcc acctgacgtc taagaaacca ttattatcat    3540
gacattaacc tataaaaata ggcgtatcac gaggcccttt cgtctcgcgc gtttcggtga    3600
```

```
tgacggtgaa aacctctgac acatgcagct cccggagacg gtcacagctt gtctgtaagc    3660
ggatgccggg agcagacaag cccgtcaggg cgcgtcagcg ggtgttggcg ggtgtcgggg    3720
ctggcttaac tatgcggcat cagagcagat tgtactgaga gtgcaccata tgcggtgtga    3780
aataccgcac agatgcgtaa ggagaaaata ccgcatcagg cgccattcgc cattcaggct    3840
gcgcaactgt tgggaagggc gatcggtgcg ggcctcttcg ctattacgcc agctggcgaa    3900
agggggatgt gctgcaaggc gattaagttg ggtaacgcca gggttttccc agtcacgacg    3960
ttgtaaaacg acggccagtg aattcggcgc gccgagctcc tcgagcaaat ttacacattg    4020
ccactaaacg tctaaaccct tgtaatttgt ttttgtttta ctatgtgtgt tatgtatttg    4080
atttgcgata aattttata tttggtacta aatttataac acctttatg ctaacgtttg    4140 ccaacactta gcaatttgca agttgattaa ttgattctaa attattttg tcttctaaat    4200 acatatacta atcaactgga aatgtaaata tttgctaata tttctactat aggagaatta    4260
aagtgagtga atatggtacc acaaggtttg gagatttaat tgttgcaatg ctgcatggat    4320
ggcatataca ccaaacattc aataattctt gaggataata atggtaccac acaagatttg    4380
aggtgcatga acgtcacgtg gacaaaaggt ttagtaattt ttcaagacaa caatgttacc    4440
acacacaagt tttgaggtgc atgcatggat gccctgtgga aagtttaaaa atattttgga    4500
aatgatttgc atggaagcca tgtgtaaaac catgacatcc acttggagga tgcaataatg    4560
aagaaaacta caaatttaca tgcaactagt tatgcatgta gtctatataa tgaggatttt    4620
gcaatacttt cattcataca cactcactaa gttttacacg attataattt cttcatagcc    4680
agcccaccgc ggtgggcggc cgcctgcagt ctagaaggcc tcctgcttta atgagatatg    4740
cgagacgcct atgatcgcat gatatttgct ttcaattctg ttgtgcacgt tgtaaaaaac    4800
ctgagcatgt gtagctcaga tccttaccgc cggtttcggt tcattctaat gaatatatca    4860
cccgttacta tcgtatttt atgaataata ttctccgttc aatttactga ttgtccgtcg    4920
agcaaattta cacattgcca ctaaacgtct aaacccttgt aatttgtttt tgttttacta    4980
tgtgtgttat gtatttgatt tgcgataaat ttttatattt ggtactaaat ttataacacc    5040
ttttatgcta acgtttgcca acacttagca atttgcaagt tgattaattg attctaaatt    5100 attttgtct tctaaataca tatactaatc aactggaaat gtaaatattt gctaatattt    5160
ctactatagg agaattaaag tgagtgaata tggtaccaca aggtttggag atttaattgt    5220
tgcaatgctg catggatggc atatacacca acattcaat aattcttgag gataataatg    5280
gtaccacaca gatttgagg tgcatgaacg tcacgtggac aaaaggttta gtaattttc    5340 aagacaacaa tgttaccaca cacaagtttt gaggtgcatg catggatgcc tgtggaaag    5400 tttaaaaata                                                           5410
```

<210> SEQ ID NO 38
<211> LENGTH: 12093
<212> TYPE: DNA
<213> ORGANISM: Unknown
<220> FEATURE:
<223> OTHER INFORMATION: Plant expression vector with a
      promoter-terminator expression cassette

<400> SEQUENCE: 38

```
gatctggcgc cggccagcga gacgagcaag attggccgcc gcccgaaacg atccgacagc      60
gcgcccagca caggtgcgca ggcaaattgc accaacgcat acagcgccag cagaatgcca     120
tagtgggcgg tgacgtcgtt cgagtgaacc agatcgcgca ggaggcccgg cagcaccggc     180
```

```
ataatcaggc cgatgccgac agcgtcgagc gcgacagtgc tcagaattac gatcaggggt    240
atgttgggtt tcacgtctgg cctccggacc agcctccgct ggtccgattg aacgcgcgga    300
ttctttatca ctgataagtt ggtggacata ttatgtttat cagtgataaa gtgtcaagca    360
tgacaaagtt gcagccgaat acagtgatcc gtgccgccct ggacctgttg aacgaggtcg    420
gcgtagacgg tctgacgaca cgcaaactgg cggaacggtt gggggttcag cagccggcgc    480
tttactggca cttcaggaac aagcgggcgc tgctcgacgc actggccgaa gccatgctgg    540
cggagaatca tacgcattcg gtgccgagag ccgacgacga ctggcgctca tttctgatcg    600
ggaatgcccg cagcttcagg caggcgctgc tcgcctaccg cgatggcgcg cgcatccatg    660
ccggcacgcg accgggcgca ccgcagatgg aaacggccga cgcgcagctt cgcttcctct    720
gcgaggcggg ttttcggcc ggggacgccg tcaatgcgct gatgacaatc agctacttca    780
ctgttggggc cgtgcttgag gagcaggccg gcgacagcga tgccggcgag gcgggcggca    840
ccgttgaaca ggctccgctc tcgccgctgt tgcgggccgc gatagacgcc ttcgacgaag    900
ccggtccgga cgcagcgttc gagcagggac tcgcggtgat tgtcgatgga ttggcgaaaa    960
ggaggctcgt tgtcaggaac gttgaaggac cgagaaaggg tgacgattga tcaggaccgc   1020
tgccggagcg caacccactc actacagcag agccatgtag acaacatccc ctcccccttt   1080
ccaccgcgtc agacgcccgt agcagcccgc tacgggcttt tcatgccct gcctagcgt     1140 ccaagcctca cggccgcgct cggcctctct ggcggccttc tggcgctctt ccgcttcctc   1200
gctcactgac tcgctgcgct cggtcgttcg gctgcggcga gcggtatcag ctcactcaaa   1260
ggcggtaata cggttatcca cagaatcagg ggataacgca ggaaagaaca tgtgagcaaa   1320
aggccagcaa aaggccagga accgtaaaaa ggccgcgttg ctggcgtttt tccataggct   1380 ccgccccct gacgagcatc acaaaaatcg acgctcaagt cagaggtggc gaaacccgac   1440
aggactataa agataccagg cgtttccccc tggaagctcc ctcgtgcgct ctcctgttcc   1500
gaccctgccg cttaccggat acctgtccgc ctttctccct cgggaagcg tggcgctttt    1560 ccgctgcata cccctgcttc ggggtcatta tagcgatttt ttcggtatat ccatcctttt   1620
tcgcacgata tacaggattt tgccaaaggg ttcgtgtaga cttccttgg tgtatccaac    1680 ggcgtcagcc gggcaggata ggtgaagtag gcccacccgc gagcgggtgt tccttcttca   1740
ctgtccctta ttcgcacctg gcggtgctca acgggaatcc tgctctgcga ggctggccgg   1800
ctaccgccgg cgtaacagat gagggcaagc ggatggctga tgaaaccaag ccaaccagga   1860
agggcagccc acctatcaag gtgtactgcc ttccagacga acgaagagcg attgaggaaa   1920
aggcggcggc ggccggcatg agcctgtcgg cctacctgct ggccgtcggc cagggctaca   1980
aaatcacggg cgtcgtggac tatgagcacg tccgcgagct ggcccgcatc aatgcgacc    2040 tgggccgcct gggcggcctg ctgaaactct ggctcaccga cgacccgcgc acggcgcggt   2100
tcggtgatgc cacgatcctc gccctgctgg cgaagatcga agagaagcag gacgagcttg   2160
gcaaggtcat gatgggcgtg gtccgcccga gggcagagcc atgactttt tagccgctaa    2220 aacggccggg gggtgcgcgt gattgccaag cacgtcccca tgcgctccat caagaagagc   2280
gacttcgcgg agctggtgaa gtacatcacc gacgagcaag gcaagaccga gcgcctttgc   2340
gacgctcacc gggctggttg ccctcgccgc tgggctggcg gccgtctatg gcctgcaaa    2400 cgcgccagaa acgccgtcga agccgtgtgc gagacaccgc ggccgccggc gttgtggata   2460
cctcgcggaa aacttggccc tcactgacag atgaggggcg gacgttgaca cttgaggggc   2520
cgactcaccc ggcgcggcgt tgacagatga ggggcaggct cgatttcggc cggcgacgtg   2580
```

```
gagctggcca gcctcgcaaa tcggcgaaaa cgcctgattt tacgcgagtt tcccacagat    2640
gatgtggaca agcctgggga taagtgccct gcggtattga cacttgaggg gcgcgactac    2700
tgacagatga ggggcgcgat ccttgacact tgaggggcag agtgctgaca gatgaggggc    2760
gcacctattg acatttgagg ggctgtccac aggcagaaaa tccagcattt gcaagggttt    2820
ccgcccgttt ttcggccacc gctaacctgt cttttaacct gcttttaaac caatatttat    2880
aaaccttgtt tttaaccagg gctgcgccct gtgcgcgtga ccgcgcacgc cgaaggggggg   2940 tgcccccccct tctcgaaccc tcccggcccg ctaacgcggg cctcccatcc ccccaggggc    3000
tgcgcccctc ggccgcgaac ggcctcaccc caaaaatggc agcgctggca gtccttgcca    3060
ttgccgggat cggggcagta acgggatggg cgatcagccc gagcgcgacg cccggaagca    3120
ttgacgtgcc gcaggtgctg gcatcgacat tcagcgacca ggtgccgggc agtgagggcg    3180
gcggcctggg tggcggcctg cccttcactt cggccgtcgg ggcattcacg gacttcatgg    3240
cggggccggc aattttttacc ttgggcattc ttggcatagt ggtcgcgggt gccgtgctcg    3300
tgttcggggg tgcgataaac ccagcgaacc atttgaggtg ataggtaaga ttataccgag    3360
gtatgaaaac gagaattgga cctttacaga attactctat gaagcgccat atttaaaaag    3420
ctaccaagac gaagaggatg aagaggatga ggaggcagat tgccttgaat atattgacaa    3480
tactgataag ataatatatc ttttatatag aagatatcgc cgtatgtaag gatttcaggg    3540
ggcaaggcat aggcagcgcg cttatcaata tatctataga atgggcaaag cataaaaact    3600
tgcatggact aatgcttgaa acccaggaca ataaccttat agcttgtaaa ttctatcata    3660
attgggtaat gactccaact tattgatagt gttttatgtt cagataatgc ccgatgactt    3720
tgtcatgcag ctccaccgat tttgagaacg acagcgactt ccgtcccagc cgtgccaggt    3780
gctgcctcag attcaggtta tgccgctcaa ttcgctgcgt atatcgcttg ctgattacgt    3840 gcagcttttcc cttcaggcgg gattcataca gcggccagcc atccgtcatc catatccacca   3900 cgtcaaaggg tgacagcagg ctcataagac gccccagcgt cgccatagtg cgttcaccga    3960
atacgtgcgc aacaaccgtc ttccggagac tgtcatacgc gtaaaacagc cagcgctggc    4020
gcgatttagc cccgacatag ccccactgtt cgtccatttc cgcgcagacg atgacgtcac    4080
tgcccggctg tatgcgcgag gttaccgact gcggcctgag ttttttaagt gacgtaaaat    4140
cgtgttgagg ccaacgccca taatgcgggc tgttgcccgg catccaacgc cattcatggc    4200
catatcaatg attttctggt gcgtaccggg ttgagaagcg gtgtaagtga actgcagttg    4260
ccatgtttta cggcagtgag agcagagata gcgctgatgt ccggcggtgc ttttgccgtt    4320
acgcaccacc ccgtcagtag ctgaacagga gggacagctg atagacacag aagccactgg    4380
agcacctcaa aaacaccatc atacactaaa tcagtaagtt ggcagcatca cccataattg    4440
tggtttcaaa atcggctccg tcgatactat gttatacgcc aactttgaaa caactttga    4500 aaaagctgtt ttctggtatt taaggttta gaatgcaagg aacagtgaat tggagttcgt    4560
cttgttataa ttagcttctt ggggtatctt taaatactgt agaaaagagg aaggaaataa    4620
taaatggcta aaatgagaat atcaccggaa ttgaaaaaac tgatcgaaaa ataccgctgc    4680
gtaaaagata cggaaggaat gtctcctgct aaggtatata agctggtggg agaaaatgaa    4740
aacctatatt taaaaatgac ggacagccgg tataaaggga ccacctatga tgtggaacgg    4800
gaaaaggaca tgatgctatg gctggaagga agctgcctg ttccaaaggt cctgcacttt    4860
gaacggcatg atggctggag caatctgctc atgagtgagg ccgatggcgt cctttgctcg    4920
```

```
gaagagtatg aagatgaaca aagccctgaa aagattatcg agctgtatgc ggagtgcatc    4980
aggctctttc actccatcga catatcggat tgtccctata cgaatagctt agacagccgc    5040
ttagccgaat tggattactt actgaataac gatctggccg atgtggattg cgaaaactgg    5100
gaagaagaca ctccatttaa agatccgcgc gagctgtatg atttttttaaa gacggaaaag   5160 cccgaagagg aacttgtctt ttcccacggc gacctgggag acagcaacat ctttgtgaaa    5220
gatggcaaag taagtggctt tattgatctt gggagaagcg gcagggcgga caagtggtat    5280
gacattgcct tctgcgtccg gtcgatcagg gaggatatcg gggaagaaca gtatgtcgag    5340 ctatttttttg acttactggg gatcaagcct gattgggaga aaataaaata ttatattttta  5400 ctggatgaat tgttttagta cctagatgtg gcgcaacgat gccggcgaca agcaggagcg    5460
caccgacttc ttccgcatca agtgttttgg ctctcaggcc gaggcccacg gcaagtattt    5520
gggcaagggg tcgctggtat tcgtgcaggg caagattcgg aataccaagt acgagaagga    5580
cggccagacg gtctacggga ccgacttcat tgccgataag gtggattatc tggacaccaa    5640
ggcaccaggc gggtcaaatc aggaataagg gcacattgcc ccggcgtgag tcgggcaat     5700 cccgcaagga gggtgaatga atcggacgtt tgaccggaag gcatacaggc aagaactgat    5760
cgacgcgggg ttttccgccg aggatgccga aaccatcgca agccgcaccg tcatgcgtgc    5820
gccccgcgaa accttccagt ccgtcggctc gatggtccag caagctacgg ccaagatcga    5880
gcgcgacagc gtgcaactgg ctcccccctgc cctgcccgcg ccatcggccg ccgtggagcg    5940
ttcgcgtcgt ctcgaacagg aggcggcagg tttggcgaag tcgatgacca tcgacacgcg    6000
aggaactatg acgaccaaga agcgaaaaac cgccggcgag gacctggcaa aacaggtcag    6060
cgaggccaag caggccgcgt tgctgaaaca cacgaagcag cagatcaagg aaatgcagct    6120
ttccttgttc gatattgcgc cgtggccgga cacgatgcga gcgatgccaa cgacacggc     6180 ccgctctgcc ctgttcacca cgcgcaacaa gaaaatcccg cgcgaggcgc tgcaaaacaa    6240
ggtcattttc cacgtcaaca aggacgtgaa gatcacctac accggcgtcg agctgcgggc    6300
cgacgatgac gaactggtgt ggcagcaggt gttggagtac gcgaagcgca ccctatcgg     6360 cgagccgatc accttcacgt tctacgagct ttgccaggac ctgggctggt cgatcaatgg    6420
ccggtattac acgaaggccg aggaatgcct gtcgcgccta caggcgacgg cgatgggctt    6480
cacgtccgac cgcgttgggc acctggaatc ggtgtcgctg ctgcaccgct tccgcgtcct    6540
ggaccgtggc aagaaaacgt cccgttgcca ggtcctgatc gacgaggaaa tcgtcgtgct    6600
gtttgctggc gaccactaca cgaaattcat atgggagaag taccgcaagc tgtcgccgac    6660
ggcccgacgg atgttcgact atttcagctc gcaccggag ccgtacccgc tcaagctgga    6720
aaccttccgc ctcatgtgcg gatcggattc cacccgcgtg aagaagtggc gcgagcaggt    6780
cggcgaagcc tgcgaagagt tgcgaggcag cggcctggtg aacacgcct gggtcaatga    6840 tgacctggtg cattgcaaac gctagggcct tgtggggtca gttccggctg ggggttcagc    6900
agccagcgct ttactggcat ttcaggaaca agcgggcact gctcgacgca cttgcttcgc    6960
tcagtatcgc tcgggacgca cggcgcgctc tacgaactgc cgataaacag aggattaaaa    7020
ttgacaattg tgattaaggc tcagattcga cggcttggag cggccgacgt gcaggatttc    7080
cgcgagatcc gattgtcggc cctgaagaaa gctccagaga tgttcgggtc cgtttacgag    7140
cacgaggaga aaaagcccat ggaggcgttc gctgaacggt tgcgagatgc cgtggcattc    7200
ggcgcctaca tcgacggcga gatcattggg ctgtcggtct tcaaacagga ggacggcccc    7260
aaggacgctc acaaggcgca tctgtccggc gttttcgtgg agcccgaaca gcgaggccga    7320
```

```
ggggtcgccg gtatgctgct gcgggcgttg ccggcgggtt tattgctcgt gatgatcgtc    7380
cgacagattc caacgggaat ctggtggatg cgcatcttca tcctcggcgc acttaatatt    7440
tcgctattct ggagcttgtt gtttatttcg gtctaccgcc tgccgggcgg ggtcgcggcg    7500
acggtaggcg ctgtgcagcc gctgatggtc gtgttcatct ctgccgctct gctaggtagc    7560
ccgatacgat tgatggcggt cctgggggct atttgcggaa ctgcgggcgt ggcgctgttg    7620
gtgttgacac caaacgcagc gctagatcct gtcggcgtcg cagcgggcct ggcggggggcg   7680 gtttccatgg cgttcggaac cgtgctgacc cgcaagtggc aacctcccgt gcctctgctc    7740
acctttaccg cctggcaact ggcggccgga ggacttctgc tcgttccagt agctttagtg    7800
tttgatccgc caatcccgat gcctacagga accaatgttc tcggcctggc gtggctcggc    7860
ctgatcggag cgggtttaac ctacttcctt tggttccggg ggatctcgcg actcgaacct    7920
acagttgttt ccttactggg cttttctcagc cccagatctg gggtcgatca gccggggatg    7980
catcaggccg acagtcggaa cttcgggtcc ccgacctgta ccattcggtg agcaatggat    8040
aggggagttg atatcgtcaa cgttcacttc taaagaaata cgccactca gcttcctcag    8100 cggctttatc cagcgatttc ctattatgtc ggcatagttc tcaagatcga cagcctgtca    8160
cggttaagcg agaaatgaat aagaaggctg ataattcgga tctctgcgag ggagatgata    8220
tttgatcaca ggcagcaacg ctctgtcatc gttacaatca acatgctacc ctccgcgaga    8280
tcatccgtgt ttcaaacccg gcagcttagt tgccgttctt ccgaatagca tcggtaacat    8340
gagcaaagtc tgccgcctta caacggctct cccgctgacg ccgtcccgga ctgatgggct    8400
gcctgtatcg agtggtgatt ttgtgccgag ctgccggtcg gggagctgtt ggctggctgg    8460
tggcaggata tattgtggtg taaacaaatt gacgcttaga caacttaata acacattgcg    8520
gacgttttta atgtactggg gtggtttttc ttttcaccag tgagacgggc aacagctgat    8580
tgcccttcac cgcctggccc tgagagagtt gcagcaagcg gtccacgctg gtttgcccca    8640
gcaggcgaaa atcctgtttg atggtggttc cgaaatcggc aaaatccctt ataaatcaaa    8700
agaatagccc gagatagggt tgagtgttgt tccagtttgg aacaagagtc cactattaaa    8760
gaacgtggac tccaacgtca aagggcgaaa aaccgtctat cagggcgatg gcccactacg    8820
tgaaccatca cccaaatcaa gttttttggg gtcgaggtgc cgtaaagcac taaatcggaa    8880
ccctaaaggg agcccccgat ttagagcttg acggggaaag ccggcgaacg tggcgagaaa    8940
ggaagggaag aaagcgaaag gagcgggcgc cattcaggct gcgcaactgt gggaagggc     9000 gatcggtgcg ggcctcttcg ctattacgcc agctggcgaa aggggggatgt gctgcaaggc   9060 gattaagttg ggtaacgcca gggttttccc agtcacgacg ttgtaaaacg acggccagtg    9120
aattaattcc catcttgaaa gaaatatagt ttaaatattt attgataaaa taacaagtca    9180
ggtattatag tccaagcaaa aacataaatt tattgatgca agtttaaatt cagaaatatt    9240
tcaataactg attatatcag ctggtacatt gccgtagatg aaagactgag tgcgatatta    9300
tgtgtaatac ataaattgat gatatagcta gcttagctca tcgggggatc cgtcgaagct    9360
agcttgggtc ccgctcagaa gaactcgtca agaaggcgat agaaggcgat gcgctgcgaa    9420
tcgggagcgg cgataccgta agcacgagg aagcggtcag cccattcgcc gccaagctct    9480
tcagcaatat cacgggtagc caacgctatg tcctgatagc ggtccgccac acccagccgg    9540
ccacagtcga tgaatccaga aaagcggcca ttttccacca tgatattcgg caagcaggca    9600
tcgccatggg tcacgacgag atcctcgccg tcgggcatgc gcgccttgag cctggcgaac    9660
```

```
agttcggctg gcgcgagccc ctgatgctct tcgtccagat catcctgatc gacaagaccg   9720
gcttccatcc gagtacgtgc tcgctcgatg cgatgtttcg cttggtggtc gaatgggcag   9780
gtagccggat caagcgtatg cagccgccgc attgcatcag ccatgatgga tactttctcg   9840
gcaggagcaa ggtgagatga caggagatcc tgccccggca cttcgcccaa tagcagccag   9900
tcccttcccg cttcagtgac aacgtcgagc acagctgcgc aaggaacgcc cgtcgtggcc   9960
agccacgata gccgcgctgc ctcgtcctgc agttcattca gggcaccgga caggtcggtc  10020
ttgacaaaaa gaaccgggcg ccctgcgct gacagccgga acacggcggc atcagagcag  10080
ccgattgtct gttgtgccca gtcatagccg aatagcctct ccacccaagc ggccggagaa  10140
cctgcgtgca atccatcttg ttcaatccaa gctcccatgg gccctcgact agagtcgaga  10200
tctggattga gagtgaatat gagactctaa ttggataccg aggggaattt atggaacgtc  10260
agtggagcat ttttgacaag aaatatttgc tagctgatag tgaccttagg cgacttttga  10320
acgcgcaata atggtttctg acgtatgtgc ttagctcatt aaactccaga aacccgcggc  10380
tgagtggctc cttcaacgtt gcggttctgt cagttccaaa cgtaaaacgg cttgtcccgc  10440
gtcatcggcg ggggtcataa cgtgactccc ttaattctcc gctcatgatc ttgatcccct  10500
gcgccatcag atccttggcg gcaagaaagc catccagttt actttgcagg gcttcccaac  10560
cttaccagag ggcgcccag ctggcaattc cggttcgctt gctgtccata aaaccgccca  10620
gtctagctat cgccatgtaa gcccactgca agctacctgc tttctctttg cgcttgcgtt  10680
ttcccttgtc cagatagccc agtagctgac attcatccgg ggtcagcacc gtttctgcgg  10740
actggctttc tacgtgttcc gcttccttta gcagcccttg cgccctgagt gcttgcggca  10800
gcgtgaagct tgcatgcctg caggtcgacg gcgcgccgag ctcctcgagc aaatttacac  10860
attgccacta aacgtctaaa cccttgtaat ttgttttttgt tttactatgt gtgttatgta  10920
tttgatttgc gataaatttt tatatttggt actaaattta taacacccttt tatgctaacg  10980
tttgccaaca cttagcaatt tgcaagttga ttaattgatt ctaaattatt tttgtcttct  11040
aaatacatat actaatcaac tggaaatgta aatatttgct aatatttcta ctataggaga  11100
attaaagtga gtgaatatgg taccacaagg tttggagatt taattgttgc aatgctgcat  11160
ggatggcata tacaccaaac attcaataat tcttgaggat aataatggta ccacacaaga  11220
tttgaggtgc atgaacgtca cgtggacaaa aggtttagta atttttcaag acaacaatgt  11280
taccacacac aagttttgag gtgcatgcat ggatgccctg tggaaagttt aaaaatattt  11340
tggaaatgat ttgcatggaa gccatgtgta aaaccatgac atccacttgg aggatgcaat  11400
aatgaagaaa actacaaatt tacatgcaac tagttatgca tgtagtctat ataatgagga  11460
ttttgcaata ctttcattca tacacactca ctaagtttta cacgattata atttcttcat  11520
agccagccca ccgcggtggg cggccgcctg cagtctagaa ggcctcctgc tttaatgaga  11580
tatgcgagac gcctatgatc gcatgatatt tgctttcaat tctgttgtgc acgttgtaaa  11640
aaacctgagc atgtgtagct cagatcctta ccgccggttt cggttcattc taatgaatat  11700
atcacccgtt actatcgtat ttttatgaat aatattctcc gttcaattta ctgattgtcc  11760
gtcgacgaat tcgagctcgg cgcgcctcta gaggatcgat gaattcagat cggctgagtg  11820
gctccttcaa cgttgcggtt ctgtcagttc caaacgtaaa acggcttgtc ccgcgtcatc  11880
ggcgggggtc ataacgtgac tcccttaatt ctccgctcat gatcagattg tcgtttcccg  11940
ccttcagttt aaactatcag tgtttgacag gatatattgg cgggtaaacc taagagaaaa  12000
gagcgtttat tagaataatc ggatatttaa aagggcgtga aaaggtttat ccttcgtcca  12060
```

-continued

```
tttgtatgtg catgccaacc acagggttcc cca                          12093

<210> SEQ ID NO 39
<211> LENGTH: 12085
<212> TYPE: DNA
<213> ORGANISM: Unknown
<220> FEATURE:
<223> OTHER INFORMATION: Plant expression vector with a
      promoter-terminator expression cassette

<400> SEQUENCE: 39
gatctggcgc cggccagcga gacgagcaag attggccgcc gcccgaaacg atccgacagc     60
gcgcccagca caggtgcgca ggcaaattgc accaacgcat acagcgccag cagaatgcca    120
tagtgggcgg tgacgtcgtt cgagtgaacc agatcgcgca ggaggcccgg cagcaccggc    180
ataatcaggc cgatgccgac agcgtcgagc gcgacagtgc tcagaattac gatcaggggt    240
atgttgggtt tcacgtctgg cctccggacc agcctccgct ggtccgattg aacgcgcgga    300
ttctttatca ctgataagtt ggtggacata ttatgtttat cagtgataaa gtgtcaagca    360
tgacaaagtt gcagccgaat acagtgatcc gtgccgccct ggacctgttg aacgaggtcg    420
gcgtagacgg tctgacgaca cgcaaactgg cggaacggtt ggggggttcag cagccggcgc    480 tttactggca cttcaggaac aagcgggcgc tgctcgacgc actggccgaa gccatgctgg    540
cggagaatca tacgcattcg gtgccgagag ccgacgacga ctggcgctca tttctgatcg    600
ggaatgcccg cagcttcagg caggcgctgc tcgcctaccg cgatgcgcg cgcatccatg    660 ccggcacgcg accgggcgca ccgcagatgg aaacggccga cgcgcagctt cgcttcctct    720
gcgaggcggg ttttcggcc ggggacgccg tcaatgcgct gatgacaatc agctacttca    780
ctgttggggc cgtgcttgag gagcaggccg gcgacagcga tgccggcgag cgcggcggca    840
ccgttgaaca ggctccgctc tcgccgctgt tgcgggccgc gatagacgcc ttcgacgaag    900
ccggtccgga cgcagcgttc gagcagggac tcgcggtgat tgtcgatgga ttggcgaaaa    960
ggaggctcgt tgtcaggaac gttgaaggac cgagaaaggg tgacgattga tcaggaccgc   1020
tgccggagcg caacccactc actacagcag agccatgtag acaacatccc ctcccccttt   1080
ccaccgcgtc agacgcccgt agcagcccgc tacgggcttt tcatgccct gccctagcgt    1140 ccaagcctca cggccgcgct cggcctctct ggcggccttc tggcgctctt ccgcttcctc   1200
gctcactgac tcgctgcgct cggtcgttcg gctgcggcga gcggtatcag ctcactcaaa   1260
ggcggtaata cggttatcca cagaatcagg ggataacgca ggaaagaaca tgtgagcaaa   1320
aggccagcaa aaggccagga accgtaaaaa ggccgcgttg ctggcgtttt tccataggct   1380
ccgcccccct gacgagcatc acaaaaatcg acgctcaagt cagaggtggc gaaacccgac   1440
aggactataa agataccagg cgtttccccc tggaagctcc ctcgtgcgct ctcctgttcc   1500
gaccctgccg cttaccggat acctgtccgc ctttctccct tcgggaagcg tggcgctttt   1560
ccgctgcata accctgcttc ggggtcatta tagcgatttt tcggtatat ccatccttt    1620 tcgcacgata tacaggattt tgccaaaggg ttcgtgtaga cttccttgg tgtatccaac    1680 ggcgtcagcc gggcaggata ggtgaagtag gcccacccgc gagcgggtgt tccttcttca   1740
ctgtccctta ttcgcacctg gcggtgctca acgggaatcc tgctctgcga ggctggccgg   1800
ctaccgccgg cgtaacagat gagggcaagc ggatggctga tgaaaccaag ccaaccagga   1860
agggcagccc acctatcaag gtgtactgcc ttccagacga acgaagagcg attgaggaaa   1920
aggcggcggc ggccggcatg agcctgtcgg cctacctgct ggccgtcggc cagggctaca   1980
```

```
aaatcacggg cgtcgtggac tatgagcacg tccgcgagct ggcccgcatc aatggcgacc    2040
tgggccgcct gggcggcctg ctgaaactct ggctcaccga cgacccgcgc acggcgcggt    2100
tcggtgatgc cacgatcctc gccctgctgg cgaagatcga agagaagcag gacgagcttg    2160
gcaaggtcat gatgggcgtg gtccgcccga gggcagagcc atgactttt tagccgctaa    2220 aacggccggg gggtgcgcgt gattgccaag cacgtcccca tgcgctccat caagaagagc    2280
gacttcgcgg agctggtgaa gtacatcacc gacgagcaag gcaagaccga gcgcctttgc    2340
gacgctcacc gggctggttg ccctcgccgc tgggctggcg gccgtctatg gccctgcaaa    2400
cgcgccagaa acgccgtcga agccgtgtgc gagacaccgc ggccgccggc gttgtggata    2460
cctcgcggaa aacttggccc tcactgacag atgaggggcg gacgttgaca cttgaggggc    2520
cgactcaccc ggcgcggcgt tgacagatga ggggcaggct cgatttcggc cggcgacgtg    2580
gagctggcca gcctcgcaaa tcggcgaaaa cgcctgattt tacgcgagtt tcccacagat    2640
gatgtggaca agcctgggga taagtgccct gcggtattga cacttgaggg gcgcgactac    2700
tgacagatga ggggcgcgat ccttgacact tgaggggcag agtgctgaca gatgaggggc    2760
gcacctattg acatttgagg ggctgtccac aggcagaaaa tccagcattt gcaagggttt    2820
ccgcccgttt tcggccaccg ctaacctgt cttttaacct gctttaaac caatatttat    2880 aaaccttgtt tttaaccagg gctgcgccct gtgcgcgtga ccgcgcacgc cgaaggggg    2940 tgccccccct tctcgaaccc tcccggcccg ctaacgcggg cctccatcc ccccaggggc    3000 tgcgcccctc ggccgcgaac ggcctcaccc caaaaatggc agcgctggca gtccttgcca    3060 ttgcccgggat cggggcagta acgggatggg cgatcagccc gagcgcgacg cccggaagca    3120
ttgacgtgcc gcaggtgctg gcatcgacat tcagcgacca ggtgccgggc agtgagggcg    3180
gcggcctggg tggcggcctg cccttcactt cggccgtcgg ggcattcacg gacttcatgg    3240
cggggccggc aattttacc ttgggcattc ttggcatagt ggtcgcgggt gccgtgctcg    3300
tgttcggggg tgcgataaac ccagcgaacc atttgaggtg ataggtaaga ttataccgag    3360
gtatgaaaac gagaattgga cctttacaga attactctat gaagcgccat atttaaaaag    3420
ctaccaagac gaagaggatg aagaggatga ggaggcagat tgccttgaat atattgacaa    3480
tactgataag ataatatatc ttttatatag aagatatcgc cgtatgtaag gatttcaggg    3540
ggcaaggcat aggcagcgcg cttatcaata tatctataga atgggcaaag cataaaaact    3600
tgcatggact aatgcttgaa acccaggaca ataaccttat agcttgtaaa ttctatcata    3660
attgggtaat gactccaact tattgatagt gttttatgtt cagataatgc ccgatgactt    3720
tgtcatgcag ctccaccgat tttgagaacg acagcgactt ccgtcccagc cgtgccaggt    3780
gctgcctcag attcaggtta tgccgctcaa ttcgctgcgt atatcgcttg ctgattacgt    3840
gcagctttcc cttcaggcgg gattcataca gcggccagcc atccgtcatc catatccacca    3900 cgtcaaaggg tgacagcagg ctcataagac gccccagcgt cgccatagtg cgttcaccga    3960
atacgtgcgc aacaaccgtc ttccggagac tgtcatacgc gtaaaacagc cagcgctggc    4020
gcgatttagc cccgacatag ccccactgtt cgtccatttc gcgcagacg atgacgtcac    4080 tgcccggctg tatgcgcgag gttaccgact gcggcctgag tttttaagt gacgtaaaat    4140 cgtgttgagg ccaacgccca taatgcgggc tgttgcccgg catccaacgc cattcatggc    4200
catatcaatg attttctggt gcgtaccggg ttgagaagcg gtgtaagtga actgcagttg    4260
ccatgtttta cggcagtgag agcagagata gcgctgatgt ccggcggtgc ttttgccgtt    4320
```

```
acgcaccacc ccgtcagtag ctgaacagga gggacagctg atagacacag aagccactgg    4380
agcacctcaa aaacaccatc atacactaaa tcagtaagtt ggcagcatca cccataattg    4440
tggtttcaaa atcggctccg tcgatactat gttatacgcc aactttgaaa acaactttga    4500
aaaagctgtt ttctggtatt taaggtttta gaatgcaagg aacagtgaat tggagttcgt    4560
cttgttataa ttagcttctt ggggtatctt taaatactgt agaaaagagg aaggaaataa    4620
taaatggcta aaatgagaat atcaccggaa ttgaaaaaac tgatcgaaaa ataccgctgc    4680
gtaaaagata cggaaggaat gtctcctgct aaggtatata agctggtggg agaaaatgaa    4740
aacctatatt taaaaatgac ggacagccgg tataaaggga ccacctatga tgtggaacgg    4800
gaaaaggaca tgatgctatg gctggaagga aagctgcctg ttccaaaggt cctgcacttt    4860
gaacggcatg atggctggag caatctgctc atgagtgagg ccgatggcgt cctttgctcg    4920
gaagagtatg aagatgaaca aagccctgaa aagattatcg agctgtatgc ggagtgcatc    4980
aggctctttc actccatcga catatcggat tgtccctata cgaatagctt agacagccgc    5040
ttagccgaat tggattactt actgaataac gatctggccg atgtggattg cgaaaactgg    5100
gaagaagaca ctccatttaa agatccgcgc gagctgtatg attttttaaa gacggaaaag    5160
cccgaagagg aacttgtctt ttcccacggc gacctgggag acagcaacat ctttgtgaaa    5220
gatggcaaag taagtggctt tattgatctt gggagaagcg gcagggcgga caagtggtat    5280
gacattgcct tctgcgtccg gtcgatcagg gaggatatcg gggaagaaca gtatgtcgag    5340 ctatttttg acttactggg gatcaagcct gattgggaga aaataaaata ttatattta    5400 ctggatgaat tgttttagta cctagatgtg gcgcaacgat gccggcgaca agcaggagcg    5460
caccgacttc ttccgcatca agtgttttgg ctctcaggcc gaggcccacg gcaagtattt    5520
gggcaagggg tcgctggtat tcgtgcaggg caagattcgg aataccaagt acgagaagga    5580
cggccagacg gtctacggga ccgacttcat tgccgataag gtggattatc tggacaccaa    5640
ggcaccaggc gggtcaaatc aggaataagg gcacattgcc ccggcgtgag tcggggcaat    5700
cccgcaagga gggtgaatga atcggacgtt tgaccggaag gcatacaggc aagaactgat    5760
cgacgcgggg ttttccgccg aggatgccga aaccatcgca agccgcaccg tcatgcgtgc    5820
gccccgcgaa accttccagt ccgtcggctc gatggtccag caagctacgg ccaagatcga    5880
gcgcgacagc gtgcaactgg ctccccctgc cctgcccgcg ccatcggccg ccgtggagcg    5940
ttcgcgtcgt ctcgaacagg aggcggcagg tttggcgaag tcgatgacca tcgacacgcg    6000
aggaactatg acgaccaaga agcgaaaaac cgccggcgga gacctggcaa aacaggtcag    6060
cgaggccaag caggccgcgt tgctgaaaca cacgaagcag cagatcaagg aaatgcagct    6120
ttccttgttc gatattgcgc cgtggccgga cacgatgcga gcgatgccaa cgacacggc    6180 ccgctctgcc ctgttcacca cgcgcaacaa gaaaatcccg cgcgaggcgc tgcaaaacaa    6240
ggtcattttc cacgtcaaca aggacgtgaa gatcacctac accggcgtcg agctgcgggc    6300
cgacgatgac gaactggtgt ggcagcaggt gttggagtac gcgaagcgca ccctatcgg    6360 cgagccgatc accttcacgt tctacgagct ttgccaggac ctgggctggt cgatcaatgg    6420
ccggtattac acgaaggccg aggaatgcct gtcgcgccta caggcgacgg cgatgggctt    6480
cacgtccgac cgcgttgggc acctggaatc ggtgtcgctg ctgcaccgct ccgcgtcct    6540 ggaccgtggc aagaaaacgt cccgttgcca ggtcctgatc gacgaggaaa tcgtcgtgct    6600
gtttgctggc gaccactaca cgaaattcat atggagaag taccgcaagc tgtcgccgac    6660 ggccccgacgg atgttcgact atttcagctc gcaccgggag ccgtacccgc tcaagctgga    6720
```

```
aaccttccgc ctcatgtgcg gatcggattc cacccgcgtg aagaagtggc gcgagcaggt    6780
cggcgaagcc tgcgaagagt tgcgaggcag cggcctggtg gaacacgcct gggtcaatga    6840
tgacctggtg cattgcaaac gctagggcct tgtggggtca gttccggctg ggggttcagc    6900
agccagcgct ttactggcat tcaggaaca agcgggcact gctcgacgca cttgcttcgc     6960
tcagtatcgc tcgggacgca cggcgcgctc tacgaactgc cgataaacag aggattaaaa    7020
ttgacaattg tgattaaggc tcagattcga cggcttggag cggccgacgt gcaggatttc    7080
cgcgagatcc gattgtcggc cctgaagaaa gctccagaga tgttcgggtc cgtttacgag    7140
cacgaggaga aaaagcccat ggaggcgttc gctgaacggt tgcgagatgc cgtggcattc    7200
ggcgcctaca tcgacggcga gatcattggg ctgtcggtct tcaaacagga ggacggcccc    7260
aaggacgctc acaaggcgca tctgtccggc gttttcgtgg agcccgaaca gcgaggccga    7320
ggggtcgccg gtatgctgct gcgggcgttg ccggcgggtt tattgctcgt gatgatcgtc    7380
cgacagattc caacgggaat ctggtggatg cgcatcttca tcctcggcgc acttaatatt    7440
tcgctattct ggagcttgtt gtttatttcg gtctaccgcc tgccgggcgg ggtcgcggcg    7500
acggtaggcg ctgtgcagcc gctgatggtc gtgttcatct ctgccgctct gctaggtagc    7560
ccgatacgat tgatggcggt cctgggggct atttgcggaa ctgcgggcgt ggcgctgttg    7620
gtgttgacac caaacgcagc gctagatcct gtcgcgtcg cagcgggcct ggcggggggcg    7680
gtttccatgg cgttcggaac cgtgctgacc cgcaagtggc aacctccccgt gcctctgctc    7740
acctttaccg cctggcaact ggcggccgga ggacttctgc tcgttccagt agctttagtg    7800
tttgatccgc caatcccgat gcctacagga accaatgttc tcggcctggc gtggctcggc    7860
ctgatcggag cgggtttaac ctacttcctt tggttccggg ggatctcgcg actcgaacct    7920
acagttgttt ccttactggg ctttctcagc cccagatctg gggtcgatca gccggggatg    7980
catcaggccg acagtcggaa cttcgggtcc ccgacctgta ccattcggtg agcaatggat    8040
aggggagttg atatcgtcaa cgttcacttc taaagaaata gcgccactca gcttcctcag    8100
cggctttatc cagcgatttc ctattatgtc ggcatagttc tcaagatcga cagcctgtca    8160
cggttaagcg agaaatgaat aagaaggctg ataattcgga tctctgcgag ggagatgata    8220
tttgatcaca ggcagcaacg ctctgtcatc gttacaatca acatgctacc ctccgcgaga    8280
tcatccgtgt ttcaaacccg gcagcttagt tgccgttctt ccgaatagca tcggtaacat    8340
gagcaaagtc tgccgcctta caacggctct cccgctgacg ccgtcccgga ctgatgggct    8400
gcctgtatcg agtggtgatt ttgtgccgag ctgccggtcg gggagctgtt ggctggctgg    8460
tggcaggata tattgtggtg taaacaaatt gacgcttaga caacttaata acacattgcg    8520
gacgtttta atgtactggg gtggtttttc ttttcaccag tgagacgggc aacagctgat    8580
tgcccttcac cgcctggccc tgagagagtt gcagcaagcg gtccacgctg gtttgcccca    8640
gcaggcgaaa atcctgtttg atggtggttc cgaaatcggc aaaatcccttt ataaatcaaa    8700
agaatagccc gagatagggt tgagtgttgt tccagtttgg aacaagagtc cactattaaa    8760
gaacgtggac tccaacgtca aagggcgaaa accgtctat cagggcgatg ccccactacg      8820
tgaaccatca cccaaatcaa gttttttggg gtcgaggtgc cgtaaagcac taaatcggaa    8880
ccctaaaggg agccccgat ttagagcttg acggggaaag ccggcgaacg tggcgagaaa     8940
ggaagggaag aaagcgaaag gagcgggcgc cattcaggct gcgcaactgt tgggaagggc    9000
gatcggtgcg ggcctcttcg ctattacgcc agctggcgaa aggggggatgt gctgcaaggc    9060
```

```
gattaagttg ggtaacgcca gggttttccc agtcacgacg ttgtaaaacg acggccagtg   9120
aattaattcc catcttgaaa gaaatatagt ttaaatattt attgataaaa taacaagtca   9180
ggtattatag tccaagcaaa aacataaatt tattgatgca agtttaaatt cagaaatatt   9240
tcaataactg attatatcag ctggtacatt gccgtagatg aaagactgag tgcgatatta   9300
tgtgtaatac ataaattgat gatatagcta gcttagctca tcgggggatc cgtcgaagct   9360
agcttgggtc ccgctcagaa gaactcgtca agaaggcgat agaaggcgat gcgctgcgaa   9420
tcgggagcgg cgataccgta aagcacgagg aagcggtcag cccattcgcc gccaagctct   9480
tcagcaatat cacgggtagc caacgctatg tcctgatagc ggtccgccac acccagccgg   9540
ccacagtcga tgaatccaga aaagcggcca ttttccacca tgatattcgg caagcaggca   9600
tcgccatggg tcacgacgag atcctcgccg tcgggcatgc gcgccttgag cctggcgaac   9660
agttcggctg gcgcgagccc ctgatgctct tcgtccagat catcctgatc gacaagaccg   9720
gcttccatcc gagtacgtgc tcgctcgatg cgatgtttcg cttggtggtc gaatgggcag   9780
gtagccggat caagcgtatg cagccgccgc attgcatcag ccatgatgga tactttctcg   9840
gcaggagcaa ggtgagatga caggagatcc tgccccggca cttcgcccaa tagcagccag   9900
tcccttcccg cttcagtgac aacgtcgagc acagctgcgc aaggaacgcc cgtcgtggcc   9960
agccacgata gccgcgctgc ctcgtcctgc agttcattca gggcaccgga caggtcggtc   10020
ttgacaaaaa gaaccgggcg cccctgcgct gacagccgga acacggcggc atcagagcag   10080
ccgattgtct gttgtgccca gtcatagccg aatagcctct ccacccaagc ggccggagaa   10140
cctgcgtgca atccatcttg ttcaatccaa gctcccatgg gccctcgact agagtcgaga   10200
tctggattga gagtgaatat gagactctaa ttggataccg aggggaattt atggaacgtc   10260
agtggagcat ttttgacaag aaatatttgc tagctgatag tgaccttagg cgacttttga   10320
acgcgcaata atggtttctg acgtatgtgc ttagctcatt aaactccaga aacccgcggc   10380
tgagtggctc cttcaacgtt gcggttctgt cagttccaaa cgtaaaacgg cttgtcccgc   10440
gtcatcggcg ggggtcataa cgtgactccc ttaattctcc gctcatgatc ttgatcccct   10500
gcgccatcag atccttggcg gcaagaaagc catccagttt actttgcagg gcttcccaac   10560
cttaccagag ggcgcccag ctggcaattc cggttcgctt gctgtccata aaaccgccca   10620
gtctagctat cgccatgtaa gcccactgca agctacctgc tttctctttg cgcttgcgtt   10680
ttcccttgtc cagatagccc agtagctgac attcatccgg ggtcagcacc gtttctgcgg   10740
actggctttc tacgtgttcc gcttccttta gcagcccttg cgccctgagt gcttgcggca   10800
gcgtgaagct tgcatgcctg caggtcgacg gcgcgccgag ctcctcgagc aaatttacac   10860
attgccacta aacgtctaaa cccttgtaat ttgttttttgt tttactatgt gtgttatgta   10920
tttgatttgc gataaatttt tatatttggt actaaattta taacaccttt tatgctaacg   10980
tttgccaaca cttagcaatt tgcaagttga ttaattgatt ctaaattatt tttgtcttct   11040
aaatacatat actaatcaac tggaaatgta aatatttgct aatatttcta ctataggaga   11100
attaaagtga gtgaatatgg taccacaagg tttggagatt taattgttgc aatgctgcat   11160
ggatggcata taccaaaac attcaataat tcttgaggat aataatggta ccacacaaga   11220
tttgaggtgc atgaacgtca cgtggacaaa aggtttagta atttttcaag acaacaatgt   11280
taccacacac aagttttgag gtgcatgcat ggatgccctg tggaaagttt aaaaatattt   11340
tggaaatgat ttgcatggaa gccatgtgta aaaccatgac atccacttgg aggatgcaat   11400
aatgaagaaa actacaaaat tacatgcaac tagttatgca tgtagtctat ataatgagga   11460
```

-continued

| | |
|---|---|
| ttttgcaata ctttcattca tacacactca ctaagttttta cacgattata atttcttcat | 11520 |
| agccagcgga tccgatatcg ggcccgctag cgttaaccct gctttaatga gatatgcgag | 11580 |
| acgcctatga tcgcatgata tttgctttca attctgttgt gcacgttgta aaaaacctga | 11640 |
| gcatgtgtag ctcagatcct taccgccggt ttcggttcat tctaatgaat atatcacccg | 11700 |
| ttactatcgt attttatga ataatattct ccgttcaatt tactgattgt ccgtcgacga | 11760 |
| attcgagctc ggcgcgcctc tagaggatcg atgaattcag atcggctgag tggctccttc | 11820 |
| aacgttgcgg ttctgtcagt tccaaacgta aaacggcttg tcccgcgtca tcggcggggg | 11880 |
| tcataacgtg actcccttaa ttctccgctc atgatcagat tgtcgtttcc cgccttcagt | 11940 |
| ttaaactatc agtgtttgac aggatatatt ggcgggtaaa cctaagagaa aagagcgttt | 12000 |
| attagaataa tcggatattt aaaagggcgt gaaaaggttt atccttcgtc catttgtatg | 12060 |
| tgcatgccaa ccacagggtt cccca | 12085 |

<210> SEQ ID NO 40
<211> LENGTH: 12079
<212> TYPE: DNA
<213> ORGANISM: Unknown
<220> FEATURE:
<223> OTHER INFORMATION: Plant expression vector with a
      promoter-terminator expression cassette

<400> SEQUENCE: 40

| | |
|---|---|
| gatctggcgc cggccagcga gacgagcaag attggccgcc gcccgaaacg atccgacagc | 60 |
| gcgcccagca caggtgcgca ggcaaattgc accaacgcat acagcgccag cagaatgcca | 120 |
| tagtgggcgg tgacgtcgtt cgagtgaacc agatcgcgca ggaggcccgg cagcaccggc | 180 |
| ataatcaggc cgatgccgac agcgtcgagc gcgacagtgc tcagaattac gatcaggggt | 240 |
| atgttgggtt tcacgtctgg cctccggacc agcctccgct ggtccgattg aacgcgcgga | 300 |
| ttctttatca ctgataagtt ggtggacata ttatgtttat cagtgataaa gtgtcaagca | 360 |
| tgacaaagtt gcagccgaat acagtgatcc gtgccgccct ggacctgttg aacgaggtcg | 420 |
| gcgtagacgg tctgacgaca cgcaaactgg cggaacggtt gggggttcag cagccggcgc | 480 |
| tttactggca cttcaggaac aagcgggcgc tgctcgacgc actggccgaa gccatgctgg | 540 |
| cggagaatca tacgcattcg gtgccgagag ccgacgacga ctggcgctca tttctgatcg | 600 |
| ggaatgcccg cagcttcagg caggcgctgc tcgcctaccg cgatggcgcg cgcatccatg | 660 |
| ccggcacgcg accgggcgca ccgcagatgg aaacggccga cgcgcagctt cgcttcctct | 720 |
| gcgaggcggg ttttcggcc ggggacgccg tcaatgcgct gatgacaatc agctacttca | 780 |
| ctgttggggc cgtgcttgag gagcaggccg gcgacagcga tgccggcgag cgcggcggca | 840 |
| ccgttgaaca ggctccgctc tcgccgctgt tgcgggccgc gatagacgcc ttcgacgaag | 900 |
| ccggtccgga cgcagcgttc gagcagggac tcgcggtgat tgtcgatgga ttggcgaaaa | 960 |
| ggaggctcgt tgtcaggaac gttgaaggac cgagaaaggg tgacgattga tcaggaccgc | 1020 |
| tgccggagcg caacccactc actacagcag agccatgtag acaacatccc ctccccctt | 1080 |
| ccaccgcgtc agacgcccgt agcagcccgc tacgggcttt ttcatgccct gccctagcgt | 1140 |
| ccaagcctca cggccgcgct cggcctctct ggcggcttc tggcgctctt ccgcttcctc | 1200 |
| gctcactgac tcgctgcgct cggtcgttcg gctgcggcga gcggtatcag ctcactcaaa | 1260 |
| ggcggtaata cggttatcca cagaatcagg ggataacgca ggaaagaaca tgtgagcaaa | 1320 |
| aggccagcaa aaggccagga accgtaaaaa ggccgcgttg ctggcgtttt tccataggct | 1380 |

```
ccgcccccct gacgagcatc acaaaaatcg acgctcaagt cagaggtggc gaaacccgac  1440
aggactataa agataccagg cgtttccccc tggaagctcc ctcgtgcgct ctcctgttcc  1500
gaccctgccg cttaccggat acctgtccgc ctttctccct tcgggaagcg tggcgctttt  1560
ccgctgcata accctgcttc ggggtcatta tagcgatttt ttcggtatat ccatccttt  1620 tcgcacgata tacaggattt tgccaaaggg ttcgtgtaga ctttccttgg tgtatccaac  1680
ggcgtcagcc gggcaggata ggtgaagtag gcccacccgc gagcgggtgt tccttcttca  1740
ctgtccctta ttcgcacctg gcggtgctca acgggaatcc tgctctgcga ggctggccgg  1800
ctaccgccgg cgtaacagat gagggcaagc ggatggctga tgaaaccaag ccaaccagga  1860
agggcagccc acctatcaag gtgtactgcc ttccagacga acgaagagcg attgaggaaa  1920
aggcggcggc ggccggcatg agcctgtcgg cctacctgct ggccgtcggc cagggctaca  1980
aaatcacggg cgtcgtggac tatgagcacg tccgcgagct ggcccgcatc aatggcgacc  2040
tgggccgcct gggcggcctg ctgaaactct ggctcaccga cgacccgcgc acggcgcggt  2100
tcggtgatgc cacgatcctc gccctgctgg cgaagatcga agagaagcag gacgagcttg  2160
gcaaggtcat gatgggcgtg gtccgcccga gggcagagcc atgacttttt tagccgctaa  2220
aacggccggg gggtgcgcgt gattgccaag cacgtcccca tgcgctccat caagaagagc  2280
gacttcgcgg agctggtgaa gtacatcacc gacgagcaag gcaagaccga gcgcctttgc  2340
gacgctcacc gggctggttg ccctcgccgc tgggctggcg gccgtctatg gccctgcaaa  2400
cgcgccagaa acgcgtcga agccgtgtgc gagacaccgc ggccgccggc gttgtggata  2460
cctcgcggaa aacttggccc tcactgacag atgaggggcg gacgttgaca cttgaggggc  2520
cgactcaccc ggcgcggcgt tgacagatga ggggcaggct cgatttcggc cggcgacgtg  2580
gagctggcca gcctcgcaaa tcggcgaaaa cgcctgattt tacgcgagtt cccacagat  2640 gatgtggaca agcctgggga taagtgccct gcggtattga cacttgaggg gcgcgactac  2700
tgacagatga ggggcgcgat ccttgacact tgaggggcag agtgctgaca gatgaggggc  2760
gcacctattg acatttgagg ggctgtccac aggcagaaaa tccagcattt gcaagggttt  2820
ccgcccgttt ttcggccacc gctaacctgt cttttaacct gcttttaaac caatatttat  2880
aaaccttgtt tttaaccagg gctgcgccct gtgcgcgtga ccgcgcacgc cgaaggggg  2940 tgccccccct tctcgaaccc tcccggcccg ctaacgcggg cctcccatcc ccccagggc  3000 tgcgcccctc ggccgcgaac ggcctcaccc caaaaatggc agcgctggca gtccttgcca  3060
ttgccgggat cggggcagta acgggatggg cgatcagccc gagcgcgacg cccggaagca  3120
ttgacgtgcc gcaggtgctg gcatcgacat tcagcgacca ggtgccgggc agtgagggcg  3180
gcggcctggg tggcggcctg cccttcactt cggccgtcgg ggcattcacg gacttcatgg  3240
cggggccggc aattttttacc ttgggcattc ttggcatagt ggtcgcgggt gccgtgctcg  3300
tgttcggggg tgcgataaac ccagcgaacc atttgaggtg ataggtaaga ttataccgag  3360
gtatgaaaac gagaattgga cctttacaga attactctat gaagcgccat atttaaaaag  3420
ctaccaagac gaagaggatg aagaggatga ggaggcagat tgccttgaat atattgacaa  3480
tactgataag ataatatatc ttttatatag aagatatcgc cgtatgtaag gatttcaggg  3540
ggcaaggcat aggcagcgcg cttatcaata tatctataga atgggcaaag cataaaaact  3600
tgcatggact aatgcttgaa acccaggaca ataaccttat agcttgtaaa ttctatcata  3660
attgggtaat gactccaact tattgatagt gttttatgtt cagataatgc ccgatgactt  3720
```

```
tgtcatgcag ctccaccgat tttgagaacg acagcgactt ccgtcccagc cgtgccaggt    3780
gctgcctcag attcaggtta tgccgctcaa ttcgctgcgt atatcgcttg ctgattacgt    3840
gcagctttcc cttcaggcgg gattcataca gcggccagcc atccgtcatc catatcacca    3900
cgtcaaaggg tgacagcagg ctcataagac gccccagcgt cgccatagtg cgttcaccga    3960
atacgtgcgc aacaaccgtc ttccggagac tgtcatacgc gtaaaacagc cagcgctggc    4020
gcgatttagc cccgacatag ccccactgtt cgtccatttc cgcgcagacg atgacgtcac    4080
tgcccggctg tatgcgcgag gttaccgact gcggcctgag ttttttaagt gacgtaaaat    4140
cgtgttgagg ccaacgccca taatgcgggc tgttgcccgg catccaacgc cattcatggc    4200
catatcaatg attttctggt gcgtaccggg ttgagaagcg gtgtaagtga actgcagttg    4260
ccatgtttta cggcagtgag agcagagata gcgctgatgt ccggcggtgc ttttgccgtt    4320
acgcaccacc ccgtcagtag ctgaacagga gggacagctg atagacacag aagccactgg    4380
agcacctcaa aaaccatcc atacactaaa tcagtaagtt ggcagcatca cccataattg    4440
tggtttcaaa atcggctccg tcgatactat gttatacgcc aactttgaaa caactttga    4500 aaaagctgtt ttctggtatt taaggtttta gaatgcaagg aacagtgaat tggagttcgt    4560
cttgttataa ttagcttctt ggggtatctt taaatactgt agaaagagg aaggaaataa    4620 taaatggcta aaatgagaat atcaccggaa ttgaaaaaac tgatcgaaaa ataccgctgc    4680
gtaaaagata cggaaggaat gtctcctgct aaggtatata agctggtggg agaaaatgaa    4740
aacctatatt taaaaatgac ggacagccgg tataagggga ccacctatga tgtggaacgg    4800
gaaaaggaca tgatgctatg gctggaagga agctgcctg ttccaaaggt cctgcacttt    4860
gaacggcatg atggctggag caatctgctc atgagtgagg ccgatggcgt cctttgctcg    4920
gaagagtatg aagatgaaca aagccctgaa aagattatcg agctgtatgc ggagtgcatc    4980
aggctctttc actccatcga catatcggat tgtccctata cgaatagctt agacagccgc    5040
ttagccgaat tggattactt actgaataac gatctggccg atgtggattg cgaaaactgg    5100
gaagaagaca ctccatttaa agatccgcgc gagctgtatg atttttaaa gacggaaaag    5160 cccgaagagg aacttgtctt ttcccacggc gacctgggag acagcaacat ctttgtgaaa    5220
gatggcaaag taagtggctt tattgatctt gggagaagcg gcagggcgga caagtggtat    5280
gacattgcct tctgcgtccg gtcgatcagg gaggatatcg gggaagaaca gtatgtcgag    5340 ctatttttg acttactggg gatcaagcct gattgggaga aaataaaata ttatatttta    5400
ctggatgaat tgttttagta cctagatgtg gcgcaacgat gccggcgaca agcaggagcg    5460
caccgacttc ttccgcatca agtgttttgg ctctcaggcc gaggcccacg gcaagtattt    5520
gggcaagggg tcgctggtat tcgtgcaggg caagattcgg ataccaagt acgagaagga    5580 cggccagacg gtctacggga ccgacttcat tgccgataag gtggattatc tggacaccaa    5640
ggcaccaggc gggtcaaatc aggaataagg gcacattgcc ccggcgtgag tcggggcaat    5700
cccgcaagga gggtgaatga atcggacgtt tgaccggaag gcatacaggc aagaactgat    5760
cgacgcgggg ttttccgccg aggatgccga accatcgca agccgcaccg tcatgcgtgc    5820
gccccgcgaa accttccagt ccgtcggctc gatggtccag caagctacgg ccaagatcga    5880
gcgcgacagc gtgcaactgg ctcccctgc cctgccgcg ccatcggccg ccgtggagcg    5940
ttcgcgtcgt ctcgaacagg aggcggcagg tttggcgaag tcgatgacca tcgacacgcg    6000
aggaactatg acgaccaaga agcgaaaaac cgcggcgag gacctggcaa acaggtcag    6060 cgaggccaag caggccgcgt tgctgaaaca cacgaagcag cagatcaagg aaatgcagct    6120
```

```
ttccttgttc gatattgcgc cgtggccgga cacgatgcga gcgatgccaa acgacacggc    6180
ccgctctgcc ctgttcacca cgcgcaacaa gaaaatcccg cgcgaggcgc tgcaaaacaa    6240
ggtcattttc cacgtcaaca aggacgtgaa gatcacctac accggcgtcg agctgcgggc    6300
cgacgatgac gaactggtgt ggcagcaggt gttggagtac gcgaagcgca cccctatcgg    6360
cgagccgatc accttcacgt tctacgagct ttgccaggac ctgggctggt cgatcaatgg    6420
ccggtattac acgaaggccg aggaatgcct gtcgcgccta caggcgacgg cgatgggctt    6480
cacgtccgac cgcgttgggc acctggaatc ggtgtcgctg ctgcaccgct tccgcgtcct    6540
ggaccgtggc aagaaaacgt cccgttgcca ggtcctgatc gacgaggaaa tcgtcgtgct    6600
gtttgctggc gaccactaca cgaaattcat atgggagaag taccgcaagc tgtcgccgac    6660
ggcccgacgg atgttcgact atttcagctc gcaccgggag ccgtacccgc tcaagctgga    6720
aaccttccgc ctcatgtgcg gatcggattc caccgcgtg aagaagtggc gcgagcaggt    6780
cggcgaagcc tgcgaagagt tgcgaggcag cggcctggtg gaacacgcct gggtcaatga    6840
tgacctggtg cattgcaaac gctagggcct tgtggggtca gttccggctg ggggttcagc    6900
agccagcgct ttactggcat tcaggaaca agcgggcact gctcgacgca cttgcttcgc    6960
tcagtatcgc tcgggacgca cggcgcgctc tacgaactgc cgataaacag aggattaaaa    7020
ttgacaattg tgattaaggc tcagattcga cggcttggag cggccgacgt gcaggatttc    7080
cgcgagatcc gattgtcggc cctgaagaaa gctccagaga tgttcgggtc cgtttacgag    7140
cacgaggaga aaaagcccat ggaggcgttc gctgaacggt tgcgagatgc cgtggcattc    7200
ggcgcctaca tcgacggcga gatcattggg ctgtcggtct tcaaacagga ggacggcccc    7260
aaggacgctc acaaggcgca tctgtccggc gttttcgtgg agcccgaaca gcgaggccga    7320
ggggtcgccg gtatgctgct gcgggcgttg ccggcgggtt tattgctcgt gatgatcgtc    7380
cgacagattc caacgggaat ctggtggatg cgcatcttca tcctcggcgc acttaatatt    7440
tcgctattct ggagcttgtt gtttatttcg gtctaccgcc tgccgggcgg ggtcgcggcg    7500
acggtaggcg ctgtgcagcc gctgatggtc gtgttcatct ctgccgctct gctaggtagc    7560
ccgatacgat tgatggcggt cctggggct atttgcggaa ctgcgggcgt ggcgctgttg    7620
gtgttgacac caaacgcagc gctagatcct gtcggcgtcg cagcgggcct ggcggggcg    7680
gtttccatgg cgttcggaac cgtgctgacc cgcaagtggc aacctcccgt gcctctgctc    7740
acctttaccg cctggcaact ggcggccgga ggacttctgc tcgttccagt agctttagtg    7800
tttgatccgc caatcccgat gcctacagga accaatgttc tcggcctggc gtggctcggc    7860
ctgatcggag cgggtttaac ctacttcctt tggttccggg gatctcgcg actcgaacct    7920
acagttgttt ccttactggg cttttctcagc cccagatctg gggtcgatca gccggggatg    7980
catcaggccg acagtcggaa cttcgggtcc ccgacctgta ccattcggtg agcaatggat    8040
agggagttg atatcgtcaa cgttcacttc taaagaaata gcgccactca gcttcctcag    8100
cggctttatc cagcgatttc ctattatgtc ggcatagttc tcaagatcga cagcctgtca    8160
cggttaagcg agaaatgaat aagaaggctg ataattcgga tctctgcgag ggagatgata    8220
tttgatcaca ggcagcaacg ctctgtcatc gttacaatca acatgctacc ctccgcgaga    8280
tcatccgtgt ttcaaacccg gcagcttagt tgccgttctt ccgaatagca tcggtaacat    8340
gagcaaagtc tgccgcctta caacggctct cccgctgacg ccgtcccgga ctgatgggct    8400
gcctgtatcg agtggtgatt ttgtgccgag ctgccggtcg gggagctgtt ggctggctgg    8460
```

```
tggcaggata tattgtggtg taaacaaatt gacgcttaga caacttaata acacattgcg    8520
gacgttttta atgtactggg gtggttttc ttttcaccag tgagacgggc aacagctgat    8580
tgcccttcac cgcctggccc tgagagagtt gcagcaagcg gtccacgctg gtttgcccca    8640
gcaggcgaaa atcctgtttg atggtggttc cgaaatcggc aaaatccctt ataaatcaaa    8700
agaatagccc gagatagggt tgagtgttgt tccagtttgg aacaagagtc cactattaaa    8760
gaacgtggac tccaacgtca aagggcgaaa aaccgtctat cagggcgatg gcccactacg    8820
tgaaccatca cccaaatcaa gttttttggg gtcgaggtgc cgtaaagcac taaatcggaa    8880
ccctaaaggg agcccccgat ttagagcttg acggggaaag ccggcgaacg tggcgagaaa    8940
ggaagggaag aaagcgaaag gagcgggcgc cattcaggct gcgcaactgt tgggaagggc    9000
gatcggtgcg ggcctcttcg ctattacgcc agctggcgaa aggggatgt gctgcaaggc    9060
gattaagttg ggtaacgcca gggttttccc agtcacgacg ttgtaaaacg acggccagtg    9120
aattaattcc catcttgaaa gaaatatagt ttaaatattt attgataaaa taacaagtca    9180
ggtattatag tccaagcaaa aacataaatt tattgatgca agtttaaatt cagaaatatt    9240
tcaataactg attatatcag ctggtacatt gccgtagatg aaagactgag tgcgatatta    9300
tgtgtaatac ataaattgat gatatagcta gcttagctca tcggggatc cgtcgaagct    9360
agcttgggtc ccgctcagaa gaactcgtca agaaggcgat agaaggcgat gcgctgcgaa    9420
tcgggagcgg cgataccgta agcacgagg aagcggtcag cccattcgcc gccaagctct    9480
tcagcaatat cacgggtagc caacgctatg tcctgatagc ggtccgccac acccagccgg    9540
ccacagtcga tgaatccaga aaagcggcca ttttccacca tgatattcgg caagcaggca    9600
tcgccatggg tcacgacgag atcctcgccg tcgggcatgc gcgccttgag cctggcgaac    9660
agttcggctg gcgcgagccc ctgatgctct tcgtccagat catcctgatc gacaagaccg    9720
gcttccatcc gagtacgtgc tcgctcgatg cgatgtttcg cttggtggtc gaatgggcag    9780
gtagccggat caagcgtatg cagccgccgc attgcatcag ccatgatgga tactttctcg    9840
gcaggagcaa ggtgagatga caggagatcc tgccccggca cttcgcccaa tagcagccag    9900
tccccttcccg cttcagtgac aacgtcgagc acagctgcgc aaggaacgcc cgtcgtggcc    9960
agccacgata gccgcgctgc ctcgtcctgc agttcattca gggcaccgga caggtcggtc    10020
ttgacaaaaa gaaccgggcg cccctgcgct gacagccgga acacggcggc atcagagcag    10080
ccgattgtct gttgtgccca gtcatagccg aatagcctct ccacccaagc ggccggagaa    10140
cctgcgtgca atccatcttg ttcaatccaa gctcccatgg gccctcgact agagtcgaga    10200
tctggattga gagtgaatat gagactctaa ttggataccg aggggaattt atggaacgtc    10260
agtggagcat ttttgacaag aaatatttgc tagctgatag tgaccttagg cgacttttga    10320
acgcgcaata atggtttctg acgtatgtgc ttagctcatt aaactccaga aacccgcggc    10380
tgagtggctc cttcaacgtt gcggttctgt cagttccaaa cgtaaaacgg cttgtcccgc    10440
gtcatcggcg ggggtcataa cgtgactccc ttaattctcc gctcatgatc ttgatcccct    10500
gcgccatcag atccttggcg gcaagaaagc catccagttt actttgcagg gcttcccaac    10560
cttaccagag ggcgccccag ctggcaattc cggttcgctt gctgtccata aaaccgccca    10620
gtctagctat cgccatgtaa gcccactgca agctacctgc tttctctttg cgcttgcgtt    10680
ttcccttgtc cagatagccc agtagctgac attcatccgg ggtcagcacc gtttctgcgg    10740
actggctttc tacgtgttcc gcttccttta gcagcccttg cgccctgagt gcttgcggca    10800
gcgtgaagct tgcatgcctg caggtcgacg gcgcgccgag ctcctcgagc aaatttacac    10860
```

```
attgccacta aacgtctaaa cccttgtaat ttgttttttgt tttactatgt gtgttatgta    10920
tttgatttgc gataaatttt tatatttggt actaaattta taacacctttt tatgctaacg    10980
```

```
attgccacta aacgtctaaa cccttgtaat ttgttttttgt tttactatgt gtgttatgta    10920
tttgatttgc gataaatttt tatatttggt actaaattta taacacccttt tatgctaacg    10980 tttgccaaca cttagcaatt tgcaagttga ttaattgatt ctaaattatt tttgtcttct    11040
aaatacatat actaatcaac tggaaatgta aatatttgct aatatttcta ctataggaga    11100
attaaagtga gtgaatatgg taccacaagg tttggagatt taattgttgc aatgctgcat    11160
ggatggcata tacaccaaac attcaataat tcttgaggat aataatggta ccacacaaga    11220
tttgaggtgc atgaacgtca cgtggacaaa aggtttagta atttttcaag acaacaatgt    11280
taccacacac aagttttgag gtgcatgcat ggatgccctg tggaaagttt aaaaatattt    11340
tggaaatgat ttgcatggaa gccatgtgta aaaccatgac atccacttgg aggatgcaat    11400
aatgaagaaa actacaaatt tacatgcaac tagttatgca tgtagtctat ataatgagga    11460
ttttgcaata ctttcattca tacacactca ctaagtttta cacgattata atttcttcat    11520
agccagcaga tctgccggca tcgatcccgg gccatggcct gctttaatga gatatgcgag    11580
acgcctatga tcgcatgata tttgctttca attctgttgt gcacgttgta aaaaacctga    11640
gcatgtgtag ctcagatcct taccgccggt ttcggttcat tctaatgaat atatcacccg    11700
ttactatcgt atttttatga ataatattct ccgttcaatt tactgattgt ccgtcgacga    11760
gctcggcgcg cctctagagg atcgatgaat tcagatcggc tgagtggctc cttcaacgtt    11820
gcggttctgt cagttccaaa cgtaaaacgg cttgtcccgc gtcatcggcg ggggtcataa    11880
cgtgactccc ttaattctcc gctcatgatc agattgtcgt ttcccgcctt cagttttaaac   11940
```

```
cgtgactccc ttaattctcc gctcatgatc agattgtcgt ttcccgcctt cagttttaaac   11940 tatcagtgtt tgacaggata tattggcggg taaacctaag agaaagagc gtttattaga     12000 ataatcggat atttaaaagg gcgtgaaaag gtttatcctt cgtccatttg tatgtgcatg    12060
ccaaccacag ggttcccca                                                  12079
```

<210> SEQ ID NO 41
<211> LENGTH: 13002
<212> TYPE: DNA
<213> ORGANISM: Unknown
<220> FEATURE:
<223> OTHER INFORMATION: Plant expression vector with two
    promoter-terminator expression cassettes

<400> SEQUENCE: 41

```
gatctggcgc cggccagcga gacgagcaag attggccgcc gcccgaaacg atccgacagc      60
gcgcccagca caggtgcgca ggcaaattgc accaacgcat acagcgccag cagaatgcca     120
tagtgggcgg tgacgtcgtt cgagtgaacc agatcgcgca ggaggcccgg cagcaccggc    180
ataatcaggc cgatgccgac agcgtcgagc gcgacagtgc tcagaattac gatcaggggt    240
atgttgggtt tcacgtctgg cctccggacc agcctccgct ggtccgattg aacgcgcgga    300
ttctttatca ctgataagtt ggtggacata ttatgtttat cagtgataaa gtgtcaagca    360
tgacaaagtt gcagccgaat acagtgatcc gtgccgccct ggacctgttg aacgaggtcg    420
gcgtagacgc tctgacgaca cgcaaactgg cggaacggtt gggggttcag cagccggcgc    480
tttactggca cttcaggaac aagcgggcgc tgctcgacgc actggccgaa gccatgctgg    540
cggagaatca tacgcattcg gtgccagagc ccgacgacga ctggcgctca tttctgatcg    600
ggaatgcccg cagcttcagg caggcgctgc tcgcctaccg cgatggcgcg cgcatccatg    660
ccggcacgcg accgggcgca ccgcagatgg aaacggccga cgcgcagctt cgcttcctct    720
gcgaggcggg tttttcggcc ggggacgccg tcaatgcgct gatgacaatc agctactcca    780
```

```
ctgttggggc cgtgcttgag gagcaggccg gcgacagcga tgccggcgag cgcggcggca    840
ccgttgaaca ggctccgctc tcgccgctgt tgcgggccgc gatagacgcc ttcgacgaag    900
ccggtccgga cgcagcgttc gagcaggacc tcgcggtgat tgtcgatgga ttggcgaaaa    960
ggaggctcgt tgtcaggaac gttgaaggac cgagaaaggg tgacgattga tcaggaccgc   1020
tgccggagcg caacccactc actacagcag agccatgtag acaacatccc ctccccottt   1080
ccaccgcgtc agacgcccgt agcagcccgc tacgggcttt ttcatgccct gccctagcgt   1140
ccaagcctca cggccgcgct cggcctctct ggcggccttc tggcgctctt ccgcttcctc   1200
gctcactgac tcgctgcgct cggtcgttcg gctgcggcga gcggtatcag ctcactcaaa   1260
ggcggtaata cggttatcca cagaatcagg ggataacgca ggaaagaaca tgtgagcaaa   1320
aggccagcaa aaggccagga accgtaaaaa ggccgcgttg ctggcgtttt tccataggct   1380
ccgcccccct gacgagcatc acaaaaatcg acgctcaagt cagaggtggc gaaacccgac   1440
aggactataa agataccagg cgtttccccc tggaagctcc ctcgtgcgct ctcctgttcc   1500
gaccctgccg cttaccggat acctgtccgc ctttctccct tcgggaagcg tggcgctttt   1560
ccgctgcata accctgcttc ggggtcatta tagcgatttt tcggtatat ccatcctttt    1620
tcgcacgata tacaggattt tgccaaaggg ttcgtgtaga cttttccttgg tgtatccaac   1680
ggcgtcagcc gggcaggata ggtgaagtag gcccacccgc gagcgggtgt tccttcttca   1740
ctgtccctta ttcgcacctg gcggtgctca acgggaatcc tgctctgcga ggctggccgg   1800
ctaccgccgg cgtaacagat gagggcaagc ggatggctga tgaaaccaag ccaaccagga   1860
agggcagccc acctatcaag gtgtactgcc ttccagacga acgaagagcg attgaggaaa   1920
aggcggcggg ggccggcatg agcctgtcgg cctacctgct ggccgtcggc cagggctaca   1980
aaatcacggg cgtcgtggac tatgagcacg tccgcgagct ggcccgcatc aatggcgacc   2040
tgggccgcct gggcggcctg ctgaaactct ggctcaccga cgacccgcgc acggcgcggt   2100
tcggtgatgc cacgatcctc gccctgctgg cgaagatcga agagaagcag gacgagcttg   2160
gcaaggtcat gatgggcgtg gtccgcccga gggcagagcc atgactttt tagccgctaa    2220
aacggccggg gggtgcgcgt gattgccaag cacgtcccca tgcgctccat caagaagagc   2280
gacttcgcgc agctggtgaa gtacatcacc gacgagcaag gcaagaccga gcgccttgc    2340
gacgctcacc gggctggttg ccctcgccgc tgggctggcg gccgtctatg gccctgcaaa   2400
cgcgccagaa acgccgtcga agccgtgtgc gagacaccgc ggccgccggc gttgtggata   2460
cctcgcggaa aacttggccc tcactgacag atgaggggcg gacgttgaca cttgaggggc   2520
cgactcaccc ggcgcggcgt tgacagatga ggggcaggct cgatttcggc cggcgacgtg   2580
gagctggcca gcctcgcaaa tcggcgaaaa cgcctgattt tacgcgagtt tcccacagat   2640
gatgtggaca agcctgggga taagtgccct gcggtattga cacttgaggg gcgcgactac   2700
tgacagatga ggggcgcgat ccttgacact tgaggggcag agtgctgaca gatgaggggc   2760
gcacctattg acatttgagg ggctgtccac aggcagaaaa tccagcattt gcaagggttt   2820
ccgcccgttt ttcggccacc gctaacctgt cttttaacct gcttttaaac caatatttat   2880
aaaccttgtt tttaaccagg gctgcgccct gtgcgcgtga ccgcgcacgc cgaagggggg   2940
tgcccccct tctcgaaccc tcccggcccg ctaacgcggg cctcccatcc cccagggggc    3000
tgcgcccctc ggccgcgaac ggcctcaccc caaaaatggc agcgctggca gtccttgcca   3060
ttgccgggat cggggcagta acgggatggg cgatcagccc gagcgcgacg cccggaagca   3120
```

```
ttgacgtgcc gcaggtgctg gcatcgacat tcagcgacca ggtgccgggc agtgagggcg    3180
gcggcctggg tggcggcctg cccttcactt cggccgtcgg ggcattcacg gacttcatgg    3240
cggggccggc aattttacc ttgggcattc ttggcatagt ggtcgcgggt gccgtgctcg     3300
tgttcggggg tgcgataaac ccagcgaacc atttgaggtg ataggtaaga ttataccgag    3360
gtatgaaaac gagaattgga cctttacaga attactctat gaagcgccat atttaaaaag   3420
ctaccaagac gaagaggatg aagaggatga ggaggcagat tgccttgaat atattgacaa   3480
tactgataag ataatatatc ttttatatag aagatatcgc cgtatgtaag gatttcaggg   3540
ggcaaggcat aggcagcgcg cttatcaata tatctataga atgggcaaag cataaaaact   3600
tgcatggact aatgcttgaa acccaggaca ataaccttat agcttgtaaa ttctatcata   3660
attgggtaat gactccaact tattgatagt gttttatgtt cagataatgc ccgatgactt   3720
tgtcatgcag ctccaccgat tttgagaacg acagcgactt ccgtcccagc cgtgccaggt   3780
gctgcctcag attcaggtta tgccgctcaa ttcgctgcgt atatcgcttg ctgattacgt   3840
gcagctttcc cttcaggcgg gattcataca gcggccagcc atccgtcatc catatcacca   3900
cgtcaaaggg tgacagcagg ctcataagac gccccagcgt cgccatagtg cgttcaccga   3960
atacgtgcgc aacaaccgtc ttccggagac tgtcatacgc gtaaaacagc cagcgctggc   4020
gcgatttagc cccgacatag ccccactgtt cgtccatttc cgcgcagacg atgacgtcac   4080
tgcccggctg tatgcgcgag gttaccgact gcggcctgag tttttaagt gacgtaaaat    4140 cgtgttgagg ccaacgccca taatgcgggc tgttgcccgg catccaacgc cattcatggc   4200
catatcaatg atttttctggt gcgtaccggg ttgagaagcg gtgtaagtga actgcagttg   4260
ccatgtttta cggcagtgag agcagagata gcgctgatgt ccggcggtgc ttttgccgtt   4320
acgcaccacc ccgtcagtag ctgaacagga gggacagctg atagacacag aagccactgg   4380
agcacctcaa aaacaccatc atacactaaa tcagtaagtt ggcagcatca cccataattg   4440
tggtttcaaa atcggctccg tcgatactat gttatacgcc aactttgaaa acaactttga   4500
aaaagctgtt ttctggtatt taaggtttta gaatgcaagg aacagtgaat tggagttcgt   4560
cttgttataa ttagcttctt ggggtatctt taaatactgt agaaaagagg aaggaaataa   4620
taaatggcta aaatgagaat atcaccggaa ttgaaaaaac tgatcgaaaa ataccgctgc   4680
gtaaaagata cggaaggaat gtctcctgct aaggtatata agctggtggg agaaaatgaa   4740
aacctatatt taaaaatgac ggacagccgg tataaaggga ccacctatga tgtggaacgg   4800
gaaaaggaca tgatgctatg gctggaagga aagctgcctg ttccaaaggt cctgcacttt   4860
gaacggcatg atggctggag caatctgctc atgagtgagg ccgatggcgt cctttgctcg   4920
gaagagtatg aagatgaaca aagccctgaa aagattatcg agctgtatgc ggagtgcatc   4980
aggctctttc actccatcga catatcggat tgtccctata cgaatagctt agacagccgc   5040
ttagccgaat tggattactt actgaataac gatctggccg atgtggattg cgaaactgg    5100 gaagaagaca ctccatttaa agatccgcgc gagctgtatg attttttaaa gacggaaaag   5160
cccgaagagg aacttgtctt ttcccacggc gacctgggag acagcaacat ctttgtgaaa   5220
gatggcaaag taagtggctt tattgatctt gggagaagcg gcagggcgga caagtggtat   5280
gacattgcct tctgcgtccg gtcgatcagg gaggatatcg gggaagaaca gtatgtcgag   5340
ctattttttg acttactggg gatcaagcct gattgggaga aaataaaata ttatatttta   5400
ctggatgaat tgttttagta cctagatgtg gcgcaacgat gccggcgaca agcaggagcg   5460
caccgacttc ttccgcatca agtgttttgg ctctcaggcc gaggcccacg gcaagtattt   5520
```

-continued

```
gggcaagggg tcgctggtat tcgtgcaggg caagattcgg aataccaagt acgagaagga    5580
cggccagacg gtctacggga ccgacttcat tgccgataag gtggattatc tggacaccaa    5640
ggcaccaggc gggtcaaatc aggaataagg gcacattgcc ccggcgtgag tcggggcaat    5700
cccgcaagga gggtgaatga atcggacgtt tgaccggaag gcatacaggc aagaactgat    5760
cgacgcgggg ttttccgccg aggatgccga aaccatcgca agccgcaccg tcatgcgtgc    5820
gccccgcgaa accttccagt ccgtcggctc gatggtccag caagctacgg ccaagatcga    5880
gcgcgacagc gtgcaactgg ctcccccctgc cctgcccgcg ccatcggccg ccgtgggagcg    5940 ttcgcgtcgt ctcgaacagg aggcggcagg tttggcgaag tcgatgacca tcgacacgcg    6000
aggaactatg acgaccaaga agcgaaaaac cgccggcgag gacctggcaa acaggtcag    6060 cgaggccaag caggccgcgt tgctgaaaca cacgaagcag cagatcaagg aaatgcagct    6120
ttccttgttc gatattgcgc cgtggccgga cacgatgcga gcgatgccaa acgacacggc    6180
ccgctctgcc ctgttcacca cgcgcaacaa gaaaatcccg cgcgaggcgc tgcaaaacaa    6240
ggtcattttc cacgtcaaca aggacgtgaa gatcacctac accggcgtcg agctgcgggc    6300
cgacgatgac gaactggtgt ggcagcaggt gttggagtac gcgaagcgca ccctatcgg    6360 cgagccgatc accttcacgt tctacgagct ttgccaggac ctgggctggt cgatcaatgg    6420
ccggtattac acgaaggccg aggaatgcct gtcgcgccta caggcgacgg cgatgggctt    6480
cacgtccgac cgcgttgggc acctggaatc ggtgtcgctg ctgcaccgct tccgcgtcct    6540
ggaccgtggc aagaaaacgt cccgttgcca ggtcctgatc gacgaggaaa tcgtcgtgct    6600
gtttgctggc gaccactaca cgaaattcat atgggagaag taccgcaagc tgtcgccgac    6660
ggcccgacgg atgttcgact atttcagctc gcaccgggag ccgtacccgc tcaagctgga    6720
aaccttccgc ctcatgtgcg gatcggattc cacccgcgtg aagaagtggc gcgagcaggt    6780
cggcgaagcc tgcgaagagt tgcgaggcag cggcctggtg aacacgcct gggtcaatga    6840 tgacctggtg cattgcaaac gctagggcct tgtgggggtca gttccggctg ggggttcagc    6900
agccagcgct ttactggcat tcaggaaca agcgggcact gctcgacgca cttgcttcgc    6960
tcagtatcgc tcgggacgca cggcgcgctc tacgaactgc cgataaacag aggattaaaa    7020
ttgacaattg tgattaaggc tcagattcga cggcttggag cggccgacgt gcaggatttc    7080
cgcgagatcc gattgtcggc cctgaagaaa gctccagaga tgttcgggtc cgtttacgag    7140
cacgaggaga aaaagcccat ggaggcgttc gctgaacggt tgcgagatgc cgtggcattc    7200
ggcgcctaca tcgacggcga gatcattggg ctgtcggtct tcaaacagga ggacggcccc    7260
aaggacgctc acaaggcgca tctgtccggc gttttcgtgg agcccgaaca gcgaggccga    7320
ggggtcgccg gtatgctgct gcgggcgttg ccggcgggtt tattgctcgt gatgatcgtc    7380
cgacagattc caacgggaat ctggtggatg cgcatcttca tcctcggcgc acttaatatt    7440
tcgctattct ggagcttgtt gtttatttcg gtctaccgcc tgccgggcgg ggtcgcggcg    7500
acggtaggcg ctgtgcagcc gctgatggtc gtgttcatct ctgccgctct gctaggtagc    7560
ccgatacgat tgatggcggt cctggggggct atttgcggaa ctgcgggcgt ggcgctgttg    7620
gtgttgacac caaacgcagc gctagatcct gtcggcgtcg cagcgggcct ggcggggggcg    7680 gtttccatgg cgttcggaac cgtgctgacc cgcaagtggc aacctcccgt gcctctgctc    7740
acctttaccg cctggcaact ggcggccgga ggacttctgc tcgttccagt agctttagtg    7800
tttgatccgc caatcccgat gcctacagga accaatgttc tcggcctggc gtggctcggc    7860
```

```
ctgatcggag cgggtttaac ctacttcctt tggttccggg ggatctcgcg actcgaacct    7920
acagttgttt ccttactggg cttctcagc cccagatctg gggtcgatca gccggggatg     7980
catcaggccg acagtcggaa cttcgggtcc ccgacctgta ccattcggtg agcaatggat    8040
aggggagttg atatcgtcaa cgttcacttc taaagaaata gcgccactca gcttcctcag   8100
cggctttatc cagcgatttc ctattatgtc ggcatagttc tcaagatcga cagcctgtca    8160
cggttaagcg agaaatgaat aagaaggctg ataattcgga tctctgcgag ggagatgata   8220
tttgatcaca ggcagcaacg ctctgtcatc gttacaatca acatgctacc ctccgcgaga   8280
tcatccgtgt ttcaaacccg gcagcttagt tgccgttctt ccgaatagca tcggtaacat    8340
gagcaaagtc tgccgcctta aacggctct cccgctgacg ccgtcccgga ctgatgggct    8400
gcctgtatcg agtggtgatt ttgtgccgag ctgccggtcg gggagctgtt ggctggctgg   8460
tggcaggata tattgtggtg taaacaaatt gacgcttaga caacttaata acacattgcg   8520
gacgttttta atgtactggg gtggttttc ttttcaccag tgagacgggc aacagctgat    8580
tgcccttcac cgcctggccc tgagagagtt gcagcaagcg gtccacgctg gtttgcccca   8640
gcaggcgaaa atcctgtttg atggtggttc cgaaatcggc aaaatccctt ataaatcaaa   8700
agaatagccc gagatagggt tgagtgttgt tccagtttgg aacaagagtc cactattaaa   8760
gaacgtggac tccaacgtca aagggcgaaa aaccgtctat cagggcgatg gcccactacg    8820
tgaaccatca cccaaatcaa gtttttggg gtcgaggtgc cgtaaagcac taaatcggaa    8880
ccctaaaggg agccccgat ttagagcttg acggggaaag ccggcgaacg tggcgagaaa     8940
ggaagggaag aaagcgaaag gagcgggcgc cattcaggct gcgcaactgt gggaagggc    9000 gatcggtgcg ggcctcttcg ctattacgcc agctggcgaa aggggatgt gctgcaaggc     9060 gattaagttg ggtaacgcca gggttttccc agtcacgacg ttgtaaaacg acggccagtg    9120
aattaattcc catcttgaaa gaaatatagt ttaaatattt attgataaaa taacaagtca   9180
ggtattatag tccaagcaaa aacataaatt tattgatgca agtttaaatt cagaaatatt   9240
tcaataactg attatatcag ctggtacatt gccgtagatg aaagactgag tgcgatatta   9300
tgtgtaatac ataaattgat gatatagcta gcttagctca tcgggggatc cgtcgaagct   9360
agcttgggtc ccgctcagaa gaactcgtca agaaggcgat agaaggcgat gcgctgcgaa   9420
tcgggagcgg cgataccgta aagcacgagg aagcggtcag cccattcgcc gccaagctct   9480
tcagcaatat cacgggtagc caacgctatg tcctgatagc ggtccgccac acccagccgg   9540
ccacagtcga tgaatccaga aaagcggcca ttttccacca tgatattcgg caagcaggca   9600
tcgccatggg tcacgacgag atcctcgccg tcgggcatgc gcgccttgag cctggcgaac   9660
agttcggctg gcgcgagccc ctgatgctct tcgtccagat catcctgatc gacaagaccg   9720
gcttccatcc gagtacgtgc tcgctcgatg cgatgtttcg cttggtggtc gaatgggcag   9780
gtagccggat caagcgtatg cagccgccgc attgcatcag ccatgatgga ctttctcg     9840 gcaggagcaa ggtgagatga caggagatcc tgccccggca cttcgcccaa tagcagccag   9900
tcccttcccg cttcagtgac aacgtcgagc acagctgcgc aaggaacgcc cgtcgtggcc   9960
agccacgata ccgcgctgc ctcgtcctgc agttcattca gggcaccgga caggtcggtc    10020
ttgacaaaaa gaaccgggcg cccctgcgct gacagccgga acacgcggc atcagagcag   10080 ccgattgtct gttgtgccca gtcatagccg aatagcctct ccacccaagc ggccggagaa   10140
cctgcgtgca atccatcttg ttcaatccaa gctcccatgg gccctcgact agagtcgaga   10200
tctggattga gagtgaatat gagactctaa ttggataccg aggggaattt atggaacgtc   10260
```

```
agtggagcat ttttgacaag aaatatttgc tagctgatag tgaccttagg cgacttttga   10320
acgcgcaata atggtttctg acgtatgtgc ttagctcatt aaactccaga aacccgcggc   10380
tgagtggctc cttcaacgtt gcggttctgt cagttccaaa cgtaaaacgg cttgtcccgc   10440
gtcatcggcg ggggtcataa cgtgactccc ttaattctcc gctcatgatc ttgatcccct   10500
gcgccatcag atccttggcg gcaagaaagc catccagttt actttgcagg gcttcccaac   10560
cttaccagag ggcgccccag ctggcaattc cggttcgctt gctgtccata aaaccgccca   10620
gtctagctat cgccatgtaa gcccactgca agctacctgc tttctctttg cgcttgcgtt   10680
ttcccttgtc cagatagccc agtagctgac attcatccgg ggtcagcacc gtttctgcgg   10740
actggctttc tacgtgttcc gcttccttta gcagcccttg cgccctgagt gcttgcggca   10800
gcgtgaagct tgcatgcctg caggtcgacg gcgcgccgag ctcctcgagc aaatttacac   10860
attgccacta aacgtctaaa cccttgtaat ttgttttttgt tttactatgt gtgttatgta   10920
tttgatttgc gataaatttt tatatttggt actaaattta taacacccttt tatgctaacg   10980
tttgccaaca cttagcaatt tgcaagttga ttaattgatt ctaaattatt tttgtcttct   11040
aaatacatat actaatcaac tggaaatgta aatatttgct aatatttcta ctataggaga   11100
attaaagtga gtgaatatgg taccacaagg tttggagatt taattgttgc aatgctgcat   11160
ggatggcata taccaaaac attcaataat tcttgaggat aataatggta ccacacaaga   11220
tttgaggtgc atgaacgtca cgtggacaaa aggtttagta attttcaag acaacaatgt   11280
taccacacac aagttttgag gtgcatgcat ggatgccctg tggaaagttt aaaaatattt   11340
tggaaatgat ttgcatggaa gccatgtgta aaaccatgac atccacttgg aggatgcaat   11400
aatgaagaaa actacaaatt tacatgcaac tagttatgca tgtagtctat ataatgagga   11460
ttttgcaata ctttcattca tacacactca ctaagtttta cacgattata atttcttcat   11520
agccagccca ccgcggtggg cggccgcctg cagtctagaa ggcctcctgc tttaatgaga   11580
tatgcgagac gcctatgatc gcatgatatt tgctttcaat tctgttgtgc acgttgtaaa   11640
aaacctgagc atgtgtagct cagatcctta ccgccggttt cggttcattc taatgaatat   11700
atcacccgtt actatcgtat ttttatgaat aatattctcc gttcaattta ctgattgtcc   11760
gtcgagcaaa tttacacatt gccactaaac gtctaaaccc ttgtaatttg ttttttgttt   11820
actatgtgtg ttatgtattt gatttgcgat aaatttttat atttggtact aaatttataa   11880
cacctttttat gctaacgttt gccaacactt agcaatttgc aagttgatta attgattcta   11940
aattattttt gtcttctaaa tacatatact aatcaactgg aaatgtaaat atttgctaat   12000
atttctacta taggagaatt aaagtgagtg aatatggtac cacaaggttt ggagatttaa   12060
ttgttgcaat gctgcatgga tggcatatac accaaacatt caataattct tgaggataat   12120
aatggtacca cacaagattt gaggtgcatg aacgtcacgt ggacaaaagg tttagtaatt   12180
tttcaagaca acaatgttac cacacacaag ttttgaggtg catgcatgga tgccctgtgg   12240
aaagtttaaa aatattttgg aaatgatttg catggaagcc atgtgtaaaa ccatgacatc   12300
cacttggagg atgcaataat gaagaaaact acaaatttac atgcaactag ttatgcatgt   12360
agtctatata tgaggatttt gcaaatactt tcattcatac acactcacta agttttacac   12420
gattataatt tcttcatagc cagcggatcc gatatcgggc ccgctagcgt taaccctgct   12480
ttaatgagat atgcgagacg cctatgatcg catgatattt gctttcaatt ctgttgtgca   12540
cgttgtaaaa aacctgagca tgtgtagctc agatccttac cgccggtttc ggttcattct   12600
```

| | |
|---|---|
| aatgaatata tcacccgtta ctatcgtatt tttatgaata atattctccg ttcaatttac | 12660 |
| tgattgtccg tcgacgaatt cgagctcggc gcgcctctag aggatcgatg aattcagatc | 12720 |
| ggctgagtgg ctccttcaac gttgcggttc tgtcagttcc aaacgtaaaa cggcttgtcc | 12780 |
| cgcgtcatcg gcgggggtca taacgtgact cccttaattc tccgctcatg atcagattgt | 12840 |
| cgtttcccgc cttcagttta aactatcagt gtttgacagg atatattggc gggtaaacct | 12900 |
| aagagaaaag agcgtttatt agaataatcg gatatttaaa agggcgtgaa aaggtttatc | 12960 |
| cttcgtccat ttgtatgtgc atgccaacca cagggttccc ca | 13002 |

<210> SEQ ID NO 42
<211> LENGTH: 13905
<212> TYPE: DNA
<213> ORGANISM: Unknown
<220> FEATURE:
<223> OTHER INFORMATION: Plant expression vector with three
      promoter-terminator expression cassettes

<400> SEQUENCE: 42

| | |
|---|---|
| gatctggcgc cggccagcga gacgagcaag attggccgcc gcccgaaacg atccgacagc | 60 |
| gcgcccagca caggtgcgca ggcaaattgc accaacgcat acagcgccag cagaatgcca | 120 |
| tagtgggcgg tgacgtcgtt cgagtgaacc agatcgcgca ggaggcccgg cagcaccggc | 180 |
| ataatcaggc cgatgccgac agcgtcgagc gcgacagtgc tcagaattac gatcaggggt | 240 |
| atgttgggtt tcacgtctgg cctccggacc agcctccgct ggtccgattg aacgcgcgga | 300 |
| ttctttatca ctgataagtt ggtggacata ttatgtttat cagtgataaa gtgtcaagca | 360 |
| tgacaaagtt gcagccgaat acagtgatcc gtgccgccct ggacctgttg aacgaggtcg | 420 |
| gcgtagacgg tctgacgaca cgcaaactgg cggaacggtt gggggttcag cagccggcgc | 480 |
| tttactggca cttcaggaac aagcgggcgc tgctcgacgc actggccgaa gccatgctgg | 540 |
| cggagaatca tacgcattcg gtgccgagag ccgacgacga ctggcgctca tttctgatcg | 600 |
| ggaatgcccg cagcttcagg caggcgctgc tcgcctaccg cgatggcgcg cgcatccatg | 660 |
| ccggcacgcg accgggcgca ccgcagatgg aaacggccga cgcgcagctt cgcttcctct | 720 |
| gcgaggcggg ttttccggcc ggggacgccg tcaatgcgct gatgacaatc agctacttca | 780 |
| ctgttggggc cgtgcttgag gagcaggccg gcgacagcga tgccggcgag cgcggcggca | 840 |
| ccgttgaaca ggctccgctc tcgccgctgt tgcgggccgc gatagacgcc ttcgacgaag | 900 |
| ccggtccgga cgcagcgttc gagcaggacc tcgcggtgat tgtcgatgga ttggcgaaaa | 960 |
| ggaggctcgt tgtcaggaac gttgaaggac cgagaaaggg tgacgattga tcaggaccgc | 1020 |
| tgccggagcg caaccactc actacagcag agccatgtag acaacatccc ctccccttt | 1080 |
| ccaccgcgtc agacgcccgt agcagcccgc tacgggcttt tcatgccct gccctagcgt | 1140 |
| ccaagcctca cggccgcgct cggcctctct ggcggccttc tggcgctctt ccgcttcctc | 1200 |
| gctcactgac tcgctgcgct cggtcgttcg gctgcggcga gcggtatcag ctcactcaaa | 1260 |
| ggcggtaata cggttatcca cagaatcagg ggataacgca ggaaagaaca tgtgagcaaa | 1320 |
| aggccagcaa aaggccagga accgtaaaaa ggccgcgttg ctggcgtttt tccataggct | 1380 |
| ccgccccct gacgagcatc acaaaaatcg acgctcaagt cagaggtggc gaaacccgac | 1440 |
| aggactataa agataccagg cgtttccccc tggaagctcc ctcgtgcgct ctcctgttcc | 1500 |
| gaccctgccg cttaccggat acctgtccgc ctttctccct tcgggaagcg tggcgctttt | 1560 |
| ccgctgcata ccctgcttc ggggtcatta tagcgatttt ttcggtatat ccatcctttt | 1620 |

```
tcgcacgata tacaggattt tgccaaaggg ttcgtgtaga cttttccttgg tgtatccaac    1680
ggcgtcagcc gggcaggata ggtgaagtag cccacccgc gagcgggtgt tccttcttca     1740
ctgtccctta ttcgcacctg gcggtgctca acgggaatcc tgctctgcga ggctggccgg    1800
ctaccgccgg cgtaacagat gagggcaagc ggatggctga tgaaaccaag ccaaccagga    1860
agggcagccc acctatcaag gtgtactgcc ttccagacga acgaagagcg attgaggaaa    1920
aggcggcggc ggccggcatg agcctgtcgg cctacctgct ggccgtcggc cagggctaca    1980
aaatcacggg cgtcgtggac tatgagcacg tccgcgagct ggcccgcatc aatggcgacc    2040
tgggccgcct gggcggcctg ctgaaactct ggctcaccga cgacccgcgc acggcgcggt    2100
tcggtgatgc cacgatcctc gccctgctgg cgaagatcga agagaagcag gacgagcttg    2160
gcaaggtcat gatgggcgtg gtccgcccga gggcagagcc atgactttt tagccgctaa     2220
aacggccggg gggtgcgcgt gattgccaag cacgtcccca tgcgctccat caagaagagc    2280
gacttcgcga agctggtgaa gtacatcacc gacgagcaag gcaagaccga cgcctttgc     2340
gacgctcacc gggctggttg ccctcgccgc tgggctggcg gccgtctatg gccctgcaaa    2400
cgcgccagaa acgccgtcga agccgtgtgc gagacaccgc ggccgccggc gttgtggata    2460
cctcgcggaa aacttggccc tcactgacag atgaggggcg gacgttgaca cttgaggggc    2520
cgactcaccc ggcgcggcgt tgacagatga ggggcaggct cgatttcggc cggcgacgtg    2580
gagctggcca gcctcgcaaa tcggcgaaaa cgcctgattt tacgcgagtt tcccacagat    2640
gatgtggaca gcctgggga taagtgcccct gcggtattga cacttgaggg gcgcgactac    2700
tgacagatga ggggcgcgat ccttgacact tgaggggcag agtgctgaca gatgaggggc    2760
gcacctattg acatttgagg ggctgtccac aggcagaaaa tccagcatt gcaagggttt      2820
ccgcccgttt ttcggccacc gctaacctgt cttttaacct gcttttaaac caatatttat    2880
aaaccttgtt tttaaccagg gctgcgccct gtgcgcgtga ccgcgcacgc cgaagggggg    2940
tgcccccccct tctcgaaccc tcccggcccg ctaacgcggg cctccatcc ccccagggc     3000
tgcgccctc ggccgcgaac ggcctcaccc caaaaatggc agcgctggca gtccttgcca    3060
ttgccgggat cggggcagta acgggatggg cgatcagccc gagcgcgacg cccggaagca    3120
ttgacgtgcc gcaggtgctg gcatcgacat tcagcgacca ggtgccgggc agtgagggcg    3180
gcggcctggg tggcggcctg cccttcactt cggccgtcgg ggcattcacg gacttcatgg    3240
cggggccggc aattttttacc ttgggcattc ttggcatagt ggtcgcgggt gccgtgctcg    3300
tgttcgggg tgcgataaac ccagcgaacc atttgaggtg ataggtaaga ttataccgag    3360
gtatgaaaac gagaattgga cctttacaga attactctat gaagcgccat atttaaaaag    3420
ctaccaagac gaagaggatg aagaggatga ggaggcagat tgccttgaat atattgacaa    3480
tactgataag ataatatatc ttttatatag aagatatcgc cgtatgtaag gatttcaggg    3540
ggcaaggcat aggcagcgcg cttatcaata tatctataga atgggcaaag cataaaaact    3600
tgcatggact aatgcttgaa acccaggaca ataaccttat agcttgtaaa ttctatcata    3660
attgggtaat gactccaact tattgatagt gttttatgtt cagataatgc ccgatgactt    3720
tgtcatgcag ctccaccgat tttgagaacg acagcgactt ccgtcccagc cgtgccaggt    3780
gctgcctcag attcaggtta tgccgctcaa ttcgctgcgt atatcgcttg ctgattacgt    3840
gcagctttcc cttcaggcgg gattcataca gcggccagcc atccgtcatc catatcacca    3900
cgtcaaaggg tgacagcagg ctcataagac gccccagcgt cgccatagtg cgttcaccga    3960
atacgtgcgc aacaaccgtc ttccggagac tgtcatacgc gtaaaacagc cagcgctggc    4020
```

```
gcgatttagc cccgacatag ccccactgtt cgtccatttc cgcgcagacg atgacgtcac    4080
tgcccggctg tatgcgcgag gttaccgact gcggcctgag ttttttaagt gacgtaaaat    4140
cgtgttgagg ccaacgccca taatgcgggc tgttgcccgg catccaacgc cattcatggc    4200
catatcaatg attttctggt gcgtaccggg ttgagaagcg gtgtaagtga actgcagttg    4260
ccatgtttta cggcagtgag agcagagata gcgctgatgt ccggcggtgc ttttgccgtt    4320
acgcaccacc ccgtcagtag ctgaacagga gggacagctg atagacacag aagccactgg    4380
agcacctcaa aaacaccatc atacactaaa tcagtaagtt ggcagcatca cccataattg    4440
tggtttcaaa atcggctccg tcgatactat gttatacgcc aactttgaaa acaactttga    4500
aaaagctgtt ttctggtatt taaggtttta gaatgcaagg aacagtgaat tggagttcgt    4560
cttgttataa ttagcttctt ggggtatctt taaatactgt agaaagagg aaggaaataa    4620 taaatggcta aaatgagaat atcaccggaa ttgaaaaaac tgatcgaaaa ataccgctgc    4680
gtaaaagata cggaaggaat gtctcctgct aaggtatata agctggtggg agaaaatgaa    4740
aacctatatt taaaaatgac ggacagccgg tataaaggga ccacctatga tgtggaacgg    4800
gaaaaggaca tgatgctatg gctggaagga aagctgcctg ttccaaaggt cctgcacttt    4860
gaacggcatg atggctggag caatctgctc atgagtgagg ccgatggcgt cctttgctcg    4920
gaagagtatg aagatgaaca aagccctgaa aagattatcg agctgtatgc ggagtgcatc    4980
aggctctttc actccatcga catatcggat tgtccctata cgatagctt agacagccgc    5040 ttagccgaat tggattactt actgaataac gatctggccg atgtggattg cgaaaactgg    5100
gaagaagaca ctccatttaa agatccgcgc gagctgtatg attttttaaa gacggaaaag    5160
cccgaagagg aacttgtctt ttcccacggc gacctgggga cagcaacat ctttgtgaaa    5220 gatggcaaag taagtggctt tattgatctt gggagaagcg gcagggcgga caagtggtat    5280
gacattgcct tctgcgtccg gtcgatcagg gaggatatcg gggaagaaca gtatgtcgag    5340 ctatttttg acttactggg gatcaagcct gattgggaga aaataaaata ttatatttta    5400
ctggatgaat tgttttagta cctagatgtg gcgcaacgat gccggcgaca agcaggagcg    5460
caccgacttc ttccgcatca agtgttttgg ctctcaggcc gaggcccacg gcaagtattt    5520
gggcaagggg tcgctggtat tcgtgcaggg caagattcgg aataccaagt acgagaagga    5580
cggccagacg gtctacggga ccgacttcat tgccgataag gtggattatc tggacaccaa    5640
ggcaccaggc gggtcaaatc aggaataagg gcacattgcc ccggcgtgag tcggggcaat    5700
cccgcaagga gggtgaatga atcggacgtt tgaccggaag gcatacaggc aagaactgat    5760
cgacgcgggg ttttccgccg aggatgccga aaccatcgca agccgcaccg tcatgcgtgc    5820
gccccgcgaa accttccagt ccgtcggctc gatggtccag caagctacgg ccaagatcga    5880
gcgcgacagc gtgcaactgg ctcccccctgc cctgcccgcg ccatcggccg ccgtggagcg    5940
ttcgcgtcgt ctcgaacagg aggcggcagg tttggcgaag tcgatgacca tcgacacgcg    6000
aggaactatg acgaccaaga agcgaaaaac cgccggcgag gacctggcaa acaggtcag    6060 cgaggccaag caggccgcgt tgctgaaaca cacgaagcag cagatcaagg aaatgcagct    6120
ttccttgttc gatattgcgc cgtgccgga cacgatgcga gcgatgccaa cgacacggc    6180 ccgctctgcc ctgttcacca cgcgcaacaa gaaaatcccg cgcgaggcgc tgcaaaacaa    6240
ggtcattttc cacgtcaaca aggacgtgaa gatcacctac accggcgtcg agctgcgggc    6300
cgacgatgac gaactggtgt ggcagcaggt gttggagtac gcgaagcgca cccctatcgg    6360
```

```
cgagccgatc accttcacgt tctacgagct ttgccaggac ctgggctggt cgatcaatgg   6420
ccggtattac acgaaggccg aggaatgcct gtcgcgccta caggcgacgg cgatgggctt   6480
cacgtccgac cgcgttgggc acctggaatc ggtgtcgctg ctgcaccgct tccgcgtcct   6540
ggaccgtggc aagaaaacgt cccgttgcca ggtcctgatc gacgaggaaa tcgtcgtgct   6600
gtttgctggc gaccactaca cgaaattcat atgggagaag taccgcaagc tgtcgccgac   6660
ggcccgacgg atgttcgact atttcagctc gcaccgggag ccgtacccgc tcaagctgga   6720
aaccttccgc ctcatgtgcg gatcggattc caccccgcgtg aagaagtggc gcgagcaggt   6780
cggcgaagcc tgcgaagagt tgcgaggcag cggcctggtg aacacgcct gggtcaatga   6840 tgacctggtg cattgcaaac gctagggcct tgtgggtca gttccggctg ggggttcagc   6900
agccagcgct ttactggcat ttcaggaaca agcgggcact gctcgacgca cttgcttcgc   6960
tcagtatcgc tcgggacgca cggcgcgctc tacgaactgc cgataaacag aggattaaaa   7020
ttgacaattg tgattaaggc tcagattcga cggcttggag cggccgacgt gcaggatttc   7080
cgcgagatcc gattgtcggc cctgaagaaa gctccagaga tgttcgggtc cgtttacgag   7140
cacgaggaga aaaagcccat ggaggcgttc gctgaacggt tgcgagatgc cgtggcattc   7200
ggcgcctaca tcgacggcga gatcattggg ctgtcggtct tcaaacagga ggacggcccc   7260
aaggacgctc acaaggcgca tctgtccggc gttttcgtgg agcccgaaca gcgaggccga   7320
ggggtcgccg gtatgctgct gcgggcgttg ccggcgggtt tattgctcgt gatgatcgtc   7380
cgacagattc caacgggaat ctggtggatg cgcatcttca tcctcggcgc acttaatatt   7440
tcgctattct ggagcttgtt gtttattccg gtctaccgcc tgccgggcgg ggtcgcggcg   7500
acggtaggcg ctgtgcagcc gctgatggtc gtgttcatct ctgccgctct gctaggtagc   7560
ccgatacgat tgatggcggt cctgggggct atttgcggaa ctgcgggcgt ggcgctgttg   7620
gtgttgacac caaacgcagc gctagatcct gtcggcgtcg cagcgggcct ggcggggcg   7680 gtttccatgg cgttcggaac cgtgctgacc cgcaagtggc aacctcccgt gcctctgctc   7740
acctttaccg cctggcaact ggcggccgga ggacttctgc tcgttccagt agctttagtg   7800
tttgatccgc caatcccgat gcctacagga accaatgttc tcggcctggc gtggctcggc   7860
ctgatcggag cgggtttaac ctacttcctt tggttccggg ggatctcgcg actcgaacct   7920
acagttgttt ccttactggg cttttctcagc cccagatctg gggtcgatca gccggggatg   7980
catcaggccg acagtcggaa cttcgggtcc ccgacctgta ccattcggtg agcaatggat   8040
aggggagttg atatcgtcaa cgttcacttc taaagaaata gcgccactca gcttcctcag   8100
cggctttatc cagcgatttc ctattatgtc ggcatagttc tcaagatcga cagcctgtca   8160
cggttaagcg agaaatgaat aagaaggctg ataattcgga tctctgcgag ggagatgata   8220
tttgatcaca ggcagcaacg ctctgtcatc gttacaatca acatgctacc ctccgcgaga   8280
tcatccgtgt ttcaaacccg gcagcttagt tgccgttctt ccgaatagca tcggtaacat   8340
gagcaaagtc tgccgcctta caacggctct cccgctgacg ccgtcccgga ctgatgggct   8400
gcctgtatcg agtggtgatt ttgtgccgag ctgccggtcg gggagctgtt ggctggctgg   8460
tggcaggata tattgtggtg taaacaaatt gacgcttaga caacttaata acacattgcg   8520
gacgttttta atgtactggg gtggtttttc ttttcaccag tgagacgggc aacagctgat   8580
tgcccttcac cgcctggccc tgagagagtt gcagcaagcg gtccacgctg gtttgcccca   8640
gcaggcgaaa atcctgtttg atggtggttc cgaaatcggc aaaatccctt ataaatcaaa   8700
agaatagccc gagatagggt tgagtgttgt tccagtttgg aacaagagtc cactattaaa   8760
```

```
gaacgtggac tccaacgtca aagggcgaaa aaccgtctat cagggcgatg gcccactacg   8820
tgaaccatca cccaaatcaa gttttttggg gtcgaggtgc cgtaaagcac taaatcggaa   8880
ccctaaaggg agcccccgat ttagagcttg acggggaaag ccggcgaacg tggcgagaaa   8940
ggaagggaag aaagcgaaag gagcgggcgc cattcaggct gcgcaactgt tgggaagggc   9000
gatcggtgcg ggcctcttcg ctattacgcc agctggcgaa aggggatgt gctgcaaggc    9060 gattaagttg ggtaacgcca gggttttccc agtcacgacg ttgtaaaacg acggccagtg   9120
aattaattcc catcttgaaa gaaatatagt ttaaatattt attgataaaa taacaagtca   9180
ggtattatag tccaagcaaa aacataaatt tattgatgca agtttaaatt cagaaatatt   9240
tcaataactg attatatcag ctggtacatt gccgtagatg aaagactgag tgcgatatta   9300
tgtgtaatac ataaattgat gatatagcta gcttagctca tcgggggatc cgtcgaagct   9360
agcttgggtc ccgctcagaa gaactcgtca agaaggcgat agaaggcgat gcgctgcgaa   9420
tcgggagcgg cgataccgta aagcacgagg aagcggtcag cccattcgcc gccaagctct   9480
tcagcaatat cacgggtagc caacgctatg tcctgatagc ggtccgccac acccagccgg   9540
ccacagtcga tgaatccaga aaagcggcca ttttccacca tgatattcgg caagcaggca   9600
tcgccatggg tcacgacgag atcctcgccg tcgggcatgc gcgccttgag cctggcgaac   9660
agttcggctg gcgcgagccc ctgatgctct tcgtccagat catcctgatc gacaagaccg   9720
gcttccatcc gagtacgtgc tcgctcgatg cgatgtttcg cttggtggtc gaatgggcag   9780
gtagccggat caagcgtatg cagccgccgc attgcatcag ccatgatgga tactttctcg   9840
gcaggagcaa ggtgagatga caggagatcc tgccccggca cttcgcccaa tagcagccag   9900
tcccttcccg cttcagtgac aacgtcgagc acagctgcgc aaggaacgcc cgtcgtggcc   9960
agccacgata gccgcgctgc ctcgtcctgc agttcattca gggcaccgga caggtcggtc  10020
ttgacaaaaa gaaccgggcg cccctgcgct gacagccgga acacggcggc atcagagcag  10080
ccgattgtct gttgtgccca gtcatagccg aatagcctct ccacccaagc ggccggagaa  10140
cctgcgtgca atccatcttg ttcaatccaa gctcccatgg gccctcgact agagtcgaga  10200
tctggattga gagtgaatat gagactctaa ttggataccg agggaatttt atggaacgtc  10260
agtggagcat ttttgacaag aaatatttgc tagctgatag tgaccttagg cgacttttga  10320
acgcgcaata atggtttctg acgtatgtgc ttagctcatt aaactccaga aacccgcggc  10380
tgagtggctc cttcaacgtt gcggttctgt cagttccaaa cgtaaaacgg cttgtcccgc  10440
gtcatcggcg ggggtcataa cgtgactccc ttaattctcc gctcatgatc ttgatcccct  10500
gcgccatcag atccttggcg gcaagaaagc catccagttt actttgcagg gcttcccaac  10560
cttaccagag ggcgccccag ctggcaattc cggttcgctt gctgtccata aaaccgccca  10620
gtctagctat cgccatgtaa gcccactgca agctacctgc tttctctttg cgcttgcgtt  10680
ttcccttgtc cagatagccc agtagctgac attcatccgg ggtcagcacc gtttctgcgg  10740
actggctttc tacgtgttcc gcttccttta gcagcccttg cgccctgagt gcttgcggca  10800
gcgtgaagct tgcatgcctg caggtcgacg gcgcgccgag ctcctcgagc aaatttacac  10860
attgccacta aacgtctaaa cccttgtaat ttgttttgt tttactatgt gtgttatgta   10920
tttgatttgc gataaatttt tatatttggt actaaattta taacacccttt tatgctaacg  10980 tttgccaaca cttagcaatt tgcaagttga ttaattgatt ctaaattatt tttgtcttct  11040
aaatacatat actaatcaac tggaaatgta aatatttgct aatatttcta ctataggaga  11100
```

```
attaaagtga gtgaatatgg taccacaagg tttggagatt taattgttgc aatgctgcat    11160
ggatggcata tacaccaaac attcaataat tcttgaggat aataatggta ccacacaaga    11220
tttgaggtgc atgaacgtca cgtggacaaa aggtttagta attttttcaag acaacaatgt   11280 taccacacac aagttttgag gtgcatgcat ggatgccctg tggaaagttt aaaaatattt    11340
tggaaatgat ttgcatggaa gccatgtgta aaaccatgac atccacttgg aggatgcaat    11400
aatgaagaaa actacaaatt tacatgcaac tagttatgca tgtagtctat ataatgagga    11460
ttttgcaata ctttcattca tacacactca ctaagttttta cacgattata atttcttcat    11520
agccagccca ccgcggtggg cggccgcctg cagtctagaa ggcctcctgc tttaatgaga    11580
tatgcgagac gcctatgatc gcatgatatt tgctttcaat tctgttgtgc acgttgtaaa    11640
aaacctgagc atgtgtagct cagatcctta ccgccggttt cggttcattc taatgaatat    11700
atcacccgtt actatcgtat tttatgaat  aatattctcc gttcaattta ctgattgtcc    11760
gtcgagcaaa tttacacatt gccactaaac gtctaaaccc ttgtaatttg tttttgtttt    11820
actatgtgtg ttatgtattt gatttgcgat aaattttttat atttggtact aaatttataa    11880
caccttttat gctaacgttt gccaacactt agcaatttgc aagttgatta attgattcta    11940 aattatttttt gtcttctaaa tacatatact aatcaactgg aaatgtaaat atttgctaat    12000
atttctacta taggagaatt aaagtgagtg aatatggtac cacaaggttt ggagatttaa    12060
ttgttgcaat gctgcatgga tggcatatac accaaacatt caataattct tgaggataat    12120
aatggtacca cacaagattt gaggtgcatg aacgtcacgt ggacaaaagg tttagtaatt    12180
tttcaagaca acaatgttac cacacacaag ttttgaggtg catgcatgga tgccctgtgg    12240
aaagtttaaa aatattttgg aaatgatttg catggaagcc atgtgtaaaa ccatgacatc    12300
cacttggagg atgcaataat gaagaaaact acaaatttac atgcaactag ttatgcatgt    12360
agtctatata tgaggatttt gcaatacttt cattcatac acactcacta agttttacac    12420
gattataatt tcttcatagc cagcggatcc gatatcgggc ccgctagcgt taaccctgct    12480
ttaatgagat atgcgagacg cctatgatcg catgatattt gctttcaatt ctgttgtgca    12540
cgttgtaaaa aacctgagca tgtgtagctc agatccttac cgccggtttc ggttcattct    12600
aatgaatata tcacccgtta ctatcgtatt tttatgaata atattctccg ttcaatttac    12660
tgattgtccg tcgagcaaat ttacacattg ccactaaacg tctaaaccct tgtaatttgt    12720
ttttgtttta ctatgtgtgt tatgtatttg atttgcgata aattttttata tttggtacta    12780 aatttataac accttttatg ctaacgtttg ccaacactta gcaatttgca agttgattaa    12840
ttgattctaa attattttttg tcttctaaat acatatacta atcaactgga aatgtaaata    12900
tttgctaata tttctactat aggagaatta aagtgagtga atatggtacc acaaggtttg    12960
gagatttaat tgttgcaatg ctgcatggat ggcatataca ccaaacattc aataattctt    13020
gaggataata atggtaccac acaagatttg aggtgcatga acgtcacgtg gacaaaaggt    13080
ttagtaattt ttcaagacaa caatgttacc acacacaagt tttgaggtgc atgcatggat    13140
gccctgtgga aagtttaaaa atattttgga aatgatttgc atggaagcca tgtgtaaaac    13200
catgacatcc acttggagga tgcaataatg aagaaaacta caaatttaca tgcaactagt    13260
tatgcatgta gtctatataa tgaggatttt gcaatacttt cattcataca cactcactaa    13320
gttttacacg attataattt cttcatagcc agcagatctg ccggcatcga tcccgggcca    13380
tggcctgctt taatgagata tgcgagacgc ctatgatcgc atgatatttg ctttcaattc    13440
tgttgtgcac gttgtaaaaa acctgagcat gtgtagctca gatccttacc gccggtttcg    13500
```

-continued

| | |
|---|---|
| gttcattcta atgaatatat cacccgttac tatcgtattt ttatgaataa tattctccgt | 13560 |
| tcaatttact gattgtccgt cgacgagctc ggcgcgcctc tagaggatcg atgaattcag | 13620 |
| atcggctgag tggctccttc aacgttgcgg ttctgtcagt tccaaacgta aaacggcttg | 13680 |
| tcccgcgtca tcggcggggg tcataacgtg actcccttaa ttctccgctc atgatcagat | 13740 |
| tgtcgtttcc cgccttcagt ttaaactatc agtgtttgac aggatatatt ggcgggtaaa | 13800 |
| cctaagagaa aagagcgttt attagaataa tcggatattt aaaagggcgt gaaaaggttt | 13860 |
| atccttcgtc catttgtatg tgcatgccaa ccacagggtt cccca | 13905 |

<210> SEQ ID NO 43
<211> LENGTH: 15430
<212> TYPE: DNA
<213> ORGANISM: Unknown
<220> FEATURE:
<223> OTHER INFORMATION: Plant expression vector with two
    promoter-terminator expression cassettes,
    inserted is Physcomitrella patens elongase and desaturase
<220> FEATURE:
<221> NAME/KEY: CDS
<222> LOCATION: (11543)..(12415)
<220> FEATURE:
<221> NAME/KEY: CDS
<222> LOCATION: (13313)..(14890)

<400> SEQUENCE: 43

| | |
|---|---|
| gatctggcgc cggccagcga gacgagcaag attggccgcc gcccgaaacg atccgacagc | 60 |
| gcgcccagca caggtgcgca ggcaaattgc accaacgcat acagcgccag cagaatgcca | 120 |
| tagtgggcgg tgacgtcgtt cgagtgaacc agatcgcgca ggaggcccgg cagcaccggc | 180 |
| ataatcaggc cgatgccgac agcgtcgagc gcgacagtgc tcagaattac gatcaggggt | 240 |
| atgttgggtt tcacgtctgg cctccggacc agcctccgct ggtccgattg aacgcgcgga | 300 |
| ttctttatca ctgataagtt ggtggacata ttatgtttat cagtgataaa gtgtcaagca | 360 |
| tgacaaagtt gcagccgaat acagtgatcc gtgccgccct ggacctgttg aacgaggtcg | 420 |
| gcgtagacgt tctgacgaca cgcaaactgg cggaacggtt ggggggttcag cagccggcgc | 480 |
| tttactggca cttcaggaac aagcgggcgc tgctcgacgc actggccgaa gccatgctgg | 540 |
| cggagaatca tacgcattcg gtgccgagag ccgacgacga ctggcgctca tttctgatcg | 600 |
| ggaatgcccg cagcttcagg caggcgctgc tcgcctaccg cgatggcgcg cgcatccatg | 660 |
| ccggcacgcg accgggcgca ccgcagatgg aaacggccga cgcgcagctt cgcttcctct | 720 |
| gcgaggcggg ttttcggcc ggggacgccg tcaatgcgct gatgacaatc agctacttca | 780 |
| ctgttggggc cgtgcttgag gagcaggccg cgacagcga tgccggcgag cgcggcggca | 840 |
| ccgttgaaca ggctccgctc tcgccgctgt tgcgggccgc gatagacgcc ttcgacgaag | 900 |
| ccggtccgga cgcagcgttc gagcaggac tcgcggtgat tgtcgatgga ttggcgaaaa | 960 |
| ggaggctcgt tgtcaggaac gttgaaggac cgagaaaggg tgacgattga tcaggaccgc | 1020 |
| tgccggagcg caacccactc actacagcag agccatgtag acaacatccc ctcccccttt | 1080 |
| ccaccgcgtc agacgcccgt agcagcccgc tacgggcttt ttcatgccct gccctagcgt | 1140 |
| ccaagcctca cggccgcgct cggcctctct ggcggccttc tggcgctctt ccgcttcctc | 1200 |
| gctcactgac tcgctgcgct cggtcgttcg gctgcggcga gcggtatcag ctcactcaaa | 1260 |
| ggcggtaata cggttatcca cagaatcagg ggataacgca ggaaagaaca tgtgagcaaa | 1320 |
| aggccagcaa aaggccagga accgtaaaaa ggccgcgttg ctggcgtttt tccataggct | 1380 |

```
ccgccccct  gacgagcatc  acaaaaatcg  acgctcaagt  cagaggtggc  gaaacccgac    1440
aggactataa  agataccagg  cgtttccccc  tggaagctcc  ctcgtgcgct  ctcctgttcc    1500
gaccctgccg  cttaccggat  acctgtccgc  ctttctccct  tcgggaagcg  tggcgctttt    1560
ccgctgcata  accctgcttc  ggggtcatta  tagcgatttt  ttcggtatat  ccatccttt    1620 tcgcacgata  tacaggattt  tgccaaaggg  ttcgtgtaga  ctttccttgg  tgtatccaac    1680
ggcgtcagcc  gggcaggata  ggtgaagtag  gcccacccgc  gagcgggtgt  tccttcttca    1740 ctgtcctta   ttcgcacctg  gcggtgctca  acgggaatcc  tgctctgcga  ggctggccgg    1800
ctaccgccgg  cgtaacagat  gagggcaagc  ggatggctga  tgaaaccaag  ccaaccagga    1860
agggcagccc  acctatcaag  gtgtactgcc  ttccagacga  acgaagagcg  attgaggaaa    1920 aggcggcgg   ggccggcatg  agcctgtcgg  cctacctgct  ggccgtcggc  cagggctaca    1980
aaatcacggg  cgtcgtggac  tatgagcacg  tccgcgagct  ggcccgcatc  aatggcgacc    2040
tgggccgcct  gggcggcctg  ctgaaactct  ggctcaccga  cgaccgcgc   acggcgcggt    2100 tcggtgatgc  cacgatcctc  gccctgctgg  cgaagatcga  agagaagcag  gacgagcttg    2160
gcaaggtcat  gatgggcgtg  gtccgcccga  gggcagagcc  atgacttttt  tagccgctaa    2220
aacggccggg  gggtgcgcgt  gattgccaag  cacgtcccca  tgcgctccat  caagaagagc    2280
gacttcgcgg  agctggtgaa  gtacatcacc  gacgagcaag  gcaagaccga  gcgcctttgc    2340
gacgctcacc  gggctggttg  ccctcgccgc  tgggctggcg  gccgtctatg  gccctgcaaa    2400
cgcgccagaa  acgccgtcga  agccgtgtgc  gagacaccgc  ggccgccggc  gttgtggata    2460
cctcgcggaa  aacttggccc  tcactgacag  atgaggggcg  gacgttgaca  cttgagggc    2520 cgactcaccc  ggcgcggcgt  tgacagatga  ggggcaggct  cgatttcggc  cggcgacgtg    2580
gagctggcca  gcctcgcaaa  tcggcgaaaa  cgcctgattt  tacgcgagtt  tcccacagat    2640
gatgtggaca  agcctgggga  taagtgccct  gcggtattga  cacttgaggg  gcgcgactac    2700
tgacagatga  ggggcgcgat  ccttgacact  tgaggggcag  agtgctgaca  gatgaggggc    2760
gcacctattg  acatttgagg  ggctgtccac  aggcagaaaa  tccagcattt  gcaagggttt    2820
ccgcccgttt  ttcggccacc  gctaacctgt  cttttaacct  gcttttaaac  caatatttat    2880
aaaccttgtt  tttaaccagg  gctgcgccct  gtgcgcgtga  ccgcgcacgc  cgaagggggg    2940
tgccccccct  tctcgaaccc  tcccggcccg  ctaacgcggg  cctcccatcc  ccccaggggc    3000
tgcgcccctc  ggccgcgaac  ggcctcaccc  caaaaatggc  agcgctggca  gtccttgcca    3060
ttgccgggat  cggggcagta  acgggatggg  cgatcagccc  gagcgcgacg  cccggaagca    3120
ttgacgtgcc  gcaggtgctg  gcatcgacat  tcagcgacca  ggtgccgggc  agtgagggcg    3180
gcggcctggg  tggcggcctg  cccttcactt  cggccgtcgg  ggcattcacg  gacttcatgg    3240
cggggccggc  aattttacc   ttgggcattc  ttggcatagt  ggtcgcgggt  gccgtgctcg    3300
tgttcggggg  tgcgataaac  ccagcgaacc  atttgaggtg  ataggtaaga  ttataccgag    3360
gtatgaaaac  gagaattgga  cctttacaga  attactctat  gaagcgccat  atttaaaaag    3420
ctaccaagac  gaagaggatg  aagaggatga  ggagcagat   tgccttgaat  atattgacaa    3480
tactgataag  ataatatatc  ttttatatag  aagatatcgc  cgtatgtaag  gatttcaggg    3540
ggcaaggcat  aggcagcgcg  cttatcaata  tatctataga  atgggcaaag  cataaaaact    3600
tgcatggact  aatgcttgaa  acccaggaca  ataaccttat  agcttgtaaa  ttctatcata    3660
attgggtaat  gactccaact  tattgatagt  gttttatgtt  cagataatgc  ccgatgactt    3720
tgtcatgcag  ctccaccgat  tttgagaacg  acagcgactt  ccgtcccagc  cgtgccaggt    3780
```

```
gctgcctcag attcaggtta tgccgctcaa ttcgctgcgt atatcgcttg ctgattacgt      3840
gcagctttcc cttcaggcgg gattcataca gcggccagcc atccgtcatc catatcacca      3900
cgtcaaaggg tgacagcagg ctcataagac gccccagcgt cgccatagtg cgttcaccga      3960
atacgtgcgc aacaaccgtc ttccggagac tgtcatacgc gtaaaacagc cagcgctggc      4020
gcgatttagc cccgacatag ccccactgtt cgtccatttc cgcgcagacg atgacgtcac      4080
tgcccggctg tatgcgcgag gttaccgact gcggcctgag ttttttaagt gacgtaaaat      4140
cgtgttgagg ccaacgccca taatgcgggc tgttgcccgg catccaacgc cattcatggc      4200
catatcaatg attttctggt gcgtaccggg ttgagaagcg gtgtaagtga actgcagttg      4260
ccatgtttta cggcagtgag agcagagata gcgctgatgt ccggcggtgc ttttgccgtt      4320
acgcaccacc ccgtcagtag ctgaacagga gggacagctg atagacacag aagccactgg      4380
agcacctcaa aaacaccatc atacactaaa tcagtaagtt ggcagcatca cccataattg      4440
tggtttcaaa atcggctccg tcgatactat gttatacgcc aactttgaaa caactttga       4500 aaaagctgtt ttctggtatt taaggtttta gaatgcaagg aacagtgaat tggagttcgt      4560
cttgttataa ttagcttctt ggggtatctt taaatactgt agaaagagg aaggaaataa       4620 taaatggcta aaatgagaat atcaccggaa ttgaaaaaac tgatcgaaaa ataccgctgc      4680 gtaaagata cggaaggaat gtctcctgct aaggtatata agctggtggg agaaaatgaa       4740
aacctatatt taaaaatgac ggacagccgg tataaaggga ccacctatga tgtggaacgg      4800
gaaaaggaca tgatgctatg gctggaagga agctgcctg ttccaaaggt cctgcacttt       4860
gaacggcatg atggctggag caatctgctc atgagtgagg ccgatggcgt cctttgctcg      4920
gaagagtatg aagatgaaca aagccctgaa aagattatcg agctgtatgc ggagtgcatc      4980
aggctctttc actccatcga catatcggat tgtccctata cgaatagctt agacagccgc      5040
ttagccgaat tggattactt actgaataac gatctggccg atgtggattg cgaaaactgg      5100
gaagaagaca ctccatttaa agatccgcgc gagctgtatg atttttttaaa gacggaaaag      5160 cccgaagagg aacttgtctt ttcccacggc gacctgggag acagcaacat ctttgtgaaa      5220
gatggcaaag taagtggctt tattgatctt gggagaagcg gcagggcgga caagtggtat      5280
gacattgcct tctgcgtccg gtcgatcagg gaggatatcg gggaagaaca gtatgtcgag      5340 ctatttttg acttactggg gatcaagcct gattgggaga aaataaaata ttatatttta       5400
ctggatgaat tgttttagta cctagatgtg gcgcaacgat gccggcgaca agcaggagcg      5460
caccgacttc ttccgcatca agtgttttgg ctctcaggcc gaggcccacg gcaagtattt      5520
gggcaagggt cgctggtat tcgtgcaggg caagattcgg aataccaagt acgaaagga       5580 cggccagacg gtctacggga ccgacttcat gccgataag gtggattatc tggacaccaa       5640
ggcaccaggc gggtcaaatc aggaataagg gcacattgcc ccggcgtgag tcggggcaat      5700
cccgcaagga gggtgaatga atcggacgtt tgaccggaag gcatacaggc aagaactgat      5760
cgacgcgggg ttttccgccg aggatgccga aaccatcgca agccgcaccg tcatgcgtgc      5820
gccccgcgaa accttccagt ccgtcggctc gatggtccag caagctacgg ccaagatcga      5880
gcgcgacagc gtgcaactgg ctccccctgc cctgcccgcg ccatcggccg ccgtggagcg      5940
ttcgcgtcgt ctcgaacagg aggcggcagg tttggcgaag tcgatgacca tcgacacgcg      6000
aggaactatg acgaccaaga agcgaaaaac cgccggcgag gacctggcaa acaggtcag      6060 cgaggccaag caggccgcgt tgctgaaaca cacgaagcag cagatcaagg aaatgcagct      6120
```

```
ttccttgttc gatattgcgc cgtggccgga cacgatgcga gcgatgccaa acgacacggc    6180
ccgctctgcc ctgttcacca cgcgcaacaa gaaaatcccg cgcgaggcgc tgcaaaacaa    6240
ggtcattttc cacgtcaaca aggacgtgaa gatcacctac accggcgtcg agctgcgggc    6300
cgacgatgac gaactggtgt ggcagcaggt gttggagtac gcgaagcgca cccctatcgg    6360
cgagccgatc accttcacgt tctacgagct ttgccaggac ctgggctggt cgatcaatgg    6420
ccggtattac acgaaggccg aggaatgcct gtcgcgccta caggcgacgg cgatgggctt    6480
cacgtccgac cgcgttgggc acctggaatc ggtgtcgctg ctgcaccgct tccgcgtcct    6540
ggaccgtggc aagaaaacgt cccgttgcca ggtcctgatc gacgaggaaa tcgtcgtgct    6600
gtttgctggc gaccactaca cgaaattcat atgggagaag taccgcaagc tgtcgccgac    6660
ggcccgacgg atgttcgact atttcagctc gcaccgggag ccgtacccgc tcaagctgga    6720
aaccttccgc ctcatgtgcg gatcggattc cacccgcgtg aagaagtggc gcgagcaggt    6780
cggcgaagcc tgcgaagagt tgcgaggcag cggcctggtg gaacacgcct gggtcaatga    6840
tgacctggtg cattgcaaac gctagggcct tgtggggtca gttccggctg ggggttcagc    6900
agccagcgct ttactggcat ttcaggaaca agcgggcact gctcgacgca cttgcttcgc    6960
tcagtatcgc tcgggacgca cggcgcgctc tacgaactgc cgataaacag aggattaaaa    7020
ttgacaattg tgattaaggc tcagattcga cggcttggag cggccgacgt gcaggatttc    7080
cgcgagatcc gattgtcggc cctgaagaaa gctccagaga tgttcgggtc cgtttacgag    7140
cacgaggaga aaaagcccat ggaggcgttc gctgaacggt tgcgagatgc cgtggcattc    7200
ggcgcctaca tcgacggcga gatcattggg ctgtcggtct tcaaacagga ggacggcccc    7260
aaggacgctc acaaggcgca tctgtccggc gttttcgtgg agcccgaaca gcgaggccga    7320
ggggtcgccg gtatgctgct gcgggcgttg ccggcgggtt tattgctcgt gatgatcgtc    7380
cgacagattc caacgggaat ctggtggatg cgcatcttca tcctcggcgc acttaatatt    7440
tcgctattct ggagcttgtt gtttatttcg gtctaccgcc tgccgggcgg ggtcgcggcg    7500
acggtaggcg ctgtgcagcc gctgatggtc gtgttcatct ctgccgctct gctaggtagc    7560
ccgatacgat tgatggcggt cctggggggct atttgcggaa ctgcgggcgt ggcgctgttg    7620
gtgttgacac aaacgcagc gctagatcct gtcggcgtcg cagcgggcct ggcggggggcg    7680
gtttccatgg cgttcggaac cgtgctgacc cgcaagtggc aacctcccgt gcctctgctc    7740
acctttaccg cctggcaact ggcggccgga ggacttctgc tcgttccagt agctttagtg    7800
tttgatccgc caatcccgat gcctacagga accaatgttc tcggcctggc gtggctcggc    7860
ctgatcggag cgggtttaac ctacttcctt tggttccggg ggatctcgcg actcgaacct    7920
acagttgttt ccttactggg ctttctcagc cccagatctg gggtcgatca gccggggatg    7980
catcaggccg acagtcggaa cttcgggtcc ccgacctgta ccattcggtg agcaatggat    8040
aggggagttg atatcgtcaa cgttcacttc taaagaaata gcgccactca gcttcctcag    8100
cggctttatc cagcgatttc ctattatgtc ggcatagttc tcaagatcga cagcctgtca    8160
cggttaagcg agaaatgaat aagaaggctg ataattcgga tctctgcgag ggagatgata    8220
tttgatcaca ggcagcaacg ctctgtcatc gttacaatca acatgctacc ctccgcgaga    8280
tcatccgtgt ttcaaacccg gcagcttagt tgccgttctt ccgaatagca tcggtaacat    8340
gagcaaagtc tgccgcctta aacggctctc ccgctgacg ccgtcccgga ctgatgggct    8400
gcctgtatcg agtggtgatt ttgtgccgag ctgccggtcg gggagctgtt ggctggctgg    8460
tggcaggata tattgtggtg taaacaaatt gacgcttaga caacttaata acacattgcg    8520
```

```
gacgttttta atgtactggg gtggttttt ttttcaccag tgagacgggc aacagctgat   8580
tgcccttcac cgcctggccc tgagagagtt gcagcaagcg gtccacgctg gtttgcccca   8640
gcaggcgaaa atcctgtttg atggtggttc cgaaatcggc aaaatccctt ataaatcaaa   8700
agaatagccc gagatagggt tgagtgttgt tccagtttgg aacaagagtc cactattaaa   8760
gaacgtggac tccaacgtca aagggcgaaa aaccgtctat cagggcgatg gcccactacg   8820
tgaaccatca cccaaatcaa gttttttggg gtcgaggtgc cgtaaagcac taaatcggaa   8880
ccctaaaggg agcccccgat ttagagcttg acggggaaag ccggcgaacg tggcgagaaa   8940
ggaagggaag aaagcgaaag gagcgggcgc cattcaggct gcgcaactgt tgggaagggc   9000
gatcggtgcg ggcctcttcg ctattacgcc agctggcgaa aggggggatgt gctgcaaggc   9060
gattaagttg ggtaacgcca gggttttccc agtcacgacg ttgtaaaacg acggccagtg   9120
aattaattcc catcttgaaa gaaatatagt ttaaatattt attgataaaa taacaagtca   9180
ggtattatag tccaagcaaa aacataaatt tattgatgca agtttaaatt cagaaatatt   9240
tcaataactg attatatcag ctggtacatt gccgtagatg aaagactgag tgcgatatta   9300
tgtgtaatac ataaattgat gatatagcta gcttagctca tcggggatc cgtcgaagct   9360
agcttgggtc ccgctcagaa gaactcgtca agaaggcgat agaaggcgat gcgctgcgaa   9420
tcgggagcgg cgataccgta aagcacgagg aagcggtcag cccattcgcc gccaagctct   9480
tcagcaatat cacgggtagc caacgctatg tcctgatagc ggtccgccac acccagccgg   9540
ccacagtcga tgaatccaga aaagcggcca ttttccacca tgatattcgg caagcaggca   9600
tcgccatggg tcacgacgag atcctcgccg tcgggcatgc gcgccttgag cctggcgaac   9660
agttcggctg cgcgagccc ctgatgctct tcgtccagat catcctgatc gacaagaccg   9720
gcttccatcc gagtacgtgc tcgctcgatg cgatgtttcg cttggtggtc gaatgggcag   9780
gtagccggat caagcgtatg cagccgccgc attgcatcag ccatgatgga tactttctcg   9840
gcaggagcaa ggtgagatga caggagatcc tgccccggca cttcgcccaa tagcagccag   9900
tcccttcccg cttcagtgac aacgtcgagc acagctgcgc aaggaacgcc cgtcgtggcc   9960
agccacgata gccgcgctgc ctcgtcctgc agttcattca gggcaccgga caggtcggtc   10020
ttgacaaaaa gaaccgggcg cccctgcgct gacagccgga acacggcggc atcagagcag   10080
ccgattgtct gttgtgccca gtcatagccg aatagcctct ccacccaagc ggccggagaa   10140
cctgcgtgca atccatcttg ttcaatccaa gctcccatgg gccctcgact agagtcgaga   10200
tctggattga gagtgaatat gagactctaa ttggataccg aggggaattt atggaacgtc   10260
agtggagcat ttttgacaag aaatatttgc tagctgatag tgaccttagg cgacttttga   10320
acgcgcaata atggtttctg acgtatgtgc ttagctcatt aaactccaga aacccgcggc   10380
tgagtggctc cttcaacgtt gcggttctgt cagttccaaa cgtaaaacgg cttgtcccgc   10440
gtcatcggcg ggggtcataa cgtgactccc ttaattctcc gctcatgatc ttgatcccct   10500
gcgccatcag atccttggcg gcaagaaagc catccagttt actttgcagg gcttcccaac   10560
cttaccagag ggcgccccag ctggcaattc cggttcgctt gctgtccata aaccgccca   10620
gtctagctat cgccatgtaa gcccactgca agctacctgc tttctctttg cgcttgcgtt   10680
ttcccttgtc cagatagccc agtagctgac attcatccgg ggtcagcacc gtttctgcgg   10740
actggctttc tacgtgttcc gcttccttta gcagcccttg cgccctgagt gcttgcggca   10800
gcgtgaagct tgcatgcctg caggtcgacg gcgcgccgag ctcctcgagc aaatttacac   10860
```

-continued

```
attgccacta aacgtctaaa cccttgtaat ttgttttttgt tttactatgt gtgttatgta    10920
tttgatttgc gataaatttt tatatttggt actaaattta taacacctttt tatgctaacg    10980 tttgccaaca cttagcaatt tgcaagttga ttaattgatt ctaaattatt tttgtcttct    11040
aaatacatat actaatcaac tggaaatgta aatatttgct aatatttcta ctataggaga    11100
attaaagtga gtgaatatgg taccacaagg tttggagatt taattgttgc aatgctgcat    11160
ggatggcata tacaccaaac attcaataat tcttgaggat aataatggta ccacacaaga    11220
tttgaggtgc atgaacgtca cgtggacaaa aggtttagta attttttcaag caacaatgt    11280 taccacacac aagttttgag gtgcatgcat ggatgccctg tggaaagttt aaaaatattt    11340
tggaaatgat ttgcatggaa gccatgtgta aaaccatgac atccacttgg aggatgcaat    11400
aatgaagaaa actacaaatt tacatgcaac tagttatgca tgtagtctat ataatgagga    11460
ttttgcaata ctttcattca tacacactca ctaagttttta cacgattata atttcttcat    11520
agccagccca ccgcggtgga aa atg gag gtc gtg gag aga ttc tac ggt gag    11572
                        Met Glu Val Val Glu Arg Phe Tyr Gly Glu
                         1               5                  10 ttg gat ggg aag gtc tcg cag ggc gtg aat gca ttg ctg ggt agt ttt    11620
Leu Asp Gly Lys Val Ser Gln Gly Val Asn Ala Leu Leu Gly Ser Phe
             15                  20                  25 ggg gtg gag ttg acg gat acg ccc act acc aaa ggc ttg ccc ctc gtt    11668
Gly Val Glu Leu Thr Asp Thr Pro Thr Thr Lys Gly Leu Pro Leu Val
         30                  35                  40 gac agt ccc aca ccc atc gtc ctc ggt gtt tct gta tac ttg act att    11716
Asp Ser Pro Thr Pro Ile Val Leu Gly Val Ser Val Tyr Leu Thr Ile
     45                  50                  55 gtc att gga ggg ctt ttg tgg ata aag gcc agg gat ctg aaa ccg cgc    11764
Val Ile Gly Gly Leu Leu Trp Ile Lys Ala Arg Asp Leu Lys Pro Arg
 60                  65                  70 gcc tcg gag cca ttt ttg ctc caa gct ttg gtg ctt gtg cac aac ctg    11812
Ala Ser Glu Pro Phe Leu Leu Gln Ala Leu Val Leu Val His Asn Leu
 75                  80                  85                  90 ttc tgt ttt gcg ctc agt ctg tat atg tgc gtg ggc atc gct tat cag    11860
Phe Cys Phe Ala Leu Ser Leu Tyr Met Cys Val Gly Ile Ala Tyr Gln
                 95                 100                 105 gct att acc tgg cgg tac tct ctc tgg ggc aat gca tac aat cct aaa    11908
Ala Ile Thr Trp Arg Tyr Ser Leu Trp Gly Asn Ala Tyr Asn Pro Lys
             110                 115                 120 cat aaa gag atg gcg att ctg gta tac ttg ttc tac atg tct aag tac    11956
His Lys Glu Met Ala Ile Leu Val Tyr Leu Phe Tyr Met Ser Lys Tyr
         125                 130                 135 gtg gaa ttc atg gat acc gtt atc atg ata ctg aag cgc agc acc agg    12004
Val Glu Phe Met Asp Thr Val Ile Met Ile Leu Lys Arg Ser Thr Arg
     140                 145                 150 caa ata agc ttc ctc cac gtt tat cat cat tct tca att tcc ctc att    12052
Gln Ile Ser Phe Leu His Val Tyr His His Ser Ser Ile Ser Leu Ile
155                 160                 165                 170 tgg tgg gct att gct cat cac gct cct ggc ggt gaa gca tat tgg tct    12100
Trp Trp Ala Ile Ala His His Ala Pro Gly Gly Glu Ala Tyr Trp Ser
                 175                 180                 185 gcg gct ctg aac tca gga gtg cat gtt ctc atg tat gcg tat tac ttc    12148
Ala Ala Leu Asn Ser Gly Val His Val Leu Met Tyr Ala Tyr Tyr Phe
             190                 195                 200 ttg gct gcc tgc ctt cga agt agc cca aag tta aaa aat aag tac ctt    12196
Leu Ala Ala Cys Leu Arg Ser Ser Pro Lys Leu Lys Asn Lys Tyr Leu
         205                 210                 215 ttt tgg ggc agg tac ttg aca caa ttc caa atg ttc cag ttt atg ctg    12244
```

```
                Phe Trp Gly Arg Tyr Leu Thr Gln Phe Gln Met Phe Gln Phe Met Leu
                    220                 225                 230 aac tta gtg cag gct tac tac gac atg aaa acg aat gcg cca tat cca    12292
Asn Leu Val Gln Ala Tyr Tyr Asp Met Lys Thr Asn Ala Pro Tyr Pro
235                 240                 245                 250 caa tgg ctg atc aag att ttg ttc tac tac atg atc tcg ttg ctg ttt    12340
Gln Trp Leu Ile Lys Ile Leu Phe Tyr Tyr Met Ile Ser Leu Leu Phe
                    255                 260                 265 ctt ttc ggc aat ttt tac gta caa aaa tac atc aaa ccc tct gac gga    12388
Leu Phe Gly Asn Phe Tyr Val Gln Lys Tyr Ile Lys Pro Ser Asp Gly
                270                 275                 280 aag caa aag gga gct aaa act gag tga tctagaaggc ctcctgcttt          12435
Lys Gln Lys Gly Ala Lys Thr Glu
            285                 290 aatgagatat gcgagacgcc tatgatcgca tgatatttgc tttcaattct gttgtgcacg   12495
ttgtaaaaaa cctgagcatg tgtagctcag atccttaccg ccggtttcgg ttcattctaa   12555
tgaatatatc acccgttact atcgtatttt tatgaataat attctccgtt caatttactg   12615
attgtccgtc gagcaaattt acacattgcc actaaacgtc taaacccttg taatttgttt   12675
ttgttttact atgtgtgtta tgtatttgat ttgcgataaa ttttttatatt tggtactaaa   12735 tttataacac cttttatgct aacgtttgcc aacacttagc aatttgcaag ttgattaatt   12795
gattctaaat tattttgtc ttctaaatac atatactaat caactggaaa tgtaaatatt    12855
tgctaatatt tctactatag gagaattaaa gtgagtgaat atggtaccac aaggtttgga   12915
gatttaattg ttgcaatgct gcatggatgg catatacacc aaacattcaa taattcttga   12975
ggataataat ggtaccacac aagatttgag gtgcatgaac gtcacgtgga caaaaggttt   13035
agtaattttt caagacaaca atgttaccac acacaagttt tgaggtgcat gcatggatgc   13095
cctgtggaaa gtttaaaaat attttggaaa tgatttgcat ggaagccatg tgtaaaacca   13155
tgacatccac ttggaggatg caataatgaa gaaaactaca aatttacatg caactagtta   13215
tgcatgtagt ctatataatg aggattttgc aatactttca ttcatacaca ctcactaagt   13275
tttacacgat tataatttct tcatagccag cggatcc atg gta ttc gcg ggc ggt   13330
                                       Met Val Phe Ala Gly Gly
                                                           295 gga ctt cag cag ggc tct ctc gaa gaa aac atc gac gtc gag cac att    13378
Gly Leu Gln Gln Gly Ser Leu Glu Glu Asn Ile Asp Val Glu His Ile
            300                 305                 310 gcc agt atg tct ctc ttc agc gac ttc ttc agt tat gtg tct tca act    13426
Ala Ser Met Ser Leu Phe Ser Asp Phe Phe Ser Tyr Val Ser Ser Thr
        315                 320                 325 gtt ggt tcg tgg agc gta cac agt ata caa cct ttg aag cgc ctg acg    13474
Val Gly Ser Trp Ser Val His Ser Ile Gln Pro Leu Lys Arg Leu Thr
    330                 335                 340 agt aag aag cgt gtt tcg gaa agc gct gcc gtg caa tgt ata tca gct    13522
Ser Lys Lys Arg Val Ser Glu Ser Ala Ala Val Gln Cys Ile Ser Ala
345                 350                 355                 360 gaa gtt cag aga aat tcg agt acc cag gga act gcg gag gca ctc gca    13570
Glu Val Gln Arg Asn Ser Ser Thr Gln Gly Thr Ala Glu Ala Leu Ala
                365                 370                 375 gaa tca gtc gtg aag ccc acg aga cga agg tca tct cag tgg aag aag    13618
Glu Ser Val Val Lys Pro Thr Arg Arg Arg Ser Ser Gln Trp Lys Lys
            380                 385                 390 tcg aca cac ccc cta tca gaa gta gca gta cac aac aag cca agc gat    13666
Ser Thr His Pro Leu Ser Glu Val Ala Val His Asn Lys Pro Ser Asp
        395                 400                 405
```

| | | | | | | | | | | | | | | | |
|---|---|---|---|---|---|---|---|---|---|---|---|---|---|---|---|
| tgc | tgg | att | gtt | gta | aaa | aac | aag | gtg | tat | gat | gtt | tcc | aat | ttt | gcg |
| Cys | Trp | Ile | Val | Val | Lys | Asn | Lys | Val | Tyr | Asp | Val | Ser | Asn | Phe | Ala |
| | 410 | | | | 415 | | | | 420 | | | | | | |

```
tgc tgg att gtt gta aaa aac aag gtg tat gat gtt tcc aat ttt gcg         13714
Cys Trp Ile Val Val Lys Asn Lys Val Tyr Asp Val Ser Asn Phe Ala
    410             415             420 gac gag cat ccc gga gga tca gtt att agt act tat ttt gga cga gac         13762
Asp Glu His Pro Gly Gly Ser Val Ile Ser Thr Tyr Phe Gly Arg Asp
425             430              435             440 ggc aca gat gtt ttc tct agt ttt cat gca gct tct aca tgg aaa att         13810
Gly Thr Asp Val Phe Ser Ser Phe His Ala Ala Ser Thr Trp Lys Ile
                445             450             455 ctt caa gac ttt tac att ggt gac gtg gag agg gtg gag ccg act cca         13858
Leu Gln Asp Phe Tyr Ile Gly Asp Val Glu Arg Val Glu Pro Thr Pro
            460             465             470 gag ctg ctg aaa gat ttc cga gaa atg aga gct ctt ttc ctg agg gag         13906
Glu Leu Leu Lys Asp Phe Arg Glu Met Arg Ala Leu Phe Leu Arg Glu
        475             480             485 caa ctt ttc aaa agt tcg aaa ttg tac tat gtt atg aag ctg ctc acg         13954
Gln Leu Phe Lys Ser Ser Lys Leu Tyr Tyr Val Met Lys Leu Leu Thr
    490             495             500 aat gtt gct att ttt gct gcg agc att gca ata ata tgt tgg agc aag         14002
Asn Val Ala Ile Phe Ala Ala Ser Ile Ala Ile Ile Cys Trp Ser Lys
505             510             515             520 act att tca gcg gtt ttg gct tca gct tgt atg atg gct ctg tgt ttc         14050
Thr Ile Ser Ala Val Leu Ala Ser Ala Cys Met Met Ala Leu Cys Phe
            525             530             535 caa cag tgc gga tgg cta tcc cat gat ttt ctc cac aat cag gtg ttt         14098
Gln Gln Cys Gly Trp Leu Ser His Asp Phe Leu His Asn Gln Val Phe
        540             545             550 gag aca cgc tgg ctt aat gaa gtt gtc ggg tat gtg atc ggc aac gcc         14146
Glu Thr Arg Trp Leu Asn Glu Val Val Gly Tyr Val Ile Gly Asn Ala
    555             560             565 gtt ctg ggg ttt agt aca ggg tgg tgg aag gag aag cat aac ctt cat         14194
Val Leu Gly Phe Ser Thr Gly Trp Trp Lys Glu Lys His Asn Leu His
570             575             580 cat gct gct cca aat gaa tgc gat cag act tac caa cca att gat gaa         14242
His Ala Ala Pro Asn Glu Cys Asp Gln Thr Tyr Gln Pro Ile Asp Glu
585             590             595             600 gat att gat act ctc ccc ctc att gcc tgg agc aag gac ata ctg gcc         14290
Asp Ile Asp Thr Leu Pro Leu Ile Ala Trp Ser Lys Asp Ile Leu Ala
            605             610             615 aca gtt gag aat aag aca ttc ttg cga atc ctc caa tac cag cat ctg         14338
Thr Val Glu Asn Lys Thr Phe Leu Arg Ile Leu Gln Tyr Gln His Leu
        620             625             630 ttc ttc atg ggt ctg tta ttt ttc gcc cgt ggt agt tgg ctc ttt tgg         14386
Phe Phe Met Gly Leu Leu Phe Phe Ala Arg Gly Ser Trp Leu Phe Trp
    635             640             645 agc tgg aga tat acc tct aca gca gtg ctc tca cct gtc gac agg ttg         14434
Ser Trp Arg Tyr Thr Ser Thr Ala Val Leu Ser Pro Val Asp Arg Leu
650             655             660 ttg gag aag gga act gtt ctg ttt cac tac ttt tgg ttc gtc ggg aca         14482
Leu Glu Lys Gly Thr Val Leu Phe His Tyr Phe Trp Phe Val Gly Thr
665             670             675             680 gcg tgc tat ctt ctc cct ggt tgg aag cca tta gta tgg atg gcg gtg         14530
Ala Cys Tyr Leu Leu Pro Gly Trp Lys Pro Leu Val Trp Met Ala Val
            685             690             695 act gag ctc atg tcc ggc atg ctg ctg ggc ttt gta ttt gta ctt agc         14578
Thr Glu Leu Met Ser Gly Met Leu Leu Gly Phe Val Phe Val Leu Ser
        700             705             710 cac aat ggg atg gag gtt tat aat tcg tct aaa gaa ttc gtg agt gca         14626
His Asn Gly Met Glu Val Tyr Asn Ser Ser Lys Glu Phe Val Ser Ala
    715             720             725
```

```
cag atc gta tcc aca cgg gat atc aaa gga aac ata ttc aac gac tgg      14674
Gln Ile Val Ser Thr Arg Asp Ile Lys Gly Asn Ile Phe Asn Asp Trp
    730                 735                 740 ttc act ggt ggc ctt aac agg caa ata gag cat cat ctt ttc cca aca      14722
Phe Thr Gly Gly Leu Asn Arg Gln Ile Glu His His Leu Phe Pro Thr
745                 750                 755                 760 atg ccc agg cat aat tta aac aaa ata gca cct aga gtg gag gtg ttc      14770
Met Pro Arg His Asn Leu Asn Lys Ile Ala Pro Arg Val Glu Val Phe
                765                 770                 775 tgt aag aaa cac ggt ctg gtg tac gaa gac gta tct att gct acc ggc      14818
Cys Lys Lys His Gly Leu Val Tyr Glu Asp Val Ser Ile Ala Thr Gly
            780                 785                 790 act tgc aag gtt ttg aaa gca ttg aag gaa gtc gcg gag gct gcg gca      14866
Thr Cys Lys Val Leu Lys Ala Leu Lys Glu Val Ala Glu Ala Ala Ala
        795                 800                 805 gag cag cat gct acc acc agt taa gctagcgtta accctgcttt aatgagatat    14920
Glu Gln His Ala Thr Thr Ser
    810                 815 gcgagacgcc tatgatcgca tgatatttgc tttcaattct gttgtgcacg ttgtaaaaaa    14980
cctgagcatg tgtagctcag atccttaccg ccggtttcgg ttcattctaa tgaatatatc    15040
acccgttact atcgtatttt tatgaataat attctccgtt caatttactg attgtccgtc    15100
gacgaattcg agctcggcgc gcctctagag gatcgatgaa ttcagatcgg ctgagtggct    15160
ccttcaacgt tgcggttctg tcagttccaa acgtaaaacg gcttgtcccg cgtcatcggc    15220
gggggtcata acgtgactcc cttaattctc cgctcatgat cagattgtcg tttcccgcct    15280
tcagtttaaa ctatcagtgt ttgacaggat atattggcgg gtaaacctaa gagaaaagag    15340
cgtttattag aataatcgga tatttaaaag ggcgtgaaaa ggtttatcct tcgtccattt    15400
gtatgtgcat gccaaccaca gggttcccca                                     15430
```

<210> SEQ ID NO 44
<211> LENGTH: 290
<212> TYPE: PRT
<213> ORGANISM: Unknown
<220> FEATURE:
<223> OTHER INFORMATION: vector

<400> SEQUENCE: 44

```
Met Glu Val Val Glu Arg Phe Tyr Gly Glu Leu Asp Gly Lys Val Ser
1               5                   10                  15

Gln Gly Val Asn Ala Leu Leu Gly Ser Phe Gly Val Glu Leu Thr Asp
                20                  25                  30

Thr Pro Thr Thr Lys Gly Leu Pro Leu Val Asp Ser Pro Thr Pro Ile
            35                  40                  45

Val Leu Gly Val Ser Val Tyr Leu Thr Ile Val Ile Gly Gly Leu Leu
        50                  55                  60

Trp Ile Lys Ala Arg Asp Leu Lys Pro Arg Ala Ser Glu Pro Phe Leu
65                  70                  75                  80

Leu Gln Ala Leu Val Leu Val His Asn Leu Phe Cys Phe Ala Leu Ser
                85                  90                  95

Leu Tyr Met Cys Val Gly Ile Ala Tyr Gln Ala Ile Thr Trp Arg Tyr
                100                 105                 110

Ser Leu Trp Gly Asn Ala Tyr Asn Pro Lys His Lys Glu Met Ala Ile
            115                 120                 125

Leu Val Tyr Leu Phe Tyr Met Ser Lys Tyr Val Glu Phe Met Asp Thr
        130                 135                 140
```

```
Val Ile Met Ile Leu Lys Arg Ser Thr Arg Gln Ile Ser Phe Leu His
145                 150                 155                 160

Val Tyr His His Ser Ser Ile Ser Leu Ile Trp Trp Ala Ile Ala His
                165                 170                 175

His Ala Pro Gly Gly Glu Ala Tyr Trp Ser Ala Ala Leu Asn Ser Gly
            180                 185                 190

Val His Val Leu Met Tyr Ala Tyr Tyr Phe Leu Ala Ala Cys Leu Arg
        195                 200                 205

Ser Ser Pro Lys Leu Lys Asn Lys Tyr Leu Phe Trp Gly Arg Tyr Leu
210                 215                 220

Thr Gln Phe Gln Met Phe Gln Phe Met Leu Asn Leu Val Gln Ala Tyr
225                 230                 235                 240

Tyr Asp Met Lys Thr Asn Ala Pro Tyr Pro Gln Trp Leu Ile Lys Ile
                245                 250                 255

Leu Phe Tyr Tyr Met Ile Ser Leu Leu Phe Leu Phe Gly Asn Phe Tyr
                260                 265                 270

Val Gln Lys Tyr Ile Lys Pro Ser Asp Gly Lys Gln Lys Gly Ala Lys
            275                 280                 285

Thr Glu
    290

<210> SEQ ID NO 45
<211> LENGTH: 525
<212> TYPE: PRT
<213> ORGANISM: Unknown
<220> FEATURE:
<223> OTHER INFORMATION: vector

<400> SEQUENCE: 45

Met Val Phe Ala Gly Gly Leu Gln Gln Gly Ser Leu Glu Glu Asn
 1               5                  10                  15

Ile Asp Val Glu His Ile Ala Ser Met Ser Leu Phe Ser Asp Phe Phe
                20                  25                  30

Ser Tyr Val Ser Ser Thr Val Gly Ser Trp Ser Val His Ser Ile Gln
            35                  40                  45

Pro Leu Lys Arg Leu Thr Ser Lys Lys Arg Val Ser Glu Ser Ala Ala
        50                  55                  60

Val Gln Cys Ile Ser Ala Glu Val Gln Arg Asn Ser Ser Thr Gln Gly
65                  70                  75                  80

Thr Ala Glu Ala Leu Ala Glu Ser Val Val Lys Pro Thr Arg Arg Arg
                85                  90                  95

Ser Ser Gln Trp Lys Lys Ser Thr His Pro Leu Ser Glu Val Ala Val
            100                 105                 110

His Asn Lys Pro Ser Asp Cys Trp Ile Val Lys Asn Lys Val Tyr
        115                 120                 125

Asp Val Ser Asn Phe Ala Asp Glu His Pro Gly Gly Ser Val Ile Ser
    130                 135                 140

Thr Tyr Phe Gly Arg Asp Gly Thr Asp Val Phe Ser Ser Phe His Ala
145                 150                 155                 160

Ala Ser Thr Trp Lys Ile Leu Gln Asp Phe Tyr Ile Gly Asp Val Glu
                165                 170                 175

Arg Val Glu Pro Thr Pro Glu Leu Leu Lys Asp Phe Arg Glu Met Arg
            180                 185                 190

Ala Leu Phe Leu Arg Glu Gln Leu Phe Lys Ser Ser Lys Leu Tyr Tyr
        195                 200                 205
```

Val Met Lys Leu Leu Thr Asn Val Ala Ile Phe Ala Ala Ser Ile Ala
    210                 215                 220

Ile Ile Cys Trp Ser Lys Thr Ile Ser Ala Val Leu Ala Ser Ala Cys
225                 230                 235                 240

Met Met Ala Leu Cys Phe Gln Gln Cys Gly Trp Leu Ser His Asp Phe
                245                 250                 255

Leu His Asn Gln Val Phe Glu Thr Arg Trp Leu Asn Glu Val Val Gly
                260                 265                 270

Tyr Val Ile Gly Asn Ala Val Leu Gly Phe Ser Thr Gly Trp Trp Lys
            275                 280                 285

Glu Lys His Asn Leu His His Ala Ala Pro Asn Glu Cys Asp Gln Thr
290                 295                 300

Tyr Gln Pro Ile Asp Glu Asp Ile Asp Thr Leu Pro Leu Ile Ala Trp
305                 310                 315                 320

Ser Lys Asp Ile Leu Ala Thr Val Glu Asn Lys Thr Phe Leu Arg Ile
                325                 330                 335

Leu Gln Tyr Gln His Leu Phe Phe Met Gly Leu Leu Phe Phe Ala Arg
                340                 345                 350

Gly Ser Trp Leu Phe Trp Ser Trp Arg Tyr Thr Ser Thr Ala Val Leu
            355                 360                 365

Ser Pro Val Asp Arg Leu Leu Glu Lys Gly Thr Val Leu Phe His Tyr
370                 375                 380

Phe Trp Phe Val Gly Thr Ala Cys Tyr Leu Leu Pro Gly Trp Lys Pro
385                 390                 395                 400

Leu Val Trp Met Ala Val Thr Glu Leu Met Ser Gly Met Leu Leu Gly
                405                 410                 415

Phe Val Phe Val Leu Ser His Asn Gly Met Glu Val Tyr Asn Ser Ser
                420                 425                 430

Lys Glu Phe Val Ser Ala Gln Ile Val Ser Thr Arg Asp Ile Lys Gly
            435                 440                 445

Asn Ile Phe Asn Asp Trp Phe Thr Gly Gly Leu Asn Arg Gln Ile Glu
450                 455                 460

His His Leu Phe Pro Thr Met Pro Arg His Asn Leu Asn Lys Ile Ala
465                 470                 475                 480

Pro Arg Val Glu Val Phe Cys Lys Lys His Gly Leu Val Tyr Glu Asp
                485                 490                 495

Val Ser Ile Ala Thr Gly Thr Cys Lys Val Leu Lys Ala Leu Lys Glu
            500                 505                 510

Val Ala Glu Ala Ala Ala Glu Gln His Ala Thr Thr Ser
515                 520                 525

<210> SEQ ID NO 46
<211> LENGTH: 17752
<212> TYPE: DNA
<213> ORGANISM: Unknown
<220> FEATURE:
<223> OTHER INFORMATION: Plant expression vector with 3
      promoter-terminator expression cassettes,
      inserted with Physcomitrella elongase + desaturase
      + Phaeodactylum desaturase
<220> FEATURE:
<221> NAME/KEY: CDS
<222> LOCATION: (11543)..(12415)
<220> FEATURE:
<221> NAME/KEY: CDS
<222> LOCATION: (13313)..(14890)
<220> FEATURE:
<221> NAME/KEY: CDS

<222> LOCATION: (15791)..(17200)

<400> SEQUENCE: 46

| | | | | | |
|---|---|---|---|---|---|
| gatctggcgc | cggccagcga | gacgagcaag | attggccgcc | gcccgaaacg | atccgacagc | 60 |
| gcgcccagca | caggtgcgca | ggcaaattgc | accaacgcat | acagcgccag | cagaatgcca | 120 |
| tagtgggcgg | tgacgtcgtt | cgagtgaacc | agatcgcgca | ggaggccagg | cagcaccggc | 180 |
| ataatcaggc | cgatgccgac | agcgtcgagc | gcgacagtgc | tcagaattac | gatcaggggt | 240 |
| atgttgggtt | tcacgtctgg | cctccggacc | agcctccgct | ggtccgattg | aacgcgcgga | 300 |
| ttctttatca | ctgataagtt | ggtggacata | ttatgtttat | cagtgataaa | gtgtcaagca | 360 |
| tgacaaagtt | gcagccgaat | acagtgatcc | gtgccgccct | ggacctgttg | aacgaggtcg | 420 |
| gcgtagacgg | tctgacgaca | cgcaaactgg | cggaacggtt | gggggttcag | cagccggcgc | 480 |
| tttactggca | cttcaggaac | aagcgggcgc | tgctcgacgc | actggccgaa | gccatgctgg | 540 |
| cggagaatca | tacgcattcg | gtgccgagag | ccgacgacga | ctggcgctca | tttctgatcg | 600 |
| ggaatgcccg | cagcttcagg | caggcgctgc | tcgcctaccg | cgatggcgcg | cgcatccatg | 660 |
| ccggcacgcg | accgggcgca | ccgcagatgg | aaacggccga | cgcgcagctt | cgcttcctct | 720 |
| gcgaggcggg | ttttcggcc | ggggacgccg | tcaatgcgct | gatgacaatc | agctacttca | 780 |
| ctgttgggc | cgtgcttgag | gagcaggccg | gcgacagcga | tgccggcgag | gcggcggca | 840 |
| ccgttgaaca | ggctccgctc | tcgccgctgt | tgcgggccgc | gatagacgcc | ttcgacgaag | 900 |
| ccggtccgga | cgcagcgttc | gagcagggac | tcgcggtgat | tgtcgatgga | ttggcgaaaa | 960 |
| ggaggctcgt | tgtcaggaac | gttgaaggac | cgagaaaggg | tgacgattga | tcaggaccgc | 1020 |
| tgccggagcg | caacccactc | actacagcag | agccatgtag | acaacatccc | ctccccttt | 1080 |
| ccaccgcgtc | agacgcccgt | agcagcccgc | tacgggcttt | ttcatgccct | gccctagcgt | 1140 |
| ccaagcctca | cggccgcgct | cggcctctct | ggcggccttc | tggcgctctt | ccgcttcctc | 1200 |
| gctcactgac | tcgctgcgct | cggtcgttcg | gctgcggcga | gcggtatcag | ctcactcaaa | 1260 |
| ggcggtaata | cggttatcca | cagaatcagg | ggataacgca | ggaaagaaca | tgtgagcaaa | 1320 |
| aggccagcaa | aaggccagga | accgtaaaaa | ggccgcgttg | ctggcgtttt | tccataggct | 1380 |
| ccgcccccct | gacgagcatc | acaaaaatcg | acgctcaagt | cagaggtggc | gaaacccgac | 1440 |
| aggactataa | agataccagg | cgtttccccc | tggaagctcc | ctcgtgcgct | ctcctgttcc | 1500 |
| gaccctgccg | cttaccggat | acctgtccgc | ctttctccct | tcgggaagcg | tggcgctttt | 1560 |
| ccgctgcata | accctgcttc | ggggtcatta | tagcgatttt | ttcggtatat | ccatcctttt | 1620 |
| tcgcacgata | tacaggattt | tgccaaaggg | ttcgtgtaga | ctttccttgg | tgtatccaac | 1680 |
| ggcgtcagcc | gggcaggata | ggtgaagtag | gcccacccgc | gagcgggtgt | tccttcttca | 1740 |
| ctgtccctta | ttcgcacctg | gcggtgctca | acgggaatcc | tgctctgcga | ggctggccgg | 1800 |
| ctaccgccgg | cgtaacagat | gagggcaagc | ggatggctga | tgaaaccaag | ccaaccagga | 1860 |
| agggcagccc | acctatcaag | gtgtactgcc | ttccagacga | acgaagagcg | attgaggaaa | 1920 |
| aggcggcggc | ggccggcatg | agcctgtcgg | cctacctgct | ggccgtcggc | cagggctaca | 1980 |
| aaatcacggg | cgtcgtggac | tatgagcacg | tccgcgagct | ggcccgcatc | aatggcgacc | 2040 |
| tgggccgcct | gggcggcctg | ctgaaactct | ggctcaccga | cgaccgcgc | acggcgcggt | 2100 |
| tcggtgatgc | cacgatcctc | gccctgctgg | cgaagatcga | agagaagcag | gacgagcttg | 2160 |
| gcaaggtcat | gatgggcgtg | gtccgcccga | gggcagagcc | atgactttt | tagccgctaa | 2220 |
| aacggccggg | gggtgcgcgt | gattgccaag | cacgtcccca | tgcgctccat | caagaagagc | 2280 |

```
gacttcgcgg agctggtgaa gtacatcacc gacgagcaag gcaagaccga gcgcctttgc   2340
gacgctcacc gggctggttg ccctcgccgc tgggctggcg gccgtctatg gccctgcaaa   2400
cgcgccagaa acgccgtcga agccgtgtgc gagacaccgc ggccgccggc gttgtggata   2460
cctcgcggaa aacttggccc tcactgacag atgaggggcg gacgttgaca cttgaggggc   2520
cgactcaccc ggcgcggcgt tgacagatga ggggcaggct cgatttcggc cggcgacgtg   2580
gagctggcca gcctcgcaaa tcggcgaaaa cgcctgattt tacgcgagtt tcccacagat   2640
gatgtggaca gcctgggga taagtgccct gcggtattga cacttgaggg gcgcgactac   2700
tgacagatga ggggcgcgat ccttgacact tgaggggcag agtgctgaca gatgaggggc   2760
gcacctattg acatttgagg ggctgtccac aggcagaaaa tccagcattt gcaagggttt   2820
ccgcccgttt ttcggccacc gctaacctgt cttttaacct gcttttaaac caatatttat   2880
aaaccttgtt tttaaccagg gctgcgccct gtgcgcgtga ccgcgcacgc cgaagggggg   2940 tgcccccct tctcgaaccc tcccggcccg ctaacgcggg cctccatcc ccccagggc    3000 tgcgcccctc ggccgcgaac ggcctcaccc caaaaatggc agcgctggca gtccttgcca   3060
ttgccgggat cggggcagta acgggatggg cgatcagccc gagcgcgacg cccggaagca   3120
ttgacgtgcc gcaggtgctg gcatcgacat tcagcgacca ggtgccgggc agtgagggcg   3180
gcggcctggg tggcggcctg cccttcactt cggccgtcgg ggcattcacg gacttcatgg   3240
cggggccggc aattttttacc ttgggcattc ttggcatagt ggtcgcgggt gccgtgctcg   3300
tgttcggggg tgcgataaac ccagcgaacc atttgaggtg ataggtaaga ttataccgag   3360
gtatgaaaac gagaattgga cctttacaga attactctat gaagcgccat atttaaaaag   3420
ctaccaagac gaagaggatg aagaggatga ggaggcagat tgccttgaat atattgacaa   3480
tactgataag ataatatatc ttttatatag aagatatcgc cgtatgtaag gatttcaggg   3540
ggcaaggcat aggcagcgcg cttatcaata tatctataga atgggcaaag cataaaaact   3600
tgcatggact aatgcttgaa acccaggaca ataaccttat agcttgtaaa ttctatcata   3660
attgggtaat gactccaact tattgatagt gttttatgtt cagataatgc ccgatgactt   3720
tgtcatgcag ctccaccgat tttgagaacg acagcgactt ccgtcccagc cgtgccaggt   3780
gctgcctcag attcaggtta tgccgctcaa ttcgctgcgt atatcgcttg ctgattacgt   3840
gcagctttcc cttcaggcgg gattcataca gcggccagcc atccgtcatc catatcacca   3900
cgtcaaaggg tgacacagg ctcataagac gccccagcgt cgccatagtg cgttcaccga   3960
atacgtgcgc aacaaccgtc ttccggagac tgtcatacgc gtaaaacagc cagcgctggc   4020
gcgatttagc cccgacatag ccccactgtt cgtccatttc cgcgcagacg atgacgtcac   4080
tgcccggctg tatgcgcgag gttaccgact gcggcctgag ttttttaagt gacgtaaaat   4140
cgtgttgagg ccaacgccca taatgcgggc tgttgcccgg catccaacgc cattcatggc   4200
catatcaatg attttctggt gcgtaccggg ttgagaagcg gtgtaagtga actgcagttg   4260
ccatgtttta cggcagtgag agcagagata gcgctgatgt ccggcggtgc ttttgccgtt   4320
acgcaccacc ccgtcagtag ctgaacagga gggacagctg atagacacag aagccactgg   4380
agcacctcaa aaacaccatc atacactaaa tcagtaagtt ggcagcatca cccataattg   4440
tggtttcaaa atcggctccg tcgatactat gttatacgcc aactttgaaa caactttga    4500 aaaagctgtt ttctggtatt taaggtttta gaatgcaagg aacagtgaat tggagttcgt   4560
cttgttataa ttagcttctt ggggtatctt taaatactgt agaaaagagg aaggaaataa   4620
```

```
taaatggcta aaatgagaat atcaccggaa ttgaaaaaac tgatcgaaaa ataccgctgc    4680
gtaaaagata cggaaggaat gtctcctgct aaggtatata agctggtggg agaaaatgaa    4740
aacctatatt taaaaatgac ggacagccgg tataagggga ccacctatga tgtggaacgg    4800
gaaaaggaca tgatgctatg gctggaagga aagctgcctg ttccaaaggt cctgcacttt    4860
gaacggcatg atggctggag caatctgctc atgagtgagg ccgatggcgt cctttgctcg    4920
gaagagtatg aagatgaaca aagccctgaa aagattatcg agctgtatgc ggagtgcatc    4980
aggctctttc actccatcga catatcggat tgtccctata cgaatagctt agacagccgc    5040
ttagccgaat tggattactt actgaataac gatctggccg atgtggattg cgaaaactgg    5100
gaagaagaca ctccatttaa agatccgcgc gagctgtatg attttttaaa gacggaaaag    5160
cccgaagagg aacttgtctt ttcccacggc gacctgggag acagcaacat ctttgtgaaa    5220
gatggcaaag taagtggctt tattgatctt gggagaagcg gcagggcgga caagtggtat    5280
gacattgcct tctgcgtccg gtcgatcagg gaggatatcg gggaagaaca gtatgtcgag    5340
ctatttttg acttactggg gatcaagcct gattgggaga aaataaaata ttatattta    5400
ctggatgaat tgttttagta cctagatgtg gcgcaacgat gccggcgaca agcaggagcg    5460
caccgacttc ttccgcatca agtgttttgg ctctcaggcc gaggcccacg gcaagtattt    5520
gggcaagggg tcgctggtat tcgtgcaggg caagattcgg aataccaagt acgaaggga    5580
cggccagacg gtctacggga ccgacttcat tgccgataag gtggattatc tggacaccaa    5640
ggcaccaggc gggtcaaatc aggaataagg gcacattgcc ccggcgtgag tcggggcaat    5700
cccgcaagga gggtgaatga atcggacgtt tgaccggaag gcatacaggc aagaactgat    5760
cgacgcgggg ttttccgccg aggatgccga aaccatcgca agccgcaccg tcatgcgtgc    5820
gccccgcgaa accttccagt ccgtcggctc gatggtccag caagctacgg ccaagatcga    5880
gcgcgacagc gtgcaactgg ctcccccgc cctgcccgcg ccatcggccg ccgtggagcg    5940
ttcgcgtcgt ctcgaacagg aggcggcagg tttggcgaag tcgatgacca tcgacacgcg    6000
aggaactatg acgaccaaga agcgaaaaac cgccggcgag gacctggcaa acaggtcag    6060
cgaggccaag caggccgcgt tgctgaaaca cacgaagcag cagatcaagg aaatgcagct    6120
ttccttgttc gatattgcgc cgtggccgga cacgatgcga gcgatgccaa acgacacggc    6180
ccgctctgcc ctgttcacca cgcgcaacaa gaaaatcccg cgcgaggcgc tgcaaaacaa    6240
ggtcattttc cacgtcaaca aggacgtgaa gatcacctac accggcgtcg agctgcgggc    6300
cgacgatgac gaactggtgt ggcagcaggt gttggagtac gcgaagcgca cccctatcgg    6360
cgagccgatc accttcacgt tctacgagct ttgccaggac ctgggctggt cgatcaatgg    6420
ccggtattac acgaaggccg aggaatgcct gtcgcgccta caggcgacgg cgatgggctt    6480
cacgtccgac cgcgttgggc acctggaatc ggtgtcgctg ctgcaccgct tccgcgtcct    6540
ggaccgtggc aagaaaacgt cccgttgcca ggtcctgatc gacgaggaaa tcgtcgtgct    6600
gtttgctggc gaccactaca cgaaattcat atgggagaag taccgcaagc tgtcgccgac    6660
ggcccgacgg atgttcgact atttcagctc gcaccgggag ccgtacccgc tcaagctgga    6720
aaccttccgc ctcatgtgcg gatcggattc caccgcgtg aagaagtggc gcgagcaggt    6780
cggcgaagcc tgcgaagagt tgcgaggcag cggcctggtg aacacgcct gggtcaatga    6840
tgacctggtg cattgcaaac gctagggcct tgtgggtca gttccggctg ggggttcagc    6900
agccagcgct ttactggcat ttcaggaaca agcgggcact gctcgacgca cttgcttcgc    6960
tcagtatcgc tcgggacgca cggcgcgctc tacgaactgc cgataaacag aggattaaaa    7020
```

```
ttgacaattg tgattaaggc tcagattcga cggcttggag cggccgacgt gcaggatttc    7080
cgcgagatcc gattgtcggc cctgaagaaa gctccagaga tgttcgggtc cgtttacgag    7140
cacgaggaga aaaagcccat ggaggcgttc gctgaacggt tgcgagatgc cgtggcattc    7200
ggcgcctaca tcgacggcga gatcattggg ctgtcggtct tcaaacagga ggacggcccc    7260
aaggacgctc acaaggcgca tctgtccggc gttttcgtgg agcccgaaca gcgaggccga    7320
ggggtcgccg gtatgctgct gcgggcgttg ccggcgggtt tattgctcgt gatgatcgtc    7380
cgacagattc caacgggaat ctggtggatg cgcatcttca tcctcggcgc acttaatatt    7440
tcgctattct ggagcttgtt gtttatttcg gtctaccgcc tgccgggcgg ggtcgcggcg    7500
acggtaggcg ctgtgcagcc gctgatggtc gtgttcatct ctgccgctct gctaggtagc    7560
ccgatacgat tgatggcggt cctgggggct atttgcggaa ctgcgggcgt ggcgctgttg    7620
gtgttgacac caaacgcagc gctagatcct gtcggcgtcg cagcgggcct ggcggggggcg    7680
gtttccatgg cgttcggaac cgtgctgacc cgcaagtggc aacctcccgt gcctctgctc    7740
acctttaccg cctggcaact ggcggccgga ggacttctgc tcgttccagt agctttagtg    7800
tttgatccgc caatcccgat gcctacagga accaatgttc tcggcctggc gtggctcggc    7860
ctgatcggag cgggtttaac ctacttcctt tggttccggg ggatctcgcg actcgaacct    7920
acagttgttt ccttactggg ctttctcagc cccagatctg gggtcgatca gccggggatg    7980
catcaggccg acagtcggaa cttcgggtcc ccgacctgta ccattcggtg agcaatggat    8040
aggggagttg atatcgtcaa cgttcacttc taaagaaata gcgccactca gcttcctcag    8100
cggctttatc cagcgatttc ctattatgtc ggcatagttc tcaagatcga cagcctgtca    8160
cggttaagcg agaaatgaat aagaaggctg ataattcgga tctctgcgag ggagatgata    8220
tttgatcaca ggcagcaacg ctctgtcatc gttacaatca acatgctacc ctccgcgaga    8280
tcatccgtgt ttcaaacccg gcagcttagt tgccgttctt ccgaatagca tcggtaacat    8340
gagcaaagtc tgccgcctta caacggctct cccgctgacg ccgtcccgga ctgatgggct    8400
gcctgtatcg agtggtgatt tgtgccgag ctgccggtcg gggagctgtt ggctggctgg    8460
tggcaggata tattgtggtg taaacaaatt gacgcttaga caacttaata acacattgcg    8520
gacgttttta atgtactggg gtggttttc ttttcaccag tgagacgggc aacagctgat    8580
tgcccttcac cgcctggccc tgagagagtt gcagcaagcg gtccacgctg gtttgcccca    8640
gcaggcgaaa atcctgtttg atggtggttc cgaaatcggc aaaatccctt ataaatcaaa    8700
agaatagccc gagataggggt tgagtgttgt tccagtttgg aacaagagtc cactattaaa    8760
gaacgtggac tccaacgtca aagggcgaaa aaccgtctat cagggcgatg cccactacg    8820
tgaaccatca cccaaatcaa gttttttggg gtcgaggtgc cgtaaagcac taaatcggaa    8880
ccctaaaggg agccccgat ttagagcttg acggggaaag ccggcgaacg tggcgagaaa    8940
ggaagggaag aaagcgaaag gagcgggcgc cattcaggct gcgcaactgt gggaagggc    9000
gatcggtgcg ggcctcttcg ctattacgcc agctggcgaa aggggatgt gctgcaaggc    9060
gattaagttg ggtaacgcca gggttttccc agtcacgacg ttgtaaaacg acggccagtg    9120
aattaattcc catcttgaaa gaaatatagt ttaaatattt attgataaaa taacaagtca    9180
ggtattatag tccaagcaaa aacataaatt tattgatgca agtttaaatt cagaaatatt    9240
tcaataactg attatatcag ctggtacatt gccgtagatg aaagactgag tgcgatatta    9300
tgtgtaatac ataaattgat gatatagcta gcttagctca tcgggggatc cgtcgaagct    9360
```

```
agcttgggtc cgctcagaa gaactcgtca agaaggcgat agaaggcgat gcgctgcgaa    9420
tcgggagcgg cgataccgta aagcacgagg aagcggtcag cccattcgcc gccaagctct    9480
tcagcaatat cacgggtagc caacgctatg tcctgatagc ggtccgccac acccagccgg    9540
ccacagtcga tgaatccaga aaagcggcca ttttccacca tgatattcgg caagcaggca    9600
tcgccatggg tcacgacgag atcctcgccg tcgggcatgc gcgccttgag cctggcgaac    9660
agttcggctg gcgcgagccc ctgatgctct tcgtccagat catcctgatc gacaagaccg    9720
gcttccatcc gagtacgtgc tcgctcgatg cgatgtttcg cttggtggtc gaatgggcag    9780
gtagccggat caagcgtatg cagccgccgc attgcatcag ccatgatgga tactttctcg    9840
gcaggagcaa ggtgagatga caggagatcc tgccccggca cttcgcccaa tagcagccag    9900
tcccttcccg cttcagtgac aacgtcgagc acagctgcgc aaggaacgcc cgtcgtggcc    9960
agccacgata gccgcgctgc ctcgtcctgc agttcattca gggcaccgga caggtcggtc    10020
ttgacaaaaa gaaccgggcg cccctgcgct gacagccgga acacggcggc atcagagcag    10080
ccgattgtct gttgtgccca gtcatagccg aatagcctct ccacccaagc ggccggagaa    10140
cctgcgtgca atccatcttg ttcaatccaa gctcccatgg gccctcgact agagtcgaga    10200
tctggattga gagtgaatat gagactctaa ttggataccg aggggaattt atggaacgtc    10260
agtggagcat ttttgacaag aaatatttgc tagctgatag tgaccttagg cgacttttga    10320
acgcgcaata atggtttctg acgtatgtgc ttagctcatt aaactccaga aacccgcggc    10380
tgagtggctc cttcaacgtt gcggttctgt cagttccaaa cgtaaaacgg cttgtcccgc    10440
gtcatcggcg ggggtcataa cgtgactccc ttaattctcc gctcatgatc ttgatcccct    10500
gcgccatcag atccttggcg gcaagaaagc catccagttt actttgcagg gcttcccaac    10560
cttaccagag ggcgccccag ctggcaattc cggttcgctt gctgtccata aaaccgccca    10620
gtctagctat cgccatgtaa gcccactgca agctacctgc tttctctttg cgcttgcgtt    10680
ttcccttgtc cagatagccc agtagctgac attcatccgg ggtcagcacc gtttctgcgg    10740
actggctttc tacgtgttcc gcttcccttta gcagcccttg cgccctgagt gcttgcggca    10800
gcgtgaagct tgcatgcctg caggtcgacg gcgcgccgag ctcctcgagc aaatttacac    10860
attgccacta aacgtctaaa cccttgtaat ttgttttttgt tttactatgt gtgttatgta    10920
tttgatttgc gataaatttt tatatttggt actaaattta taacacctttt tatgctaacg    10980 tttgccaaca cttagcaatt tgcaagttga ttaattgatt ctaaattatt tttgtcttct    11040
aaatacatat actaatcaac tggaaatgta aatatttgct aatatttcta ctataggaga    11100
attaaagtga gtgaatatgg taccacaagg tttggagatt taattgttgc aatgctgcat    11160
ggatggcata tacaccaaac attcaataat tcttgaggat aataatggta ccacacaaga    11220
tttgaggtgc atgaacgtca cgtggacaaa aggtttagta attttttcaag acaacaatgt    11280 taccacacac aagttttgag gtgcatgcat ggatgccctg tggaaagttt aaaaatattt    11340
tggaaatgat ttgcatggaa gccatgtgta aaaccatgac atccacttgg aggatgcaat    11400
aatgaagaaa actacaaatt tacatgcaac tagttatgca tgtagtctat ataatgagga    11460
ttttgcaata ctttcattca tacacactca ctaagtttta cacgattata atttcttcat    11520
agccagccca ccgcggtgga aa atg gag gtc gtg gag aga ttc tac ggt gag    11572
                          Met Glu Val Val Glu Arg Phe Tyr Gly Glu
                           1               5                  10 ttg gat ggg aag gtc tcg cag ggc gtg aat gca ttg ctg ggt agt ttt    11620
Leu Asp Gly Lys Val Ser Gln Gly Val Asn Ala Leu Leu Gly Ser Phe
         15                  20                  25
```

```
ggg gtg gag ttg acg gat acg ccc act acc aaa ggc ttg ccc ctc gtt    11668
Gly Val Glu Leu Thr Asp Thr Pro Thr Thr Lys Gly Leu Pro Leu Val
             30                  35                  40 gac agt ccc aca ccc atc gtc ctc ggt gtt tct gta tac ttg act att    11716
Asp Ser Pro Thr Pro Ile Val Leu Gly Val Ser Val Tyr Leu Thr Ile
         45                  50                  55 gtc att gga ggg ctt ttg tgg ata aag gcc agg gat ctg aaa ccg cgc    11764
Val Ile Gly Gly Leu Leu Trp Ile Lys Ala Arg Asp Leu Lys Pro Arg
         60                  65                  70 gcc tcg gag cca ttt ttg ctc caa gct ttg gtg ctt gtg cac aac ctg    11812
Ala Ser Glu Pro Phe Leu Leu Gln Ala Leu Val Leu Val His Asn Leu
75                  80                  85                  90 ttc tgt ttt gcg ctc agt ctg tat atg tgc gtg ggc atc gct tat cag    11860
Phe Cys Phe Ala Leu Ser Leu Tyr Met Cys Val Gly Ile Ala Tyr Gln
                 95                 100                 105 gct att acc tgg cgg tac tct ctc tgg ggc aat gca tac aat cct aaa    11908
Ala Ile Thr Trp Arg Tyr Ser Leu Trp Gly Asn Ala Tyr Asn Pro Lys
            110                 115                 120 cat aaa gag atg gcg att ctg gta tac ttg ttc tac atg tct aag tac    11956
His Lys Glu Met Ala Ile Leu Val Tyr Leu Phe Tyr Met Ser Lys Tyr
            125                 130                 135 gtg gaa ttc atg gat acc gtt atc atg ata ctg aag cgc agc acc agg    12004
Val Glu Phe Met Asp Thr Val Ile Met Ile Leu Lys Arg Ser Thr Arg
140                 145                 150 caa ata agc ttc ctc cac gtt tat cat cat tct tca att tcc ctc att    12052
Gln Ile Ser Phe Leu His Val Tyr His His Ser Ser Ile Ser Leu Ile
155                 160                 165                 170 tgg tgg gct att gct cat cac gct cct ggc ggt gaa gca tat tgg tct    12100
Trp Trp Ala Ile Ala His His Ala Pro Gly Gly Glu Ala Tyr Trp Ser
                175                 180                 185 gcg gct ctg aac tca gga gtg cat gtt ctc atg tat gcg tat tac ttc    12148
Ala Ala Leu Asn Ser Gly Val His Val Leu Met Tyr Ala Tyr Tyr Phe
                190                 195                 200 ttg gct gcc tgc ctt cga agt agc cca aag tta aaa aat aag tac ctt    12196
Leu Ala Ala Cys Leu Arg Ser Ser Pro Lys Leu Lys Asn Lys Tyr Leu
            205                 210                 215 ttt tgg ggc agg tac ttg aca caa ttc caa atg ttc cag ttt atg ctg    12244
Phe Trp Gly Arg Tyr Leu Thr Gln Phe Gln Met Phe Gln Phe Met Leu
220                 225                 230 aac tta gtg cag gct tac tac gac atg aaa acg aat gcg cca tat cca    12292
Asn Leu Val Gln Ala Tyr Tyr Asp Met Lys Thr Asn Ala Pro Tyr Pro
235                 240                 245                 250 caa tgg ctg atc aag att ttg ttc tac tac atg atc tcg ttg ctg ttt    12340
Gln Trp Leu Ile Lys Ile Leu Phe Tyr Tyr Met Ile Ser Leu Leu Phe
            255                 260                 265 ctt ttc ggc aat ttt tac gta caa aaa tac atc aaa ccc tct gac gga    12388
Leu Phe Gly Asn Phe Tyr Val Gln Lys Tyr Ile Lys Pro Ser Asp Gly
            270                 275                 280 aag caa aag gga gct aaa act gag tga tctagaaggc ctcctgcttt          12435
Lys Gln Lys Gly Ala Lys Thr Glu
            285                 290 aatgagatat gcgagacgcc tatgatcgca tgatatttgc tttcaattct gttgtgcacg  12495
ttgtaaaaaa cctgagcatg tgtagctcag atccttaccg ccggtttcgg ttcattctaa  12555
tgaatatatc acccgttact atcgtatttt tatgaataat attctccgtt caatttactg  12615
attgtccgtc gagcaaattt acacattgcc actaaacgtc taaacccttg taatttgttt  12675 ttgtttttact atgtgtgtta tgtatttgat ttgcgataaa ttttatatt tggtactaaa  12735
```

-continued

```
tttataacac ctttttatgct aacgtttgcc aacacttagc aatttgcaag ttgattaatt    12795
gattctaaat tattttttgtc ttctaaatac atatactaat caactggaaa tgtaaatatt    12855
tgctaatatt tctactatag gagaattaaa gtgagtgaat atggtaccac aaggtttgga    12915
gatttaattg ttgcaatgct gcatggatgg catatacacc aaacattcaa taattcttga    12975
ggataataat ggtaccacac aagatttgag gtgcatgaac gtcacgtgga caaaaggttt    13035
agtaattttt caagacaaca atgttaccac acacaagttt tgaggtgcat gcatggatgc    13095
cctgtggaaa gtttaaaaat attttggaaa tgatttgcat ggaagccatg tgtaaaacca    13155
tgacatccac ttggaggatg caataatgaa gaaaactaca aatttacatg caactagtta    13215
tgcatgtagt ctatataatg aggattttgc aatactttca ttcatacaca ctcactaagt    13275
tttacacgat tataatttct tcatagccag cggatcc atg gta ttc gcg ggc ggt    13330
                                      Met Val Phe Ala Gly Gly
                                                        295 gga ctt cag cag ggc tct ctc gaa gaa aac atc gac gtc gag cac att    13378
Gly Leu Gln Gln Gly Ser Leu Glu Glu Asn Ile Asp Val Glu His Ile
        300                 305                 310 gcc agt atg tct ctc ttc agc gac ttc ttc agt tat gtg tct tca act    13426
Ala Ser Met Ser Leu Phe Ser Asp Phe Phe Ser Tyr Val Ser Ser Thr
    315                 320                 325 gtt ggt tcg tgg agc gta cac agt ata caa cct ttg aag cgc ctg acg    13474
Val Gly Ser Trp Ser Val His Ser Ile Gln Pro Leu Lys Arg Leu Thr
330                 335                 340 agt aag aag cgt gtt tcg gaa agc gct gcc gtg caa tgt ata tca gct    13522
Ser Lys Lys Arg Val Ser Glu Ser Ala Ala Val Gln Cys Ile Ser Ala
345                 350                 355                 360 gaa gtt cag aga aat tcg agt acc cag gga act gcg gag gca ctc gca    13570
Glu Val Gln Arg Asn Ser Ser Thr Gln Gly Thr Ala Glu Ala Leu Ala
                365                 370                 375 gaa tca gtc gtg aag ccc acg aga cga agg tca tct cag tgg aag aag    13618
Glu Ser Val Val Lys Pro Thr Arg Arg Arg Ser Ser Gln Trp Lys Lys
            380                 385                 390 tcg aca cac ccc cta tca gaa gta gca gta cac aac aag cca agc gat    13666
Ser Thr His Pro Leu Ser Glu Val Ala Val His Asn Lys Pro Ser Asp
        395                 400                 405 tgc tgg att gtt gta aaa aac aag gtg tat gat gtt tcc aat ttt gcg    13714
Cys Trp Ile Val Val Lys Asn Lys Val Tyr Asp Val Ser Asn Phe Ala
    410                 415                 420 gac gag cat ccc gga gga tca gtt att agt act tat ttt gga cga gac    13762
Asp Glu His Pro Gly Gly Ser Val Ile Ser Thr Tyr Phe Gly Arg Asp
425                 430                 435                 440 ggc aca gat gtt ttc tct agt ttt cat gca gct tct aca tgg aaa att    13810
Gly Thr Asp Val Phe Ser Ser Phe His Ala Ala Ser Thr Trp Lys Ile
                445                 450                 455 ctt caa gac ttt tac att ggt gac gtg gag agg gtg gag ccg act cca    13858
Leu Gln Asp Phe Tyr Ile Gly Asp Val Glu Arg Val Glu Pro Thr Pro
            460                 465                 470 gag ctg ctg aaa gat ttc cga gaa atg aga gct ctt ttc ctg agg gag    13906
Glu Leu Leu Lys Asp Phe Arg Glu Met Arg Ala Leu Phe Leu Arg Glu
        475                 480                 485 caa ctt ttc aaa agt tcg aaa ttg tac tat gtt atg aag ctg ctc acg    13954
Gln Leu Phe Lys Ser Ser Lys Leu Tyr Tyr Val Met Lys Leu Leu Thr
    490                 495                 500 aat gtt gct att ttt gct gcg agc att gca ata ata tgt tgg agc aag    14002
Asn Val Ala Ile Phe Ala Ala Ser Ile Ala Ile Ile Cys Trp Ser Lys
505                 510                 515                 520 act att tca gcg gtt ttg gct tca gct tgt atg atg gct ctg tgt ttc    14050
```

```
Thr Ile Ser Ala Val Leu Ala Ser Ala Cys Met Met Ala Leu Cys Phe
            525                 530                 535 caa cag tgc gga tgg cta tcc cat gat ttt ctc cac aat cag gtg ttt      14098
Gln Gln Cys Gly Trp Leu Ser His Asp Phe Leu His Asn Gln Val Phe
            540                 545                 550 gag aca cgc tgg ctt aat gaa gtt gtc ggg tat gtg atc ggc aac gcc      14146
Glu Thr Arg Trp Leu Asn Glu Val Val Gly Tyr Val Ile Gly Asn Ala
            555                 560                 565 gtt ctg ggg ttt agt aca ggg tgg tgg aag gag aag cat aac ctt cat      14194
Val Leu Gly Phe Ser Thr Gly Trp Trp Lys Glu Lys His Asn Leu His
            570                 575                 580 cat gct gct cca aat gaa tgc gat cag act tac caa cca att gat gaa      14242
His Ala Ala Pro Asn Glu Cys Asp Gln Thr Tyr Gln Pro Ile Asp Glu
585                 590                 595                 600 gat att gat act ctc ccc ctc att gcc tgg agc aag gac ata ctg gcc      14290
Asp Ile Asp Thr Leu Pro Leu Ile Ala Trp Ser Lys Asp Ile Leu Ala
                605                 610                 615 aca gtt gag aat aag aca ttc ttg cga atc ctc caa tac cag cat ctg      14338
Thr Val Glu Asn Lys Thr Phe Leu Arg Ile Leu Gln Tyr Gln His Leu
                620                 625                 630 ttc ttc atg ggt ctg tta ttt ttc gcc cgt ggt agt tgg ctc ttt tgg      14386
Phe Phe Met Gly Leu Leu Phe Phe Ala Arg Gly Ser Trp Leu Phe Trp
                635                 640                 645 agc tgg aga tat acc tct aca gca gtg ctc tca cct gtc gac agg ttg      14434
Ser Trp Arg Tyr Thr Ser Thr Ala Val Leu Ser Pro Val Asp Arg Leu
            650                 655                 660 ttg gag aag gga act gtt ctg ttt cac tac ttt tgg ttc gtc ggg aca      14482
Leu Glu Lys Gly Thr Val Leu Phe His Tyr Phe Trp Phe Val Gly Thr
665                 670                 675                 680 gcg tgc tat ctt ctc cct ggt tgg aag cca tta gta tgg atg gcg gtg      14530
Ala Cys Tyr Leu Leu Pro Gly Trp Lys Pro Leu Val Trp Met Ala Val
                685                 690                 695 act gag ctc atg tcc ggc atg ctg ctg ggc ttt gta ttt gta ctt agc      14578
Thr Glu Leu Met Ser Gly Met Leu Leu Gly Phe Val Phe Val Leu Ser
                700                 705                 710 cac aat ggg atg gag gtt tat aat tcg tct aaa gaa ttc gtg agt gca      14626
His Asn Gly Met Glu Val Tyr Asn Ser Ser Lys Glu Phe Val Ser Ala
            715                 720                 725 cag atc gta tcc aca cgg gat atc aaa gga aac ata ttc aac gac tgg      14674
Gln Ile Val Ser Thr Arg Asp Ile Lys Gly Asn Ile Phe Asn Asp Trp
            730                 735                 740 ttc act ggt ggc ctt aac agg caa ata gag cat cat ctt ttc cca aca      14722
Phe Thr Gly Gly Leu Asn Arg Gln Ile Glu His His Leu Phe Pro Thr
745                 750                 755                 760 atg ccc agg cat aat tta aac aaa ata gca cct aga gtg gag gtg ttc      14770
Met Pro Arg His Asn Leu Asn Lys Ile Ala Pro Arg Val Glu Val Phe
                765                 770                 775 tgt aag aaa cac ggt ctg gtg tac gaa gac gta tct att gct acc ggc      14818
Cys Lys Lys His Gly Leu Val Tyr Glu Asp Val Ser Ile Ala Thr Gly
                780                 785                 790 act tgc aag gtt ttg aaa gca ttg aag gaa gtc gcg gag gct gcg gca      14866
Thr Cys Lys Val Leu Lys Ala Leu Lys Glu Val Ala Glu Ala Ala Ala
            795                 800                 805 gag cag cat gct acc acc agt taa gctagcgtta accctgcttt aatgagatat    14920
Glu Gln His Ala Thr Thr Ser
            810                 815 gcgagacgcc tatgatcgca tgatatttgc tttcaattct gttgtgcacg ttgtaaaaaa    14980
cctgagcatg tgtagctcag atccttaccg ccggtttcgg ttcattctaa tgaatatatc    15040
```

```
                                      -continued acccgttact atcgtatttt tatgaataat attctccgtt caatttactg attgtccgtc     15100
gagcaaattt acacattgcc actaaacgtc taaacccttg taatttgttt ttgttttact     15160
atgtgtgtta tgtatttgat ttgcgataaa ttttttatatt tggtactaaa tttataacac    15220
cttttatgct aacgtttgcc aacacttagc aatttgcaag ttgattaatt gattctaaat     15280 tattttttgtc ttctaaatac atatactaat caactggaaa tgtaaatatt tgctaatatt    15340
tctactatag gagaattaaa gtgagtgaat atggtaccac aaggtttgga gatttaattg     15400
ttgcaatgct gcatggatgg catatacacc aaacattcaa taattcttga ggataataat     15460
ggtaccacac aagattgag gtgcatgaac gtcacgtgga caaaaggttt agtaattttt       15520
caagacaaca atgttaccac acacaagttt tgaggtgcat gcatggatgc cctgtggaaa     15580
gtttaaaaat atttttggaaa tgatttgcat ggaagccatg tgtaaaacca tgacatccac    15640
ttggaggatg caataatgaa gaaaactaca aatttacatg caactagtta tgcatgtagt     15700
ctatataatg aggattttgc aatacttttca ttcatacaca ctcactaagt tttacacgat    15760
tataatttct tcatagccag cagatctaaa atg gct ccg gat gcg gat aag ctt    15814
                                   Met Ala Pro Asp Ala Asp Lys Leu
                                                                820 cga caa cgc cag acg act gcg gta gcg aag cac aat gct gct acc ata       15862
Arg Gln Arg Gln Thr Thr Ala Val Ala Lys His Asn Ala Ala Thr Ile
    825                 830                 835 tcg acg cag gaa cgc ctt tgc agt ctg tct tcg ctc aaa ggc gaa gaa       15910
Ser Thr Gln Glu Arg Leu Cys Ser Leu Ser Ser Leu Lys Gly Glu Glu
840                 845                 850                 855 gtc tgc atc gac gga atc atc tat gac ctc caa tca ttc gat cat ccc       15958
Val Cys Ile Asp Gly Ile Ile Tyr Asp Leu Gln Ser Phe Asp His Pro
                860                 865                 870 ggg ggt gaa acg atc aaa atg ttt ggt ggc aac gat gtc act gta cag       16006
Gly Gly Glu Thr Ile Lys Met Phe Gly Gly Asn Asp Val Thr Val Gln
    875                 880                 885 tac aag atg att cac ccg tac cat acc gag aag cat ttg gaa aag atg       16054
Tyr Lys Met Ile His Pro Tyr His Thr Glu Lys His Leu Glu Lys Met
890                 895                 900 aag cgt gtc ggc aag gtg acg gat ttc gtc tgc gag tac aag ttc gat       16102
Lys Arg Val Gly Lys Val Thr Asp Phe Val Cys Glu Tyr Lys Phe Asp
    905                 910                 915 acc gaa ttt gaa cgc gaa atc aaa cga gaa gtc ttc aag att gtg cga       16150
Thr Glu Phe Glu Arg Glu Ile Lys Arg Glu Val Phe Lys Ile Val Arg
920                 925                 930                 935 cga ggc aag gat ttc ggt act ttg gga tgg ttc ttc cgt gcg ttt tgc       16198
Arg Gly Lys Asp Phe Gly Thr Leu Gly Trp Phe Phe Arg Ala Phe Cys
                940                 945                 950 tac att gcc att ttc ttc tac ctg cag tac cat tgg gtc acc acg gga       16246
Tyr Ile Ala Ile Phe Phe Tyr Leu Gln Tyr His Trp Val Thr Thr Gly
    955                 960                 965 acc tct tgg ctg ctg gcc gtg gcc tac gga atc tcc caa gcg atg att       16294
Thr Ser Trp Leu Leu Ala Val Ala Tyr Gly Ile Ser Gln Ala Met Ile
970                 975                 980 ggc atg aat gtc cag cac gat gcc aac cac ggg gcc acc tcc aag cgt       16342
Gly Met Asn Val Gln His Asp Ala Asn His Gly Ala Thr Ser Lys Arg
    985                 990                 995 ccc tgg gtc aac gac atg cta ggc ctc ggt gcg gat ttt att ggt ggt       16390
Pro Trp Val Asn Asp Met Leu Gly Leu Gly Ala Asp Phe Ile Gly Gly
1000                1005                1010                1015 tcc aag tgg ctc tgg cag gaa caa cac tgg acc cac cac gct tac acc       16438
Ser Lys Trp Leu Trp Gln Glu Gln His Trp Thr His His Ala Tyr Thr
                1020                1025                1030
```

```
aat cac gcc gag atg gat ccc gat agc ttt ggt gcc gaa cca atg ctc    16486
Asn His Ala Glu Met Asp Pro Asp Ser Phe Gly Ala Glu Pro Met Leu
        1035                1040                1045 cta ttc aac gac tat ccc ttg gat cat ccc gct cgt acc tgg cta cat    16534
Leu Phe Asn Asp Tyr Pro Leu Asp His Pro Ala Arg Thr Trp Leu His
    1050                1055                1060 cgc ttt caa gca ttc ttt tac atg ccc gtc ttg gct gga tac tgg ttg    16582
Arg Phe Gln Ala Phe Phe Tyr Met Pro Val Leu Ala Gly Tyr Trp Leu
1065                1070                1075 tcc gct gtc ttc aat cca caa att ctt gac ctc cag caa cgc ggc gca    16630
Ser Ala Val Phe Asn Pro Gln Ile Leu Asp Leu Gln Gln Arg Gly Ala
1080                1085                1090                1095 ctt tcc gtc ggt atc cgt ctc gac aac gct ttc att cac tcg cga cgc    16678
Leu Ser Val Gly Ile Arg Leu Asp Asn Ala Phe Ile His Ser Arg Arg
                1100                1105                1110 aag tat gcg gtt ttc tgg cgg gct gtg tac att gcg gtg aac gtg att    16726
Lys Tyr Ala Val Phe Trp Arg Ala Val Tyr Ile Ala Val Asn Val Ile
    1115                1120                1125 gct ccg ttt tac aca aac tcc ggc ctc gaa tgg tcc tgg cgt gtc ttt    16774
Ala Pro Phe Tyr Thr Asn Ser Gly Leu Glu Trp Ser Trp Arg Val Phe
        1130                1135                1140 gga aac atc atg ctc atg ggt gtg gcg gaa tcg ctc gcg ctg gcg gtc    16822
Gly Asn Ile Met Leu Met Gly Val Ala Glu Ser Leu Ala Leu Ala Val
    1145                1150                1155 ctg ttt tcg ttg tcg cac aat ttc gaa tcc gcg gat cgc gat ccg acc    16870
Leu Phe Ser Leu Ser His Asn Phe Glu Ser Ala Asp Arg Asp Pro Thr
1160                1165                1170                1175 gcc cca ctg aaa aag acg gga gaa cca gtc gac tgg ttc aag aca cag    16918
Ala Pro Leu Lys Lys Thr Gly Glu Pro Val Asp Trp Phe Lys Thr Gln
                1180                1185                1190 gtc gaa act tcc tgc act tac ggt gga ttc ctt tcc ggt tgc ttc acg    16966
Val Glu Thr Ser Cys Thr Tyr Gly Gly Phe Leu Ser Gly Cys Phe Thr
    1195                1200                1205 gga ggt ctc aac ttt cag gtt gaa cac cac ttg ttc cca cgc atg agc    17014
Gly Gly Leu Asn Phe Gln Val Glu His His Leu Phe Pro Arg Met Ser
        1210                1215                1220 agc gct tgg tat ccc tac att gcc ccc aag gtc cgc gaa att tgc gcc    17062
Ser Ala Trp Tyr Pro Tyr Ile Ala Pro Lys Val Arg Glu Ile Cys Ala
    1225                1230                1235 aaa cac ggc gtc cac tac gcc tac tac ccg tgg atc cac caa aac ttt    17110
Lys His Gly Val His Tyr Ala Tyr Tyr Pro Trp Ile His Gln Asn Phe
1240                1245                1250                1255 ctc tcc acc gtc cgc tac atg cac gcg gcc ggg acc ggt gcc aac tgg    17158
Leu Ser Thr Val Arg Tyr Met His Ala Ala Gly Thr Gly Ala Asn Trp
                1260                1265                1270 cgc cag atg gcc aga gaa aat ccc ttg acc gga cgg gcg taa             17200
Arg Gln Met Ala Arg Glu Asn Pro Leu Thr Gly Arg Ala
    1275                1280 agatctgccg gcatcgatcc cgggccatgg cctgctttaa tgagatatgc gagacgccta  17260
tgatcgcatg atatttgctt tcaattctgt tgtgcacgtt gtaaaaaacc tgagcatgtg  17320
tagctcagat ccttaccgcc ggtttcggtt cattctaatg aatatatcac ccgttactat  17380
cgtattttta tgaataatat tctccgttca atttactgat tgtccgtcga cgagctcggc  17440
gcgcctctag aggatcgatg aattcagatc ggctgagtgg ctccttcaac gttgcggttc  17500
tgtcagttcc aaacgtaaaa cggcttgtcc cgcgtcatcg gcggggggtca taacgtgact  17560 cccttaattc tccgctcatg atcagattgt cgtttccgc cttcagttta aactatcagt   17620
```

```
gtttgacagg atatattggc gggtaaacct aagagaaaag agcgtttatt agaataatcg    17680
gatatttaaa agggcgtgaa aaggtttatc cttcgtccat ttgtatgtgc atgccaacca    17740
cagggttccc ca                                                       17752
```

<210> SEQ ID NO 47
<211> LENGTH: 290
<212> TYPE: PRT
<213> ORGANISM: Unknown
<220> FEATURE:
<223> OTHER INFORMATION: vector

<400> SEQUENCE: 47

```
Met Glu Val Val Glu Arg Phe Tyr Gly Glu Leu Asp Gly Lys Val Ser
 1               5                  10                  15

Gln Gly Val Asn Ala Leu Leu Gly Ser Phe Gly Val Glu Leu Thr Asp
             20                  25                  30

Thr Pro Thr Thr Lys Gly Leu Pro Leu Val Asp Ser Pro Thr Pro Ile
         35                  40                  45

Val Leu Gly Val Ser Val Tyr Leu Thr Ile Val Ile Gly Gly Leu Leu
     50                  55                  60

Trp Ile Lys Ala Arg Asp Leu Lys Pro Arg Ala Ser Glu Pro Phe Leu
 65                  70                  75                  80

Leu Gln Ala Leu Val Leu Val His Asn Leu Phe Cys Phe Ala Leu Ser
                 85                  90                  95

Leu Tyr Met Cys Val Gly Ile Ala Tyr Gln Ala Ile Thr Trp Arg Tyr
            100                 105                 110

Ser Leu Trp Gly Asn Ala Tyr Asn Pro Lys His Lys Glu Met Ala Ile
        115                 120                 125

Leu Val Tyr Leu Phe Tyr Met Ser Lys Tyr Val Glu Phe Met Asp Thr
    130                 135                 140

Val Ile Met Ile Leu Lys Arg Ser Thr Arg Gln Ile Ser Phe Leu His
145                 150                 155                 160

Val Tyr His His Ser Ser Ile Ser Leu Ile Trp Trp Ala Ile Ala His
                165                 170                 175

His Ala Pro Gly Gly Glu Ala Tyr Trp Ser Ala Ala Leu Asn Ser Gly
            180                 185                 190

Val His Val Leu Met Tyr Ala Tyr Tyr Phe Leu Ala Ala Cys Leu Arg
        195                 200                 205

Ser Ser Pro Lys Leu Lys Asn Lys Tyr Leu Phe Trp Gly Arg Tyr Leu
    210                 215                 220

Thr Gln Phe Gln Met Phe Gln Phe Met Leu Asn Leu Val Gln Ala Tyr
225                 230                 235                 240

Tyr Asp Met Lys Thr Asn Ala Pro Tyr Pro Gln Trp Leu Ile Lys Ile
                245                 250                 255

Leu Phe Tyr Tyr Met Ile Ser Leu Leu Phe Leu Phe Gly Asn Phe Tyr
            260                 265                 270

Val Gln Lys Tyr Ile Lys Pro Ser Asp Gly Lys Gln Lys Gly Ala Lys
        275                 280                 285

Thr Glu
    290
```

<210> SEQ ID NO 48
<211> LENGTH: 525
<212> TYPE: PRT
<213> ORGANISM: Unknown
<220> FEATURE:

<223> OTHER INFORMATION: vector

<400> SEQUENCE: 48

```
Met Val Phe Ala Gly Gly Leu Gln Gln Gly Ser Leu Glu Glu Asn
 1               5                  10                  15

Ile Asp Val Glu His Ile Ala Ser Met Ser Leu Phe Ser Asp Phe Phe
             20                  25                  30

Ser Tyr Val Ser Ser Thr Val Gly Ser Trp Ser Val His Ser Ile Gln
         35                  40                  45

Pro Leu Lys Arg Leu Thr Ser Lys Lys Arg Val Ser Glu Ser Ala Ala
     50                  55                  60

Val Gln Cys Ile Ser Ala Glu Val Gln Arg Asn Ser Ser Thr Gln Gly
 65                  70                  75                  80

Thr Ala Glu Ala Leu Ala Glu Ser Val Val Lys Pro Thr Arg Arg Arg
                 85                  90                  95

Ser Ser Gln Trp Lys Lys Ser Thr His Pro Leu Ser Glu Val Ala Val
                100                 105                 110

His Asn Lys Pro Ser Asp Cys Trp Ile Val Lys Asn Lys Val Tyr
            115                 120                 125

Asp Val Ser Asn Phe Ala Asp Glu His Pro Gly Gly Ser Val Ile Ser
        130                 135                 140

Thr Tyr Phe Gly Arg Asp Gly Thr Asp Val Phe Ser Ser Phe His Ala
145                 150                 155                 160

Ala Ser Thr Trp Lys Ile Leu Gln Asp Phe Tyr Ile Gly Asp Val Glu
                165                 170                 175

Arg Val Glu Pro Thr Pro Glu Leu Leu Lys Asp Phe Arg Glu Met Arg
            180                 185                 190

Ala Leu Phe Leu Arg Glu Gln Leu Phe Lys Ser Ser Lys Leu Tyr Tyr
        195                 200                 205

Val Met Lys Leu Leu Thr Asn Val Ala Ile Phe Ala Ala Ser Ile Ala
210                 215                 220

Ile Ile Cys Trp Ser Lys Thr Ile Ser Ala Val Leu Ala Ser Ala Cys
225                 230                 235                 240

Met Met Ala Leu Cys Phe Gln Gln Cys Gly Trp Leu Ser His Asp Phe
                245                 250                 255

Leu His Asn Gln Val Phe Glu Thr Arg Trp Leu Asn Glu Val Val Gly
            260                 265                 270

Tyr Val Ile Gly Asn Ala Val Leu Gly Phe Ser Thr Gly Trp Trp Lys
        275                 280                 285

Glu Lys His Asn Leu His His Ala Ala Pro Asn Glu Cys Asp Gln Thr
290                 295                 300

Tyr Gln Pro Ile Asp Glu Asp Ile Asp Thr Leu Pro Leu Ile Ala Trp
305                 310                 315                 320

Ser Lys Asp Ile Leu Ala Thr Val Glu Asn Lys Thr Phe Leu Arg Ile
                325                 330                 335

Leu Gln Tyr Gln His Leu Phe Phe Met Gly Leu Leu Phe Phe Ala Arg
            340                 345                 350

Gly Ser Trp Leu Phe Trp Ser Trp Arg Tyr Thr Ser Thr Ala Val Leu
        355                 360                 365

Ser Pro Val Asp Arg Leu Leu Glu Lys Gly Thr Val Leu Phe His Tyr
370                 375                 380

Phe Trp Phe Val Gly Thr Ala Cys Tyr Leu Leu Pro Gly Trp Lys Pro
385                 390                 395                 400
```

-continued

```
Leu Val Trp Met Ala Val Thr Glu Leu Met Ser Gly Met Leu Leu Gly
            405                 410                 415

Phe Val Phe Val Leu Ser His Asn Gly Met Glu Val Tyr Asn Ser Ser
        420                 425                 430

Lys Glu Phe Val Ser Ala Gln Ile Val Ser Thr Arg Asp Ile Lys Gly
            435                 440                 445

Asn Ile Phe Asn Asp Trp Phe Thr Gly Gly Leu Asn Arg Gln Ile Glu
    450                 455                 460

His His Leu Phe Pro Thr Met Pro Arg His Asn Leu Asn Lys Ile Ala
465                 470                 475                 480

Pro Arg Val Glu Val Phe Cys Lys Lys His Gly Leu Val Tyr Glu Asp
                485                 490                 495

Val Ser Ile Ala Thr Gly Thr Cys Lys Val Leu Lys Ala Leu Lys Glu
            500                 505                 510

Val Ala Glu Ala Ala Glu Gln His Ala Thr Thr Ser
            515                 520                 525

<210> SEQ ID NO 49
<211> LENGTH: 469
<212> TYPE: PRT
<213> ORGANISM: Unknown
<220> FEATURE:
<223> OTHER INFORMATION: vector

<400> SEQUENCE: 49

Met Ala Pro Asp Ala Asp Lys Leu Arg Gln Arg Gln Thr Thr Ala Val
1               5                   10                  15

Ala Lys His Asn Ala Ala Thr Ile Ser Thr Gln Glu Arg Leu Cys Ser
            20                  25                  30

Leu Ser Ser Leu Lys Gly Glu Glu Val Cys Ile Asp Gly Ile Ile Tyr
        35                  40                  45

Asp Leu Gln Ser Phe Asp His Pro Gly Gly Glu Thr Ile Lys Met Phe
    50                  55                  60

Gly Gly Asn Asp Val Thr Val Gln Tyr Lys Met Ile His Pro Tyr His
65                  70                  75                  80

Thr Glu Lys His Leu Glu Lys Met Lys Arg Val Gly Lys Val Thr Asp
                85                  90                  95

Phe Val Cys Glu Tyr Lys Phe Asp Thr Glu Phe Glu Arg Glu Ile Lys
            100                 105                 110

Arg Glu Val Phe Lys Ile Val Arg Arg Gly Lys Asp Phe Gly Thr Leu
        115                 120                 125

Gly Trp Phe Phe Arg Ala Phe Cys Tyr Ile Ala Ile Phe Phe Tyr Leu
    130                 135                 140

Gln Tyr His Trp Val Thr Thr Gly Thr Ser Trp Leu Leu Ala Val Ala
145                 150                 155                 160

Tyr Gly Ile Ser Gln Ala Met Ile Gly Met Asn Val Gln His Asp Ala
                165                 170                 175

Asn His Gly Ala Thr Ser Lys Arg Pro Trp Val Asn Asp Met Leu Gly
            180                 185                 190

Leu Gly Ala Asp Phe Ile Gly Gly Ser Lys Trp Leu Trp Gln Glu Gln
        195                 200                 205

His Trp Thr His His Ala Tyr Thr Asn His Ala Glu Met Asp Pro Asp
    210                 215                 220

Ser Phe Gly Ala Glu Pro Met Leu Leu Phe Asn Asp Tyr Pro Leu Asp
225                 230                 235                 240
```

```
His Pro Ala Arg Thr Trp Leu His Arg Phe Gln Ala Phe Phe Tyr Met
                245                 250                 255
Pro Val Leu Ala Gly Tyr Trp Leu Ser Ala Val Phe Asn Pro Gln Ile
            260                 265                 270
Leu Asp Leu Gln Gln Arg Gly Ala Leu Ser Val Gly Ile Arg Leu Asp
        275                 280                 285
Asn Ala Phe Ile His Ser Arg Arg Lys Tyr Ala Val Phe Trp Arg Ala
    290                 295                 300
Val Tyr Ile Ala Val Asn Val Ile Ala Pro Phe Tyr Thr Asn Ser Gly
305                 310                 315                 320
Leu Glu Trp Ser Trp Arg Val Phe Gly Asn Ile Met Leu Met Gly Val
                325                 330                 335
Ala Glu Ser Leu Ala Leu Ala Val Leu Phe Ser Leu Ser His Asn Phe
            340                 345                 350
Glu Ser Ala Asp Arg Asp Pro Thr Ala Pro Leu Lys Lys Thr Gly Glu
        355                 360                 365
Pro Val Asp Trp Phe Lys Thr Gln Val Glu Thr Ser Cys Thr Tyr Gly
    370                 375                 380
Gly Phe Leu Ser Gly Cys Phe Thr Gly Gly Leu Asn Phe Gln Val Glu
385                 390                 395                 400
His His Leu Phe Pro Arg Met Ser Ser Ala Trp Tyr Pro Tyr Ile Ala
                405                 410                 415
Pro Lys Val Arg Glu Ile Cys Ala Lys His Gly Val His Tyr Ala Tyr
            420                 425                 430
Tyr Pro Trp Ile His Gln Asn Phe Leu Ser Thr Val Arg Tyr Met His
        435                 440                 445
Ala Ala Gly Thr Gly Ala Asn Trp Arg Gln Met Ala Arg Glu Asn Pro
    450                 455                 460
Leu Thr Gly Arg Ala
465

<210> SEQ ID NO 50
<211> LENGTH: 26
<212> TYPE: DNA
<213> ORGANISM: Artificial sequence
<220> FEATURE:
<223> OTHER INFORMATION: Polylinker

<400> SEQUENCE: 50
gaattcggcg cgccgagctc ctcgag                                          26

<210> SEQ ID NO 51
<211> LENGTH: 265
<212> TYPE: DNA
<213> ORGANISM: Artificial sequence
<220> FEATURE:
<223> OTHER INFORMATION: Polylinker-terminator-polylinker

<400> SEQUENCE: 51
ccaccgcggt gggcggccgc ctgcagtcta gaaggcctcc tgctttaatg agatatgcga      60
gacgcctatg atcgcatgat atttgctttc aattctgttg tgcacgttgt aaaaaacctg     120
agcatgtgta gctcagatcc ttaccgccgg tttcggttca ttctaatgaa tatatcaccc     180
gttactatcg tatttttatg aataatattc tccgttcaat ttactgattg tccgtcgacg     240
aattcgagct cggcgcgcca agctt                                          265

<210> SEQ ID NO 52
```

-continued

```
<211> LENGTH: 257
<212> TYPE: DNA
<213> ORGANISM: Artificial sequence
<220> FEATURE:
<223> OTHER INFORMATION: Polylinker-terminator-polylinker

<400> SEQUENCE: 52
ggatccgata tcgggcccgc tagcgttaac cctgctttaa tgagatatgc gagacgccta      60
tgatcgcatg atatttgctt tcaattctgt tgtgcacgtt gtaaaaaacc tgagcatgtg     120
tagctcagat ccttaccgcc ggtttcggtt cattctaatg aatatatcac ccgttactat     180
cgtattttta tgaataatat tctccgttca atttactgat tgtccgtcga cgaattcgag     240
ctcggcgcgc caagctt                                                    257

<210> SEQ ID NO 53
<211> LENGTH: 257
<212> TYPE: DNA
<213> ORGANISM: Artificial sequence
<220> FEATURE:
<223> OTHER INFORMATION: Polylinker-terminator-polylinker

<400> SEQUENCE: 53
agatctgccg gcatcgatcc cgggccatgg cctgctttaa tgagatatgc gagacgccta      60
tgatcgcatg atatttgctt tcaattctgt tgtgcacgtt gtaaaaaacc tgagcatgtg     120
tagctcagat ccttaccgcc ggtttcggtt cattctaatg aatatatcac ccgttactat     180
cgtattttta tgaataatat tctccgttca atttactgat tgtccgtcga cgaattcgag     240
ctcggcgcgc caagctt                                                    257

<210> SEQ ID NO 54
<211> LENGTH: 47
<212> TYPE: DNA
<213> ORGANISM: Artificial sequence
<220> FEATURE:
<223> OTHER INFORMATION: Synthetic oligonucleotide

<400> SEQUENCE: 54
ccggaattcg gcgcgccgag ctcctcgagc aaatttacac attgcca                    47

<210> SEQ ID NO 55
<211> LENGTH: 47
<212> TYPE: DNA
<213> ORGANISM: Artificial sequence
<220> FEATURE:
<223> OTHER INFORMATION: Synthetic oligonucleotide

<400> SEQUENCE: 55
ccggaattcg gcgcgccgag ctcctcgagc aaatttacac attgcca                    47

<210> SEQ ID NO 56
<211> LENGTH: 47
<212> TYPE: DNA
<213> ORGANISM: Artificial sequence
<220> FEATURE:
<223> OTHER INFORMATION: Synthetic oligonucleotide

<400> SEQUENCE: 56
ccggaattcg gcgcgccgag ctcctcgagc aaatttacac attgcca                    47

<210> SEQ ID NO 57
<211> LENGTH: 48
<212> TYPE: DNA
<213> ORGANISM: Artificial sequence
```

```
<220> FEATURE:
<223> OTHER INFORMATION: Synthetic oligonucleotide

<400> SEQUENCE: 57
aaaactgcag gcggccgccc accgcggtgg gctggctatg aagaaatt                    48

<210> SEQ ID NO 58
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 58
cgcggatccg ctggctatga agaaatt                                          27

<210> SEQ ID NO 59
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 59
tcccccggga tcgatgccgg cagatctgct ggctatgaag aaatt                      45

<210> SEQ ID NO 60
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 60
aaaactgcag tctagaaggc ctcctgcttt aatgagatat                            40

<210> SEQ ID NO 61
<211> LENGTH: 51
<212> TYPE: DNA
<213> ORGANISM: Artificial sequence
<220> FEATURE:
<223> OTHER INFORMATION: Synthetic oligonucleotide

<400> SEQUENCE: 61
cgcggatccg atatcgggcc cgctagcgtt aaccctgctt taatgagata t               51

<210> SEQ ID NO 62
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 62
tcccccgggc catggcctgc tttaatgaga tat                                   33

<210> SEQ ID NO 63
<211> LENGTH: 53
<212> TYPE: DNA
<213> ORGANISM: Artificial sequence
<220> FEATURE:
<223> OTHER INFORMATION: Synthetic oligonucleotide

<400> SEQUENCE: 63
cccaagcttg gcgcgccgag ctcgaattcg tcgacggaca atcagtaaat tga             53
```

```
<210> SEQ ID NO 64
<211> LENGTH: 53
<212> TYPE: DNA
<213> ORGANISM: Artificial sequence
<220> FEATURE:
<223> OTHER INFORMATION: Synthetic oligonucleotide

<400> SEQUENCE: 64
cccaagcttg gcgcgccgag ctcgaattcg tcgacggaca atcagtaaat tga          53

<210> SEQ ID NO 65
<211> LENGTH: 47
<212> TYPE: DNA
<213> ORGANISM: Artificial sequence
<220> FEATURE:
<223> OTHER INFORMATION: Synthetic oligonucleotide

<400> SEQUENCE: 65
cccaagcttg gcgcgccgag ctcgtcgacg gacaatcagt aaattga                 47
```

METHOD FOR PRODUCING MULTIPLE UNSATURATED FATTY ACIDS IN PLANTS

RELATED APPLICATIONS

This application is a national stage application (under 35 U.S.C. 371) of PCT/EP03/04297 filed Apr. 25, 2003, which claims benefit of German application 102 19 203.0 filed Apr. 29, 2002.

INCORPORATION OF SEQUENCE LISTING

The contents of the following submission on compact discs are incorporated herein by reference in its entirety: two copies of the Sequence Listing (COPY 1 and COPY 2) and a computer-readable form of the Sequence Listing (CRF COPY), all on CD-ROMs, each containing: file name: Final Sequence list-12810-00043-US, date recorded: May 16, 2006, size: 668 KB.

FIELD OF THE INVENTION

The present invention relates to a method for the production of fatty acid esters which comprise unsaturated fatty acids with at least three double bonds, and to free unsaturated fatty acids with a content of at least 1% by weight based on the total fatty acids present in the plants, by expressing at least one nucleic acid sequence which encodes a polypeptide with Δ6-desaturase activity and at least one nucleic acid sequence which encodes a polypeptide with Δ6-elongase activity. Advantageously, these nucleic acid sequences can, if appropriate, be expressed in the transgenic plant together with a third nucleic acid sequence which encodes a polypeptide with Δ5-desaturase activity.

The invention furthermore relates to the use of defined nucleic acid sequences which encode polypeptides with a Δ6-desaturase activity, Δ6-elongase activity or Δ5-desaturase activity selected from a group of nucleic acid sequences, and/or to the use of nucleic acid constructs comprising the abovementioned nucleic acid sequences.

DESCRIPTION OF THE BACKGROUND

Certain products and by-products of naturally occurring metabolic processes in microbial cells or in the cells of animals and, advantageously plants, have utility for a wide range of industries, including the feed, food, cosmetics and pharmaceutical industries. These molecules, which are collectively termed "fine chemicals", also include, for example, lipids and fatty acids, one representative class of which are the polyunsaturated fatty acids. Polyunsaturated fatty acids (PUFAs) are added for example to infant formula for increasing the nutritional value of these foods. PUFAs have, for example, a positive effect on the cholesterol level in the blood of humans and are therefore useful for protection against heart disease. Fine chemicals such as polyunsaturated fatty acids (PUFAs) can be isolated from animal sources such as, for example, fish, or produced by microorganisms by culturing microorganisms which have been developed such that they produce and accumulate or secrete large amounts of one or more desired molecules.

Fatty acids and triglycerides have a multiplicity of uses in the food industry, in animal nutrition, in cosmetics and in the pharmacological sector. Depending on whether they take the form of free saturated or unsaturated fatty acids or triglycerides with an increased content of saturated or unsaturated fatty acids, they are suitable for a variety of uses. Polyunsaturated Ω3-fatty acids and Ω6-fatty acids constitute an important part of animal and human nutrition. Owing to the present-day composition of human nutrition, an addition of polyunsaturated Ω3-fatty acids, which are predominantly found in fish oils, to the food is of particular importance. Thus, for example, polyunsaturated fatty acids such as docosahexaenoic acid (=DHA, $C22:6^{\Delta 4,7,10,13,16,19}$) or eisosapentaenoic acid (=EPA, $C20:5^{\Delta 5,8,11,14,17}$) is added to baby formula for increasing the nutritional value. DHA is said to have a positive effect on brain development.

The various acids and triglycerides are obtained mainly from microorganisms such as *Mortierella* or from oil-producing plants such as soybeans, oilseed rape, sunflower, algae such as *Cryptocodinium* or *Phaeodactylum* and others, the products being obtained, as a rule, in the form of their triacylglycerides (=triglycerides=triglycerols). However, they can also be obtained from animals such as, for example, fish. The free fatty acids are advantageously prepared by hydrolysis. Higher polyunsaturated fatty acids such as DHA, EPA, arachidonic acid (=ARA, $C20:4^{\Delta 5,8,11,14}$), dihomo-γ-linolenic acid ($C20:3^{\Delta 8,11,14}$) or docosapentaenoic acid (DPA, $C22:5^{\Delta 7,10,13,16,19}$) cannot be isolated from oil crops such as oilseed rape, soybeans, sunflower, safflower or others. Conventional natural sources of these fatty acids are fish such as herring, salmon, sardine, redfish, eel, carp, trout, halibut, mackerel, zander or tuna, or algae.

Depending on the intended purpose, oils with saturated or with unsaturated fatty acids are preferred; thus, for example, lipids with unsaturated fatty acids, specifically polyunsaturated fatty acids, are preferred in human nutrition. The polyunsaturated Ω3-fatty acids are said to have a positive effect on the cholesterol level in the blood and thus on the possibility of preventing heart disease. The risk of heart disease, stroke or hypertension can be reduced markedly by adding these ω3-fatty acids to the food. Also, Ω3-fatty acids can have a positive effect on inflammatory processes, specifically chronically inflammatory processes in connection with immunological diseases such as rheumatoid arthritis. These fatty acids are therefore added to foodstuffs, specifically dietetic foodstuffs, or are used in medicaments.

In connection with these rheumatic diseases due to the usual composition of our foods, Ω6-fatty acids such as arachidonic acid tend to have a negative effect on these diseases.

Ω3- and Ω6-fatty acids are precursors of tissue hormones, what are known as eicosanoids such as the postaglandins, which are derived from dihomo-γ-linolenic acid, arachidonic acid and eicosapentaenoic acid, the thromoxanes and the leukotrienes, which are derived from arachidonic acid and eicosapentaenoic acid. Eicosanoids (known as the $PG_2$ series), which are formed from Ω6-fatty acids, promote, as a rule, inflammatory reactions, while eicosanoids (known as the $PG_3$ series) from Ω3-fatty acids have a minor, or no, proinflammatory action.

Owing to the positive properties, there has been no lack of attempts in the past to make available genes which are involved in the synthesis of fatty acids or triglycerides, for the production, in various organisms, of oils with a modified content of unsaturated fatty acids. Thus, WO 91/13972 and its US equivalent describe a Δ9-desaturase. A Δ15-desaturase is claimed in WO 93/11245 and a Δ12-desaturase is claimed in WO 94/11516. Further desaturases are described, for example, in EP-A-0 550 162, WO 94/18337, WO 97/30582, WO 97/21340, WO 95/18222, EP-A-0 794 250, Stukey et al., J. Biol. Chem., 265, 1990: 20144-20149, Wada et al., Nature 347, 1990: 200-203 or Huang et al., Lipids 34, 1999: 649-659. However, the biochemical characterization of the various desaturases is incomplete as yet since the enzymes, being membrane-bound proteins, can only be isolated and characterized with great difficulty (McKeon et al., Methods in Enzymol. 71, 1981: 12141-12147, Wang et-al., Plant Physiol. Biochem., 26, 1988: 777-792). As a rule, membrane-bound desaturases are characterized by introduction into a suitable organism which is subsequently analyzed for enzyme activity by means of analyses of the starting material and the product. Δ6-Desaturases are described in WO 93/06712, U.S. Pat. No. 5,614,393, U.S. Pat. No. 5,614,393, WO 96/21022, WO00/21557 and WO 99/27111, and their application for the production in transgenic organisms has also been described, such as in WO98/46763 WO98/46764, WO9846765. In this context, the expression of various desaturases is also described and claimed, as is the case in WO99/64616 or WO98/46776, as is the formation of polyunsaturated fatty acids. As regards the efficacy of the expression of desaturases and their effect on the formation of polyunsaturated fatty acids, it must be noted that only minor contents of Δ6-unsaturated fatty acids/lipids, such as, for example, gamma-linolenic acid and stearidonic acid, have been obtained by expression of a single desaturase, as described to date. Moreover, a mixture of ω3- and ω6-fatty acids has been obtained as a rule, since all of the Δ6-desaturases described to date converted for example not only linoleic acid (ω6-fatty acid), but also α-linolenic acid (ω3-fatty acid).

Particularly suitable microorganisms for the production of PUFAs are microorganisms such as *Thraustochytrium* species or *Schizochytrium* species, algae such as *Phaeodactylum tricornutum* or *Crypthecodinium* species, ciliates such as *Stylonychia* or *Colpidium*, fungi such as *Mortierella, Entomophthora* or *Mucor*. Strain selection has made possible the development of mutant strains of the microorganisms in question which produce a series of desirable compounds, including PUFAs. The mutation and selection of strains with an improved production of a particular molecule, such as the polyunsaturated fatty acids, is, however, a time-consuming and difficult procedure. This is why recombinant methods are preferred whenever possible, as described above. However, only limited amounts of the desired polyunsaturated fatty acids such as DPA, EPA or APA can be produced with the aid of the abovementioned microorganisms, these unsaturated fatty acids being obtained, as a rule, as fatty acid mixtures of, for example, EPA, DPA and DHA, depending on the microorganism used.

As an alternative, the production of fine chemicals can suitably be carried out on a large scale via the production in plants which have been developed such that they produce the abovementioned PUFAs. Plants which are particularly suited to this purpose are oil crops, which comprise large amounts of lipid compounds, such as oilseed rape, canola, linseed, soyabeans, sunflowers, borage and evening primrose. However, other crop plants which comprise oils or lipids and fatty acids are also well suited, as mentioned in the extensive description of the present invention. Conventional breeding has given rise to a series of mutant plants which produce a spectrum of desirable lipids and fatty acids, cofactors and enzymes. However, the selection of new plant varieties with improved production of a particular molecule is a time-consuming and difficult procedure or is indeed impossible if the compound does not occur naturally in the plant in question, as in the case of polyunsaturated $C_{18}$-, $C_{20}$-fatty acids and $C_{22}$-fatty acids and those with longer carbon chains.

Owing to the positive properties of unsaturated fatty acids, there has been no lack of attempts in the past to make available these genes which are involved in the synthesis of fatty acids or triglycerides for the production, in various plants, of oils with a modified content of polyunsaturated fatty acids. However, it has been impossible as yet to produce longer-chain polyunsaturated $C_{20}$- and/or $C_{22}$-fatty acids such as EPA or ARA in plants.

SUMMARY OF THE INVENTION

The present invention provides, generally, methods for production of polyunsaturated acids in plants.

One embodiment of the invention is directed to processes for the production of compounds in transgenic plants wherein the compounds comprise the formula of Formula I:

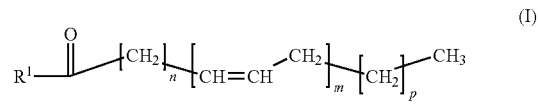

wherein: $R^1$=-OH, coenzyme A (thioester), phosphatidylcholine, phosphatidylethanolamine, phoshatidylglycerol, diphosphatidylglycerol, phosphatidylserine, phosphatidylinositol, sphingolipid, glycoshingolipid or a radical of Formula II;

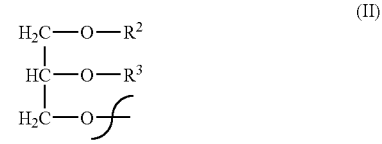

wherein $R^2$=H, phosphatidylcholine-, phosphatidylethanolamine-, phosphatidylglycerol-, diphosphatidylglycerol-, phosphatidylserine-, phosphatidylinositol-, sphingolipid-, glycoshingolipid-, glycoshingolipid- or saturated or unsaturated $C_2$-$C_{24}$-alkylcarbonyl-; and $R^3$=H, saturated or unsaturated $C_2$-$C_{24}$-alkylcarbonyl-. Preferably, $R^2$ and $R^3$ are independent of one another and represent a radical of Formula Ia:

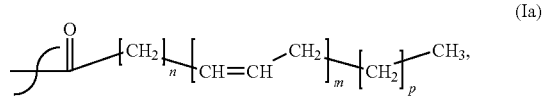

wherein n=3, 4 or 6; m=3, 4 or 5; and p=0 or 3.

The compounds preferably have a content in the transgenic plant of at least 1% by weight based on the total fatty acid content of the plant or, more preferably, 5% by weight. The process generally comprises introducing into a plant: at least one first nucleic acid sequence which encodes a polypeptide with an Δ6-desaturase activity; at least one second nucleic acid sequence which encodes a polypeptide with a Δ6-elongase activity; and, optionally, at least one third nucleic acid sequence which encodes a polypeptide with a Δ5-desaturase activity. The process further comprises growing and harvesting the transgenic plants.

Preferably, variables $R^2$ and $R^3$ are independent of one another and are $C_{10}$-$C_{22}$-alkylcarbonyl-, or are $C_{16}$-, $C_{18}$-, $C_{20}$- or $C_{22}$-alkylcarbonyl-, wherein any of the preceding may have one, two, three, four or five double bonds. Preferably, the plant is a plant of an oil crop, or a plant selected from the group soya, peanut, oilseed rape, canola, linseed, evening primrose, verbascum, thistle, hazelnut, almond, macadamia, avocado, bay, wild roses, pumpkin/squash, pistachios, sesame, sunflower, safflower, borage, maize, poppy, mustard, hemp, castor-oil plant, olive, Calendula, Punica, oil palm, walnut and coconut.

Preferably, the compounds are obtained from the oils, fats, lipids or free fatty acids of the transgenic plants by pressing or extraction, and once obtained may be further refined. Also preferably, the saturated or unsaturated fatty acids present in the compounds may be liberated such as, for example, by alkaline hydrolysis or enzymatic cleavage.

Preferably, one or more of the nucleic acid sequences which encode the polypeptides with Δ6-desaturase activity, Δ6-elongase activity or Δ5-desaturase activity, may be selected from the group consisting of: a) a nucleic acid sequence with the sequence shown in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29 or SEQ ID NO: 31, b) nucleic acid sequences which, owing to the degeneracy of the genetic code, are obtained by back translation of the amino acid sequences shown in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30 or SEQ ID NO: 32, or c) derivatives of the nucleic acid sequences shown in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29 or SEQ ID NO: 31 which encode polypeptides with the amino acid sequences shown in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30 or SEQ ID NO: 32 and which have at least 50% homology at the amino acid level, without the enzymatic activity of the polypeptide being substantially reduced. Nucleic acid sequences may be linked with one or more regulatory signals in a nucleic acid construct and, nucleic acid constructs may additional biosynthetic genes of the fatty acid or lipid metabolism such as, preferably, acyl-CoA dehydrogenase(s), acyl-ACP [=acyl carrier protein] desaturase(s), acyl-ACP thioesterase(s), fatty acid acyl transferase(s), fatty acid synthase(s), fatty acid hydroxylase(s), acetyl-coenzyme A carboxylase(s), acyl-coenzyme A oxidase(s), fatty acid desaturase(s), fatty acid acetylenases, lipoxygenases, triacylglycerol lipases, allene oxide synthases, hydroperoxide lyases or fatty acid elongase(s).

Other embodiments and advantages of the invention are set forth in part in the description, which follows, and in part, may be obvious from this description, or may be learned from the practice of the invention.

DESCRIPTION OF THE DRAWINGS

FIG. 1. Biosynthesis chain.
FIG. 2. Fatty acid profile of transgenic tobacco seeds.
FIG. 3. Fatty acid profile of wild tobacco seeds as control.

DESCRIPTION OF THE INVENTION

It was therefore an object to develop a method for the production of polyunsaturated fatty acid esters and/or free polyunsaturated fatty acids with at least three double bonds in the fatty acid molecule. This object was achieved by the method according to the invention for the production of compounds of the general formula I:

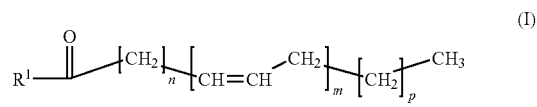

in transgenic plants with a content of at least 1% by weight based on the total fatty acids, which process comprises the following steps:

a) introducing, into a plant, at least one nucleic acid sequence which encodes a polypeptide with a Δ6-desaturase activity; and b) introducing at least one second nucleic acid sequence which encodes a polypeptide with a Δ6-elongase activity; and, c) if appropriate, introducing a third nucleic acid sequence which encodes a polypeptide with a Δ5-desaturase activity;

d) followed by growing and harvesting the plants; and where the variables and substituents in the formula I have the following meanings:

$R^1$=—OH, coenzyme A (thioester), phosphatidylcholine, phosphatidylethanolamine, phoshatidylglycerol, diphosphatidylglycerol, phosphatidylserine, phosphatidylinositol, sphingolipid, glycoshingolipid or a radical of the following general formula II

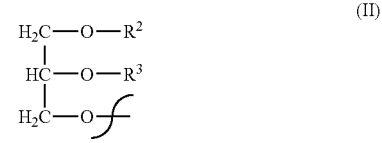

$R^2$=H, phosphatidylcholine-, phosphatidylethanolamine-, phosphatidylglycerol-, diphosphatidylglycerol-, phosphatidylserine-, phosphatidylinositol-, shingolipid-, glycoshingolipid-, glycoshingolipid- or saturated or unsaturated $C_2$-$C_{24}$-alkylcarbonyl-, $R^3$=H, saturated or unsaturated $C_2$-$C_{24}$-alkylcarbonyl-, or $R^2$ and $R^3$ independently of one another represent a radical of the general formula Ia

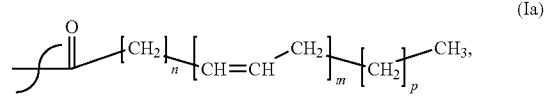

n=3, 4 or 6, m=3, 4 or 5 and p=0 or 3, preferably n=3, m=4 or 5 and p=0 or 3.

$R^1$ in the compounds of the formula I denotes —OH (hydroxyl-), acetyl-coenzyme A-, phosphatidylcholine-, phosphatidylethanolamine-, phoshatidylglycerol-, diphosphatidylglycerol-, phosphatidylserine-, phosphatidylinositol-, sphingolipid-, glycoshingolipid- or a radical of the following general formula II

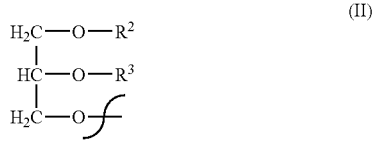

The abovementioned radicals for $R^1$ are in each case bound to the compounds of the formula I in the form of esters or thioesters.

$R^2$ in the compounds of the formula II denotes hydrogen, phosphatidylcholine-, phosphatidylethanolamine-, phoshatidylglycerol-, diphosphatidylglycerol-, phosphatidylserine-, phosphatidylinositol-, shingolipid-, glycoshingolipid-, glycoshingolipid- or saturated or unsaturated $C_2$-$C_{24}$-alkylcarbonyl-.

Unsaturated or saturated $C_2$-$C_{22}$-alkylcarbonyl which may be mentioned are radicals such as ethylcarbonyl, n-propylcarbonyl, n-butylcarbonyl, n-pentylcarbonyl, n-hexylcarbonyl, n-heptylcarbonyl, n-octylcarbonyl, n-nonylcarbonyl, n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl, n-nonadecylcarbonyl, n-eicosylcarbonyl, n-docosanylcarbonyl or n-tetracosanylcarbonyl, all of which may comprise one or more double bonds. Preferred are saturated or unsaturated $C_{10}$-$C_{22}$-alkylcarbonyl radicals such as n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl, n-nonadecylcarbonyl, n-eicosylcarbonyl, n-docosanylcarbonyl or n-tetracosanylcarbonyl, all of which comprise one or more double bonds. Especially preferred are saturated or unsaturated $C_{10}$-$C_{22}$-alkylcarbonyl radicals such as $C_{10}$-alkylcarbonyl, $C_{11}$-alkylcarbonyl, $C_{12}$-alkylcarbonyl, $C_{13}$-alkylcarbonyl, $C_{14}$-alkylcarbonyl, $C_{16}$-alkylcarbonyl, $C_{18}$-alkylcarbonyl, $C_{20}$-alkylcarbonyl, $C_{22}$-alkylcarbonyl or $C_{24}$-alkylcarbonyl radicals, all of which comprise one or more double bonds. Very especially preferred are saturated or unsaturated $C_{16}$-$C_{22}$-alkylcarbonyl radicals such as $C_{16}$-alkylcarbonyl, $C_{18}$-alkylcarbonyl, $C_{20}$-alkylcarbonyl or $C_{22}$-alkylcarbonyl radicals, all of which comprise one or more double bonds. Preferably, the abovementioned radicals comprise two, three, four or five double bonds. Especially preferably, the radicals comprise three, four or five double bonds. Very especially preferred are $C_{18}$-alkylcarbonyl radicals which comprise one, two, three or four double bonds and $C_{20}$-alkylcarbonyl radicals which comprise three, four or five double bonds. All of the abovementioned radicals are derived from the corresponding fatty acids.

$R^3$ denotes hydrogen or saturated or unsaturated $C_2$-$C_{24}$-alkylcarbonyl.

$R^2$ and $R^3$ in the compounds of the formula II independently of one another furthermore denote a radical of the general formula Ia

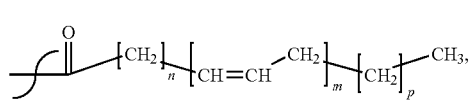

where n=3, 4 or 6, m=3, 4 or 5 and p=0 or 3, preferably n=3, m=4 or 5 and p=0 or 3.

The abovementioned radicals $R^1$, $R^2$ and $R^3$ may also have attached to them substituents such as hydroxyl or epoxy groups or else comprise triple bonds.

The nucleic acid sequences used in the method according to the invention are isolated nucleic acid sequences which encode polypeptides with Δ5-, Δ6-desaturase or Δ6-elongase activity.

The compounds of the formula I which are produced in this method advantageously comprise a mixture of differing radicals $R^1$, $R^2$ or $R^3$ which can be derived from differing glycerides. Moreover, the abovementioned radicals can be derived from different fatty acids such as short-chain fatty acids having 4 to 6 carbon atoms, medium-chain fatty acids having 8 to 12 carbon atoms or long-chain fatty acids having 14 to 24 carbon atoms; the long-chain fatty acids are preferred.

The method according to the invention advantageously gives fatty acid esters (=compounds of the formula I) with polyunsaturated $C_{18}$-, $C_{20}$- and/or $C_{22}$-fatty acid molecules with at least two double bonds in the fatty acid ester. Preferably, these fatty acid molecules comprise three, four or five double bonds and advantageously lead to the synthesis of γ-linolenic acid (=GLA, $C18:3^{\Delta6,9,12}$), stearidonic acid (=SDA, $C18:4^{\Delta6,9,12,15}$), dihomo-γ-linolenic acid (=DGLA, $20:3^{\Delta8,11,14}$), eicosatetraenoic acid (=ETA, $C20:4^{\Delta5,8,11,14}$), arachidonic acid (ARA), eicosapentaenoic acid (EPA) or their mixtures, preferably EPA and/or ARA.

The fatty acid esters with polyunsaturated $C_{18}$-, $C_{20}$- and/or $C_{22}$-fatty acid molecules can be isolated from the organisms which have been used for the production of the fatty acid esters in the form of an oil or lipid, for example in the form of compounds such as sphingolipids, phosphoglycerides, lipids, glycolipids such as glycoshingolipid, phospholipids such as phosphatidylethanolamine, phosphatidylcholine, phoshatidylserine, phosphatidylglycerol, phosphatidylinositol or diphosphatidylglycerol, monoacylglycerides, diacylglycerides, triacylglycerides or other fatty acid-esters such as the acetyl-coenzyme A esters which comprise the polyunsaturated fatty acids having at least two, preferably three, double bonds. In addition to these esters, the polyunsaturated fatty acids are also present in the plants as free fatty acids or bound in other compounds. As a rule, the different abovementioned compounds (fatty acid esters and free fatty acids) are present in the plant in an approximate distribution of 80 to 90% by weight of triglycerides, 2 to 5% by weight of diglycerides, 5 to 10% by weight of monoglycerides, 1 to 5% by weight of free fatty acids, 2 to 8% by weight of phospholipids, the total of the different compounds making 100% by weight.

When the compounds of the general formula I are produced in the method according to the invention, they are produced in a content of at least 1% by weight, advantageously at least 2% by weight, preferably at least 3% by weight, especially preferably at least 5% by weight, very especially preferably at least 10% by weight based on the total of the fatty acids in the transgenic plant. Since, in the method according to the invention, the starting compounds linoleic acid (C18:2) and/or linolenic acid (C18:3) undergo several reaction steps, the end products of the method, such as, for example, arachidonic acid (ARA) or eicosapentaenoic acid (EPA) are not obtained as pure products, but there are always minor amounts of the precursors still present in the end product. If both linoleic acid and linolenic acid are present in the original plant, the end products such as ARA and EPA are present as mixtures. The precursors should advantageously not amount to more than 20% by weight, preferably not more than 15% by weight, especially preferably not more than 10% by weight, very especially preferably not more than 5% by weight, based on the amount of the end product in question. Advantageously, the end products which are produced in the method according to the invention in a transgenic plant are only ARA or only EPA, either bound or as free acids (see compounds of the general formula I). If both compounds (ARA+EPA) are produced simultaneously, they are advantageously prduced in a ratio of at least 1:2 (EPA:ARA), advantageously at least 1:3, preferably 1:4, especially preferably 1:5.

Suitable organisms for the production in the method according to the invention are, in principle, all plants such as mosses, algae, dicots or monocots. It is advantageous to use, in the method according to the invention, organisms which belong to the oil-producing organisms, i.e. which are used for the production of oils, such as algae like *Crypthecodinium*, *Phaeodactylum* or plants, in particular plants, preferably oil crops, which comprise large amounts of lipid compounds, such as peanut, oilseed rape, canola, sunflower, safflower, poppy, mustard, hemp, castor-oil plant, olive, sesame, *Calendula*, *Punica*, evening primrose, verbascum, thistle, wild roses, hazelnut, almond, macadamia, avocado, bay, pumpkin/squash, linseed, soybean, pistachios, borage, trees (oil palm, coconut or walnut) or field crops such as maize, wheat, rye, oats, triticale, rice, barley, cotton, cassava, pepper, Tagetes, Solanaceae plants such as potato, tobacco, eggplant and tomato, *Vicia* species, pea, alfalfa or bush plants (coffee, cacao, tea), *Salix* species and perennial grasses and fodder crops. Preferred plants according to the invention are oil crops such as peanut, oilseed rape, canola, sunflower, safflower, pea, mustard, hemp, castor-oil plants, olive, Calendula, Punica, evening primrose, pumpkin/squash, linseed, soybean, borage, trees (oil palm, coconut). Especially preferred are plants which are high in C18:2- and/or C18:3-fatty acid, such as sunflower, safflower, tobacco, verbascum, sesame, cotton, pumpkin/squash, poppy, evening primrose, walnut, linseed, hemp, thistle or safflower. Very especially preferred are plants such as safflower, sunflower, poppy, evening primrose, walnut, linseed or hemp.

Owing to the enzymatic activity of the nucleic acids used in the method according to the invention, which encode polypeptides with $\Delta 5$-, $\Delta 6$-desaturase or $\Delta 6$-longase activity, different compounds of the formula I can be produced. Depending on the choice of the plant used for the method according to the invention, mixtures of the different compounds of the general formula I or individual compounds, such as EPA or ARA, can be produced in free or bound form. Depending on the fatty acid composition which prevails in the original plant (C18:2- or C18:3-fatty acids), this gives compounds of the general formula I which are derived from C18:2-fatty acids, such as GLA-, DGLA- or ARA-comprising compounds of the formula I, or compounds which are derived from C18:3-fatty acids, such as SDA-, ETA- or EPA-comprising compounds of the formula I. If linoleic acid (=LA, $C18:2^{\Delta 9,12}$) is the only unsaturated fatty acid present in the plant used for the method, only GLA, DGLA and ARA can be formed as products of the method, all of which can be present as free fatty acids or in bound form. If $\alpha$-linolenic acid (=ALA, $C18:3^{\Delta 9,12,15}$) is the only unsaturated fatty acid present in the plant used in the method, for example such as in linseed, only SDA, ETA and EPA can be formed as products of the method, all of which can be present as free fatty acids or in bound form, as described above. By modifying the activity of the enzymes implicated in the synthesis ($\Delta 5$-, $\Delta 6$-desaturase and $\Delta 6$-elongase), or by introducing only the first two genes ($\Delta 6$-desaturase and $\Delta 6$-elongase) of the synthetic cascade, it is possible to produce in a targeted manner only individual products in the abovementioned plants (see FIG. I). Due to the activity of the enzymes $\Delta 6$-desaturase and $\Delta 6$-elongase, GLA and DGLA, or SDA and ETA, respectively, form, depending on the original plant and the unsaturated fatty acid. DGLA or ETA, respectively, or mixtures of these are formed preferentially. If the enzyme $\Delta 5$-desaturase is additionally introduced into the plant, ARA or EPA are additionally formed. It is advantageous only to synthesize ARA or EPA or their mixtures, depending on the fatty acid which is present in the plant and which acts as starting material for the synthesis. Since biosynthetic cascades are involved, the end products in question are not present in pure form in the plants. There are always minor amounts of the precursor compounds present in the end product. These minor amounts amount to less than 20% by weight, advantageously less than 15% by weight, especially advantageously less than 10% by weight, very especially advantageously less than 5, 4, 3, 2 or 1% by weight, based on the end product DGLA, ETA or their mixtures, or ARA, EPA or their mixtures, respectively.

For the purposes of the method according to the invention, transgenic plants are also understood as meaning plant cells, plant organs or intact plants which are grown for the production of compounds of the general formula I. Growing is understood as meaning for example culturing of the transgenic plant cells, plant tissue or plant organs on a nutrient medium or the intact plant on or in a substrate, for example in hydroponic culture or on an arable soil.

Nucleic acids which can be used in the method according to the invention are, in principle, all those which encode polypeptides with $\Delta 5$-, $\Delta 6$-desaturase- or $\Delta 6$-elongase activity. These nucleic acids are advantageously derived from plants such as algae, such as *Isochrysis* or *Crypthecodinium*, diatoms such as *Phaeodactylum*, mosses such as *Physcomitrella*, *Ceratodon* or higher plants such as the primulaceae, such as *Aleuritia, Calendula stellata, Osteospermum spinescens* or *Osteospermum hyoseroides*, microorganisms such as fungi, such as *Aspergillus, Thraustochytrium, Phytophtora, Entomophthora, Mucor* or *Mortierella*, yeasts or animals such as nematodes, such as *Caenorhabditis*, insects or humans. The $\Delta 5$-, $\Delta 6$-desaturase or $\Delta 6$-elongase genes are advantageously derived from fungi or from plants such as algae or mosses, preferably from plants.

It is advantageous to in the method according to the invention, a nucleic acid sequence selected from the group of the in SEQ ID NO: 1, 3, 5, 7, 9, 11, 13, 15, 17, 19, 21, 23, 25, 27, 29 or 31 or their derivative or homologs which encode polypeptides which retain the enzymatic activity. These sequences, individually or in combination, are cloned into expression constructs; these expression constructs are represented in the sequences SEQ ID NO: 33-37. These expression constructs make possible an optimal synthesis of the compounds of the general formula I produced in the method according to the invention.

In a preferred embodiment, the method furthermore comprises the step of obtaining a cell which comprises the nucleic acid sequences which are used in the method and which encode a $\Delta 5$- or $\Delta 6$-desaturase and a $\Delta 6$-elongase, where a cell is transformed with the nucleic acid sequence, a gene construct or a vector which bring about the expression of the $\Delta 5$-, $\Delta 6$-desaturase or $\Delta 6$-elongase nucleic acid, alone or in combination. In a further preferred embodiment, the method furthermore comprises the step of obtaining the fine chemical from the culture. The cell generated thus is advantageously a cell of an oil crop such as, for example, peanut, oilseed rape, canola, linseed, soybean, safflower, hemp, sunflowers or borage.

A transgenic plant is understood as meaning, for the purposes of the invention, that the nucleic acids used in the method are not at their natural locus in the genome of an organism; in this context, the nucleic acids can be expressed homologously or heterologously. However, transgenic also means that, while the nucleic acids according to the invention are at their natural locus in the genome of an organism, the sequence has been modified in comparison with the natural sequence and/or the regulatory sequences of the natural sequences have been modified. Preferably, transgenic is understood as meaning that the nucleic acids according to the invention are not expressed at their natural locus in the genome, that is to say that homologous or preferably heterologous expression of the nucleic acids takes place. Preferred transgenic plants are the oil crops.

Transgenic plants which comprise the compounds of the formula I which have been synthesized in the method according to the invention can be marketed directly without isolation of the compounds which have been synthesized. Plants are understood as meaning, in the method according to the invention, all plant parts, plant organs such as leaf, stem, root, tuber or seeds, or all of the plant. In this context, the seed comprises all parts of the seed such as the seed coats, epidermis cells and seed cells, endosperm or embyro tissue. However, the compounds produced in the method according to the invention can also be isolated from the plants in the form of their oils, fat, lipids and/or free fatty acids. Compounds of the formula I which have been produced by this method can be harvested by harvesting the organisms either from the culture in which they grow or from the field. This can be done by pressing or extracting the plant parts, preferably the plant seeds. In this context, the oils, fats, lipids and/or free fatty acids can be obtained by pressing by what is known as cold-beating or cold-pressing, without supplying heat. The plant parts, specifically the seeds, are beforehand comminuted, steam-treated or toasted in order to facilitate their disruption. The seeds pretreated thus can subsequently be pressed or else extracted with solvents such as warm hexane. The solvent is subsequently removed. In this manner, more than 96% of the compounds produced in the method can be isolated. The resulting products are subsequently processed further, i.e. refined. Here, the plant mucilages and turbid matter are first. What is known as degumming can be performed enzymatically or, for example, chemico-physically by adding acid such as phosphoric acid. The free fatty acids are subsequently removed by treatment with a base, for example sodium hydroxide solution. The resulting product is washed thoroughly with water to remove the alkali remaining in the product, and dried. To remove the coloring matter which still remains in the product, the products are bleached, for example using bleaching earth or active charcoal. At the end, the product is deodorized, for example by using steam.

The PUFAs produced by this method are preferentially $C_{18}$- or $C_{20-22}$-fatty acid molecules having at least two double bonds in the fatty acid molecule, preferably three, four, in combination with a further elongases and a Δ4-desaturase five or six double bonds. These $C_{18}$- or $C_{20-22}$-fatty acid molecules can be isolated from the organism in the form of an oil, lipid or a free fatty acid. Suitable organisms are, for example, those which have been mentioned above. Preferred organisms are transgenic plants.

In a preferred embodiment, oils, lipids or fatty acids or fractions of these which have been produced by the above-described method are especially preferably oil, lipid or a fatty acid composition which comprise PUFAs or which originate from transgenic plants.

A further embodiment according to the invention is the use of the oil, lipid or the fatty acid composition in foods, feeds, cosmetics or pharmaceuticals.

The term "oil" or "fat" is understood as meaning a fatty acid mixture which comprises unsaturated, saturated, preferably esterified fatty acid(s). It is preferred that the oil or fat has a high content of unsaturated, unconjugated esterified fatty acid(s), in particular linoleic acid, γ-linolenic acid, dihomo-γ-linolenic acid, arachidonic acid, α-linolenic acid, stearidonic acid, eicosatetraenoic acid or eicosapentaenoic acid. The amount of unsaturated esterified fatty acids is preferably approximately 30%, with an amount of 50% being more preferred and an amount of 60%, 70%, 80% or more being even more preferred. For identification purposes, it is possible, for example, to determine the amount of fatty acid by gas chromatography after converting the fatty acids into the methyl esters by means of transesterification. The oil or fat can comprise various other saturated or unsaturated fatty acids, for example calendulic acid, palmitic acid, stearic acid, oleic acid and the like. The amount of the various fatty acids in oil or fat can vary in particular as a function of the original plant.

The compounds of the formula I which are produced in the method and which comprise polyunsaturated fatty acids having at least two double bonds are sphingolipids, phosphoglycerides, lipids, glycolipids, phospholipids, monoacylglycerol, diacylglycerol, triacylglycerol or other fatty acid esters.

The polyunsaturated fatty acids which are present can be liberated from the compounds of the general formula I produced thus in the method according to the invention for example via treatment with alkali, for example aqueous KOH or NaOH, or acid hydrolysis, advantageously in the presence of an alcohol such as methanol or ethanol, or via enzymatic cleavage and isolated via, for example, phase separation and subsequent acidification with, for example, $H_2SO_4$. However, the fatty acids can also be liberated directly without the above-described processing.

After they have been introduced into plant cells or plants, the nucleic acids used in the method can either be located on a separate plasmid or integrated into the genome of the host cell. In the case of integration into the genome, the integration can be random or be effected by recombination in such a way that the native gene is replaced by the copy being introduced, whereby the production of the desired compound by the cell is modulated, or by using a gene in trans, so that the gene is linked operably with a functional expression unit which comprises at least one sequence which ensures the expression of a gene and at least one sequence which ensures the polyadenylation of a functionally transcribed gene. The nucleic acids are advantageously introduced into the plants via multiexpression cassettes or constructs for the multiparallel seed-specific expression of genes.

Mosses and algae are the only known plant systems which produce substantial amounts of polyunsaturated fatty acids such as arachidonic acid (ARA) and/or eicosapentaenoic acid (EPA) and/or docosahexaenoic acid (DHA). Mosses comprise PUFAs in membrane lipids, while algae, organisms which are related to algae and some fungi also accumulate substantial amounts of PUFAs in the triacylglycerol fraction. This is why nucleic acid molecules which are isolated from such strains which also accumulate PUFAs in the triacylglycerol fraction are especially advantageously suitable for the method according to the invention and thus for the modification of the lipid and PUFA production system in a host, in particular plants, such as oil crops, for example oilseed rape, canola, linseed, hemp, soybean, sunflowers, borage. They can therefore be used advantageously in the method according to the invention.

It has been possible to date to demonstrate that a trienoic acid with $C_{18}$ carbon chain can be produced with the aid of desaturases. These methods which are known from the literature claim the production of γ-linolenic acid. However, nobody has as yet been able to demonstrate the production very long-chain polyunsaturated fatty acids (with $C_{20}$- and longer carbon chain and of trienoic acids and higher unsaturated types) by modified plants alone.

To produce the longer-chain PUFAs according to the invention, the polyunsaturated $C_{18}$-fatty acids must first be desaturated by the enzymatic activity of a desaturase and subsequently elongated by at least two carbon atoms via an elongase. After one elongation cycle, this enzyme activity gives $C_{20}$-fatty acids, and after two or three elongation cycles $C_{22}$- or $C_{24}$-fatty acids. The activity of the desaturases and elongases used method according to the invention gives by preference $C_{18}$-, $C_{20}$- and/or $C_{22}$-fatty acids having at least two double bonds in the fatty acid molecule, by preference three, four or five double bonds, especially preferably $C_{18}$- and/or $C_{20}$-fatty acids with at least two double bonds in the fatty acid molecule, preferably with three, four or five double bonds in the molecule. After a first desaturation and the elongation have taken place, further desaturation steps such as, for example, in Δ5-position, may take place. Especially preferred products of the process according to the invention are arachidonic acid and eicosapentaenoic acid. The $C_{18}$-fatty acids with at least two double bonds in the fatty acid can be elongated by the enzymatic activity according to the invention in the form of the free fatty acid or in the form of the esters, such as phospholipids, glycolipids, sphingolipids, phosphoglycerides, monoacylglycerol, diacylglycerol or triacylglycerol.

Using cloning vectors in plants and in the transformation of plants like those which are published and cited in: Plant Molecular Biology and Biotechnology (CRC Press, Boca Raton, Fla.), Chapter 6/7, pp. 71-119 (1993); F. F. White, Vectors for Gene Transfer in Higher Plants; in: Transgenic Plants, Vol. 1, Engineering and Utilization, Eds.: Kung and R. Wu, Academic Press, 1993, 15-38; B. Jenes et al., Techniques for Gene Transfer, in: Transgenic Plants, Vol. 1, Engineering and Utilization, Eds.: Kung and R. Wu, Academic Press (1993), 128-143; Potrykus, Annu. Rev. Plant Physiol. Plant Molec. Biol. 42 (1991), 205-225)), the nucleic acids can be used for the recombinant modification of a broad spectrum of plants so that this plant becomes a better or more efficient producer of one or more lipid-derived products, such as PUFAs. This improved production or production efficiency of a lipid-derived product, such as PUFAs, can be brought about by a direct action of the manipulation or an indirect action of this manipulation.

A series of mechanisms exist by means of which the modification of a desaturase protein according to the invention can have a direct effect on the yield, production and/or production efficiency of a fine chemical from an oil crop plant or a microorganism, owing to a modified protein. The number or activity of the desaturase protein or desaturase gene and of gene combinations of desaturases and elongases can be increased, so that larger amounts of these compounds are produced de novo since the organisms lacked this activity and ability to biosynthesize them prior to introduction of the gene in question. This also applies analogously to the combination with further desaturases or elongases or further enzymes of the lipid metabolism. The use of various divergent sequences, i.e. sequences which differ at the DNA sequence level, may also be advantageous, or else the use of promoters for gene expression which makes possible a different temporal gene expression, for example as a function of the degree of maturity of the seed or oil-storing tissue.

The introduction of a desaturase and/or elongase gene, or several desaturase and elongase genes, into an organism, alone or in combination with other genes into a cell can not only increase the biosynthesis flux toward the end product, but also increase, or generate de novo, the corresponding triacylglycerol composition. Likewise, the number or activity of other genes which participate in the import of nutrients required for the biosynthesis of one or more fine chemicals (for example fatty acids, polar and neutral lipids) can be increased, so that the concentration of these precursors, cofactors or intermediates ithin the cells or within the storage compartment is increased, thus further increasing the ability of the cells to produce PUFAs as described hereinbelow. Fatty acids and lipids themselves are desirable as fine chemicals; by optimizing the activity or increasing the number of one or more desaturases and/or elongases hich participate in the biosynthesis of these compounds, or by destroying the activity of one or more desaturases which participate in the breakdown of these compounds, it can be possible to increase the yield, production and/or efficiency of the production of fatty acid and lipid molecules from plants.

The isolated nucleic acid molecules used in the process according to the invention encode proteins or parts of these, the proteins, or the individual protein or parts thereof, comprising an amino acid sequence with sufficient homology with an amino acid sequence of the sequence SEQ ID NO: 2, 4, 6, 8, 10, 12, 14, 16, 18, 20, 22, 24, 26, 28, 30 or 32 so that the protein or the part thereof retains a desaturase or elongase activity. Preferably, the protein or the part thereof which is encoded by the nucleic acid molecule has its essential enzymatic activity and the capability of being implicated in the metabolism of compounds which are required for the synthesis of plant cell membranes or in the transport of molecules across these membranes. Advantageously, the protein encoded by the nucleic acid molecules is at least approximately 50%, preferably at least approximately 60% and more preferably at least approximately 70%, 80% or 90% and most preferably at least approximately 95%, 96%, 97%, 98%, 99% or more homologous to an amino acid sequence of the sequence SEQ ID NO: 2, 4, 6, 8, 10, 12, 14, 16, 18, 20, 22, 24, 26, 28, 30 or 32. Preferably, the protein is a full-length protein which is essentially homologous in parts to a total amino acid sequence of SEQ ID NO: 2, 4, 6, 8, 10, 12, 14, 16, 18, 20, 22, 24, 26, 28, 30 or 32 (which is the result of the open reading frame shown in SEQ ID NO: 1, 3, 5, 7, 9, 11, 13, 15, 17, 19, 21, 23, 25, 27, 29 or 31). For the purposes of the invention, homology and homologous are understood as meaning identity or identical.

The term essential enzymatic activity of the desaturases and the elongase used is understood as meaning that, in comparison with the proteins/enzymes encoded by the sequences with SEQ ID NO: 1, 3, 5, 7, 9, 11, 13, 15, 17, 19, 21, 23, 25, 27, 29 or 31, they retain at least an enzymatic activity of at least 10%, preferably 20%, especially preferably 30% and very especially 40% and can thus be implicated in the metabolism of compounds which are required for the synthesis of fatty acids in a plant cell or in the transport of molecules across membranes, meaning desaturated $C_{18}$- or $C_{20-22}$-carbon chains with double bonds at at least two, advantageously three, four or five positions.

Nucleic acids which can advantageously be used in the process originate from fungi or plants such as algae or mosses of the genera *Physcomitrella*, *Thraustochytrium*, *Phytophtora*, *Ceratodon*, *Isochrysis*, *Aleurita*, *Muscarioides*, *Mor-* tierella, Borago, Phaeodactylum, Crypthecodinium or from nematodes such as Ceanorhabditis, specifically from the genera and species Physcomitrella patens, Phytophtora infestans, Ceratodon purpureus, Isochrysis galbana, Aleurita farinosa, Muscarioides viallii, Mortierella alpina, Borago officinalis, Phaeodactylum tricormutum or Ceanorhabditis elegans.

As an alternative, the isolated nucleotide sequences used can encode desaturases or elongases which hybridize, for example under stringent conditions, with a nucleotide sequence of the SEQ ID NO: 1, 3, 5, 7, 9, 11, 13, 15, 17, 19, 21, 23, 25, 27, 29 or 31.

The nucleic acid sequences used in the process are advantageously introduced in an expression cassette which makes possible the expression of the nucleic acids in plants.

Advantageous expression cassettes are shown in SEQ ID NO: 33 to 37. Here, the nucleic acid sequences encoding the desaturases and/or the elongases are linked operably with one or more regulatory signals, advantageously for enhancing gene expression. These regulatory sequences are intended to make possible the specific expression of genes and of protein expression. Depending on the host organism, this may mean, for example, that the gene is expressed and/or overexpressed only after induction, or else that it is immediately expressed and/or overexpressed. For example, these regulatory sequences take the form of sequences to which inductors or repressors bind and thus regulate expression of the nucleic acid. In addition to these novel regulatory sequences, or instead of these sequences, the natural regulation of these sequences before the actual structural genes may still be present and, if appropriate, may have been genetically modified so that the natural regulation has been switched off and the expression of the genes enhanced. However, the expression cassette (=expression construct=gene construct) can also be simpler in construction, that is to say no additional regulatory signals have been inserted before the nucleic acid sequence or its derivatives, and the natural promoter together with its regulation has not been removed. Instead, the natural regulatory sequence has been mutated in such a way that regulation no longer takes place and/or gene expression is enhanced. These modified promoters can also be placed before the natural gene alone in the form of part-sequences (=promoter together with parts of the nucleic acid sequences according to the invention) to enhance the activity. Moreover, the gene construct can advantageously also comprise one or more enhancer sequences in operable linkage with the promoter, which make possible an enhanced expression of the nucleic acid sequence. Also, additional advantageous sequences, such as further regulatory elements or terminators, may be inserted at the 3' terminus of the DNA sequences. The Δ5-desaturase/Δ6-desaturase and/or Δ6-elongase genes may be present in the expression cassette (=gene construct) in one or more copies. Advantageously, in each case only one copy of the genes is present in the expression cassette. This gene construct, or the gene constructs, can be expressed together in the host organism. In this context, the gene construct(s) can be inserted in one or more vectors and be present in the cell in free form or else be inserted in the genome. It is advantageous for the insertion of further genes in the host genome when the genes to be expressed are present together in one gene construct.

In this context, the regulatory sequences or factors can, as described above, preferably have a positive effect on the gene expression of the genes which have been introduced, thus enhancing it. Thus, the regulatory elements can advantageously be enhanced at transcriptional level by using strong transcription signals such as promoters and/or enhancers. In addition, however, an enhancement of translation is also possible, for example by improving the stability of the mRNA.

A further embodiment of the invention are one or more gene constructs which comprise one or more sequences which are defined by SEQ ID NO: 1, 3, 5, 7, 9, 11, 13, 15, 17, 19, 21, 23, 25, 27, 29 or 31 and which encode polypeptides of SEQ ID NO: 2, 4, 6, 8, 10, 12, 14, 16, 18, 20, 22, 24, 26, 28, 30 or 32. The abovementioned desaturases introduce a double bond into the Δ5 or Δ6 position, the substrate having one, two, three or four double bonds. Elongase (Δ6-elongase) has an enzyme activity which elongates a fatty acid by at least two carbon atoms. The same applies to its homologs, derivatives or analogs which are linked operably with one or more regulatory signals, advantageously for enhancing gene expression.

Advantageous regulatory sequences for the novel process are present, for example, in promoters such as cos, tac, trp, tet, trp-tet, lpp, lac, lpp-lac, lacI$^q$, T7, T5, T3, gal, trc, ara, SP6, $\lambda$-P$_R$ or $\lambda$-P$_L$ promoter and are advantageously used in Gram-negative bacteria. Further advantageous regulatory sequences are present, for example, in the Gram-positive promoters amy and SPO2, in the yeast or fungal promoters ADC1, MFα, AC, P-60, CYC1, GAPDH, TEF, rp28, ADH or in the plant promoters CaMV/35S [Franck et al., Cell 21 (1980) 285-294], PRP1 [Ward et al., Plant. Mol. Biol. 22 (1993)], SSU, OCS, lib4, usp, STLS1, B33, nos or in the ubiquitin or phaseolin promoter. Also advantageous in this connection are inducible promoters such as the promoters described in EP-A-0 388 186 (benzylsulfonamide-inducible), Plant J. 2, 1992:397-404 (Gatz et al., tetracyclin-inducible), EP-A-0 335 528 (abscisic acid-inducible) or WO 93/21334 (ethanol- or cyclohexenol-inducible). Further useful plant promoters are the potato cytosolic FBPase promoter or ST-LSI promoter (Stockhaus et al., EMBO J. 8, 1989, 2445), the Glycine max phosphoribosyl-pyrophosphate amidotransferase promoter (Genbank Accession No. U87999) or the node-specific promoter described in EP-A-0 249 676. Especially advantageous promoters are promoters which make possible expression in tissues which are implicated in fatty acid biosynthesis. Very especially advantageous are seed-specific promoters, such as the USP promoter in accordance with the specification, but also other promoters such as the LeB4, DC3, phaseolin or napin promoter. Further especially advantageous promoters are seed-specific promoters which can be used for monocots or dicots and which are described in U.S. Pat. No. 5,608,152 (oilseed rape napin promoter), WO 98/45461 (Arabidopsis oleosin promotor), U.S. Pat. No. 5,504,200 (Phaseolus vulgaris phaseolin promoter), WO 91/13980 (Brassica Bce4 promoter) described by Baeumlein et al., Plant J., 2, 2, 1992:233-239 (LeB4 promoter from a legume), said promoters being useful in dicots. The following promoters are suitable for example in monocots: barley lpt-2 or lpt-1 promoter (WO 95/15389 and WO 95/23230), barley hordein promoter and other suitable promoters which are described in WO 99/16890.

In principle, it is possible to use all natural promoters with their regulatory sequences like those mentioned above for the novel process. It is likewise possible and advantageous to use synthetic promoters, in addition or alone, especially when they confer seed-specific expression, such as, for example, described in WO 99/16890.

In order to achieve a particularly high PUFA content in transgenic plants, the PUFA biosynthetic genes should advantageously be expressed in oil crops in a seed-specific manner. To this end, seed-specific promoters can be used, or those promoters which are active in the embryo and/or in the endosperm. In principle, seed-specific promoters can be isolated from both dicots and monocots. Advantageous preferred promoters are detailed hereinbelow: USP (=unknown seed protein) and vicilin (*Vicia faba*) [Bäumlein et al., Mol. Gen Genet., 1991, 225(3)], napin (oilseed rape) [U.S. Pat. No. 5,608,152], Acyl-Carrier Protein (oilseed rape) [U.S. Pat. No. 5,315,001 and WO 92/18634], oleosin (*Arabidopsis thaliana*) [WO 98/45461 and WO 93/20216], phaseolin (*Phaseolus vulgaris*) [U.S. Pat. No. 5,504,200], Bce4 [WO 91/13980], legume B4 (LegB4 promoter) [Bäumlein et al., Plant J., 2, 2, 1992], Lpt2 and lpt1 (barley) [WO 95/15389 and WO95/23230], seed-specific promoters from rice, maize and wheat [WO 99/16890], Amy32b, Amy 6-6 and aleurain [U.S. Pat. No. 5,677,474], Bce4 (oilseed rape) [(U.S. Pat. No. 5,530,149], glycinin (soya) [EP 571 741], phosphoenolpyruvate carboxylase (soya) [JP 06/62870], ADR12-2 (soya) [WO 98/08962], isocitrate lyase (oilseed rape) [U.S. Pat. No. 5,689,040] or β-amylase (barley) [EP 781 849].

Plant gene expression can also be facilitated via a chemically inducible promoter (see a review in Gatz 1997, Annu. Rev. Plant Physiol. Plant Mol. Biol., 48:89-108). Chemically inducible promoters are particularly suitable when it is desired that gene expression should take place in a time-specific manner. Examples of such promoters are a salicylic-acid-inducible promoter (WO 95/19443), a tetracyclin-inducible promoter (Gatz et al. (1992) Plant J. 2, 397-404) and an ethanol-inducible promoter.

To ensure the stable integration of the biosynthesis genes into the transgenic plant over a plurality of generations, each of the nucleic acids which encode Δ6-desaturase, Δ5-desaturase, or Δ6-elongase and which are used in the process should be expressed under the control of a separate promoter, preferably a promoter which differs from the other promoters, since repeating sequence motifs can lead to instability of the T-DNA, or to recombination events. In this context, the expression cassette is advantageously constructed in such a way that a promoter is followed by a suitable cleavage site, advantageously in a polylinker, for insertion of the nucleic acid to be expressed and, if appropriate, a terminator sequence is positioned behind the polylinker. This sequence is repeated several times, preferably three, four or five times, so that up to five genes can be combined in one construct and introduced into the transgenic plant in order to be expressed. Advantageously, the sequence is repeated up to three times (see sequence listing SEQ ID NO: 33 to 37). To express the nucleic acid sequences, the latter are inserted after the promoter via a suitable cleavage site, for example in the polylinker. Advantageously, each nucleic acid sequence has its own promoter and, if appropriate, its own terminator sequence. However, it is also possible to insert a plurality of nucleic acid sequences after a promoter and, if appropriate, before a terminator sequence. Here, the insertion site, or the sequence, of the inserted nucleic acids in the expression cassette is not of critical importance, that is to say a nucleic acid sequence can be inserted at the first or last position in the cassette without its expression being substantially influenced thereby. Advantageously, different promoters such as, for example, the USP, LegB4 or DC3 promoter, and different terminator sequences can be used in the expression cassette. However, it is also possible to use only one type of promoter in the cassette, which, however, may lead to undesired recombination events.

As described above, the transcription of the genes which have been introduced should advantageously be terminated by suitable terminator sequences at the 3' end of the biosynthesic genes which have been introduced (after the stop codon). An example of a sequence which can be used in this context is the OCS1 terminator sequence. As is the case with the promoters, different terminator sequences should be used for each gene.

As described above, the gene construct can also comprise further genes to be introduced into the organisms. It is possible and advantageous to introduce into the host organisms, and to express, regulatory genes such as genes for inductors, repressors or enzymes which, owing to their enzyme activity, engage in the regulation of one or more genes of a biosynthesis pathway. These genes can be of heterologous or of homologous origin. Moreover, further biosynthesis genes of the fatty acid or lipid metabolism can advantageously be present in the nucleic acid construct, or gene construct; however, these genes can also be present on one or more further nucleic acid constructs. A biosynthesic gene of the fatty acid or lipid metabolism which is preferably chosen is a gene selected from the group acyl-CoA dehydrogenase(s), acyl-ACP [=acyl carrier protein] desaturase(s), acyl-ACP thioesterase(s), fatty acid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenases, lipoxygenases, triacylglycerol lipases, allene oxide synthases, hydroperoxide lyases or fatty acid elongase(s) or their combinations.

In this context, the abovementioned desaturases can be cloned into expression cassette according to the invention in combination with elongases and other desaturases and employed for the transformation of plants with the aid of Agrobacterium.

In this context, the regulatory sequences or factors can, as described above, have a positive effect on, preferably, the gene expression of the genes introduced, thus enhancing it. Thus, enhancement of the regulatory elements can advantageously take-place at the transcriptional level by using strong transcription signals such as promoters and/or enhancers. In addition, however, enhancement of translation is also possible, for example by improving the stability of the mRNA. In principle, the expression cassettes can be used directly for introduction into the plant, or else be introduced into a vectors.

These advantageous vectors, preferably expression vectors, comprise the nucleic acid which are used in the method and which encode Δ5- or Δ6-desatures or Δ6-elonagases, or a nucleic acid construct, which the nucleic acid used, alone or in combination with further biosynthetic genes of the fatty acid or lipid metabolism. As used in the present context, the term "vector" refers to a nucleic acid molecule which is capable of transporting another nucleic acid, to which it is bound. One type of vector is a "plasmid", which represents a circular double-stranded DNA loop into which additional DNA segments can be ligated. Another type of vector is a viral vector, it being possible for additional DNA segments to be ligated in the viral genome. Certain vectors are capable of autonomous replication in a host cell in which they have been introduced (for example bacterial vectors with bacterial origin of replication). Other vectors are advantageously integrated in the genome of a host cell when being introduced into the host cell, whereby they replicate together with the host genome. Moreover, certain vectors are capable of governing the expression of genes with which they are operably linked. These vectors are referred to herein as "expression vectors". Usually, expression vectors which are suitable for DNA recombination techniques take the form of plasmids. In the present description, "plasmid" and "vector" can be used interchangeably since the plasmid is the most frequently used vector form. However the invention is also intended to comprise these other forms of expression vectors, such as viral vectors, which have similar functions. Furthermore, the term vector is also intended to comprise other vectors which are known to the skilled worker, such as phages, viruses such as SV40, CMV, TMV, transposons, IS elements, phasmids, phagemids, cosmids, linear or circular DNA.

The recombinant expression vectors which are advantageously used in the method comprise the nucleic acids described hereinbelow or the above-described gene construct in a form suitable for expressing these nucleic acids in a host cell, which means that the recombinant expression vectors comprise one or more regulatory sequences selected on the basis of the host cells to be used for the expression, which is linked operably with the nucleic acid sequence to be expressed. "Linked operably" in a recombinant expression vector means that the nucleotide sequence of interest is bound to the regulatory sequence(s) in such a way that the expression of the nucleotide sequence is possible and that they are bound with one another so that both sequences fulfill the predicted function ascribed to the sequence (for example in an in-vitro transcription/translation system or in a host cell if the vector is introduced into the host cell). The term "regulatory sequence" is intended to comprise promoters, enhancers and other expression control elements (for example polyadenylation signals). These regulatory sequences are described for example in Goeddel: Gene Expression Technology: Methods in Enzymology 185, Academic Press, San Diego, Calif. (1990), or see: Gruber and Crosby, in: Methods in Plant Molecular Biology and Biotechnolgy, CRC Press, Boca Raton, Fla., eds.: Glick and Thompson, chapter 7, 89-108, including the references therein. Regulatory sequences comprise those which govern the constitutive expression of a nucleotide sequence in many types of host cell and those which govern the direct expression of the nucleotide sequence only in specific host cells under specific conditions. The skilled worker knows that the design of the expression vector can depend on factors such as the choice of the host cell to be transformed, the expression level of the desired protein and the like.

The recombinant expression vectors used can be designed for expressing desaturases and elongases in prokaryotic or eukaryotic cells. This is advantageous since intermediate steps of vector construction are frequently performed in microorganisms for the sake of simplicity. For example, desaturase and/or elongase genes can be expressed in bacterial cells, insect cells (using baculovirus expression vectors), yeast cells and other fungal cells (see Romanos, M. A., et al. (1992) "Foreign gene expression in yeast: a review", Yeast 8:423-488; van den Hondel, C.A.M.J.J., et al. (1991) "Heterologous gene expression in filamentous fungi", in: More Gene Manipulations in Fungi, J. W. Bennet & L. L. Lasure, ed., pp. 396-428: Academic Press: San Diego; and van den Hondel, C.A.M.J.J., & Punt, P. J. (1991) "Gene transfer systems and vector development for filamentous fungi, in: Applied Molecular Genetics of Fungi, Peberdy, J. F., et al., ed., pp. 1-28, Cambridge University Press: Cambridge), Algen (Falciatore et al., 1999, Marine Biotechnology. 1, 3:239-251), ciliates of the types: *Holotrichia, Peritrichia, Spirotrichia, Suctoria, Tetrahymena, Paramecium, Colpidium, Glaucoma, Platyophrya, Potomacus, Desaturaseudocohnilembus, Euplotes, Engelmaniella* and *Stylonychia*, in particular the genus *Stylonychia lemnae*, using vectors by a transformation method as described in WO 98/01572, and preferably in cells of: multi-celled plants (see Schmidt, R. and Willmitzer, L. (1988) "High efficiency *Agrobacterium tumefaciens*-mediated transformation of *Arabidopsis thaliana* leaf and cotyledon explants" Plant Cell Rep.: 583-586; Plant. Molecular Biology and Biotechnology, C Press, Boca Raton, Fla., chapter 6/7, pp. 71-119 (1993); F. F. White, B. Jenes et al., Techniques for Gene Transfer, in: Transgenic Plants, vol. 1, Engineering and Utilization, ed.: Kung and R. Wu, Academic Press (1993), 128-43; Potrykus, Annu. Rev. Plant Physiol. Plant Molec. Biol. 42 (1991), 205-225 (and references cited therein)). Suitable host cells are furthermore discussed in Goeddel, Gene Expression Technology: Methods in Enzymology 185, Academic Press, San Diego, Calif. (1990). As an alternative, the recombinant expression vector can be transcribed and translated in vitro, for example using T7 promoter regulation sequences and T7 polymerase.

Protein expression in prokaryotes is usually performed with the aid of vectors which comprise constitutive or inducible promoters which govern the expression of fusion proteins or nonfusion proteins. Typical fusion expression vectors are, inter alia PGEX (Pharmacia Biotech Inc; Smith, D. B., and Johnson, K. S. (1988) Gene 67:31-40), pMAL (New England Biolabs, Beverly, Mass.) and pRIT5 (Pharmacia, Piscataway, N.J.), where glutathione S-transferase (GST), maltose-E-binding protein or protein A, respectively, is fused with the recombinant target protein.

Examples of suitable inducible nonfusion *E. coli* expression vectors are, inter alia, pTrc (Amann et al. (1988) Gene 69:301-315) and pET 11d (Studier et al., Gene Expression Technology: Methods in Enzymology 185, Academic Press, San Diego, Calif. (1990) 60-89). The target gene expression of the pTrc vector is based on the transcription of host RNA polymerase by a hybrid trp-lac fusion promoter. The target gene expression from the pET 11d vector is based on the transcription of a T7-gn10-lac fusion promoter, which is mediated by a coexpressed viral RNA polymerase (T7 gn1). This viral polymerase is provided by the host strains BL21 (DE3) or HMS174 (DE3) by a resident λ prophage which harbors a T7 gn1 gene under the transcriptional control of the lacUV 5 promoter.

Other vectors which are suitable for use in prokaryotic organisms are known to the skilled worker; these vectors are, for example in *E. coli*, pLG338, pACYC184, the pBR series such as pBR322, the pUC series such as pUC18 or pUC19, the M113mp series, pKC30, pRep4, pHS1, pHS2, pPLc236, pMBL24, pLG200, pUR290, pIN-III$^{113}$-B1, λgt11 or pBdCI, in *Streptomyces* pIJ101, pIJ364, pIJ702 or pIJ361, in *Bacillus* pUB110, pC194 oder pBD214, in *Corynebacterium* pSA77 or pAJ667.

In a further embodiment, the expression vector is a yeast expression vector. Examples of vectors for expression in the yeast *S. cerevisiae* comprise pYeDesaturasec1 (Baldari et al. (1987) Embo J. 6:229-234), pMFa (Kurjan and Herskowitz (1982) Cell 30:933-943), pJRY88 (Schultz et al. (1987) Gene 54:113-123) and pYES2 (Invitrogen Corporation, San Diego, Calif.). Vectors and methods for construction of vectors which are suitable for use in other fungi, such as the filamentous fungi, comprise those which are described in detail in: van den Hondel, C.A.M.J.J., & Punt, P. J. (1991) "Gene transfer systems and vector development for filamentous fungi, in: Applied Molecular Genetics of fungi, J. F. Peberdy et al., ed., pp. 1-28, Cambridge University Press: Cambridge, or in: More Gene Manipulations in Fungi [J. W. Bennet & L. L. Lasure, ed., pp. 396-428: Academic Press: San Diego]. Further suitable yeast vectors are, for example, pAG-1, YEp6, YEpl3 or pEMBLYe23.

As an alternative, the desaturases and/or elongases can be expressed in insect cells using baculovirus expression vectors. Baculovirus vectors which are available for expressing proteins in cultured insect cells (for example Sf9 cells) comprise the pAc series (Smith et al. (1983) Mol. Cell Biol. 3:2156-2165) and the pVL series (Lucklow and Summers (1989) Virology 170:31-39).

The abovementioned vectors offer only a small overview over suitable vectors which are possible. Further plasmids are known to the skilled worker and are described, for example, in: Cloning Vectors (ed. Pouwels, P. H., et al., Elsevier, Amsterdam-New York-Oxford, 1985, ISBN 0 444 904018). Further suitable expression systems for prokaryotic and eukaryotic cells, see in the chapters 16 and 17 of Sambrook, J., Fritsch, E. F., and Maniatis, T., Molecular Cloning: A Laboratory Manual, 2nd edition, Cold Spring Harbor Laboratory, Cold Spring Harbor Laboratory Press, Cold Spring Harbor, N.Y., 1989.

In a further embodiment of the process, the desaturases and/or elongases can be expressed in single-cell plant cells (such as algae), see Falciatore et al., 1999, Marine Biotechnology 1 (3):239-251 and references cited therein, and plant cells from higher plants (for example spermatophytes such as crops). Examples of plant expression vectors comprise those which are described in detail in: Becker, D., Kemper, E., Schell, J., and Masterson, R. (1992) "New plant binary vectors with selectable markers located proximal to the left border", Plant Mol. Biol. 20:1195-1197; and Bevan, M. W. (1984) "Binary Agrobacterium vectors for plant transformation", Nucl. Acids Res. 12:8711-8721; Vectors for Gene Transfer in Higher Plants; in: Transgenic Plants, vol. 1, Engineering and Utilization, ed.: Kung and R. Wu, Academic Press, 1993, pp. 15-38.

A plant expression cassette preferably comprises regulatory sequences which are capable of governing the gene expression in plant cells and which are linked operably so that each sequence can fulfill its function, such as transcriptional termination, for example polyadenylation signals. Preferred polyadenylation signals are those which originate from *Agrobacterium tumefaciens* T-DNA, such as the gene 3 of the Ti plasmid pTiACH5, which is known as octopine synthase (Gielen et al., EMBO J. 3 (1984) 835ff.) or functional equivalents thereof, but all other terminators which are functionally active in plants are also suitable.

Since plant gene expression is very often not limited to the transcriptional levels, a plant expression cassette preferably comprises other operably linked sequences such as translation enhancers, for example the overdrive sequence which comprises the 5'-untranslated leader sequence from tobacco mosaic virus, which increases the protein/RNA ratio (Gallie et al., 1987, Nucl. Acids Research 15:8693-8711).

As described above, plant gene expression must be linked operably with a suitable promoter which performs gene expression with the correct timing or in a cell- or tissue-specific manner. Utilizable promoters are constitutive promoters (Benfey et al., EMBO J. 8 (1989) 2195-2202) such as those which are derived from plant viruses, such as 35S CAMV (Franck et al., Cell 21 (1980) 285-294), 19S CaMV (see also U.S. Pat. No. 5,352,605 and WO 84/02913) or plant promoters such as the Rubisco small subunit, which is described in U.S. Pat. No. 4,962,028.

Other sequences which are preferred for the use for operable linkage in plant gene expression cassettes are targeting sequences, which are required for targeting the gene product into its relevant cell compartment (for a review see Kermode, Crit. Rev. Plant Sci. 15, 4 (1996) 285-423 and references cited therein), for example into the vacuole, the nucleus, all types of plastids, such as amyloplasts, chloroplasts, chromoplasts, the extracellular space, the mitochondria, the endoplasmic reticulum, oil bodies, peroxisomes and other plant cell compartments.

Plant gene expression can also be facilitated as described above via a chemically inducible promoter (for a review see Gatz 1997, Annu. Rev. Plant Physiol. Plant Mol. Biol., 48:89-108). Chemically inducible promoters are suitable in particular when it is desired that gene expression is clock-specific. Examples of such promoters are a salicylic acid-inducible promoter (WO 95/19443), a tetracyclin-inducible promoter (Gatz et al. (1992) Plant J. 2, 397-404) and an ethanol-inducible promoter.

Other promoters which are suitable are promoters which respond to biotic or abiotic stress conditions, for example the pathogen-induced PRP1 gene promoter (Ward et al., Plant. Mol. Biol. 22 (1993) 361-366), the heat-inducible tomato hsp80 promoter (U.S. Pat. No. 5,187,267), the chill-inducible potato alpha-amylase promoter (WO 96/12814) or the wound-inducible pinII promoter (EP-A-0 375 091).

Preferred promoters are in particular those which bring about the expression of genes in tissues and organs in which lipid and oil biosynthesis takes place, in seed cells, such as cells of the endosperm and of the developing embryo. Suitable promoters are the oilseed rape napin gene promoter (U.S. Pat. No. 5,608,152), the *Vicia faba* USP promoter (Baeumlein et al., Mol Gen Genet, 1991, 225 (3):459-67), the *Arabidopsis oleosin* promoter (WO 98/45461), the *Phaseolus vulgaris* phaseolin promoter (U.S. Pat. No. 5,504,200), the *Brassica* Bce4 promoter (WO 91/13980) or the legumin B4 promoter LeB4; Baeumlein et al., 1992, Plant Journal, 2 (2):233-9), and promoters which bring about the seed-specific expression in monocots such as maize, barley, wheat, rye, rice and the like. Suitable promoters which should be taken into consideration are the barley lpt2 or lpt1 gene promoter (WO 95/15389 and WO 95/23230), or those described in WO 99/16890 (promoters from the barley hordein gene, the rice glutelin gene, the rice oryzin gene, the rice prolamin gene, the wheat gliadin gene, the wheat glutelin gene, the maize zein gene, the oat glutelin gene, the sorghum kasirin gene, the rye secalin gene).

In particular, it may be desired to bring about the multiparallel expression of the desaturases and/or elongases used in the method alone or in combination with other desaturases or elongases. Such expression cassettes can be introduced via the simultaneous transformation of a plurality of individual expression constructs or, preferably, by combining a plurality of expression cassettes on one construct. Also, it is possible to transform a plurality of vectors with in each case a plurality of expression cassettes and to transfer them to the host cell.

Promoters which are likewise especially suitable are those which bring about the plastid-specific expression since plastids are the compartment in which the precursors and some end products of lipid biosynthesis are synthesized. Suitable promoters such as the viral RNA polymerase promoter are described in WO 95/16783 and WO 97/06250, and the Arabidopsis clpP promoter, described in WO 99/46394.

Vector DNA can be introduced into prokaryotic or eukaryotic cells via conventional transformation or transfection techniques. The terms "transformation" and "transfection", conjugation and transduction, as used in the present context, are meant to comprise a multiplicity of methods known in the art for introducing foreign nucleic acid (for example DNA) into a host cell, including calcium phosphate or calcium chloride coprecipitation, DEAE-dextran-mediated transfection, lipofection, natural competence, chemically mediated transfer, electroporation or particle bombardment. Suitable methods for the transformation or transfection of host cells, including plant cells, can be found in Sambrook et al. (Molecular Cloning: A Laboratory Manual., 2nd edition., Cold Spring Harbor Laboratory, Cold Spring Harbor Laboratory Press, Cold Spring Harbor, N.Y., 1989) and other laboratory handbooks such as Methods in Molecular Biology, 1995, vol. 44, *Agrobacterium* protocols, ed.: Gartland and Davey, Humana Press, Totowa, N.J.

Host cells which are suitable in principle for taking up the nucleic acid according to the invention, the gene product according to the invention or the vector according to the invention are all prokaryotic or eukaryotic organisms. The host organisms which are advantageously used are organisms such as bacteria, fungi, yeasts or plant cells, preferably plants or parts thereof. Fungi, yeasts or plants are used by preference; especially preferably plants, very especially preferably plants such as oil crops which comprise large amounts of lipid compounds, such as oilseed rape, evening primrose, hemp, thistle, peanut, canola, linseed, soya, safflower, sunflower, borage or plants such as maize, wheat, rye, oats, triticale, rice, barley, cotton, cassava, pepper, Tagetes, Solanaceae plants such as potato, tobacco, eggplant and tomato, *Vicia* species, pea, alfalfa, bushy plants (coffee, cocoa, tea), *Salix* species, trees (oil palm, coconut) and perennial grasses and fodder crops. Especially preferred plants according to the invention are oil crops such as soya, peanut, oilseed rape, canola, linseed, hemp, evening primrose, sunflower, safflower, trees (oil palm, coconut).

Nucleic acid sequences which are advantageously used in the process according to the invention are those which encode polypeptides with a Δ6-desaturase activity, Δ6-elongase activity or Δ5-desaturase activity, selected from the group consisting of:
a) a nucleic acid sequence with the sequence shown in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29 or SEQ ID NO: 31,
b) nucleic acid sequences which, owing to the degeneracy of the genetic code, are obtained by back translation of the amino acid sequences shown in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30 or SEQ ID NO: 32,
c) derivatives of the nucleic acid sequences shown in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29 or SEQ ID NO: 31 which encode polypeptides with the amino acid sequences shown in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30 or SEQ ID NO: 32 and which have at least 50% homology at the amino acid level, without the enzymatic activity of the polypeptides being substantially reduced.

The abovementioned nucleic acid according to the invention originates from organisms such as animals, ciliates, fungi, plants such as algae or dinoflagellates which are capable of synthesizing PUFAs.

The term "nucleic acid (molecule)" as used in the present context also comprises the untranslated sequence located at the 3' and at the 5' end of the coding gene region: at least 500, preferably 200, especially preferably 100 nucleotides of the sequence upstream of the 5' terminus of the coding region and at least 100, preferably 50, especially preferably 20 nucleotides of the sequence downstream of the 3' end of the coding gene region. An "isolated" nucleic acid molecule is separated from other nucleic acid molecules which are present in the natural source of the nucleic acid. An "isolated" nucleic acid preferably has no sequences which naturally flank the nucleic acid in the genomic DNA of the organism from which the nucleic acid originates (for example sequences which are present at the 5' and 3' ends of the nucleic acid). In different embodiments, the isolated desaturase or elongase nucleic acid molecule may comprise, for example less than approximately 5 kb, 4 kb, 3 kb, 2 kb, 1 kb, 0.5 kb or 0.1 kb of nucleotide sequences which naturally flank the nucleic acid molecule in the genomic DNA of the cell from which the nucleic acid originates.

The nucleic acid molecules used in the process, for example a nucleic acid molecule with a nucleotide sequence of the SEQ ID NO: 1 or a part thereof, can be isolated using molecular-biological standard techniques and the sequence information provided herein. Also, for example a homologous sequence or homologous, conserved sequence regions at the DNA or amino acid level can be identified with the aid of comparative algorithms. They can be used as hybridization probe and standard hybridization techniques (as described, for example, in Sambrook et al., Molecular Cloning: A Laboratory Manual. 2nd ed., Cold Spring Harbor Laboratory, Cold Spring Harbor Laboratory Press, Cold Spring Harbor, N.Y., 1989) for the isolation of further nucleic acid sequences which are useful in the process. Moreover, a nucleic acid molecule comprising a complete sequence of the SEQ ID NO: 1, 3, 5, 7, 9, 11, 13, 15, 17, 19, 21, 23, 25, 27, 29 or 31 or a part thereof can be isolated by polymerase chain reaction, where oligonucleotide primers, which are used on the basis of this sequence or parts thereof (for example, it is possible to isolate a nucleic acid molecule comprising the complete sequence or a part thereof by means of polymerase chain reaction using oligonucleotide primers which have been generated on the basis of the same sequence). For example, mRNA can be isolated from cells (for example by means of the guanidinium thiocyanate extraction method of Chirgwin et al. (1979) Biochemistry 18:5294-5299) and cDNA can be generated by means of reverse transcriptase (for example Moloney MLV Reverse Transcriptase, available from Gibco/BRL, Bethesda, Md., or AMV Reverse Transcriptase, available from Seikagaku America, Inc., St. Petersburg, Fla.). Synthetic oligonucleotide primers for amplification by means of polymerase chain reaction can be generated based on one of the sequences shown in SEQ ID NO: 1, 3, 5, 7, 9, 11, 13, 15, 17, 19, 21, 23, 25, 27, 29 or 31 and that of FIG. 5*a*, or with the aid of the amino acid sequences shown in SEQ ID NO: 2, 4, 6, 8, 10, 12, 14, 16, 18, 20, 22, 24, 26, 28, 30 or 32. A nucleic acid according to the invention can be amplified in accordance with standard PCR amplification techniques using cDNA or, alternatively, genomic DNA as template and suitable oligonucleotide primers. The nucleic acid amplified thus can be cloned into a suitable vector and characterized by means of DNA sequence analysis. Oligonucleotides which correspond to a desaturase nucleotide sequence can be generated by means of synthetic standard methods, for example using an automatic DNA synthesizer.

Homologs of the desaturase or elongase nucleic acid sequences used, with sequence SEQ ID NO: 1, 3, 5, 7, 9, 11, 13, 15, 17, 19, 21, 23, 25, 27, 29 or 31, means for example allelic variants with at least approximately 50 to 60%, preferably at least approximately 60 to 70%, more preferably at least approximately 70 to 80%, 80 to 90% or 90 to 95% and even more preferably at least approximately 95%, 96%, 97%, 98%, 99% or more homology with one of the nucleotide sequences shown in SEQ ID NO: 1, 3, 5, 7, 9, 11, 13, 15, 17, 19, 21, 23, 25, 27, 29 or 31 or their homologs, derivatives or analogs, or parts of these. Moreover, isolated nucleic acid molecules of a nucleotide sequence which hybridize with one of the nucleotide sequences shown in SEQ ID NO: 1, 3, 5, 7, 9, 11, 13, 15, 17, 19, 21, 23, 25, 27, 29 or 31 or part thereof, hybridize for example under stringent conditions. Allelic variants comprise in particular functional variants which can be obtained by deletion, insertion or substitution of nucleotides from into the sequence shown in SEQ ID NO: 1, 3, 5, 7, 9, 11, 13, 15, 17, 19, 21, 23, 25, 27, 29 or 31, it being intended, however, that the enzyme activity of the resulting synthesized proteins is advantageously retained for the insertion of one or more genes. Proteins which retain the enzymatic activity of the desaturase or elongase, i.e. whose activity is essentially not reduced, means proteins with at least 10%, preferably 20%, especially preferably 30%, very especially preferably 40% of the original enzyme activity in comparison with the protein encoded by SEQ ID NO: 2, 4, 6, 8, 10, 12, 14, 16, 18, 20, 22, 24, 26, 28, 30 or 32.

Homologs of SEQ ID NO: 1, 3, 5, 7, 9, 11, 13, 15, 17, 19, 21, 23, 25, 27, 29 or 31 mean for example also bacterial, fungal and plant homologs, truncated sequences, single-stranded DNA or RNA of the coding and noncoding DNA sequence.

Homologs of SEQ ID NO: 1, 3, 5, 7, 9, 11, 13, 15, 17, 19, 21, 23, 25, 27, 29 or 31 also means derivatives such as, for example, promoter variants. The promoters upstream of the abovementioned nucleotide sequences can be modified by one or more nucleotide substitutions, insertion(s) and/or deletion(s) without, however, interfering with the functionality or activity of the promoters. Moreover, it is possible to increase the activity of the promoters by modifying their sequence or to replace them completely by more active promoters, including promoters from heterologous organisms.

The abovementioned nucleic acids and protein-molecules with desaturase or elongase activity which are involved in the metabolism of lipids and fatty acids, PUFA cofactors and enzymes or in the transport of lipophilic compounds across membranes are used in the process according to the invention for the modulation of the production of compounds of the general formula I in transgenic plants such as maize, wheat, rye, oats, triticale, rice, barley, soybean, peanut, cotton, *Linum* species such as linseed or flax, *Brassica* species such as oilseed rape, canola and turnip rape, pepper, sunflower, borage, evening primrose and Tagetes, Solanaceae plants such as potato, tobacco, eggplant and tomato, *Vicia* species, pea, cassava, alfalfa, bushy plants (coffee, cocoa, tea), *Salix* species, trees (oil palm, coconut) and perennial grasses and fodder crops, either directly (for example when the overexpression or optimization of a fatty acid biosynthesis protein has a direct effect on the yield, production and/or production efficiency of the fatty acid from modified organisms) and/or can have an indirect effect which nevertheless leads to an increase in the yield, production and/or production efficiency of a desired compound or a decrease in undesired compounds (for example when the modulation of the metabolism of lipids and fatty acids, cofactors and enzymes leads to modifications of the yield, production and/or production efficiency or the composition of the desired compounds within the cells, which, in turn, may have an effect on the production of one or more fatty acids).

The combination of different precursor molecules and biosynthetic enzymes results in the production of different fatty acid molecules, which has a decisive effect on lipid composition. Since polyunsaturated fatty acids (=PUFAs) are not simply incorporated into triacylglycerol, but also into membrane lipids.

Lipid synthesis can be divided into two sections: the synthesis of fatty acids and their binding to sn-glycerol-3-phosphate, and the addition or modification of a polar head group. Conventional lipids which are used in membranes comprise phospholipids, glycolipids, sphingolipids and phosphoglycerides. Fatty acid synthesis starts with the conversion of acetyl-CoA into malonyl-CoA by the enzyme acetyl-CoA carboxylase or into acetyl-ACP by the enzyme acetyl transacylase. After a condensation reaction, these two product molecules together form acetoacetyl-ACP, which is converted by a series of condensation, eduction and dehydratization reactions so that a saturated fatty acid molecule with the desired chain length is obtained. The roduction of the unsaturated fatty acids from these molecules is atalyzed by specific desaturases, either aerobically by means of molecular oxygen or anaerobically (as regards the fatty acid synthesis in microorganisms, see F. C. Neidhardt et al. (1996) *E. coli* and *Salmonella*. ASM Press: Washington, D.C., pp. 612-636 and references cited therein; Lengeler et al. (ed.) (1999) Biology of Procaryotes. Thieme: Stuttgart, N.Y., and references therein, and Magnuson, K., et al. (1993) Microbiological Reviews 57:522-542 and the references therein).

Examples of precursors for PUFA biosynthesis are oleic acid, linoleic acid and linolenic acid. These $C_{18}$-carbon fatty acids must be elongated to $C_{20}$ and $C_{22}$ to obtain fatty acids of the eicosa and docosa chain type. With the aid of the desaturases used in the process, such as Δ5- and Δ6-desaturase and Δ6-elongase, it is possible to obtain arachidonic acid and eicosapentaenoic acid and various other long-chain PUFAs, to extract them and to use them for various purposes in applications in foodstuffs, feeding stuffs, cosmetics or pharmacology. Using the abovementioned enzymes, it is possible to produce preferably $C_{18}+C_{20}$ fatty acids with at least two, three, four or five double bonds in the fatty acid molecule, preferably $C_{20}$-fatty acids with advantageously three, four or five double bonds in the fatty acid molecule. Desaturation can take place before or after elongation of the fatty acid in question. This is why the products of desaturase activities and the further desaturation and elongation which are possible give rise to preferred PUFAs with a higher degree of desaturation, including a further elongation from $C_{20}$ to $C_{22}$-fatty acids, to give fatty acids such as γ-linolenic acid, dihomo-γ-linolenic acid, arachidonic acid, stearidonic acid, eicosatetraenoic acid or eicosapentaenoic acid. Substrates in the process according to the invention are, for example, linoleic acid, γ-linolenic acid, α-linolenic acid, dihomo-γ-linolenic acid, eicosatetraenoic acid or stearidonic acid. Preferred substrates are linoleic acid, γ-linolenic acid and/or α-linolenic acid, dihomo-γ-linolenic acid or arachidonic acid, eicosatetraenoic acid or eicosapentaenoic acid, respectively. The $C_{18}$- or $C_{20}$- fatty acids with at least two double bonds in the fatty acid are obtained in the process according to the invention in the form of the free fatty acid or in the form of its esters (see formula I), for example in the form of its glycerides.

The term "glyceride" is understood as meaning a glycerol which is esterified with one, two or three carboxylic acid residues (mono-, di- or triglyceride). "Glyceride" is also understood as being a mixture of various glycerides. The glyceride, or glyceride mixture, may comprise further additions, for example free fatty acids, antioxidants, proteins, carbohydrates, vitamins and/or other substances.

A "glyceride" for the purposes of the process according to the invention is furthermore understood as meaning glycerol-derived derivatives. These include, in addition to the above-described fatty acid glycerides, glycerophospholipids and glyceroglyco-lipids. Preferred examples which may be mentioned in this context are the glycerophospholipids such as lecithin (phosphatidyl-choline), cardiolipin, phosphatidylglycerol, phosphatidylserine and alkylacylglycerophospholipids.

Furthermore, fatty acids must subsequently be translocated to various sites of modification and incorporated into the triacylglycerol storage lipid. A further important step in lipid synthesis is the transfer of fatty acids on the polar head groups, for example by the enzyme glycerol fatty acid acyltransferase (see Frentzen, 1998, Lipid, 100(4-5):161-166).

Publications on plant fatty acid biosynthesis, desaturation, the lipid metabolism and membrane transport of lipidic compounds, beta-oxidation, fatty acid modification and cofactors, triacylglycerol storage and triacylglycerol assembly including the references cited therein, see the following papers: Kinney, 1997, Genetic Engeneering, ed.: J. K. Setlow, 19:149-166; Ohlrogge and Browse, 1995, Plant Cell 7:957-970; Shanklin and Cahoon, 1998, Annu. Rev. Plant Physiol. Plant Mol. Biol. 49:611-641; Voelker, 1996, Genetic Engeneering, ed.: J. K. Setlow, 18:111-13; Gerhardt, 1992, Prog. Lipid R. 31:397-417; Gühnemann-Schäfer & Kindl, 1995, Biochim. Biophys Acta 1256:181-186; Kunau et al., 1995, Prog. Lipid Res. 34:267-342; Stymne et al., 1993, in: Biochemistry and Molecular Biology of Membrane and Storage Lipids of Plants, ed.: Murata and Somerville, Rockville, American Society of Plant Physiologists, 150-158, Murphy & Ross 1998, Plant Journal. 13(1):1-16.

The PUFAs produced in the process comprise a group of molecules which higher animals are no longer capable of synthesizing and must therefore take up, or which higher animals can no longer synthesize themselves in sufficient amounts and must thus additionally take them up, although they are synthesized readily by other organisms such as bacteria; for example, cats are no longer capable of synthesizing arachidonic acid.

For the purposes of the invention, the terms "desaturase or elongase" or "desaturase or elongase polypeptide" comprises proteins which are implicated in the desaturation and elongation of fatty acids, and their homologs, derivatives or analogs. The terms desaturase or elongase nucleic acid sequence(s) comprise nucleic acid sequences which encode a desaturase or elongase and in which a part can be a coding region and likewise corresponding 5' and 3'-untranslated sequence regions. The terms production or productivity are known in the art and comprise the concentration of the fermentation product (compound of the formula I) which is formed within a specified period of time and a specified fermentation volume (for example kg of product per hour per liter). The term production efficiency comprises the time span required for obtaining a specific amount of product (for example the time required by the cell for establishing a certain throughput rate of a fine chemical). The term yield or product/carbon yield is known in the art and comprises the efficiency with which the carbon source is converted into the product (i.e. the fine chemical). This is usually expressed as, for example, kg of product per kg of carbon source. Increasing the yield or production of the compound results in increasing the amount of resulting molecules or the suitable resulting molecules of this compound in a certain amount of culture over a specified period. The terms biosynthesis or biosynthetic pathway are known in the art and comprise the synthesis of a compound, preferably an organic compound, by a cell starting from intermediates, for example in a multi-step process which is strongly regulated. The terms catabolism or catabolic pathway are known in the art and comprise the cleavage of a compound, preferably an organic compound, by a cell to give catabolites (in more general germs, smaller or less complex molecules), for example in a multi-step process which is strongly regulated. The term metabolism is known in the art and comprises the totality of the biochemical reactions which take place in an organism. The metabolism of a certain compound (for example the metabolism of a fatty acid) thus comprises the totality of the biosynthetic pathways, modified pathways and catabolic pathways of this compound in the cell which relate to this compound.

In a further embodiment, derivatives of the nucleic acid molecule according to the invention encode proteins with at least 50%, advantageously approximately 50 to 60%, preferably at least approximately 60 to 70% and more preferably at least approximately 70 to 80%, 80 to 90%, 90 to 95% and most preferably at least approximately 96%, 97%, 98%, 99% or more homology (=identity) with a complete amino acid sequence of the SEQ ID NO: 2, 4, 6, 8, 10, 12, 14, 16, 18, 20, 22, 24, 26, 28, 30 or 32. The homology of the amino acid sequence can be determined over the entire sequence region using the program PileUp (J. Mol. Evolution., 25, 351-360, 1987, Higgins et al., CABIOS, 5, 1989:151-153) or BESTFIT or GAP (Henikoff, S. and Henikoff, J. G. (1992). Amino acid substitution matrices from protein blocks. Proc. Natl. Acad. Sci. USA 89: 10915-10919.)

Moreover, the invention comprises nucleic acid molecules which differ from one of the nucleotide sequences shown in SEQ ID NO: 1, 3, 5 or 11 (and parts thereof) as the result of the degeneracy of the genetic code and which thus encode the same desaturase as the desaturase which is encoded by the nucleotide sequences shown in SEQ ID NO: 1, 3, 5, 7, 9, 11, 13, 15, 17, 19, 21, 23, 25, 27, 29 or 31.

In addition to the desaturase nucleotide sequences shown in SEQ ID NO: 1, 3, 5, 7, 9, 11, 13, 15, 17, 19, 21, 23, 25, 27, 29 or 31, the skilled worker will recognize that DNA sequence polymorphisms which result in modifications in the amino acid sequences of the desaturases or elongases may exist within a population. These genetic polymorphisms in the desaturase or elongase gene may exist between individuals within a population as the result of natural variation. These natural variants usually bring about a variance of from 1 to 5% in the nucleotide sequence of the desaturase or elongase gene. All and sundry of these nucleotide variations and resulting amino acid polymorphisms in the enzyme desaturase or elongase which are the result of natural variation and which do not modify the functional activity of desaturases or elongases are also intended to fall under the scope of the invention.

Nucleic acid molecules which are advantageous for the process according to the invention can be isolated on the basis of their homology with the desaturase or elongase nucleic acids disclosed herein using the sequences or part thereof as hybridization probe, following standard hybridization techniques under stringent hybridization conditions. In this context, it is possible for example to use isolated nucleic acid molecules which are at least 15 nucleotides in length and which hybridize under stringent conditions with the nucleic acid molecules which comprise a nucleotide sequence of SEQ ID NO: 1, 3, 5, 7, 9, 11, 13, 15, 17, 19, 21, 23, 25, 27, 29 or 31. It is also possible to use nucleic acids with at least 25, 50, 100, 250 or more nucleotides. The term "hybridizes under stringent conditions" as used in the present context is understood as describing hybridization and wash conditions under which nucleotide sequences with at least 60% homology with one another usually remain hybridized with one another. The conditions are preferably such that sequences which are at least approximately 65%, more preferably at least approximately 70% and even more preferably at least approximately 75% or more homologous with one another usually remain hybridized with one another. These stringent conditions are known to the skilled worker and can be found in Current Protocols in Molecular Biology, John Wiley & Sons, N. Y. (1989), 6.3.1-6.3.6. A preferred nonlimiting example of stringent hybridization conditions is hybridization in 6× sodium chloride/sodium citrate (SSC) at approximately 45° C., followed by one or more wash steps in 0.2×SSC, 0.1% SDS at 50 to 65° C. The skilled worker knows that these hybridization conditions differ depending on the type of the nucleic acid and, for example when organic solvents are used, with regard to the temperature and concentration of the buffer. For example, under "standard hybridization conditions" the temperature differs depending on the type of nucleic acid between 42° C. and 58° C. in aqueous buffer with a concentration of 0.1 to 5×SSC (pH 7.2). If organic solvent is present in the abovementioned buffer, for example 50% formamide, the temperature under standard conditions is approximately 42° C. The hybridization conditions for DNA:DNA hybrids preferably are for example 0.1×SSC and 20° C. to 45° C., preferably between 30° C. and 45° C. The hybridization conditions for DNA:RNA hybrids preferably are for example 0.1×SSC and 30° C. to 55° C., preferably between 45° C. and 55° C. The abovementioned hybridization temperatures are determined for example for a nucleic acid with a length of approximately 100 bp (=base pairs) and a G+C content of 50% in the absence of formamide. The skilled worker knows how to identify the hybridization conditions required with the aid of textbooks, such as the one mentioned above, or the following textbooks: Sambrook et al., "Molecular Cloning", Cold Spring Harbor Laboratory, 1989; Hames and Higgins (ed.) 1985, "Nucleic Acids Hybridization: A Practical Approach", IRL Press at Oxford University Press, Oxford; Brown (ed.) 1991, "Essential Molecular Biology: A Practical Approach", IRL Press at Oxford University Press, Oxford.

To determine the percentage homology (=identity) of two amino acid sequences (for example of the sequences of SEQ ID NO: 2, 4, 6, 8, 10, 12, 14, 16, 18, 20, 22, 24, 26, 28, 30 or 32) or of two nucleic acids (for example one of the sequences of SEQ ID NO: 1, 3, 5, 7, 9, 11, 13, 15, 17, 19, 21, 23, 25, 27, 29 or 31), the sequences are written underneath each other to provide an optimal comparison (for example, gaps may be introduced into the sequence of a protein or a nucleic acid in order to generate an optimal alignment with the other protein or the other nucleic acid). The amino residues of nucleotides at the corresponding amino acid positions or nucleotide positions are then compared. If a position in a sequence is occupied by the same amino acid residue or the same nucleotide as the corresponding position in the other sequence, the molecules are homologous at this position (i.e. amino acid or nucleic acid "homology" as used in the present context corresponds to amino acid or nucleic acid "identity"). The percentage homology between the two sequences is a function of the number of identical positions which the sequences share (i.e. percent homology=number of identical positions/total number of positions×100). The terms homology and identity are thus to be regarded as synonymous.

An isolated nucleic acid molecule which encodes a desaturase or elongase which is homologous to a protein sequence of SEQ ID NO: 2, 4, 6, 8, 10, 12, 14, 16, 18, 20, 22, 24, 26, 28, 30 or 32 can be generated by introducing one or more nucleotide substitutions, additions or deletions into a nucleotide sequence of SEQ ID NO: 1, 3, 5, 7, 9, 11, 13, 15, 17, 19, 21, 23, 25, 27, 29 or 31 so that one or more amino acid substitutions, additions or deletions are introduced into the protein which is encoded. Mutations can be introduced into one of the sequences of SEQ ID NO: 1, 3, 5, 7, 9, 11, 13, 15, 17, 19, 21, 23, 25, 27, 29 or 31 by standard techniques such as site-specific mutagenesis and PCR-mediated mutagenesis. It is preferred to generate conservative amino acid substitutions at one or more of the predicted nonessential amino acid residues. In a "conservative amino acid substitution", the amino acid residue is substituted by an amino acid residue with a similar side chain. Families of amino acid residues with similar side chains have been defined in the art. These families comprise amino acids with basic side chains (for example lysine, arginine, histidine), acidic side chains (for example aspartic acid, glutamic acid), uncharged polar side chains (for example glycine, asparagine, glutamine, serine, threonine, tyrosine, cysteine), unpolar side chains (for example alanine, valine, leucine, isoleucine, proline, phenylalanine, methionine, tryptophan), beta-branched side chains (for example threonine, valine, isoleucine) and aromatic side chains (for example tyrosine, phenylalanine, tryptophan, histidine). A predicted nonessential amino acid residue in a desaturase or elongase is thus preferably substituted by another amino acid residue from the same family of side chains. As an alternative, the mutations can, in a different embodiment, be introduced randomly over the entire desaturase-encoding sequence or part thereof, for example by means of saturation mutagenesis, and the resulting mutants can be screened for the desaturase activity described herein in order to identify mutants which retain the desaturase or elongase activity. After the mutagenesis of one of the sequences of SEQ ID NO: 1, 3, 5, 7, 9, 11, 13, 15, 17, 19, 21, 23, 25, 27, 29 or 31 the encoded protein can be expressed recombinantly, and the activity of the protein can be determined for example using the assays described herein.

The invention is illustrated further by the examples which follow, but which are not to be construed as limiting. The content of all of the references, patent applications, patents and published patent applications cited in the present patent application is herein incorporated by reference.

EXAMPLES SECTION

Example 1

General Methods a) General Cloning Methods:

Cloning methods such as, for example, restriction cleavages, agarose gel electrophoresis, purification of DNA fragments, transfer of nucleic acids onto nitrocellulose and nylon membranes, linking of DNA fragments, transformation of *Escherichia coli* and yeast cells, bacterial cultures and sequence analysis of recombinant DNA were carried out as described in Sambrook et al. (1989) (Cold Spring Harbor Laboratory Press: ISBN 0-87969-309-6) or Kaiser, Michaelis and Mitchell (1994) "Methods in Yeast Genetics" (Cold Spring Harbor Laboratory Press: ISBN 0-87969-451-3).

b) Chemicals

Unless otherwise stated in the text, the chemicals used were obtained in analytical-grade quality from Fluka (Neu-Ulm), Merck (Darmstadt), Roth (Karlsruhe), Serva (Heidelberg) and Sigma (Deisenhofen). Solutions were made with purified, pyrogen-free water, hereinbelow referred to as $H_2O$, from a Milli-Q Water System water purification system (Millipore, Eschborn). Restriction endonucleases, DNA-modifying enzymes and molecular biology kits were obtained from AGS (Heidelberg), Amersham (Braunschweig), Biometra (Göttingen), Boehringer (Mannheim), Genomed (Bad Oeynhausen), New England Biolabs (Schwalbach/Taunus), Novagen (Madison, Wis., USA), Perkin-Elmer (Weiterstadt), Pharmacia (Freiburg), Qiagen (Hilden) and Stratagene (Amsterdam, Netherlands). Unless otherwise specified, they were used in accordance with the manufacturer's instructions.

Example 2

Isolation of Total RNA and Poly(A)+-RNA from Plants

Total RNA is isolated from plants such as linseed and oilseed rape and the like following a method described by Logemann et al. (1987, Anal. Biochem. 163, 21). The total RNA can be obtained from protonemal tissue from moss using the GTC method (Reski et al., 1994, Mol. Gen. Genet., 244:352-359).

Example 3

Transformation of *Agrobacterium*

The *Agrobacterium*-mediated transformation of plants can be carried out for example using the *Agrobacterium tumefaciens* strain GV3101- (pMP90-) (Koncz and Schell, Mol. Gen. Genet. 204 (1986) 383-396) or LBA4404- (Clontech) or C58C1 pGV2260 (Deblaere et al 1984, Nucl. Acids Res. 13, 4777-4788)). The transformation can be carried out by standard transformation techniques (also Deblaere et al. 1984).

Example 4

Plant Transformation

The *Agrobacterium*-mediated transformation of plants can be carried out using standard transformation and regeneration techniques (Gelvin, Stanton B., Schilperoort, Robert A., Plant Molecular Biology Manual, 2nd ed., Dordrecht: Kluwer Academic Publ., 1995, in Sect., Ringbuch Zentrale Signatur: BT11-P ISBN 0-7923-2731-4; Glick, Bernard R., Thompson, John E., Methods in Plant Molecular Biology and Biotechnology, Boca Raton: CRC Press, 1993, 360 S., ISBN 0-8493-5164-2).

Oilseed rape can be transformed by means of cotyledon or hypocotyl-transformation (Moloney et al., Plant Cell 8 (1989) 238-242; De Block et al., Plant Physiol. 91 (1989) 694-701). The use of antibiotics for the seletion of agrobacteria and plants depends on the *Agrobacterium* strain and the binary vector used for the transformation. Normally, oilseed rape is selected using kanamycin as selectable plant marker.

The *Agrobacterium*-mediated gene transfer into linseed (*Linum usitatissimum*) can be carried out using for example a technique described by Mlynarova et al. (1994) Plant Cell Report 13:282-285.

The transformation of soya can be carried out using for example a technique described in EP-A-0 0424 047 (Pioneer Hi-Bred International) or in EP-A-0 0397 687, U.S. Pat. No. 5,376,543, U.S. Pat. No. 5,169,770 (University Toledo).

The transformation of plants using particle bombardment, polyethylene glycol mediated DNA uptake or via the silicon carbonate fiber technique is described for example by Freeling and Walbot "The maize handbook" (1993) ISBN 3-540-97826-7, Springer Verlag New York).

Example 5

Plasmids for Plant Transformation

Binary vectors such as pBinAR (Höfgen and Willmitzer, Plant Science 66 (1990) 221-230) or PGPTV (Becker et al 1992, Plant Mol. Biol. 20:1195-1197) can be used for plant transformation. The binary vectors can be constructed by ligating the cDNA in sense or antisense orientation into T-DNA. 5' of the cDNA, a plant promoter activates cDNA transcription. A polyadenylation sequence is located 3' of the cDNA. The binary vectors can bear different marker genes. In particular, the nptII marker gene, which encodes kanamycin resistance conferred by neomycin phosphotransferase, can be substituted by the herbicide-resistant form of an acetolactate synthase gene (AHAS or ALS). The ALS gene is described in Ott et al., J. Mol. Biol. 1996, 263:359-360. The v-ATPase-c1 promoter can be cloned into plasmid pBinl9 or pGPTV and used for the expression of the marker gene by cloning upstream of the ALS coding region. The abovementioned promoter corresponds to a 1153 base-pair fragment from Beta vulgaris (Plant Mol Biol, 1999, 39:463-475). In this context, not only sulfonylureas, but also imidazolinones such as imazethapyr or sulphonylureas may be used as antimetabolites for the selection.

Tissue-specific expression can be achieved using a tissue-specific promoter. For example, seed-specific expression can be achieved by cloning the DC3 or LeB4 or USP promoter or the phaseolin promoter 5' of the cDNA. However, any other seed-specific promoter element such as, for example, the napin or arcelin promoter (Goossens et al. 1999, Plant Phys. 120(4):1095-1103 and Gerhardt et al. 2000, Biochimica et Biophysica Acta 1490(1-2):87-98) may also be used. The CaMV-35S promoter or a v-ATPase C1 promoter can be used for constitutive expression in the intact plants.

In particular, genes encoding desaturases and elongases can be cloned into a binary vector one after the other by constructing a plurality of expression cassettes in order to mimic the metabolic pathway in plants.

Within an expression casette, the protein to be expressed can be targeted into a cellular compartment using a signal peptide, for example for plastids, mitochondria or the endoplasmic reticulum (Kermode, Crit. Rev. Plant Sci. 15, 4 (1996) 285-423). The signal peptide is cloned 5' in the reading frame with the cDNA to achieve the subcellular localization of the fusion protein.

Examples of multiexpression cassettes are given hereinbelow.

I.) Promoter-Terminator Cassettes

Expression cassettes consist of least two functional units such as a promoter and a terminator. Further desired gene sequences such as targeting sequences, coding regions of genes or parts thereof and the like can be inserted between promoter and terminator. To construct expression cassettes, promoters and terminators (USP promoter: Baeumlein et al., Mol Gen Genet, 1991, 225 (3):459-67); OCS terminator: Gielen et al. EMBO J. 3 (1984) 835ff.) are isolated with the aid of the polymerase chain reaction and tailor-made with flanking sequences of choice on the basis of synthetic oligonucleotides.

Examples of oligonucleotides which can be used are the following:

```
USP1 upstream:
CCGGAATTCGGCGCGCCGAGCTCCTCGAGCAAATTTACACATTGCCA
(SEQ ID NO: 54)

USP2 upstream:
CCGGAATTCGGCGCGCCGAGCTCCTCGAGCAAATTTACACATTGCCA
(SEQ ID NO: 55)
```

-continued

USP3 upstream:
CCGGAATTCGGCGCGCCGAGCTCCTCGAGCAAATTTACACATTGCCA
(SEQ ID NO: 56)

USP1 downstream:
AAAACTGCAGGCGGCCGCCCACCGCGGTGGGCTGGCTATGAAGAAATT
(SEQ ID NO: 57)

USP2 downstream:
CGCGGATCCGCTGGCTATGAAGAAATT
(SEQ ID NO: 58)

USP3 downstream:
TCCCCCGGGATCGATGCCGGCAGATCTGCTGGCTATGAAGAAATT
(SEQ ID NO: 59)

OCS1 upstream:
AAAACTGCAGTCTAGAAGGCCTCCTGCTTTAATGAGATAT
(SEQ ID NO: 60)

OCS2 upstream:
CGCGGATCCGATATCGGGCCCGCTAGCGTTAACCCTGCTTTAATGAGATA
T (SEQ ID NO: 61)

OCS3 upstream:
TCCCCCGGGCCATGGCCTGCTTTAATGAGATAT
(SEQ ID NO: 62)

The constructs are defined in accordance with the invention in SEQ ID NO: 33, 34 and 42. They comprise the USP promoter and the OCS terminator. Based on these plasmids, the construct pUT12 is generated by cutting pUT1 with SalI/ScaI and cutting pUT2 with XhoI/ScaI. The fragments in the expression cassettes are ligated and transformed into *E. coli* XLI blue MRF. After picking out ampicillin-resistant colonies, DNA is prepared, and those clones which comprise two expression cassettes are identified by restriction analysis. The XhoI/SalI ligation of compatible ends has eliminated the two cleavage sites XhoI and SalI between the expression cassettes. This gives rise to plasmid pUT12, which is defined in SEQ ID NO: 36. pUT12 is subsequently cut again with SalI/ScaI and pUT3 with XhoI/ScaI. The fragments comprising the expression cassettes are ligated and transformed into *E. coli* XLI blue MRF. After singling out ampicillin-resistant colonies, DNA is prepared, and those clones which comprise three expression cassettes are identified by restriction analysis. In this manner, a set of multiexpression cassettes is created which can be exploited for inserting the desired DNA and is described in Table 1 and can additionally incorporate further expression cassettes.

They comprise the following elements:

TABLE 1

| pUC19 derivate | Cleavage sites before the USP promoter | Multiple cloning cleavage sites | Cleavage sites behind the OCS terminator |
|---|---|---|---|
| pUT1 | EcoRI/AscI/SacI/XhoI | BstXI/NotI/PstI/XbaI/StuI | SalI/EcoRI/SacI/AscI/HindIII |
| pUT2 | EcoRI/AscI/SacI/XhoI | BamHI/EcoRV/ApaI/NheI/HpaI | SalI/EcoRI/SacI/AscI/HindIII |
| pUT3 | EcoRI/AscI/SacI/XhoI | BglII/NaeI/ClaI/SmaI/NcoI | SalI/SacI/AscI/HindIII |
| pUT12 Double expression cassette | EcoRI/AscI/SacI/XhoI | BstXI/NotI/PstI/XbaI/StuI and BamHI/EcoRV/ApaI/NheI/HpaI | SalI/EcoRI/SacI/AscI/HindIII |
| pUT123 Triple expression cassette | EcoRI/AscI/SacI/XhoI | 1. BstXI/NotI/PstI/XbaI/StuI and 2. BamHI/EcoRV/ApaI/NheI/HpaI and 3. BglII/NaeI/ClaI/SmaI/NcoI | SalI/SacI/AscI/HindIII |

-continued

OCS1 downstream:
CCCAAGCTTGGCGCGCCGAGCTCGAATTCGTCGACGGACAATCAGTAAAT
-TGA (SEQ ID NO: 63)

OCS2 downstream:
CCCAAGCTTGGCGCGCCGAGCTCGAATTCGTCGACGGACAATCAGTAAAT
TGA (SEQ ID NO: 64)

OCS3 downstream:
CCCAAGCTTGGCGCGCCGAGCTCGTCGACGGACAATCAGTAAATTGA
(SEQ ID NO: 65)

The methods are known to the specialist worker and are generally known from the literature.

In a first step, a promoter and a terminator are amplified via PCR. Then, the terminator is cloned into a recipient plasmid and, in a second step, the promoter is inserted upstream of the terminator. This gives an expression cassette on a plasmid vehicle. The plasmids pUT1, 2 and 3 are generated on the basis of the plasmid pUC19.

Furthermore, further multiexpression cassettes can be generated and employed for seed-specific gene expression, as described and as specified in greater detail in Table 2, with the aid of the i) USP promoter or with the aid of the ii) 700 base pair 3' fragment of the LeB4 promoter or with the aid of the iii) DC3 promoter.

The DC3 promoter is described in Thomas, Plant Cell 1996, 263:359-368 and consists merely of the region −117 to +26, which is why it therefore constitutes one of the smallest known seed-specific promoters. The expression cassettes can comprise several copies of the same promoter or else be constructed via three different promoters.

The vectors used for the transformation of plants and the sequences of the inserted genes/proteins can be found in sequence listing SEQ ID NO: 43 to 49.

Advantageously used polylinker or polylinker-terminator-polylinkers can be found in the sequences SEQ ID NO: 50 to 52.

TABLE 2

Multiple expression cassettes

| Plasmid name of the pUC19 derivative | Cleavage sites before the respective promoter | Multiple cloning cleavage sites | Cleavage sites behind the OCS terminator |
|---|---|---|---|
| pUT1 (pUC19 with USP-OCS1) | EcoRI/AscI/SacI/XhoI | (1) BstXI/NotI/PstI/XbaI/StuI | SalI/EcoRI/SacI/AscI/HindIII |
| pDCT (pUC19 with DC3-OCS) | EcoRI/AscI/SacI/XhoI | (2) BamHI/EcoRV/ApaI/NheI/HpaI | SalI/EcoRI/SacI/AscI/HindIII |
| pLeBT (pUC19-with LeB4(700)-OCS) | EcoRI/AscI/SacI/XhoI | (3) BglII/NaeI/ClaI/SmaI/NcoI | SalI/SacI/AscI/HindIII |
| pUD12 (pUC 19 with USP-OCS1 and with DC3-OCS) | EcoRI/AscI/SacI/XhoI | (1) BstXI/NotI/PstI/XbaI/StuI and (2) BamHI/EcoRV/ApaI/NheI/HpaI | SalI/EcoRI/SacI/AscI/HindIII |
| pUDL123 Triple expression cassette (pUC19 with USP/DC3 and LeB4-700) | EcoRI/AscI/SacI/XhoI | (1) BstXI/NotI/PstI/XbaI/StuI and (2) BamHI/(EcoRV*)/ApaI/NheI/HpaI and (3) BglII/NaeI/ClaI/SmaI/NcoI | SalI/SacI/AscI/HindIII |

*EcoRV cleavage site in the 700 base-pair fragment of the LeB4 promoter (LeB4-700)

Further promoters for multi-gene constructs can be generated analogously, in particular using the
a) 2.7 kb fragment of the LeB4 promoter or with the aid of the
b) phaseolin promoter or with the aid of the
c) constitutive v-ATPase c1 promoter.

It may be particularly desirable to use further especially suitable promoters for constructing seed-specific multi-expression cassettes such as, for example, the napin promoter or the arcelin-5 promoter.

II) Generation of Expression Constructs which Comprise Promoter, Terminator and Desired Gene Sequence for the Expression of PUFA Genes in Plant Expression Cassettes.

In pUT123, the Δ6-elongase Pp_PSE1 is first inserted into the first cassette via BstXI and XbaI. Then, the moss Δ-6-desaturase (Pp_des6) is inserted into the second cassette via BamHI/NaeI, and, finally, the *Phaeodactylum* Δ5-desaturase (Pt_des5) is inserted into the third cassette via BglII/NcoI. The triple construct is named pARA1. Taking into consideration sequence-specific restriction cleavage sites, further expression cassettes are shown in Table 3, which are named pARA2, pARA3 and pARA4, can be generated.

TABLE 3

Combinations of desaturases and elongases

| Gene plasmid | Δ6-Desaturase | Δ5-Desaturase | Δ6-Elongase |
|---|---|---|---|
| pARA1 | Pp_des6 | Pt_des5 | Pp_PSE1 |
| pARA2 | Pt_des6 | Pt_des5 | Pp_PSE1 |
| pARA3 | Pt_des6 | Ce_des5 | Pp_PSE1 |
| pARA4 | Ce_des6 | Ce_des5 | Ce_PSE1 |

Pp = *Physcomitrella patens*,
Pt = *Phaeodactylum tricornutum*
Pp_PSE1 corresponds to the sequence of SEQ ID NO: 3.
PSE = PUFA-specific Δ6-elongase
Ce_des5 = Δ5-desaturase from *Caenorhabditis elegans* (Genbank Acc. No. AF078796)
Ce_des6 = Δ6-desaturase from *Caenorhabditis elegans elegans* (Genbank Acc. No. AF031477, bases 11–1342)
Ce_PSE1 = Δ6-elongase from *Caenorhabditis elegans* (Genbank Acc. No. AF244356, bases 1–867)

Further desaturases or elongase sequences can also be inserted into the expression cassettes in the described manner, such as, for example, Genbank Acc. Nr. AF231981, NM_013402, AF206662, AF268031, AF226273, AF110510 or AF110509.

iii) Transfer of expression Cassettes into vectors for the transformation of *Agrobacterium tumefaciens* and for the transformation of Plants The constructs generated thus are inserted into the binary vector PGPTV by means of AscI. For this purpose, the multiple cloning sequence is extended by an AscI cleavage site. For this purpose, the polylinker is synthesized de novo as two double-stranded oligonucleotides, thereby introducing an additional AscI DNA sequence. The oligonucleotide is inserted into the vector pGPTV by means of EcoRI and HindIII. The cloning techniques required are known to the skilled worker and can simply be found in the literature as described in Example 1.

Example 6

Studying the Expression of a Recombinant Gene Product in a Transformed Organism

The activity of a recombinant gene product in the transformed host organism can be measured at the transcriptional and/or the translational level.

A suitable method for determining the extent to which the gene is transcribed (which indicates the amount of RNA which is available for the translation of the gene product) is to carry out a Northern blot as detailed hereinbelow (as reference, see Ausubel et al. (1988) Current Protocols in Molecular Biology, Wiley: New York, or the abovementioned Examples Section), where a primer which is designed in such a way that it binds to the gene of interest is labeled with a detectable label (usually a radioactive label or a chemiluminescent label) so that, when the total RNA of a culture of the organism is extracted, separated on a gel, transferred onto a stable matrix and incubated with this probe, the binding and extent of the binding of the probe indicates the existence and also the amount of the mRNA for this gene. This information indicates the degree to which the transformed gene has been transcribed. Cellular total RNA can be prepared from cells, tissues or organs using a plurality of methods, all of which are known in the art, such as, for example, the method of Bormann, E. R., et al. (1992) Mol. Microbiol. 6:317-326.

Northern Hybridization:

To carry out the RNA hybridization, 20 μg of total RNA or 1 μg of poly(A)+RNA were separated by gel electrophoresis in agarose gels with a strength of 1.25% using formaldehyde, as described in Amasino (1986, Anal. Biochem. 152, 304), capillary-blotted onto positively charged nylon membranes Hybond N+, Amersham, Braunschweig) using 10×SSC, immobilized using UV-light and prehybridized for 3 hours at 68° C. using hybridization buffer (10% dextran sulfate w/v, 1 M NaCl, 1% SDS, 100 mg herring sperm DNA). The DNA probe was labeled with the Highprime DNA labeling kit (Roche, Mannheim, Germany) during the prehybridization step, using alpha-$^{32}$P-dCTP (Amersham, Braunschweig, Germany). After the labeled DNA probe had been added, the hybridization was carried out overnight at 68° C. in the same buffer. The wash steps were carried out twice for 15 minutes using 2×SSC and twice for 30 minutes using 1×SSC, 1%. SDS, at 68° C. The sealed filters were exposed at −70° C. for a period of 1 to 14 days.

Standard techniques, such as a western blot, can be employed for studying the presence or the relative amount of protein translated by this mRNA (see, for example, Ausubel et al. (1988) Current Protocols in Molecular Biology, Wiley: New York). In this method, the cellular total proteins are extracted, separated by gel electrophoresis, transferred to a matrix such as nitrocellulose and incubated with a probe such as an antibody which binds specifically to the desired protein. This probe is usually provided with a chemiluminescent or calorimetric label which can be detected readily. The presence and the amount of the label observed indicates the presence and the amount of the desired mutated protein present in the cell.

Example 7

Analysis of the Effect of the Recombinant Proteins on the Production of the Desired Product The effect of the genetic modification in plants, fungi, algae, ciliates or on the production of a desired compound (such as a fatty acid) can be determined by growing the modified microorganisms or the modified plant under suitable conditions (such as those described above) and analyzing the medium and/or the cellular components for the increased production of the desired product (i.e. of lipids or a fatty acid). These analytical techniques are known to the skilled worker and comprise spectroscopy, thin-layer chromatography, various types of staining methods, enzymatic and microbiological methods, and analytical chromatography such as high-performance liquid chromatography (see, for example, Ullman, Encyclopedia of Industrial Chemistry, vol. A2, pp. 89-90 and pp. 443-613, VCH: Weinheim (1985); Fallon, A., et al., (1987) "Applications of HPLC in Biochemistry" in: Laboratory Techniques in Biochemistry and Molecular Biology, vol. 17; Rehm et al. (1993) Biotechnology, vol. 3, chapter III: "Product recovery and purification", pp. 469-714, VCH: Weinheim; Belter, P. A., et al. (1988) Bioseparations: downstream processing for Biotechnology, John Wiley and Sons; Kennedy, J. F. and Cabral, J. M. S. (1992) Recovery processes for biological Materials, John Wiley and Sons; Shaeiwitz, J. A., and Henry, J. D. (1988) Biochemical Separations, in: Ullmann's Encyclopedia of Industrial Chemistry, vol. B3; chapter 11, pp. 1-27, VCH: Weinheim; and Dechow, F. J. (1989) Separation and purification techniques in biotechnology, Noyes Publications).

In addition to the abovementioned methods, plant lipids are extracted from plant material as described by Cahoon et al. (1999) Proc. Natl. Acad. Sci. USA 96 (22):12935-12940, and Browse et al. (1986) Analytic Biochemistry 152:141-145. The qualitative and quantitative lipid and fatty acid analysis is described by Christie, William W., Advances in Lipid Methodology, Ayr/Scotland: Oily Press (Oily Press Lipid Library; 2); Christie, William W., Gas Chromatography and Lipids. A Practical Guide—Ayr, Scotland: Oily Press, 1989, Repr. 1992, IX, 307 S. (Oily Press Lipid Library; 1); "progress in Lipid Research, Oxford: Pergamon Press, 1 (1952)-16 (1977) u.d.T.: Progress in the Chemistry of Fats and Other Lipids CODEN.

To determine the overall efficiency with which the compound is produced, it is also possible, in addition to measuring the fermentation end product, to analyze other components of the metabolic pathways which are used for producing the desired compounds, such as intermediates and secondary products. The analytical methods comprise measurements of the nutrient quantities in the medium (for example sugars, hydrocarbons, nitrogen sources, phosphate and other ions), measurements of the biomass composition and the growth, analysis of the production of usual metabolites via biosynthetic pathways, and measurements of gases which are generated during the fermentation process. Standard methods for these measurements are described in Applied Microbial Physiology; A Practical Approach, P. M. Rhodes and P. F. Stanbury, ed., IRL Press, pp. 103-129; 131-163 and 165-192 (ISBN: 0199635773) and references cited therein.

One example is the analysis of fatty acids (abbreviations: FAMEs, fatty acid methyl esters; GC-MS, gas liquid chromatography/mass spectrometry; TAG, triacylglycerol; TLC, thin-layer chromatography).

Unequivocal proof for the presence of fatty acid products can be obtained by the analysis of recombinant organisms following standard analytical procedures: GC, GC-MS or TLC as variously described by Christie and references therein (1997, in: Advances on Lipid Methodology, Fourth ed.: Christie, Oily Press, Dundee, 119-169; 1998, gas-chromatography/mass-spectrometry methods, Lipids 33:343-353).

Material to be analyzed can be disintegrated via sonication, glass milling, liquid nitrogen and grinding or via other applicable methods. The material has to be centrifuged after disintegration. The sediment is resuspended in Aqua dest, heated for 10 min at 100° C., cooled on ice and centrifuged again, followed by extraction in 0.5 M sulfuric acid in methanol containing 2% dimethoxypropane for 1 h at 90° C., leading to hydrolyzed oil and liquid compounds, resulting in transmethylated lipids. These fatty acid methyl esters are extracted in petrolether and finally subjected to GC analysis using a capillary column (Chrompack, WCOT Fused Silica, CP-Wax-52 CB, 25 μm, 0.32 mm) at a temperature gradient between 170° C. and 240° C. for 20 min and 5 min at 240° C. The identity of resulting fatty acid methylesters has to be defined by the use of standards available from commercial sources (i.e. Sigma).

In the case of fatty acids where standards are not available molecule identity has to be shown via derivatization and subsequent GC MS analysis. For example the localization of triple bond fatty acids has to be shown via GC-MS after derivatization via 4,4-dimethoxyoxazoline derivatives (Christie, 1998, see above).

Expression constructs in Heterologous Microbial Systems

Strains, Growth Conditions and Plasmids

*Escherichia coli* strain XL1 Blue MRF' kan (Stratagene) was used for sub-cloning the new elongase pPDesaturase1 from *Physcomitrella patens*. For functional expression of this gene we used the *Saccharomyces cerevisiae* strain INVSc 1 (Invitrogen Co.). *E. coli* was grown in Luria-Bertini broth (LB, Duchefa, Haarlem, The Netherlands) at 37° C. When necessary, ampicillin (100 mg/liter) was added and 1.5% (w/v) agar was included for solid LB media. *S. cerevisiae* was grown at 30° C. either in YPG-medium or in complete minimal dropout uracil medium (CMdum; see in: Ausubel, F. M., Brent, R., Kingston, R. E., Moore, D. D., Seidman, J. G., Smith, J. A., Struhl, K., Albright, L. B., Coen, D. M., and Varki, A. (1995) Current Protocols in Molecular Biology, John Wiley & Sons, New York) containing either 2% (w/v) raffinose or glucose. For solid media 2% (w/v) Bacto™ agar (Difco) was included. Plasmids used for cloning and expression were pUC18 (Pharmacia) and pYES2 (Invitrogen Co.).

Example 8

Cloning and Expression of PUFA-specific Desaturases and Elongases

For expression in plants, cDNA clones from SEQ ID NO: 1, 3, 5, 7, 9, 11, 13, 15, 17, 19, 21, 23, 25, 27, 29, 31 were modified in such a way that only the coding region was amplified by means of polymerase chain reaction using two oligonucleotides. Care was taken that a consensus sequence before the start codon was maintained for efficient translation. To this end, either the base sequence ATA or AAA was chosen and introduced into the sequence before the ATG (Kozak, M. (1986) Point mutations define a sequence flanking the AUG initiator codon that modulates translation by eukaryotic ribosomes, Cell 44, 283-292). In addition, a restriction cleavage site was introduced before this consensus triplet, which restriction cleavage site must be compatible with the cleavage site of the target vector into which the fragment is to be cloned and with the aid of which the expression of genes in microorganisms or plants is to take place.

The PCR reaction was performed with plasmid DNA as template in a Thermocycler (Biometra) using the Pfu-DNA (Stratagene) polymerase and the following temperature programme: 3 minutes at 96° C., followed by 30 cycles with 30 seconds at 96° C., 30 seconds at 55° C. and 2 minutes at 72° C., 1 cycle with 10 minutes at 72° C. and stop at 4° C. The annealing temperature was varied, depending on the oligonucleotides chosen. A synthesis time of approximately one minute can be assumed per kilobase pairs DNA. Further parameters which have an effect on the PCR such as, for example, Mg ions, salt, DNA polymerase and the like are known to the specialist worker and can be varied as required.

The correct size of the amplified DNA fragment was verified by agarose-TBE gel electrophoresis. The amplified DNA was extracted from the gel using the QIAquick Gel Extraction Kit (QIAGEN) and ligated into the SmaI restriction site of the dephosphorylated vector pUC18 using the Sure Clone Ligation Kit (Pharmacia), giving rise to the pUC derivatives. After the transformation of *E. coli* XL1 Blue MRF' kan, a DNA miniprep (Riggs, M. G., & McLachlan, A. (1986) A simplified screening procedure for large numbers of plasmid mini-preparation. BioTechniques 4, 310-313) was carried out on ampicillin-resistant transformants, and positive clones were identified by means of BamHI restriction analysis. The sequence of the cloned PCR product was verified by resequencing using the ABI PRISM Big Dye Terminator Cycle Sequencing Ready Reaction Kit (Perkin-Elmer, Weiterstadt).

Fatty Acid Analysis

The total fatty acids were extracted from plant seeds and analyzed by gas chromatography.

The seeds were taken up in 1% sodium methoxide in methanol and incubated for 20 minutes at RT. Thereafter, the mixture is washed with NaCl solution, and the FAMEs are taken up in 0.3 ml heptane. The samples were separated on a ZEBRON-ZB-Wax capillary column (30 m, 0.32 mm, 0.25 μm; Phenomenex) in a Hewlett Packard-6850 gas chromatograph with flame ionization detector. The oven temperature was programmed from 70° C. (1 minute hold) to 200° C. at a rate of 20° C./minute, then to 250° C. (5 min hold) at a rate of 5° C./min and finally to 260° C. at a rate of 5° C./min. Nitrogen was used as carrier gas (4.5 ml/min at 70° C.). The fatty acids were identified by comparing the retention times with those of FAME standards (SIGMA).

Expression Analysis

Result of the expression of a *Phaeodactylum tricornutum* Δ6-acyl-lipid desaturase, a *Phaeodactylum tricornutum* Δ5-acyl-lipid desaturase and the delta-6-specific elongase in tobacco seeds:

FIG. 2: Fatty acid profile of transgenic tobacco seeds. The plants were transformed with a triple expression cassette which expresses, under the control of the USP promoter, the delta-6-, the delta-5- and the Physcomitrella patens PpPSE1 (pARA2). 100 transgenic tobacco and linseed plants are generated, of which approximately 20% synthesize arachidonic acid in the seed.

FIG. 3: Tobacco wild-type control.

Example 9

Purification of the Desired Product from Transformed Organisms

The desired product can be obtained from plant material or fungi, algae, ciliates, animal cells or from the supernatant of the above-described cultures by various methods known in the art. If the desired product is not excreted from the cells, the cells can be harvested from the culture by slow centrifugation, and the cells can be lyzed by standard techniques such as mechanical force or sonication. Plant organs can be separated mechanically from other tissue or other organs. After homogenization, the cell debris is removed by centrifugation, and the supernatant fraction, which comprises the soluble proteins, is stored for the further purification of the desired compound. If the product is excreted from desired cells, the cells are removed from the culture by slow centrifugation, and the supernatant fraction is stored for further purification.

The supernatant fraction of each purification method is subjected to chromatography with a suitable resin, the desired molecule either being retained on the chromatography resin, while many contaminations in the sample are not, or else the contaminations are retained on the resin, while the sample is not. If necessary, these chromatography steps can be repeated, using identical or different chromatography resins. The skilled worker is familiar with the selection of suitable chromatography resins and their most effective application for a particular molecule to be purified. The purified product can be concentrated by filtration or ultrafiltration and stored at a temperature which provides maximum stability of the product.

A broad spectrum of purification methods is known in the art, and the above purification method is not intended to be limiting. These purification methods are described, for example, in Bailey, J. E., & Ollis, D. F., Biochemical Engineering Fundamentals, McGraw-Hill: New York (1986).

The identity and purity of the compounds which have been isolated can be determined by standard techniques of the art. These include high-performance liquid chromatography (HPLC), spectroscopic methods, staining methods, thin-layer chromatography, in particular thin-layer chromatography and flame ionization detection (IATROSCAN, Iatron, Tokio, Japan), NIRS, enzyme assay or microbiological methods. For an overview of these analytical methods, see: Patek et al. (1994) Appl. Environ. Microbiol. 60:133-140; Malakhova-et al. (1996) Biotekhnologiya 11:27-32; and Schmidt et al. (1998) Bioprocess Engineer. 19:67-70. Ulmann's Encyclopedia of Industrial Chemistry (1996) vol. A27, VCH: Weinheim, pp. 89-90, pp. 521-540, pp. 540-547, pp. 559-566, 575-581 and pp. 581-587; Michal, G (1999) Biochemical Pathways: An Atlas of Biochemistry and Molecular Biology, John Wiley and Sons; Fallon, A., et al. (1987) Applications of HPLC in Biochemistry in: Laboratory Techniques in Biochemistry and Molecular Biology, vol. 17.

EQUIVALENTS

The skilled worker will or can recognize many equivalents of the specific embodiments according to the invention described herein by simply using routine experiments. These equivalents are intended to fall within the patent claims.

We claim:

1. A process for the production of compounds in transgenic plant cells, plants or parts thereof, wherein said compounds are comprised of general Formula I:

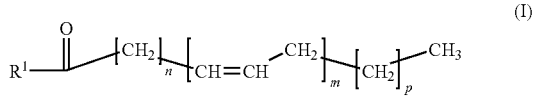

wherein $R^1$=—OH, coenzyme A (thioester), phosphatidylcholine, phosphatidylethanolamine, phoshatidylglycerol, diphosphatidylglycerol, phosphatidylserine, phosphadatidylinositol, sphingolipid, glycoshingolipid or a radical of general Formula II:

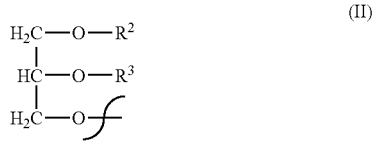

wherein $R^2$=saturated or unsaturated $C_{20}$-alkylcarbonyl-; and $R^3$=saturated or unsaturated $C_{20}$-alkylcarbonyl-;
wherein n=3, 4 or 6, m=3, 4 or 5; and p=0 or 3, and said compounds comprise at least 1% by weight of the total fatty acid content of said transgenic plants, which process comprises the following steps:

a) introducing, into a plant cell, plant or part thereof:
   i) at least one first nucleic acid sequence which encodes a polypeptide with an Δ6-desaturase activity;
   ii) at least one second nucleic acid sequence which encodes a polypeptide with a Δ6-elongase activity; and
   iii) a third nucleic acid sequence which encodes a polypeptide with a Δ5-desaturase activity; and
b) growing and harvesting the transgenic plant cell, plant or part thereof,
wherein said nucleic acid sequences are obtained from *Phaeodactylum tricornutum* or *Physcomitrella patens*, and
wherein the at least one first nucleic acid sequence comprises the sequence of SEQ ID NO: 13, a nucleic acid sequence encoding a polypeptide comprising the amino acid sequence of SEQ ID NO: 14, or a nucleic acid sequence encoding a polypeptide having at least 90% homology with the amino acid sequence of SEQ ID NO: 14 and having essentially the same enzymatic activity.

2. The process of claim 1, wherein $R^2$ and $R^3$ independently of one another are unsaturated $C_{20}$-alkylcarbonyl- with one, two, three, four or five double bonds.

3. The process of claim 1, wherein the plant is an oil crop.

4. The process of claim 1, wherein the plant is selected from the group consisting of soya, peanut, oilseed rape, canola, linseed, evening primrose, verbascum, thistle, hazelnut, almond, macadamia, avocado, bay, wild roses, pumpkin/squash, pistachios, sesame, sunflower, safflower, borage, maize, poppy, mustard, hemp, castor-oil plant, olive, Calendula, Punica, oil palm, walnut and coconut.

5. The process of claim 1, wherein the compounds of general Formula I are obtained from the transgenic plants by pressing or extraction, and said compounds are in the form of oils, fats, lipids or free fatty acids.

6. The process of claim 5, wherein the oils, fats, lipids or free fatty acids are refined.

7. The process of claim 1, wherein saturated or unsaturated fatty acids present in the compounds are liberated.

8. The process of claim 7, wherein the saturated or unsaturated fatty acids are liberated by alkaline hydrolysis or enzymatic cleavage.

9. The process of claim 1, wherein the compounds comprise at least 5% by weight, of the total fatty acid content of the transgenic plants.

10. The process of claim 1, wherein the nucleic acid sequence that encodes the polypeptide with Δ6-elongase activity or Δ5-desaturase activity comprises a nucleic acid sequence selected from the group consisting of:

a) a nucleic acid sequence comprising the sequence of SEQ ID NO: 3 or SEQ ID NO: 21, b) a nucleic acid sequence encoding a polypeptide comprising the amino acid sequence of SEQ ID NO: 4, SEQ ID NO: 11, SEQ ID NO: 18, or SEQ ID NO: 22, and c) a nucleic acid sequence encoding a polypeptide having at least 90% homology with the amino acid sequence of SEQ ID NO: 4 or SEQ ID NO: 22; wherein the polypeptide has essentially the same enzymatic activity.

11. The process of claim 1, wherein one or more of the first, second, and third nucleic acid sequences are linked with one or more regulatory signals in a nucleic acid construct.

12. The process of claim 11, wherein the nucleic acid construct comprises additional biosynthetic genes of fatty acid or lipid metabolism selected from the group consisting of acyl-CoA dehydrogenase(s), acyl-ACP [=acyl carrier protein] desaturase(s), acyl-ACP thioesterase(s), fatty acid acyl transferase(s), fatty acid synthase(s), fatty acid hydroxylase(s), acetyl-coenzyme A carboxylase(s), acyl-coenzyme A oxidase(s), fatty acid desaturase(s), fatty acid acetylenases, lipoxygenases, triacylglycerol lipases, allene oxide synthases, hydroperoxide lyases fatty acid elongase(s) and combinations thereof.

13. The process of claim 1, wherein the first, second and third nucleic acid sequences are stably integrated in the plant.

14. The process of claim 1, wherein the plant or part thereof comprises plant tissues, plant organs, plant leaves, plant roots, plant stems, intact plants, plant tubers, plant seeds, or cellular parts of any of the preceding.

15. The process of claim 5, wherein the pressing or the extraction is performed without supplying heat.

16. The process of claim 1, wherein the at least one second nucleic acid sequence comprises:

the sequence of SEQ ID NO: 3,
a nucleic acid sequence encoding a polypeptide comprising the amino acid sequence of SEQ ID NO: 4, or
a nucleic acid sequence encoding a polypeptide having at least 90% homology with the amino acid sequence of SEQ ID NO: 4, and having essentially the same enzymatic activity.

17. The process of claim 1, wherein the third nucleic acid sequence comprises:

the sequence of SEQ ID NO: 21,
a nucleic acid sequence encoding a polypeptide comprising the amino acid sequence of SEQ ID NO: 22, or
a nucleic acid sequence encoding a polypeptide having at least 90% homology with the amino acid sequence of SEQ ID NO: 22 and having essentially the same enzymatic activity.

18. The process of claim 11, wherein the first, second and third nucleic acid sequences are linked with one or more regulatory signals in said nucleic acid construct.

19. The process of claim 1, wherein the plant is a dicot.

20. The process of claim 1, wherein the plant is tobacco or linseed.

21. The process of claim 1, wherein the at least one second nucleic acid sequence comprises the sequence of SEQ ID NO: 3, a nucleic acid sequence encoding a polypeptide comprising the amino acid sequence of SEQ ID NO: 4, or a nucleic acid sequence encoding a polypeptide having at least 90% homology with the amino acid sequence of SEQ ID NO: 4 and having essentially the same enzymatic activity, and the third nucleic acid sequence comprises the sequence of SEQ ID NO: 21, a nucleic acid sequence encoding a polypeptide comprising the amino acid sequence of SEQ ID NO: 22, or a nucleic acid sequence encoding a polypeptide having at least 90% homology with the amino acid sequence of SEQ ID NO: 22 and having essentially the same enzymatic activity.

* * * * *

UNITED STATES PATENT AND TRADEMARK OFFICE
CERTIFICATE OF CORRECTION

| | | |
|---|---|---|
| PATENT NO. | : 7,893,320 B2 | Page 1 of 1 |
| APPLICATION NO. | : 10/511621 | |
| DATED | : February 22, 2011 | |
| INVENTOR(S) | : Petra Cirpus et al. | |

It is certified that error appears in the above-identified patent and that said Letters Patent is hereby corrected as shown below:

In the Claims:

In Claim 10, in column 257, on lines 4-5, "prising the amino acid sequence of SEQ ID NO: 4, SEQ ID NO: 11, SEQ ID NO: 18, or SEQ ID NO: 22, and" should read -- prising the amino acid sequence of SEQ ID NO: 4 or SEQ ID NO: 22, and --.

Signed and Sealed this
Fourteenth Day of June, 2011

David J. Kappos
*Director of the United States Patent and Trademark Office*